US009856223B2

(12) United States Patent
Treon et al.

(10) Patent No.: US 9,856,223 B2
(45) Date of Patent: Jan. 2, 2018

(54) METHODS TO TREAT LYMPHOPLASMACYTIC LYMPHOMA

(71) Applicant: Dana-Farber Cancer Institute, Inc., Boston, MA (US)

(72) Inventors: Steven P. Treon, Jamaica Plain, MA (US); Sara Jean Buhrlage, Somerville, MA (US); Nathanael S. Gray, Boston, MA (US); Li Tan, Boston, MA (US); Guang Yang, Natick, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 15/104,132

(22) PCT Filed: Dec. 12, 2014

(86) PCT No.: PCT/US2014/070162
§ 371 (c)(1),
(2) Date: Jun. 13, 2016

(87) PCT Pub. No.: WO2015/089479
PCT Pub. Date: Jun. 18, 2015

(65) Prior Publication Data
US 2016/0318878 A1 Nov. 3, 2016

Related U.S. Application Data

(60) Provisional application No. 62/036,934, filed on Aug. 13, 2014, provisional application No. 61/915,684, filed on Dec. 13, 2013.

(51) Int. Cl.
*A01N 43/54* (2006.01)
*A61K 31/505* (2006.01)
(Continued)

(52) U.S. Cl.
CPC .......... *C07D 239/47* (2013.01); *A61K 31/506* (2013.01); *A61K 45/06* (2013.01);
(Continued)

(58) Field of Classification Search
None
See application file for complete search history.

(56) References Cited

U.S. PATENT DOCUMENTS 6,455,520 B1  9/2002 Brown et al.
7,060,700 B2  6/2006 Brown et al.
(Continued)

FOREIGN PATENT DOCUMENTS

DE  WO2010026095  * 3/2010  .......... C07D 213/68
WO  WO 99/54286 A2  10/1999
(Continued)

OTHER PUBLICATIONS

Wolff et. al., "Burger's Medicinal Chemistry and Drug Discovery," 5th Ed. Part 1, pp. 975-977 (1995).*
(Continued)

Primary Examiner — Jeffrey H Murray
(74) Attorney, Agent, or Firm — Wolf, Greenfield & Sacks, P.C.

(57) ABSTRACT

The present invention provides compounds of any one of Formulae (A), (I-11), (II), and (V) (e.g., compounds of Formula (A-1)-(A-18)), and methods for treating Waldenström's macroglobulinemia (WM) and other B cell neoplasm in a subject using the compounds. The methods comprise administering to a subject in need thereof an effective amount of the compounds. Also provided are methods to treat B cell neoplasms using the compounds in combination with inhibitors of Bruton's tyrosine kinase (BTK), interleukin-1 receptor-associated kinase 1 (IRAK1), interleukin-1 receptor-associated kinase 4 (IRAK4), bone marrow on X chromosome kinase (BMX), phosphoinositide 3-kinase (PI3K), transforming growth factor b-activated kinase-1 (TAK1), and/or a Src family kinase.

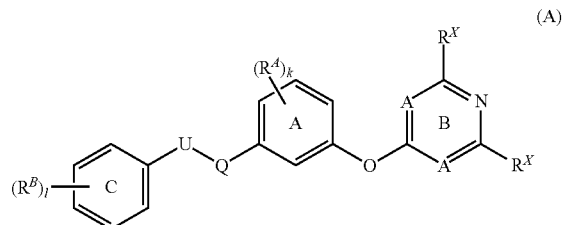

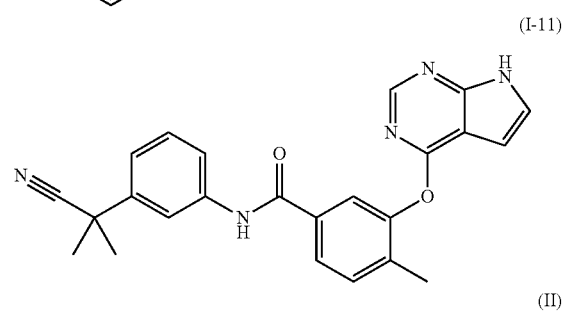

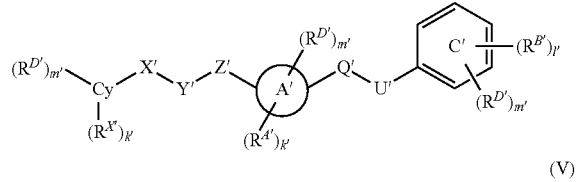

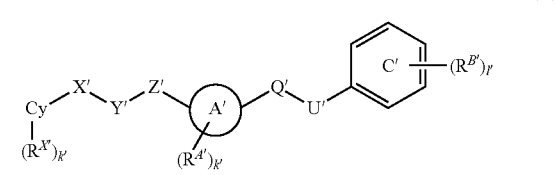

23 Claims, 1 Drawing Sheet

(51) Int. Cl.
| | |
|---|---|
| C07D 239/02 | (2006.01) |
| C07D 239/47 | (2006.01) |
| A61K 31/506 | (2006.01) |
| A61K 45/06 | (2006.01) |
| C07D 403/12 | (2006.01) |
| C07D 405/12 | (2006.01) |
| C07D 413/12 | (2006.01) |
| C07D 417/04 | (2006.01) |
| C07D 487/04 | (2006.01) |

(52) U.S. Cl.
CPC ......... *C07D 403/12* (2013.01); *C07D 405/12* (2013.01); *C07D 413/12* (2013.01); *C07D 417/04* (2013.01); *C07D 487/04* (2013.01)

(56) References Cited

U.S. PATENT DOCUMENTS

| | | |
|---|---|---|
| 2004/0106615 A1 | 6/2004 | Cochran et al. |
| 2007/0060619 A1 | 3/2007 | Burns et al. |
| 2009/0054405 A1 | 2/2009 | Booker et al. |
| 2009/0118297 A1 | 5/2009 | Simo et al. |
| 2012/0108572 A1 | 5/2012 | Wagner et al. |
| 2013/0040949 A1 | 2/2013 | Gray et al. |
| 2014/0162983 A1 | 6/2014 | Hodous et al. |
| 2016/0311807 A1 | 10/2016 | Treon et al. |

FOREIGN PATENT DOCUMENTS

| | | | |
|---|---|---|---|
| WO | WO 00/56737 | A2 | 9/2000 |
| WO | WO 03/030902 | A1 | 4/2003 |
| WO | WO 2008/144253 | A1 | 11/2008 |
| WO | WO 2008/150446 | A1 | 12/2008 |
| WO | WO 2009/137596 | A1 | 11/2009 |
| WO | WO 2010/056875 | A1 | 5/2010 |
| WO | WO 2011/029043 | A1 | 3/2011 |
| WO | WO2011090738 | * | 7/2011 ........... C07D 403/12 |
| WO | WO 2012/007375 | A1 | 1/2012 |
| WO | WO 2012/062704 | A1 | 5/2012 |
| WO | WO 2012/068096 | A2 | 5/2012 |
| WO | WO 2012/161877 | A1 | 11/2012 |
| WO | WO 2012/170976 | A2 | 12/2012 |
| WO | WO 2013/010380 | A1 | 1/2013 |
| WO | WO 2013/052699 | A2 | 4/2013 |
| WO | WO 2013/067277 | A1 | 5/2013 |
| WO | WO 2013/074986 | A1 | 5/2013 |
| WO | WO 2013/088404 | A1 | 6/2013 |

OTHER PUBLICATIONS

Banker, et. al., (1996), Modern Pharmaceuticals, p. 596.*
Chawla et. al. Current Research & Information on Pharmaceutical Science, 2004, 5(1), pp. 9-12.*
Newman et. al.; Drug Discovery Today, 2003, 8(19), pp. 898-905.*
International Search Report and Written Opinion for PCT/US2014/70167, dated Mar. 11, 2015.
International Preliminary Report on Patentability for PCT/US2014/70167, dated Jun. 23, 2016.
International Search Report and Written Opinion for PCT/US2014/70162, dated Mar. 11, 2015.
International Preliminary Report on Patentability for PCT/US2014/70162, dated Jun. 23, 2016.
International Search Report and Written Opinion for PCT/US2015/56899, dated Jan. 29, 2016.
CAS Registry No. 1298854-20-2, STN Entry Date May 22, 2011.
CAS Registry No. 1319879-27-0, STN Entry Date Aug. 19, 2011.
Buckley, et al., IRAK-4 inhibitors. Part I: A series of amides, Bioorganic & Medicinal Chemistry Letters, vol. 18, Issue 11, pp. 3211-3214.
Buckley, et al., IRAK-4 inhibitors. Part III: A series of imidazo[1,2-a]pyridines, Bioorganic & Medicinal Chemistry Letters, vol. 18, Issue 12, pp. 3656-3660.

Cheng et al., Binding of Bruton's tyrosine kinase to Fyn, Lyn, or Hck through a Src homology 3 domain-mediated interaction, Proc. Natl. Acad. Sci. USA 91 (1994).
Choi et al., Discovery and structural Bioorg Med Chem. Bioorg Med Chem Lett. Aug. 1, 2009;19(15):4467-70. doi: 10.1016/j.bmcl.2009.05.029. Epub May 13, 2009.
Davis et al., Comprehensive analysis of kinase inhibitor selectivity. Nat. Biotechnol. 2011, 29(11): 1046-1051.
Ding et al., Constitutively activated STAT3 promotes cell proliferation and survival in the activated B-cell subtype of diffuse large B-cell lymphomas. Blood. Feb. 1, 2008; 111(3): 1515-23.
Ditzel et al., Establishment of BVWM.1 cell line for Waldenstrom's macroglobulinemia with productive in vivo engraftment in SCID-hu mice, Experimental Hematology 35 (2007) 1366-1375.
Fabian et al., A small molecule-kinase interaction map for clinical kinase inhibitors. Nat. Biotechnol. 2005, 23(3): 329-336.
Hodge et al., Establishment and characterization of a novel Waldenstrom macroglobulinemia cell line, MWCL-1, Blood. 2011;117(19):e190-e197, doi:10.1182/blood-2010-12-326868.
Horwood et al., Bruton's tyrosine kinase is required for lipopolysaccharide-induced tumor necrosis factor alpha production, J. Exp. Med., Jun. 16, 2003;197(12):1603-11.
Iwaki et al., Btk Plays a Crucial Role in the Amplification of Fc RI-mediated Mast Cell Activation by Kit, J. Biol. Chem., 2005, 280(48), 40261-40270.
Jeffries et al., Bruton's Tyrosine Kinase Is a Toll/Interleukin-1 Receptor Domain-binding Protein That Participates in Nuclear Factor B Activation by Toll-like Receptor 4, J.Biol. Chem., 2003, 278, 26258-26264.
Koshiol et al., Chronic immune stimulation and subsequent Waldenstrom's macroglobulinemia, Arch Intern Med. Sep. 22, 2008; 168(17): 1903-1909. doi:10.1001/archinternmed.2008.4.
Kurosaki, Functional dissection of BCR signaling pathways, Curr Opin Immunol. Jun. 2000;12(3):276-81.
Kwarcinski et al., Irreversible inhibitors of c-Src kinase that target a nonconserved cysteine. ACS Chem Biol. Nov. 16, 2012;7(11):1910-7. doi: 10.1021/cb300337u. Epub Sep. 5, 2012.
Lam et al., Cooperative signaling through the signal transducer and activator of transcription 3 and nuclear factor-{kappa}B pathways in subtypes of diffuse large B-cell lymphoma. Blood. Apr. 1, 2008; 111(7): 3701-13.
Li et al., Creating chemical diversity to target protein kinases. Comb Chem High Throughput Screen. Aug. 2004;7(5):453-72.
Lim et al. Oncogenic MYD88 mutants require Toll-like receptors. In: Proceedings of the 104th Annual Meeting of the American Association for Cancer Research; Apr. 6-10, 2013; Washington, DC. Philadelphia: AACR; Cancer Res; (2013) 73(8 Suppl): Abst 2332. 10.1158/1538-7445.AM2013-2332.
Liu et al., Intracellular MHC class II molecules promote TLR-triggered innate immune responses by maintaining activation of the kinase Btk, Nature Immunology 12, 416-424 (2011) doi:10.1038/ni.2015.
Neparidze et al., Waldenstrom's Macroglobulinemia: Recent Advances in Biology and Therapy, Clin Adv Hematol Oncol. Oct. 2009 ; 7(10): 677-690.
Ngo et al., Oncogenically active MYD88 mutations in human lymphoma. Nature. Feb. 3, 2011; 470(7332): 115-9.
Patricelli et al., Functional interrogation of the kinome using nucleotide acyl phosphates. Biochemistry, 2007, 46(2): 350-358.
Peng-Cheng et al. Synthesis, molecular docking and evaluation of thiazolyl-pyrazoline derivatives as EGFR TK inhibitors and potential anticancer agents. Bioorg Med Chem Letts. 2011; 21:5374-5377.
Quek, et al., A role for Bruton's tyrosine kinase (Btk) in platelet activation by Collagen, Curr. Biol., 1998, 8(20), 1137-1140.
Sawasdikosol et al., HPK1 as a novel target for cancer immunotherapy, Immunol Res (2012) 54:262-265, DOI 10.1007/s12026-012-8319-1.
Schaeffer, et al., Tec family kinases in lymphocyte signaling and function, Curr Opin Immunol. Jun. 2000; 12(3): 282-88.
Vassilev, et al., Bruton's tyrosine kinase as an inhibitor of the Fas/CD95 death-inducing signaling complex, J. Biol. Chem., Jan. 15, 1999, 275(3): 1646-56.

(56) References Cited

OTHER PUBLICATIONS

Wang et al., Emerging targets in human lymphoma: targeting the MYD88 mutation. Blood Lymphat Cancer (2013) 2013:53-61.
Wang et al., Consequences of the recurrent MYD88(L265P) somatic mutation for B cell tolerance. J Exp Med. Mar. 10, 2014; 211(3): 413-26.
Wesche et al., MyD88: An Adapter That Recruits IRAK to the IL-1 Receptor Complex, Immunity, 1997, vol. 7, Issue 6, 837-847.
Yang et al, A Mutation in MYD88 (L265P) supports the survival of lymphoplasmacytic cells by activation of Bruton tyrosine kinase in Waldenstrom macroglobulinemia, Blood, Aug. 15, 2013;122(7):1222-32. doi: 10.1182/blood-2012-12-475111. Epub Jul. 8, 2013.
International Preliminary Report on Patentability for PCT/US2015/56899, dated May 4, 2017.
CAS Registry No. 1388492-05-4, STN Entry Date Aug. 9, 2012.
CAS Registry No. 1320831-41-1, STN Entry Date Aug. 21, 2011.

* cited by examiner

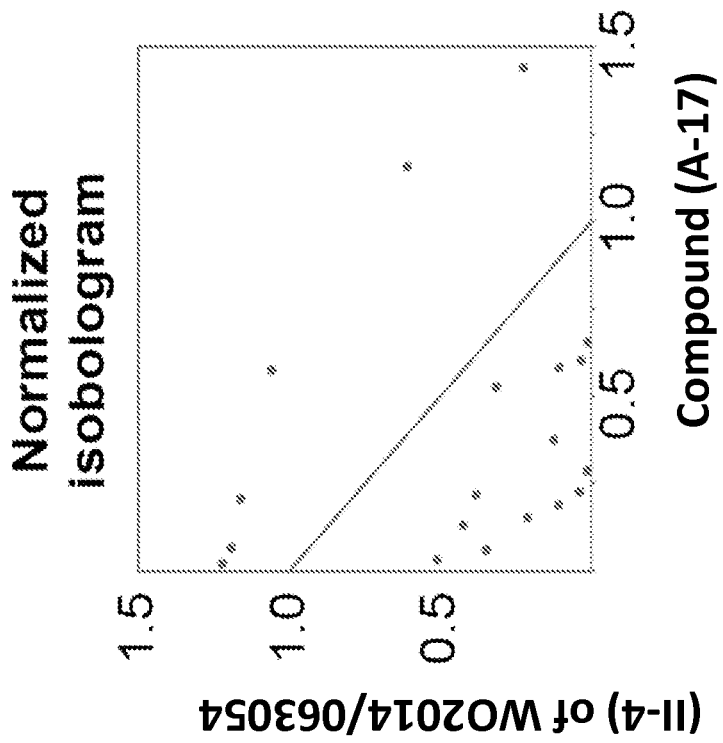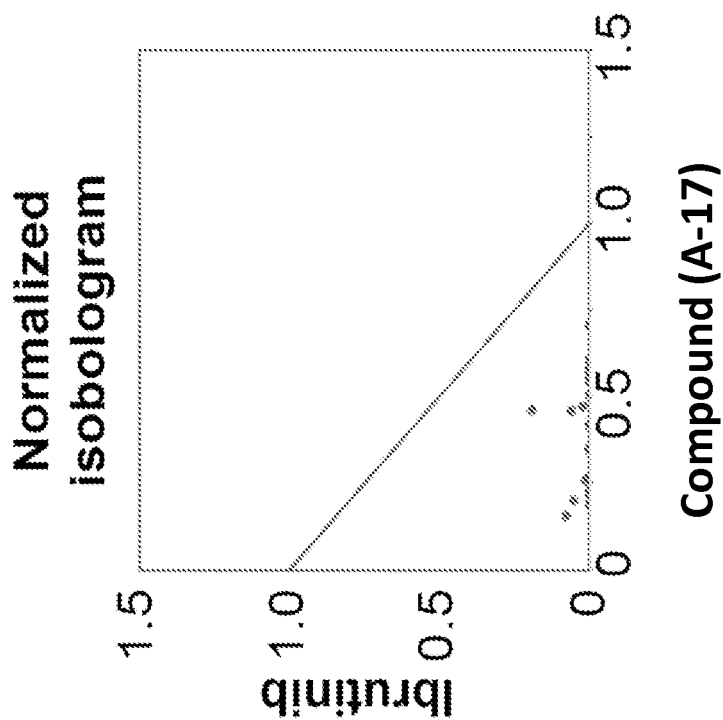

METHODS TO TREAT LYMPHOPLASMACYTIC LYMPHOMA

RELATED APPLICATIONS

The present application is a national stage filing under 35 U.S.C. §371 of international PCT application, PCT/US2014/070162, filed Dec. 12, 2014, which claims priority under 35 U.S.C. §119(e) to U.S. provisional patent applications, U.S. Ser. No. 62/036,934, filed Aug. 13, 2014, and U.S. Ser. No. 61/915,684, filed Dec. 13, 2013, the entire contents of each of which are incorporated herein by reference.

GOVERNMENT SUPPORT

This invention was made with government support under grant numbers 5R01CA130876-05, 5P50CA090578-10, 5R01CA136851-04, 2R01CA136851-05, and 1R01CA172592-01A1, awarded by the National Institutes of Health. The government has certain rights in the invention.

BACKGROUND OF THE INVENTION

Waldenström's macroglobulinemia (WM) is a distinct clinicopathological entity resulting from the accumulation, predominantly in the bone marrow, of clonally related lymphoplasmacytic cells which secrete a monoclonal IgM protein. This condition is considered to correspond to lymphoplasmacytic lymphoma (LPL) as defined by the World Health Organization classification system. WM is a rare disorder, with fewer than 1,500 cases occurring in the United States annually. There is a 2- to 3-fold risk increase of developing WM in people with a personal history of autoimmune diseases with autoantibodies and particularly elevated risks associated with hepatitis, human immunodeficiency virus, and rickettsiosis (*Arch. Intern. Med.,* 2008, 168(17), 1903-9). There is no single accepted treatment for WM, and there can be a marked variation in clinical outcome. Objective response rates are high (>80%) but complete response rates are low (0-15%) (*Clin. Adv. Hematol. Oncol.,* 2009, 7(10), 677-81, 687-90). Thus, there is a need for effective treatment of WM.

SUMMARY OF THE INVENTION

The present invention is based, at least in part, on the discovery of compounds of the Formula (A):

(A)

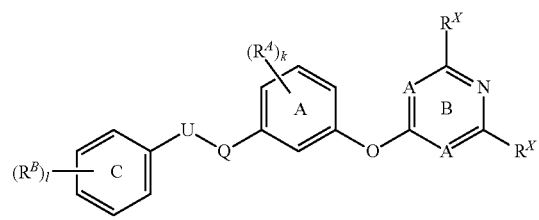

or a pharmaceutically acceptable salt thereof, wherein Q, U, $R^A$, $R^B$, $R^X$, k, and l are defined herein, for the treatment of Waldenström's macroglobulinemia. The activity of these compounds was established by in vitro screening against several kinases (e.g., BTK, HCK, TAK1, HPK1).

In certain embodiments, compounds of Formula (A) are of formula:

(A-1)

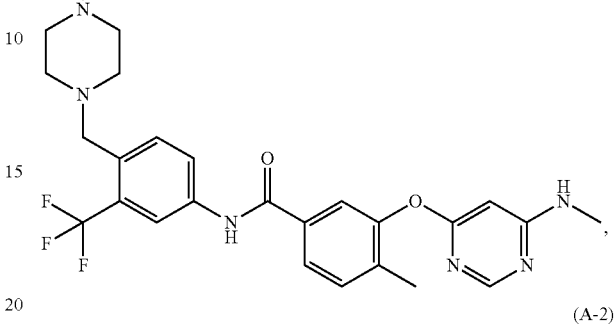

(A-2)

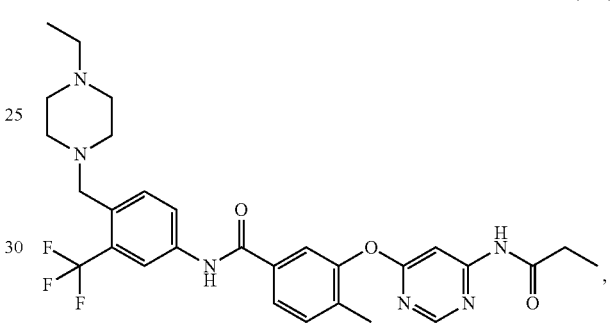

(A-3)

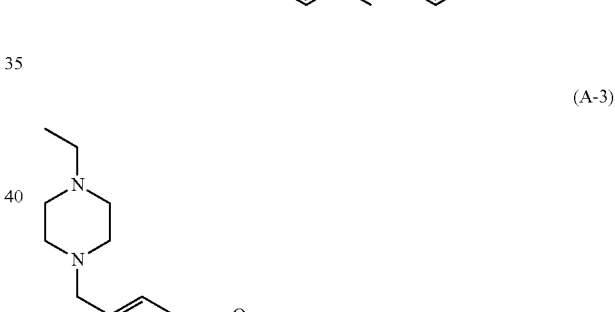

(A-4)

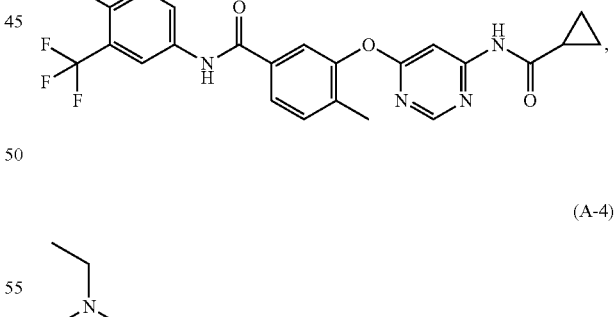

(A-5)
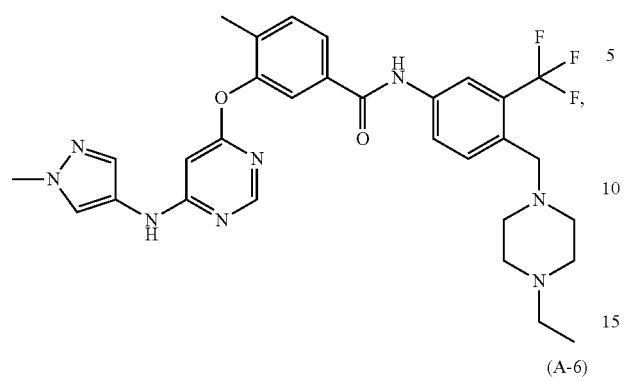
(A-9)
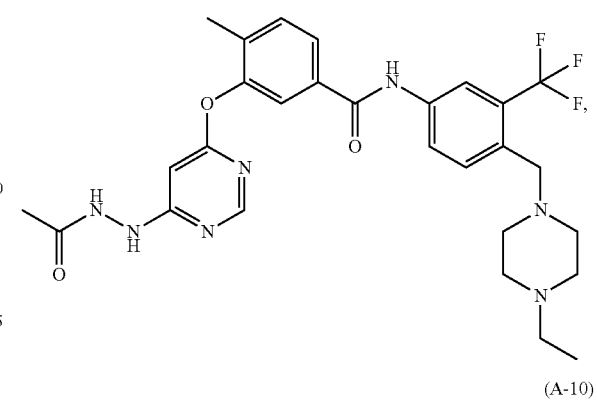
(A-6)
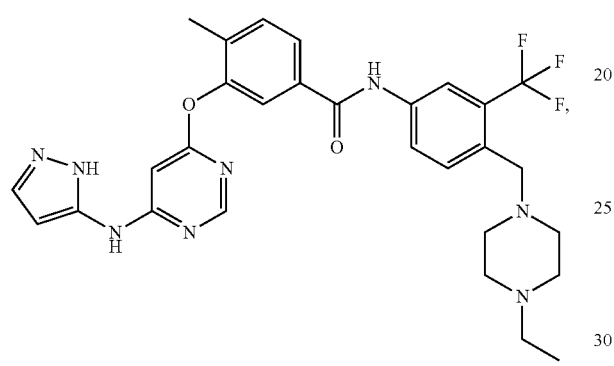
(A-10)
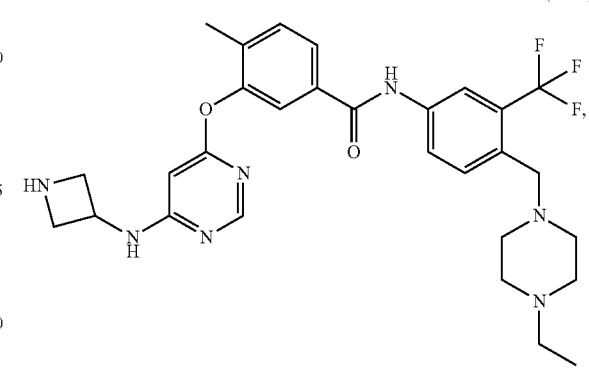
(A-7)
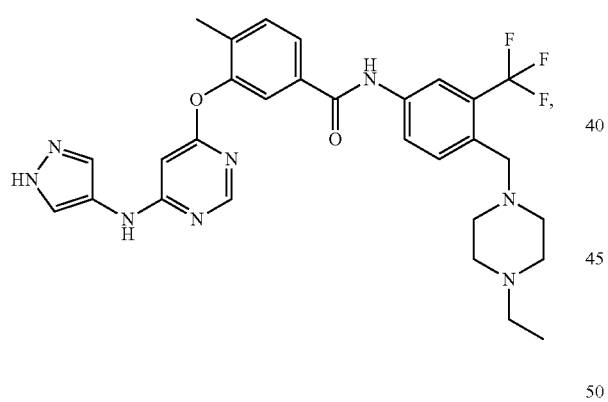
(A-11)
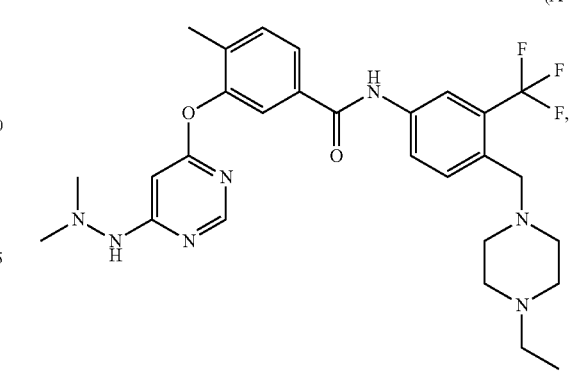
(A-8)
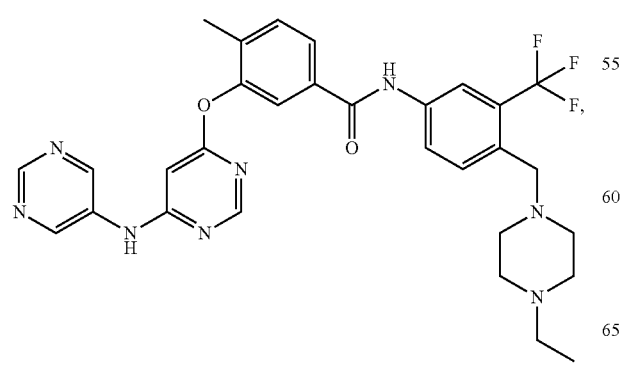
(A-12)
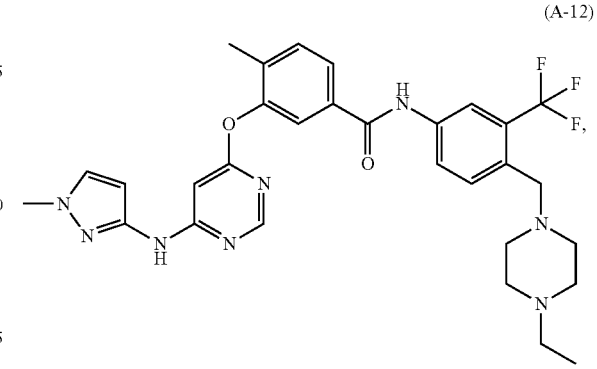

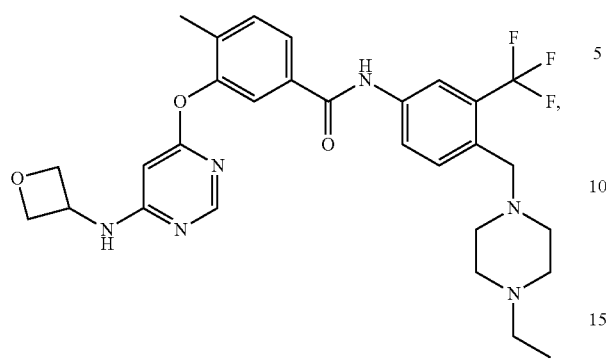
(A-13)
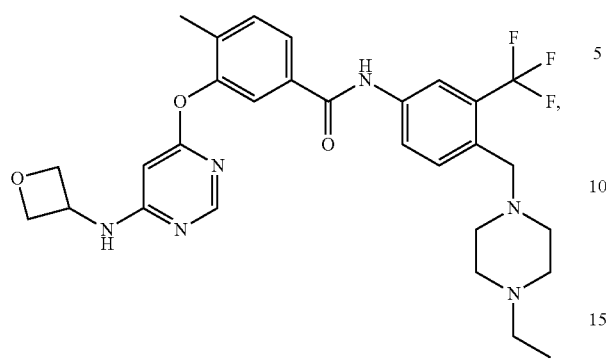
(A-14)
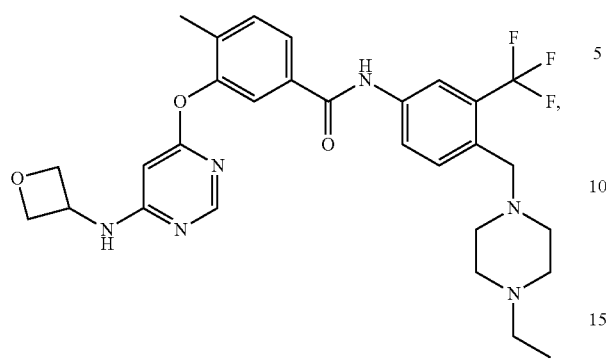
(A-15)
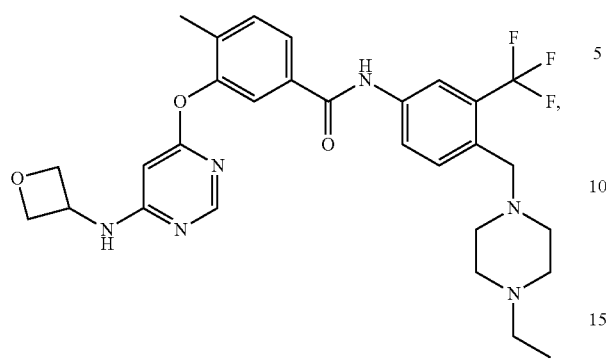
(A-16)
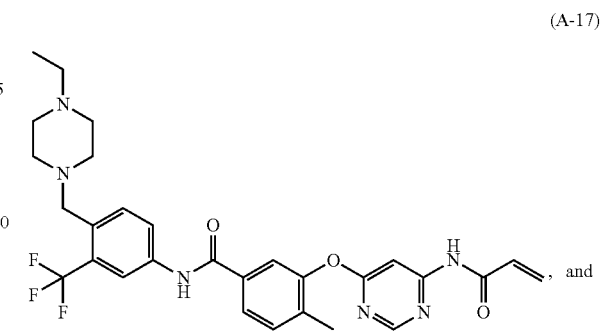
(A-17)
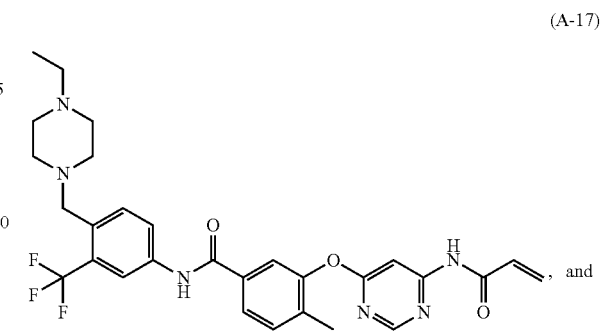
(A-18)
and pharmaceutically acceptable salts thereof.
Another aspect of the invention relates to the compound of Formula (I-11):
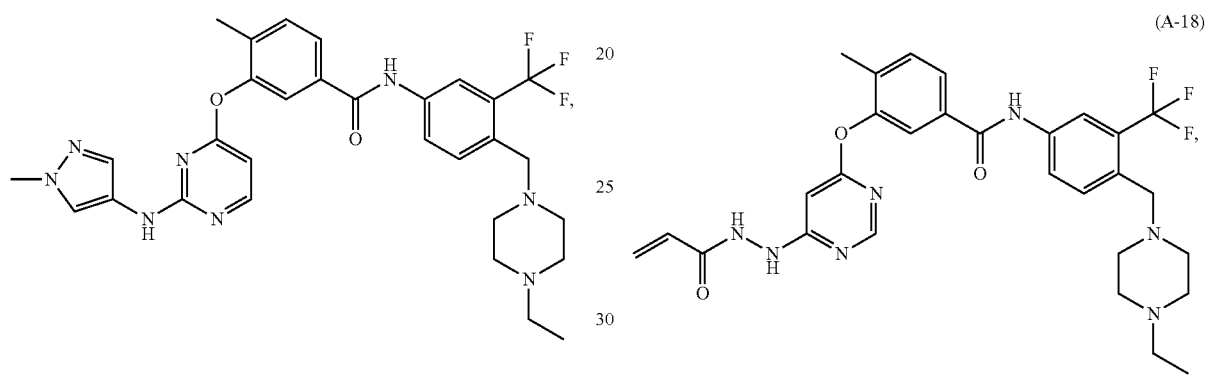
(I-11)
and pharmaceutically acceptable salts thereof.
The present invention also provides compounds of Formula (II) or (V):
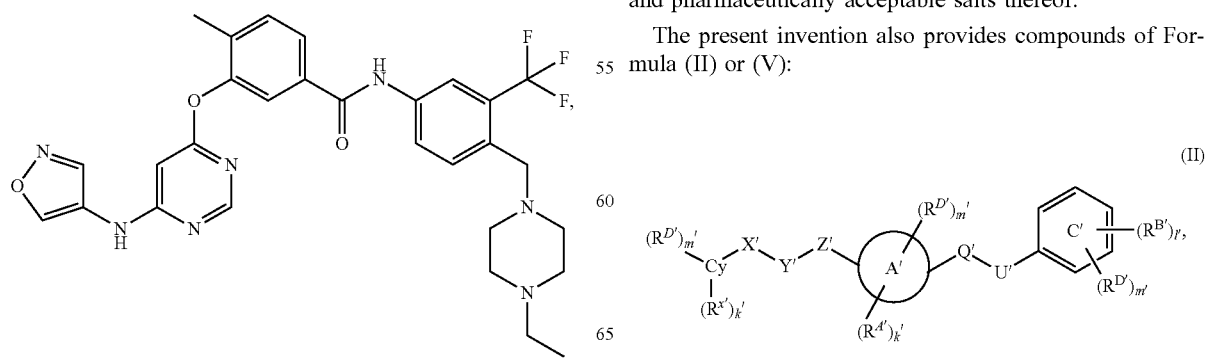
(II)

-continued

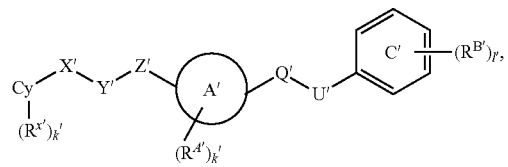

(V)

and pharmaceutically acceptable salts thereof, wherein Ring A', Ring C', Cy, X', Y', Z', Q', U', $R^{A'}$, $R^{B'}$, $R^{D'}$, $R^{X'}$, k', l', and m' are as defined herein.

The present invention is also based, at least in part, on the discovery that Waldenström's macroglobulinemia may be treated by administration of a compound of the invention to a subject in need thereof. The activity of these compounds was established by in vitro screening against several kinases (e.g., BTK, HCK, TAK1, HPK1) that are involved in the regulation of aberrant cell growth, as well as cell-based screening against several cell lines (e.g., BCWM.1, MWCL-1) that are disease state models of Waldenström's macroglobulinemia (Ditzel et al. *Exp Hematol.* 2007 September; 35(9):1366-75; Hodge et al. *Blood.* 2011 May 12; 117(19)).

The methods of treatment utilizing a compound of the invention also apply to B cell neoplasms of the group consisting of Hodgkin's lymphomas and most non-Hodgkin's lymphomas, such as diffuse large B cell lymphoma, Follicular lymphoma, mucosa-associated lymphatic tissue lymphoma (MALT), small cell lymphocytic lymphoma (overlaps with chronic lymphocytic leukemia), mantle cell lymphoma (MCL), Burkitt lymphoma, mediastinal large B cell lymphoma, nodal marginal zone B cell lymphoma (NMZL), splenic marginal zone lymphoma (SMZL), Intravascular large B-cell lymphoma, Primary effusion lymphoma, and Lymphomatoid granulomatosis.

The present invention is also based, at least in part, on pharmaceutical compositions comprising a compound of the invention (e.g., a compound of Formula (A), (I-11), (II), or (V) (e.g., compounds of Formula (A-1)-(A-18))) and a pharmaceutically acceptable excipient. In certain embodiments, the pharmaceutical composition may be useful for modulating the activity of a kinase in vitro or in a subject in need thereof, and/or for treating and/or preventing in a subject in need thereof a condition associated with aberrant activity of a kinase (e.g., a proliferative disease). In certain embodiments, the pharmaceutical composition may be useful for treatment of Waldenström's macroglobulinemia in a subject in need thereof.

The present invention also provides kits comprising a container with a compound of the invention (e.g., a compound of Formula (A), (I-11), (II), or (V) (e.g., compounds of Formula (A-1)-(A-18))), or a pharmaceutical composition thereof. The kits may include a single dose or multiple doses of a compound described herein or a pharmaceutical composition thereof. The kits may be useful for modulating the activity of a kinase in a subject in need thereof. The kits may also be useful for treating and/or preventing in a subject in need thereof a condition associated with aberrant activity of a kinase. In certain embodiments, the kits further include instructions for using the kit (e.g., for administering a compound described herein, or a pharmaceutical composition thereof).

The details of particular embodiments of the invention are set forth herein. Other features, objects, and advantages of the invention will be apparent from the Detailed Description, the FIGURES, the Examples, and the Claims.

Definitions

Chemical Definitions

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of a carbon by a $^{13}$C- or $^{14}$C-enriched carbon are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic," as used herein, refers to alkyl, alkenyl, alkynyl, and carbocyclic groups. Likewise, the term "heteroaliphatic" as used herein, refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

As used herein, "haloalkyl" is a substituted alkyl group as defined herein wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In certain embodiments, the haloalkyl moiety has 1 to 8 carbon atoms ("$C_{1-8}$ haloalkyl"). In certain embodiments, the haloalkyl moiety has 1 to 6 carbon atoms ("$C_{1-6}$ haloalkyl"). In certain embodiments, the haloalkyl moiety has 1 to 4 carbon atoms ("$C_{1-4}$ haloalkyl"). In certain embodiments, the haloalkyl moiety has 1 to 3 carbon atoms ("$C_{1-3}$ haloalkyl"). In certain embodiments, the haloalkyl moiety has 1 to 2 carbon atoms ("$C_{1-2}$ haloalkyl"). In certain embodiments, all of the haloalkyl hydrogen atoms are replaced with fluoro to provide a perfluoroalkyl group. In certain embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

As used herein, "heteroalkyl" refers to an alkyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("heteroC$_{1-10}$ alkyl"). In certain embodiments, a heteroalkyl group is a saturated group having 1 to 9 carbon atoms and 1 or more heteroatoms within the parent chain ("heteroC$_{1-9}$ alkyl"). In certain embodiments, a heteroalkyl group is a saturated group having 1 to 8 carbon atoms and 1 or more heteroatoms within the parent chain ("heteroC$_{1-8}$ alkyl"). In certain embodiments, a heteroalkyl group is a saturated group having 1 to 7 carbon atoms and 1 or more heteroatoms within the parent chain ("heteroC$_{1-7}$ alkyl"). In certain embodiments, a heteroalkyl group is a saturated group having 1 to 6 carbon atoms and 1 or more heteroatoms within the parent chain ("heteroC$_{1-6}$ alkyl"). In certain embodiments, a heteroalkyl group is a saturated group having 1 to 5 carbon atoms and 1 or 2 heteroatoms within the parent chain ("heteroC$_{1-5}$ alkyl"). In certain embodiments, a heteroalkyl group is a saturated group having 1 to 4 carbon atoms and 1 or 2 heteroatoms within the parent chain ("heteroC$_{1-4}$ alkyl"). In certain embodiments, a heteroalkyl group is a saturated group having 1 to 3 carbon atoms and 1 heteroatom within the parent chain ("heteroC$_{1-3}$ alkyl"). In certain embodiments, a heteroalkyl group is a saturated group having 1 to 2 carbon atoms and 1 heteroatom within the parent chain ("heteroC$_{1-2}$ alkyl"). In certain embodiments, a heteroalkyl group is a saturated group having 1 carbon atom and 1 heteroatom ("heteroC$_1$ alkyl"). In certain embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

As used herein, "alkenyl" refers to a radical of a straight-chain or branched hydrocarbon group having from 2 to 10 carbon atoms and one or more carbon-carbon double bonds (e.g., 1, 2, 3, or 4 double bonds). In certain embodiments, an alkenyl group has 2 to 9 carbon atoms ("$C_{2-9}$ alkenyl"). In certain embodiments, an alkenyl group has 2 to 8 carbon atoms ("$C_{2-8}$ alkenyl"). In certain embodiments, an alkenyl group has 2 to 7 carbon atoms ("$C_{2-7}$ alkenyl"). In certain embodiments, an alkenyl group has 2 to 6 carbon atoms ("$C_{2-6}$ alkenyl"). In certain embodiments, an alkenyl group has 2 to 5 carbon atoms ("$C_{2-5}$ alkenyl"). In certain embodiments, an alkenyl group has 2 to 4 carbon atoms ("$C_{2-4}$ alkenyl"). In certain embodiments, an alkenyl group has 2 to 3 carbon atoms ("$C_{2-3}$ alkenyl"). In certain embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C=C double bond for which the stereochemistry is not specified (e.g., —CH=CHCH$_3$ or

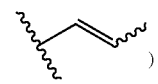

)

may be an (E)- or (Z)-double bond

As used herein, "heteroalkenyl" refers to an alkenyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2\text{-}10}$ alkenyl"). In certain embodiments, a heteroalkenyl group has 2 to 9 carbon atoms at least one double bond, and 1 or more heteroatoms within the parent chain ("heteroC$_{2\text{-}9}$ alkenyl"). In certain embodiments, a heteroalkenyl group has 2 to 8 carbon atoms, at least one double bond, and 1 or more heteroatoms within the parent chain ("heteroC$_{2\text{-}8}$ alkenyl"). In certain embodiments, a heteroalkenyl group has 2 to 7 carbon atoms, at least one double bond, and 1 or more heteroatoms within the parent chain ("heteroC$_{2\text{-}7}$ alkenyl"). In certain embodiments, a heteroalkenyl group has 2 to 6 carbon atoms, at least one double bond, and 1 or more heteroatoms within the parent chain ("heteroC$_{2\text{-}6}$ alkenyl"). In certain embodiments, a heteroalkenyl group has 2 to 5 carbon atoms, at least one double bond, and 1 or 2 heteroatoms within the parent chain ("heteroC$_{2\text{-}5}$ alkenyl"). In certain embodiments, a heteroalkenyl group has 2 to 4 carbon atoms, at least one double bond, and 1 or 2 heteroatoms within the parent chain ("heteroC$_{2\text{-}4}$ alkenyl"). In certain embodiments, a heteroalkenyl group has 2 to 3 carbon atoms, at least one double bond, and 1 heteroatom within the parent chain ("heteroC$_{2\text{-}3}$ alkenyl"). In certain embodiments, a heteroalkenyl group has 2 to 6 carbon atoms, at least one double bond, and 1 or 2 heteroatoms within the parent chain ("heteroC$_{2\text{-}6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2\text{-}10}$ alkenyl. In certain embodiments, the heteroalkenyl group is a substituted heteroC$_{2\text{-}10}$ alkenyl.

As used herein, "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2\text{-}10}$ alkynyl"). In certain embodiments, an alkynyl group has 2 to 9 carbon atoms ("C$_{2\text{-}9}$ alkynyl"). In certain embodiments, an alkynyl group has 2 to 8 carbon atoms ("C$_{2\text{-}8}$ alkynyl"). In certain embodiments, an alkynyl group has 2 to 7 carbon atoms ("C$_{2\text{-}7}$ alkynyl"). In certain embodiments, an alkynyl group has 2 to 6 carbon atoms ("C$_{2\text{-}6}$ alkynyl"). In certain embodiments, an alkynyl group has 2 to 5 carbon atoms ("C$_{2\text{-}5}$ alkynyl"). In certain embodiments, an alkynyl group has 2 to 4 carbon atoms ("C$_{2\text{-}4}$-alkynyl"). In certain embodiments, an alkynyl group has 2 to 3 carbon atoms ("C$_{2\text{-}3}$ alkynyl"). In certain embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2\text{-}4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2\text{-}6}$ alkenyl groups include the aforementioned C$_{2\text{-}4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2\text{-}10}$ alkynyl. In certain embodiments, the alkynyl group is a substituted C$_{2\text{-}10}$ alkynyl.

As used herein, "heteroalkynyl" refers to an alkynyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2\text{-}10}$ alkynyl"). In certain embodiments, a heteroalkynyl group has 2 to 9 carbon atoms, at least one triple bond, and 1 or more heteroatoms within the parent chain ("heteroC$_{2\text{-}9}$ alkynyl"). In certain embodiments, a heteroalkynyl group has 2 to 8 carbon atoms, at least one triple bond, and 1 or more heteroatoms within the parent chain ("heteroC$_{2\text{-}8}$ alkynyl"). In certain embodiments, a heteroalkynyl group has 2 to 7 carbon atoms, at least one triple bond, and 1 or more heteroatoms within the parent chain ("heteroC$_{2\text{-}7}$ alkynyl"). In certain embodiments, a heteroalkynyl group has 2 to 6 carbon atoms, at least one triple bond, and 1 or more heteroatoms within the parent chain ("heteroC$_{2\text{-}6}$ alkynyl"). In certain embodiments, a heteroalkynyl group has 2 to 5 carbon atoms, at least one triple bond, and 1 or 2 heteroatoms within the parent chain ("heteroC$_{2\text{-}5}$ alkynyl"). In certain embodiments, a heteroalkynyl group has 2 to 4 carbon atoms, at least one triple bond, and 1 or 2 heteroatoms within the parent chain ("heteroC$_{2\text{-}4}$ alkynyl"). In certain embodiments, a heteroalkynyl group has 2 to 3 carbon atoms, at least one triple bond, and 1 heteroatom within the parent chain ("heteroC$_{2\text{-}3}$ alkynyl"). In certain embodiments, a heteroalkynyl group has 2 to 6 carbon atoms, at least one triple bond, and 1 or 2 heteroatoms within the parent chain ("heteroC$_{2\text{-}6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2\text{-}10}$ alkynyl. In certain embodiments, the heteroalkynyl group is a substituted heteroC$_{2\text{-}10}$ alkynyl.

As used herein, "carbocyclyl" or "carbocyclic" refers to a radical of a non-aromatic cyclic hydrocarbon group having from 3 to 14 ring carbon atoms ("C$_{3\text{-}14}$ carbocyclyl") and zero heteroatoms in the non-aromatic ring system. In certain embodiments, a carbocyclyl group has 3 to 10 ring carbon atoms ("C$_{3\text{-}10}$ carbocyclyl"). In certain embodiments, a carbocyclyl group has 3 to 8 ring carbon atoms ("C$_{3\text{-}8}$ carbocyclyl"). In certain embodiments, a carbocyclyl group has 3 to 7 ring carbon atoms ("C$_{3\text{-}7}$ carbocyclyl"). In certain embodiments, a carbocyclyl group has 3 to 6 ring carbon atoms ("C$_{3\text{-}6}$ carbocyclyl"). In certain embodiments, a carbocyclyl group has 4 to 6 ring carbon atoms ("C$_{4\text{-}6}$ carbocyclyl"). In certain embodiments, a carbocyclyl group has 5 to 6 ring carbon atoms ("C$_{5\text{-}6}$ carbocyclyl"). In certain embodiments, a carbocyclyl group has 5 to 10 ring carbon atoms ("C$_{5\text{-}10}$ carbocyclyl"). Exemplary C$_{3\text{-}6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3\text{-}8}$ carbocyclyl groups include, without limitation, the aforementioned C$_{3\text{-}6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3\text{-}10}$ carbocyclyl groups include, without limitation, the aforementioned C$_{3\text{-}8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl. In certain embodiments, "carbocyclyl" is a monocyclic, saturated carbocyclyl group having from 3 to 14 ring carbon atoms ("$C_{3-14}$ cycloalkyl"). In certain embodiments, a cycloalkyl group has 3 to 10 ring carbon atoms ("$C_{3-10}$ cycloalkyl"). In certain embodiments, a cycloalkyl group has 3 to 8 ring carbon atoms ("$C_{3-8}$ cycloalkyl"). In certain embodiments, a cycloalkyl group has 3 to 6 ring carbon atoms ("$C_{3-6}$ cycloalkyl"). In certain embodiments, a cycloalkyl group has 4 to 6 ring carbon atoms ("$C_{4-6}$ cycloalkyl"). In certain embodiments, a cycloalkyl group has 5 to 6 ring carbon atoms ("$C_{5-10}$ cycloalkyl"). In certain embodiments, a cycloalkyl group has 5 to 10 ring carbon atoms ("$C_{5-10}$ cycloalkyl"). Examples of $C_5$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-4}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

As used herein, "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In certain embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In certain embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In certain embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In certain embodiments, the 5-6 membered heterocyclyl has 1-3 ring heteroatoms selected from nitrogen, oxygen, and sulfur. In certain embodiments, the 5-6 membered heterocyclyl has 1-2 ring heteroatoms selected from nitrogen, oxygen, and sulfur. In certain embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]

pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetra-hydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14 it electrons shared in a cyclic array) having 6-14 ring carbon atoms and zero heteroatoms provided in the aromatic ring system ("$C_{6-14}$ aryl"). In certain embodiments, an aryl group has 6 ring carbon atoms ("$C_6$ aryl"; e.g., phenyl). In certain embodiments, an aryl group has 10 ring carbon atoms ("$C_{10}$ aryl"; e.g., naphthyl such as 1-naphthyl and 2-naphthyl). In certain embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group, as defined herein, substituted by an aryl group, as defined herein, wherein the point of attachment is on the alkyl moiety.

As used herein, "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In certain embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In certain embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In certain embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In certain embodiments, the 5-6 membered heteroaryl has 1-3 ring heteroatoms selected from nitrogen, oxygen, and sulfur. In certain embodiments, the 5-6 membered heteroaryl has 1-2 ring heteroatoms selected from nitrogen, oxygen, and sulfur. In certain embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group, as defined herein, substituted by a heteroaryl group, as defined herein, wherein the point of attachment is on the alkyl moiety.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, the term "saturated" refers to a ring moiety that does not contain a double or triple bond, i.e., the ring contains all single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

As understood from the above, alkyl, alkenyl, alkynyl, heteroalkyl, heteroalkenyl, heteroalkynyl, carbocyclyl, heterocyclyl, aryl, and heteroaryl groups, as defined herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

As used herein, the term "halo" or "halogen" refers to fluorine (fluoro, —F), chlorine (chloro, —Cl), bromine (bromo, —Br), or iodine (iodo, —I).

In certain embodiments, the substituent present on the nitrogen atom is an nitrogen protecting group (also referred to herein as an "amino protecting group"). Nitrogen protecting groups include, but are not limited to, —OH, —OR, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., alkyl, aralkyl, heteroaralkyl), C$_{2-10}$ alkenyl, C$_{2-10}$ alkynyl, C$_{1-10}$ heteroalkyl, C$_{2-10}$ heteroalkenyl, C$_{2-10}$ heteroalkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as described herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as described herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as described herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

As used herein, a "leaving group", or "LG", is a term understood in the art to refer to a molecular fragment that departs with a pair of electrons upon heterolytic bond cleavage, wherein the molecular fragment is an anion or neutral molecule. See, for example, Smith, March *Advanced Organic Chemistry* 6th ed. (501-502). Examples of suitable leaving groups include, but are not limited to, halides (such as chloride, bromide, or iodide), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, haloformates, —$NO_2$, trialkylammonium, and aryliodonium salts. In certain embodiments, the leaving group is a sulfonic acid ester. In certain embodiments, the sulfonic acid ester comprises the formula —$OSO_2R^{LG1}$ wherein $R^{LG1}$ is selected from the group consisting alkyl optionally, alkenyl optionally substituted, heteroalkyl optionally substituted, aryl optionally substituted, heteroaryl optionally substituted, arylalkyl optionally substituted, and heterarylalkyl optionally substituted. In certain embodiments, $R^{LG1}$ is substituted or unsubstituted $C_1$-$C_6$ alkyl. In certain embodiments, $R^{LG1}$ is methyl. In certain embodiments, $R^{LG1}$ is —$CF_3$. In certain embodiments, $R^{LG1}$ is substituted or unsubstituted aryl. In certain embodiments, $R^{LG1}$ is substituted or unsubstituted phenyl. In certain embodiments $R^{LG1}$ is:

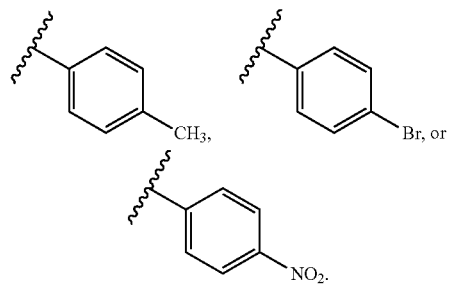

In some cases, the leaving group is toluenesulfonate (tosylate, Ts), methanesulfonate (mesylate, Ms), p-bromobenzenesulfonyl (brosylate, Bs), or trifluoromethanesulfonate (triflate, Tf). In some cases, the leaving group is a brosylate (p-bromobenzenesulfonyl). In some cases, the leaving group is a nosylate (2-nitrobenzenesulfonyl). In certain embodiments, the leaving group is a sulfonate-containing group. In certain embodiments, the leaving group is a tosylate group. The leaving group may also be a phosphineoxide (e.g., formed during a Mitsunobu reaction) or an internal leaving group such as an epoxide or cyclic sulfate.

These and other exemplary substituents are described in more detail in the Detailed Description, FIGURES, Examples, and Claims. The invention is not intended to be limited in any manner by the above exemplary listing of substituents.

Other Definitions

The following definitions are more general terms used throughout the present application.

As used herein, the term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_1$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. Compounds of the invention may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates (R.0.5$H_2O$)), and polyhydrates (x is a number greater than 1, e.g., dihydrates (R.2$H_2O$) and hexahydrates (R.6$H_2O$)).

The term "tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds of the invention, which are pharmaceutically active in vivo. Such examples include, but are not limited to, choline ester derivatives and the like, N-alkylmorpholine esters and the like. Other derivatives of the compounds of this invention have activity in both their acid and acid derivative forms, but in the acid sensitive form often offers advantages of solubility, tissue compatibility, or delayed release in the mammalian organism (see, Bundgard, H., *Design of Prodrugs, pp.* 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. Particularly the $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds of the invention (e.g., the compounds of Formula (A), (I-11), (II), or (V)).

BRIEF DESCRIPTION OF THE DRAWINGS

FIG. 1 shows isobolograms demonstrating the synergy between compound (A-17) and a BTK inhibitor. Points below the 1 to 1 line connecting the X and Y axes are 'synergistic', points near the line are 'additive', and points above it are antagonistic.

DETAILED DESCRIPTION OF THE INVENTION

In an effort to identify novel treatments for Waldenström's macroglobulinemia, in vitro screens were carried out against several kinases (e.g., BTK, HCK, TAK1, HPK1). These kinases are involved in the regulation of aberrant cell growth associated with this condition. Cell-based screening was also carried out in several disease state model lines of Waldenström's macroglobulinemia (e.g., BCWM.1, MWCL-1). Based on these screening efforts and subsequent lead optimization, compounds of any one of Formulae (A), (I-11), (II), and (V) (e.g., compounds of Formula (A-1)-(A-18)) were identified.

In one aspect, the present invention provides compounds of Formula (A):

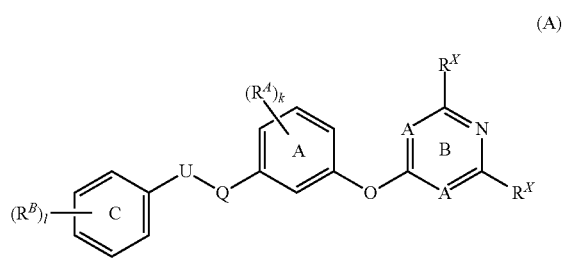

(A)

and pharmaceutically acceptable salts, solvates, hydrates, polymorphs, co-crystals, tautomers, stereoisomers, isotopically labeled derivatives, and prodrugs thereof;
wherein:
each instance of $R^A$ is independently selected from the group consisting of hydrogen, halogen, optionally substituted alkyl, optionally substituted carbocyclyl, —OR$^{A1}$, —N(R$^{A1}$)$_2$, —CN, —C(=O)R$^{A1}$, —C(=O)OR$^{A1}$, —C(=O)N(R$^{A1}$)$_2$, —NO$_2$, —NR$^{A1}$C(=O)R$^{A1}$, —NR$^{A1}$C(=O)OR$^{A1}$, —NR$^{A1}$S(=O)$_2$R$^{A1}$, —S(=O)$_2$R$^{A1}$, or —S(=O)$_2$N(R$^{A1}$)$_2$;

each instance of R$^B$ is independently selected from the group consisting of hydrogen, halogen, optionally substituted alkyl, optionally substituted carbocyclyl, optionally substituted heterocyclyl, optionally substituted aryl, optionally substituted heteroaryl, —OR$^{A1}$, —N(R$^{A1}$)$_2$, —CN, —C(=O)R$^{A1}$, —C(=O)OR$^{A1}$, —C(=O)N(R$^{A1}$)$_2$, —NO$_2$, —NR$^{A1}$C(=O)R$^{A1}$, —NR$^{A1}$C(=O)OR$^{A1}$, —NR$^{A1}$S(=O)$_2$R$^{A1}$, —S(=O)$_2$R$^{A1}$, or —S(=O)$_2$N(R$^{A1}$)$_2$;

each instance of R$^{A1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two R$^{A1}$ groups are joined to form an optionally substituted heterocyclic ring;

one instance of A that is included in Ring B is CR$^Y$;

the other instance of A that is included in Ring B is CR$^Y$ or N;

each instance of R$^Y$ is independently H, halogen, or substituted or unsubstituted C$_{1-6}$ alkyl;

each instance of R$^X$ is independently selected from the group consisting of R$^D$, optionally substituted carbocyclyl, optionally substituted heterocyclyl, optionally substituted aryl, optionally substituted heteroaryl, and —N(R$^{A1}$)(R$^{Xa}$);

each instance of R$^{Xa}$ is selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)R$^{A1}$, —C(=O)OR$^{A1}$, —C(=O)N(R$^{A1}$)$_2$, —S(=O)R$^{A1}$, —S(=O)N(R$^{A1}$)$_2$, —S(=O)$_2$R$^{A1}$, —S(=O)$_2$OR$^{A1}$, —S(=O)$_2$R$^{A1}$, —S(=O)$_2$N(R$^{A1}$)$_2$, —N(R$^{A1}$)$_2$, and a nitrogen protecting group;

k is 0, 1, 2, 3, or 4;

l is 1, 2, 3, 4, or 5;

Q and U are taken together to be —NR$^A$(C=O)— or —(C=O)NR$^A$—; and

R$^D$ is an electrophilic moiety as described herein.

In certain embodiments, the present invention provides compounds from the group consisting of:

(A-1)

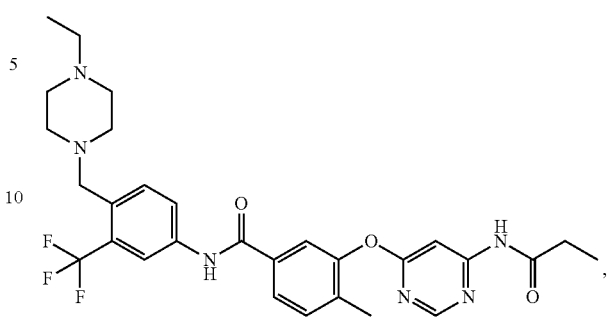

(A-2)

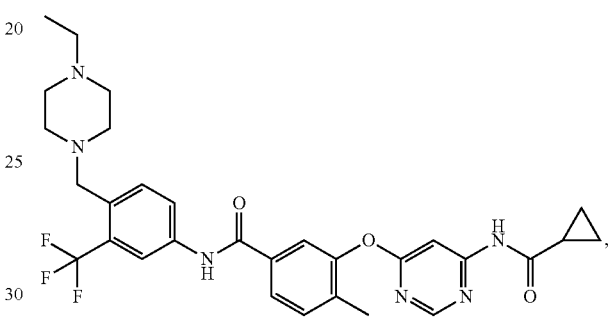

(A-3)

(A-4)

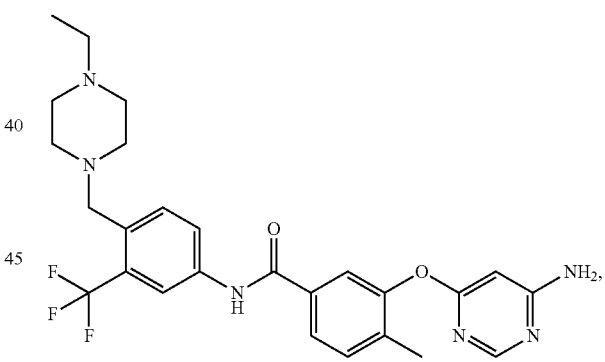

(A-5)

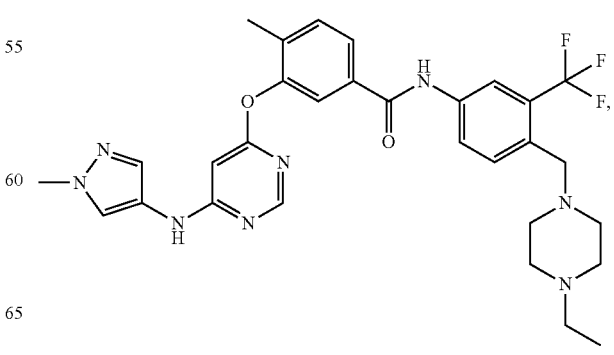

(A-6)
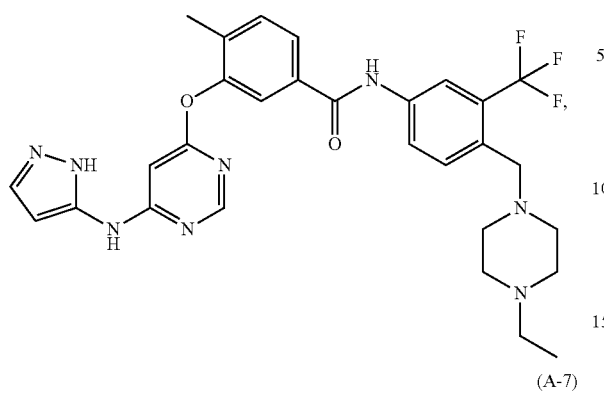
(A-10)
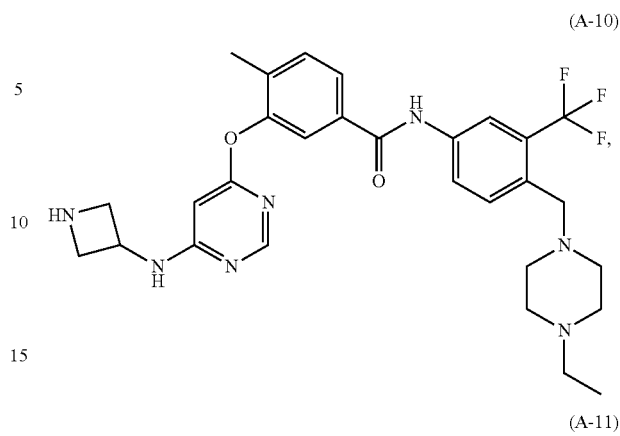
(A-7)
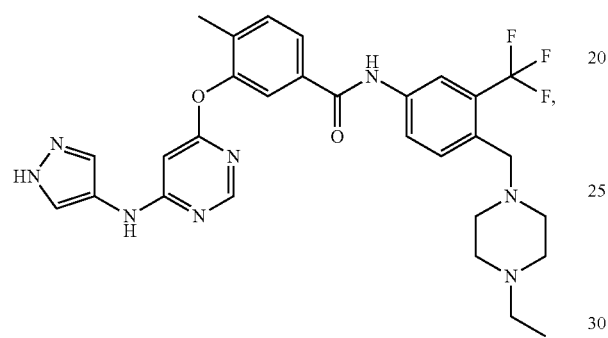
(A-11)
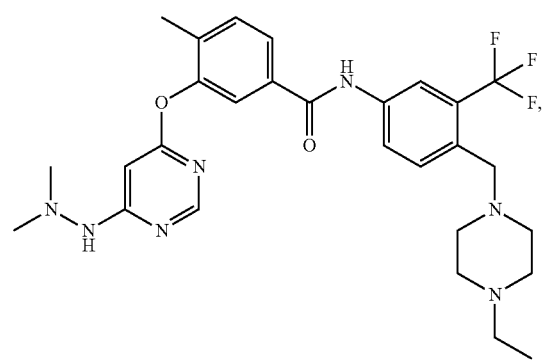
(A-8)
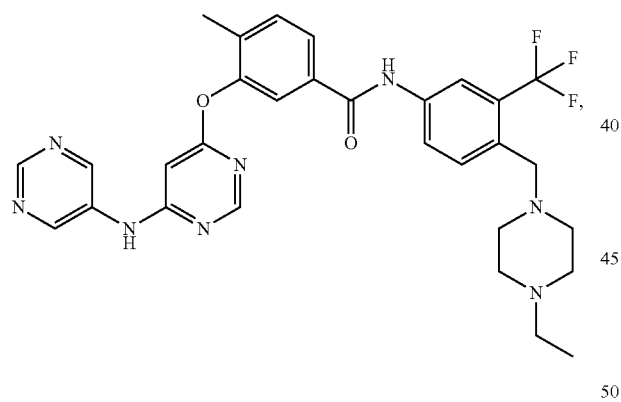
(A-12)
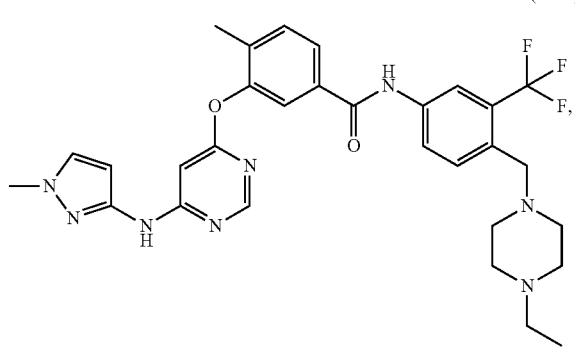
(A-9)
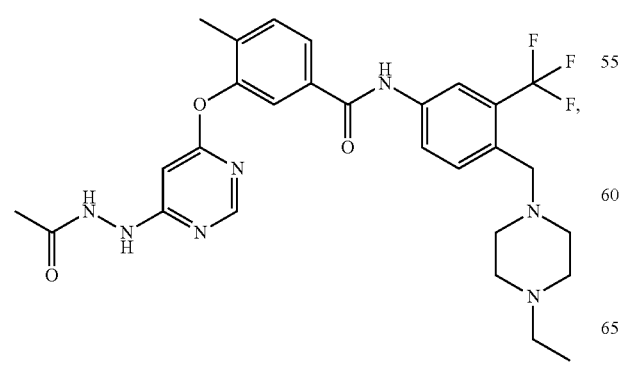
(A-13)
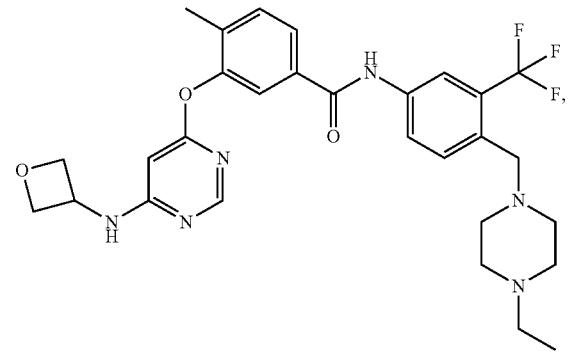

(A-14)
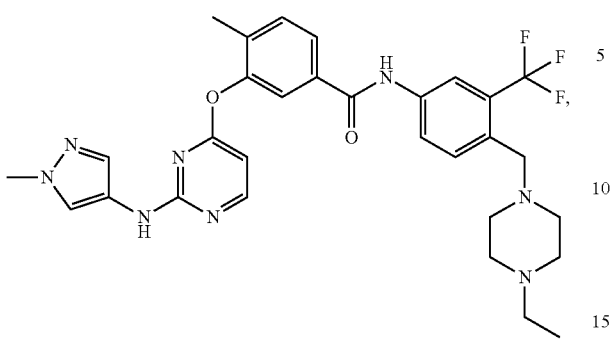

(A-18)
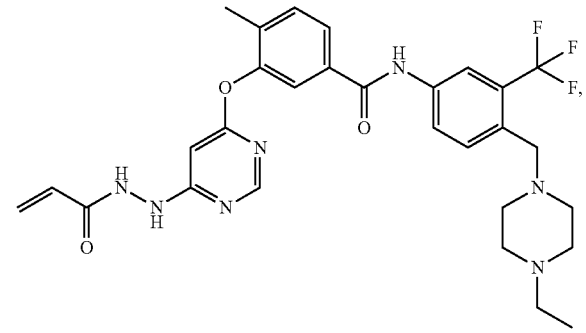

(A-15)
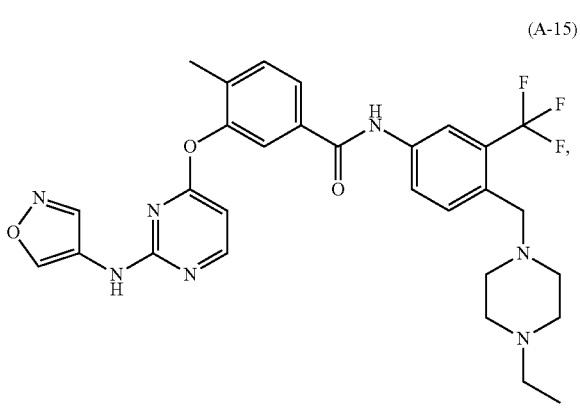

(A-16)
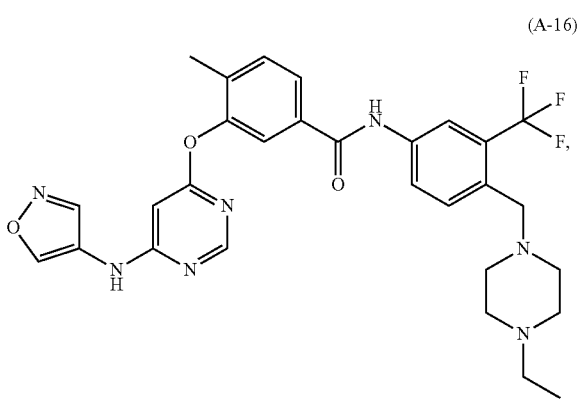

(A-17)
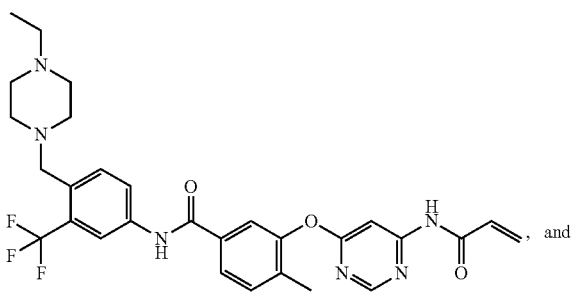
, and and pharmaceutically acceptable salts thereof.

In another aspect, the present invention provides methods for treating Waldenström's macroglobulinemia (WM) in a subject using compounds of the invention. The methods comprise administering to a subject in need thereof an effective amount of a compound of the invention. Also provided are methods to treat other B cell neoplasms using compounds of the invention in combination with inhibitors of Bruton's tyrosine kinase (BTK), interleukin-1 receptor-associated kinase 1 (IRAK1), interleukin-1 receptor-associated kinase 4 (IRAK4), bone marrow on X chromosome kinase (BMX), phosphoinositide 3-kinase (PI3K), transforming growth factor b-activated kinase-1 (TAK1), and/or a Src family kinase. In certain embodiments, one or more compounds of the invention are used in combination with an inhibitor of the phosphoinositide 3-kinase delta isoform (PI3Kδ). In certain embodiments, combinations of 2, 3, 4, 5, 6, 7, 8, 9, 10, or more of the agents described herein are used for treating WM. In certain embodiments, the agents described herein are used in combination with kinase inhibitors such as inhibitors of Bruton's tyrosine kinase (BTK), interleukin-1 receptor-associated kinase 1 (IRAK1), interleukin-1 receptor-associated kinase 4 (IRAK4), bone marrow on X chromosome kinase (BMX), and/or phosphoinositide 3-kinase (PI3K), transforming growth factor b-activated kinase-1 (TAK1), and/or a Src family kinase.

Waldenstrom's macroglobulinemia (WM) is a distinct clinicopathological entity resulting from the accumulation, predominantly in the bone marrow, of clonally related lymphoplasmacytic cells which secrete a monoclonal IgM protein. This condition is considered to correspond to lymphoplasmacytic lymphoma (LPL) as defined by the World Health Organization classification system. Genetic factors play an important role in the pathogenesis of WM, with 25% of patients demonstrating a family history. IgM monoclonal gammopathy of unknown significance (MGUS) often precedes the development of WM.

As used herein, a B cell neoplasm includes both Hodgkin's lymphoma and non-Hodgkin's lymphomas. Classical Hodgkin's lymphoma (HL) includes various subtypes such as Nodular sclerosing HL, Mixed-cellularity subtype, Lymphocyte-rich or Lymphocytic predominance and Lymphocyte depleted. Examples of B cell non-Hodgkin's lymphomas include, but are not limited to, Waldenström's macroglobulinemia, diffuse large B cell lymphoma, follicular lymphoma, mucosa-associated lymphatic tissue lymphoma (MALT), small cell lymphocytic lymphoma (overlaps with chronic lymphocytic leukemia), mantle cell lymphoma (MCL), Burkitt lymphoma, mediastinal large B cell lymphoma, nodal marginal zone B cell lymphoma (NMZL), splenic marginal zone lymphoma (SMZL), intravascular large B-cell lymphoma, primary effusion lymphoma, and lymphomatoid granulomatosis.

In certain embodiments, the subject is administered a compound of Formula (A):

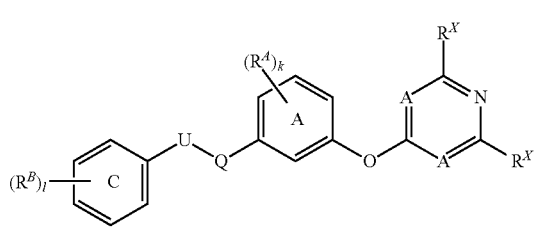

and pharmaceutically acceptable salts, solvates, hydrates, polymorphs, co-crystals, tautomers, stereoisomers, isotopically labeled derivatives, and prodrugs thereof; wherein:

each instance of $R^A$ is independently selected from the group consisting of hydrogen, halogen, optionally substituted alkyl, optionally substituted carbocyclyl, —$OR^{A1}$, —$N(R^{A1})_2$, —CN, —C(=O)$R^{A1}$, —C(=O)$OR^{A1}$, —C(=O)N($R^{A1})_2$, —$NO_2$, —$NR^{A1}$C(=O)$R^{A1}$, —$NR^{A1}$C(=O)$OR^{A1}$, —$NR^{A1}$S(=O)$_2R^{A1}$, —S(O)$_2R^{A1}$, or —S(=O)$_2$N($R^{A1})_2$;

each instance of $R^B$ is independently selected from the group consisting of hydrogen, halogen, optionally substituted alkyl, optionally substituted carbocyclyl, optionally substituted heterocyclyl, optionally substituted aryl, optionally substituted heteroaryl, —$OR^{A1}$, —N($R^{A1})_2$, —CN, —C(=O)$R^{A1}$, —C(=O)$OR^{A1}$, —C(=O)N($R^{A1})_2$, —$NO_2$, —$NR^{A1}$C(=O)$R^{A1}$, —$NR^{A1}$C(=O)$OR^{A1}$, —$NR^{A1}$S(=O)$_2R^{A1}$, —S(=O)$_2R^{A1}$, or —S(=O)$_2$N($R^{A1})_2$;

each instance of $R^{A1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two $R^{A1}$ groups are joined to form an optionally substituted heterocyclic ring;

each instance of $R^X$ is independently selected from the group consisting of $R^D$, optionally substituted carbocyclyl, optionally substituted heterocyclyl, optionally substituted aryl, optionally substituted heteroaryl, and —N($R^{A1}$)($R^{Xa}$);

each instance of $R^{Xa}$ is selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)$R^{A1}$, —C(=O)$OR^{A1}$, —C(=O)N($R^{A1})_2$, —S(=O)$R^{A1}$, —S(=O)N($R^{A1})_2$, —S(=O)$_2R^{A1}$, —S(=O)$_2OR^{A1}$, —S(=O)$_2$N($R^{A1})_2$, —S(=O)$_2$N($R^{A1})_2$, —N($R^{A1})_2$, and a nitrogen protecting group;

k is 0, 1, 2, 3, or 4;

l is 1, 2, 3, 4, or 5;

Q and U are taken together to be —$NR^A$(C=O)— or —(C=O)$NR^A$—; and $R^D$ is an electrophilic moiety as described herein.

In certain embodiments, the subject is administered compound (A-1):

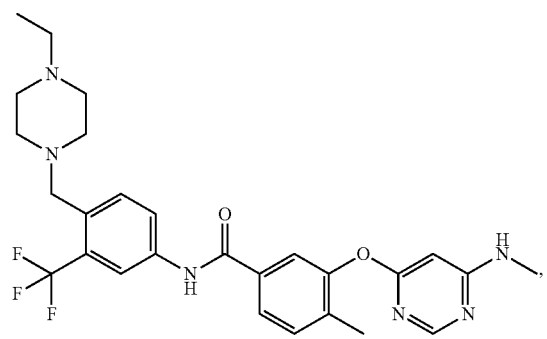

or a pharmaceutically acceptable salt thereof.

In certain embodiments, the subject is adminstered compound (A-2):

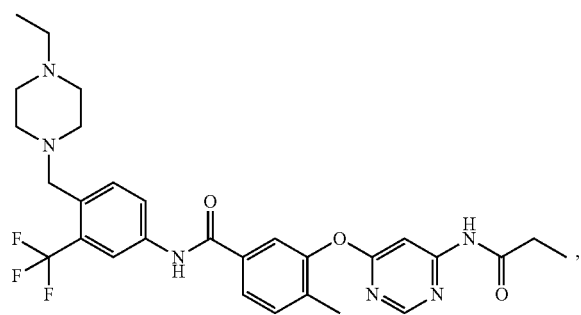

or a pharmaceutically acceptable salt thereof.

In certain embodiments, the subject is administered compound (A-3):

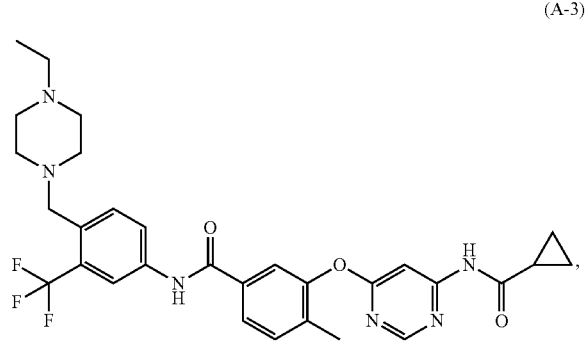 [SMILES: CCN1CCN(Cc2ccc(NC(=O)c3ccc(C)c(Oc4cc(NC(=O)C5CC5)ncn4)c3)cc2C(F)(F)F)CC1]

or a pharmaceutically acceptable salt thereof.

In certain embodiments, the subject is adminstered compound (A-4):

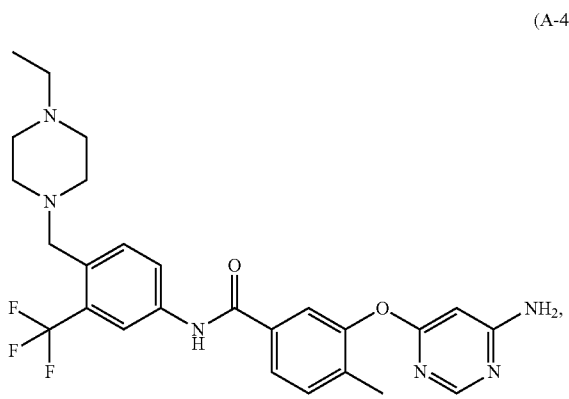 [SMILES: CCN1CCN(Cc2ccc(NC(=O)c3ccc(C)c(Oc4cc(N)ncn4)c3)cc2C(F)(F)F)CC1]
(A-4)

or a pharmaceutically acceptable salt thereof.

In certain embodiments, the subject is adminstered compound (A-5):

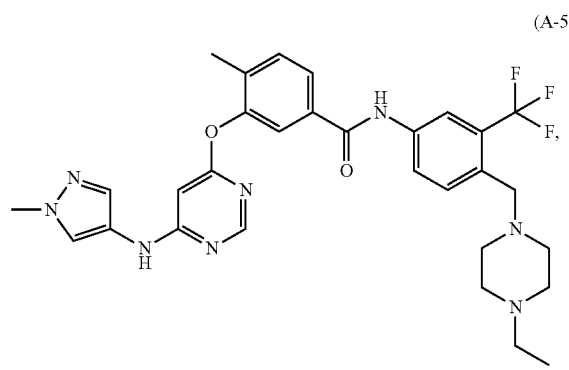
(A-5)

or a pharmaceutically acceptable salt thereof.

In certain embodiments, the subject is adminstered compound (A-6):

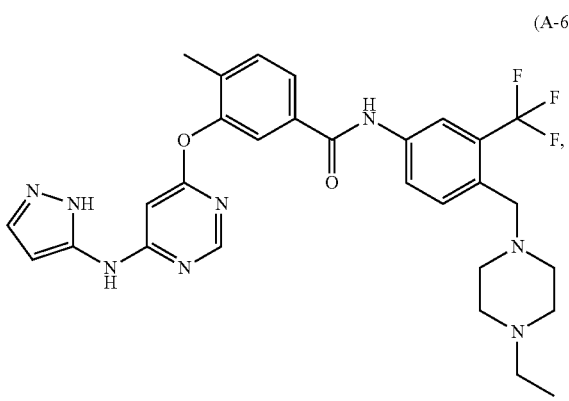
(A-6)

or a pharmaceutically acceptable salt thereof.

In certain embodiments, the subject is adminstered compound (A-7):

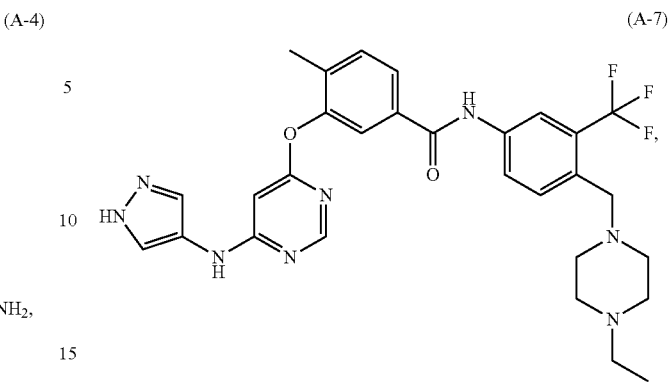
(A-7)

or a pharmaceutically acceptable salt thereof.

In certain embodiments, the subject is adminstered compound (A-8):

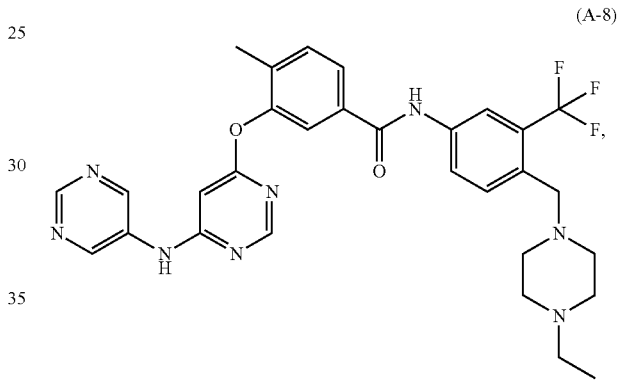
(A-8)

or a pharmaceutically acceptable salt thereof.

In certain embodiments, the subject is adminstered compound (A-9):

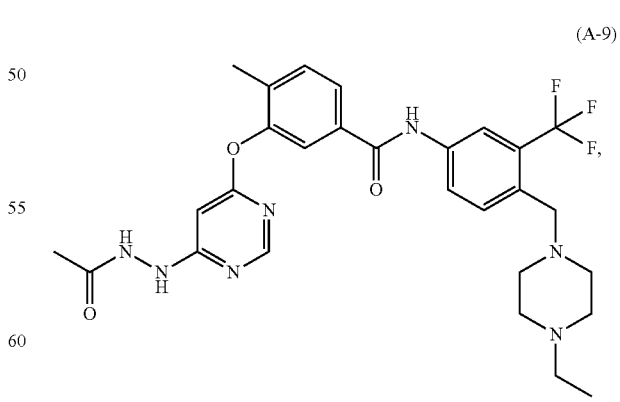
(A-9)

or a pharmaceutically acceptable salt thereof.

In certain embodiments, the subject is adminstered compound (A-10):

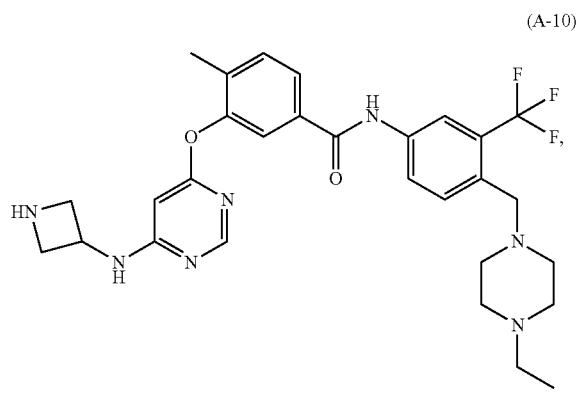 [SMILES: CCN1CCN(Cc2ccc(NC(=O)c3ccc(C)c(Oc4cc(NC5CNC5)ncn4)c3)cc2C(F)(F)F)CC1]

(A-10)

or a pharmaceutically acceptable salt thereof.

In certain embodiments, the subject is adminstered compound (A-11):

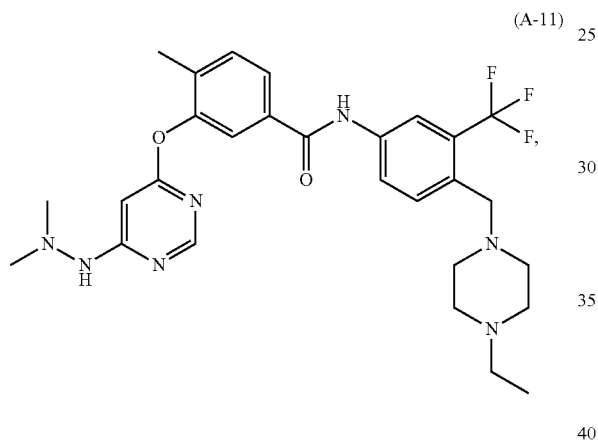

(A-11)

or a pharmaceutically acceptable salt thereof.

In certain embodiments, the subject is adminstered compound (A-12):

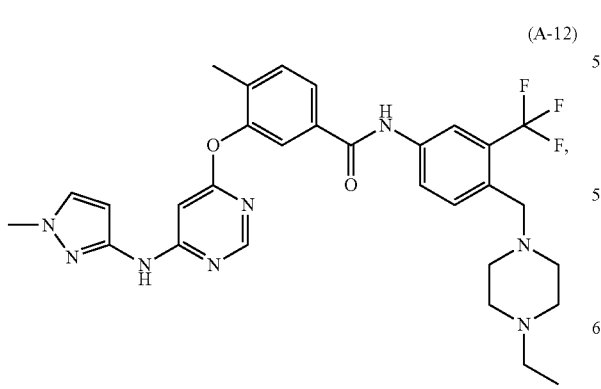

(A-12)

or a pharmaceutically acceptable salt thereof.

In certain embodiments, the subject is adminstered compound (A-13):

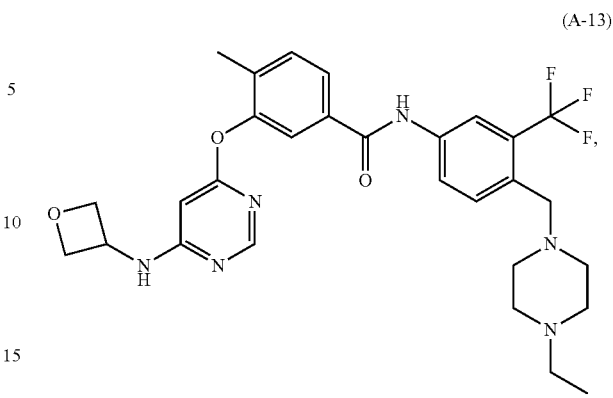

(A-13)

or a pharmaceutically acceptable salt thereof.

In certain embodiments, the subject is adminstered compound (A-14):

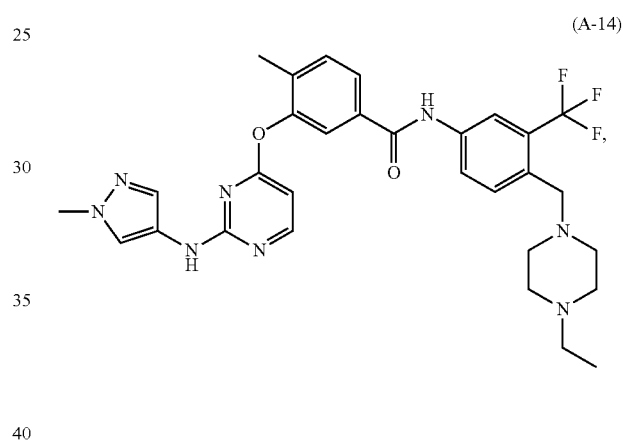

(A-14)

or a pharmaceutically acceptable salt thereof.

In certain embodiments, the subject is adminstered compound (A-15):

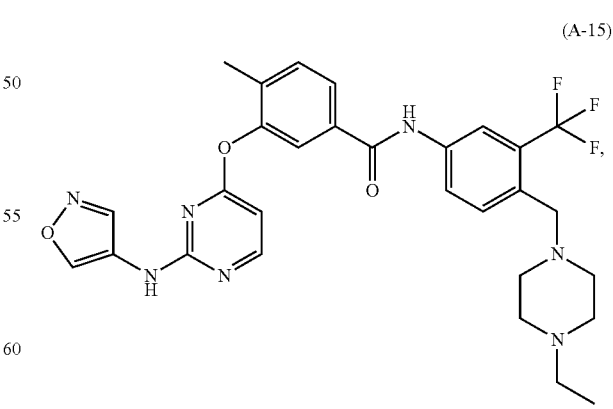

(A-15)

or a pharmaceutically acceptable salt thereof.

In certain embodiments, the subject is adminstered compound (A-16):

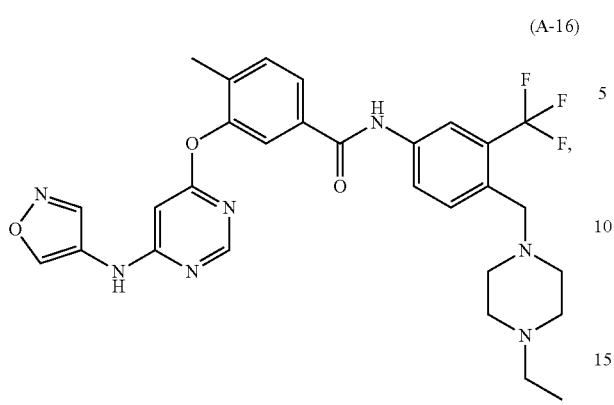

(A-16)

or a pharmaceutically acceptable salt thereof.

In certain embodiments, the subject is adminstered compound (A-17):

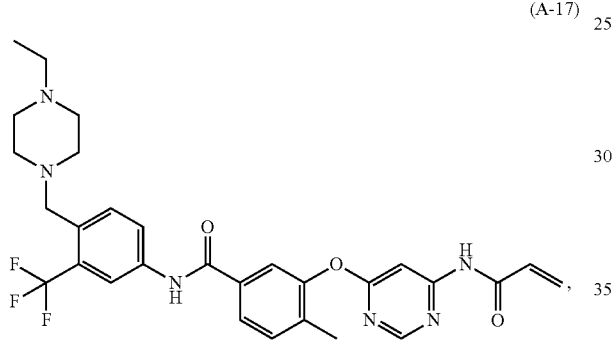

(A-17)

or a pharmaceutically acceptable salt thereof.

In certain embodiments, the subject is adminstered compound (A-18):

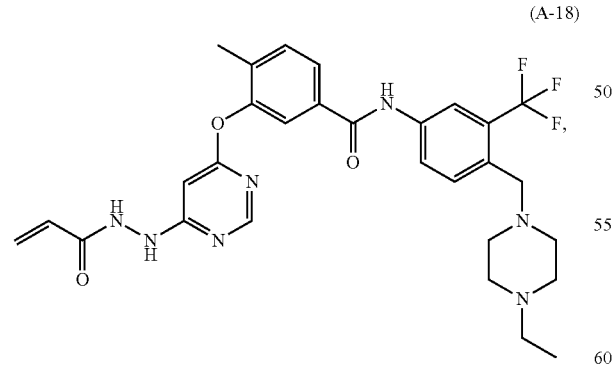

(A-18)

or a pharmaceutically acceptable salt thereof.

Compounds of Formula (A) include a phenyl Ring A optionally substituted with one or more $R^4$ groups. In certain embodiments, k is 0. In certain embodiments, Ring A is of the formula:

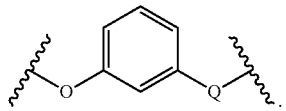

In certain embodiments, Ring A is of the formula:

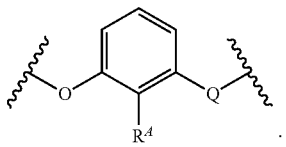

In certain embodiments, Ring A is of the formula:

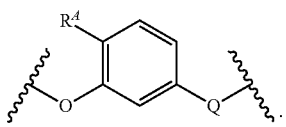

In certain embodiments, Ring A is of the formula:

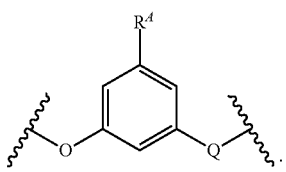

In certain embodiments, Ring A is of the formula:

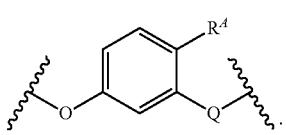

In certain embodiments, k is 2. In certain embodiments, Ring A is of the formula:

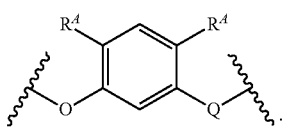

In certain embodiments, Ring A is of the formula:

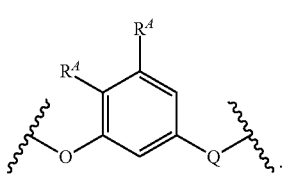

In certain embodiments, Ring A is of the formula:

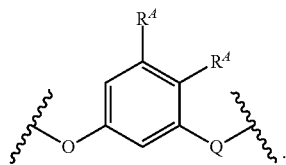

In certain embodiments, Ring A is of the formula:

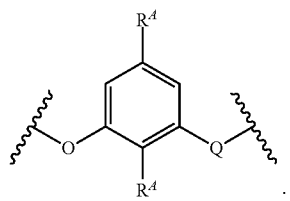

In certain embodiments, Ring A is of the formula:

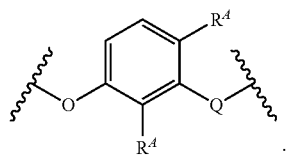

In certain embodiments, Ring A is of the formula:

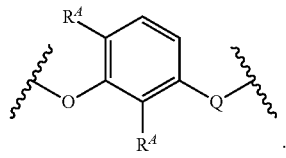

In certain embodiments, k is 3. In certain embodiments, Ring A is of the formula:

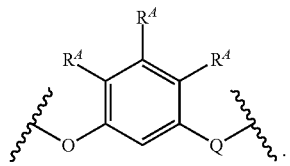

In certain embodiments, Ring A is of the formula:

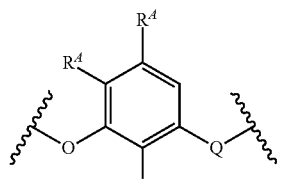

In certain embodiments, Ring A is of the formula:

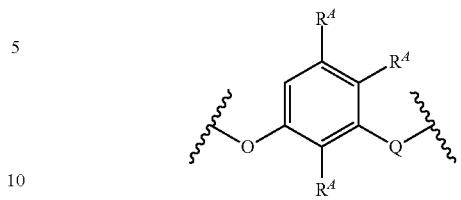

In certain embodiments, k is 4. In certain embodiments, Ring A is of the formula:

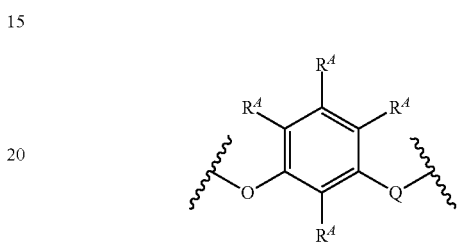

In compounds of Formula (A), Ring A may be substituted with one or more $R^A$ groups. In certain embodiments, at least one $R^A$ is H. In certain embodiments, at least two $R^A$ groups are H. In certain embodiments, at least three $R^A$ groups are H. In certain embodiments, at least four $R^A$ groups are H. In certain embodiments, at least one $R^A$ is not H. In certain embodiments, at least two $R^A$ groups are not H. In certain embodiments, at least three $R^A$ groups are not H. In certain embodiments, at least one $R^A$ is halogen. In certain embodiments, at least one $R^A$ is F. In certain embodiments, at least one $R^A$ is Cl. In certain embodiments, at least one $R^A$ is Br. In certain embodiments, at least one $R^A$ is I (iodine). In certain embodiments, one $R^A$ is F. In certain embodiments, one $R^A$ is Cl. In certain embodiments, at least one $R^A$ is substituted alkyl. In certain embodiments, at least one $R^A$ is unsubstituted alkyl. In certain embodiments, at least one $R^A$ is substituted $C_{1-6}$ alkyl. In certain embodiments, at least one $R^A$ is unsubstituted $C_{1-6}$ alkyl. In certain embodiments, at least one $R^A$ is methyl. In certain embodiments, at least one $R^A$ is ethyl. In certain embodiments, at least one $R^A$ is propyl. In certain embodiments, at least one $R^A$ is butyl. In certain embodiments, at least one $R^A$ is substituted carbocyclyl. In certain embodiments, at least one $R^A$ is unsubstituted carbocyclyl. In certain embodiments, at least one $R^A$ is —$OR^{A1}$. In certain embodiments, at least one $R^A$ is —$O(C_{1-6}$ alkyl) where the alkyl is substituted or unsubstituted. In certain embodiments, at least one $R^A$ is —OMe. In certain embodiments, at least one $R^A$ is —OH. In certain embodiments, at least one $R^A$ is —$N(R^{A1})_2$. In certain embodiments, at least one $R^A$ is —$NH_2$. In certain embodiments, at least one $R^A$ is —CN. In certain embodiments, at least one $R^A$ is —$C(=O)R^{A1}$. In certain embodiments, at least one $R^A$ is acetyl. In certain embodiments, at least one $R^A$ is —$C(=O)OR^{A1}$. In certain embodiments, at least one $R^A$ is —$C(=O)N(R^{A1})_2$. In certain embodiments, at least one $R^A$ is —$C(=O)NHR^{A1}$. In certain embodiments, at least one $R^A$ is —$C(=O)NH(C_{1-6}$ alkyl) where the alkyl is substituted or unsubstituted. In certain embodiments, at least one $R^A$ is —$C(=O)NHMe$. In certain embodiments, at least one $R^A$ is —$C(=O)NH_2$. In certain embodiments, at least one $R^A$ is —$NO_2$. In certain embodiments, at least one $R^A$ is —$NR^{A1}C(=O)R^{A1}$. In certain embodiments, at least one $R^A$ is —$NR^{A1}C(=O)OR^{A1}$. In certain embodiments, at least one $R^A$ is —$NR^{A1}S(=O)_2R^{A1}$. In certain embodiments, at least one $R^A$ is —NHS(=O)$_2R^{A1}$. In certain embodiments, at least one $R^A$ is —NHS(=O)$_2$(C$_{1-6}$ alkyl) where the alkyl is substituted or unsubstituted. In certain embodiments, at least one $R^A$ is —NHS(=O)$_2$Me. In certain embodiments, at least one $R^A$ is —S(=O)$_2R^{A1}$. In certain embodiments, at least one $R^A$ is —S(=O)$_2$N(R$^{A1}$)$_2$. In certain embodiments, at least one $R^A$ is —S(=O)$_2$N(R$^{A1}$)$_2$. In certain embodiments, at least one $R^A$ is —S(=O)$_2$N(C$_{1-6}$ alkyl)$_2$. In certain embodiments, at least one $R^A$ is —S(=O)$_2$NH(C$_{1-6}$ alkyl). In certain embodiments, at least one $R^A$ is —S(=O)$_2$NH(t-Bu). In certain embodiments, at least one $R^A$ is —S(=O)$_2$NH$_2$.

In certain embodiments, $R^A$ is —OR$^{A1}$; and k is 1. In certain embodiments, $R^A$ is —O(C$_{1-6}$ alkyl); and k is 1. In certain embodiments, $R^A$ is —OMe; and k is 1. In certain embodiments, $R^A$ is —OH; and k is 1.

In certain embodiments, $R^A$ is substituted C$_{1-6}$ alkyl; and k is 1. In certain embodiments, $R^A$ is unsubstituted C$_{1-6}$ alkyl; and k is 1. In certain embodiments, $R^A$ is methyl; and k is 1. In certain embodiments, $R^A$ is —CF$_3$; and k is 1. In certain embodiments, $R^A$ is ethyl; and k is 1. In certain embodiments, $R^A$ is propyl; and k is 1. In certain embodiments, $R^A$ is butyl; and k is 1. In certain embodiments, $R^A$ is propyl; and k is 1. In certain embodiments, $R^A$ is butyl; and k is 1.

In certain embodiments, $R^A$ is halogen; and k is 1. In certain embodiments, $R^A$ is F; and k is 1. In certain embodiments, $R^A$ is Cl; and k is 1. In certain embodiments, $R^A$ is Br; and k is 1. In certain embodiments, $R^A$ is I (iodine); and k is 1.

In certain embodiments, one instance of $R^A$ is halogen; another instance of $R^A$ is substituted C$_{1-6}$ alkyl; and k is 2. In certain embodiments, one instance of $R^A$ is F; another instance of $R^A$ is substituted C$_{1-6}$ alkyl; and k is 2. In certain embodiments, one instance of $R^A$ is Cl; another instance of $R^A$ is substituted C$_{1-6}$ alkyl; and k is 2. In certain embodiments, one instance of $R^A$ is halogen; another instance of $R^A$ is unsubstituted C$_{1-6}$ alkyl; and k is 2. In certain embodiments, one instance of $R^A$ is F; another instance of $R^A$ is unsubstituted C$_{1-6}$ alkyl; and k is 2. In certain embodiments, one instance of $R^A$ is Cl; another instance of $R^A$ is unsubstituted C$_{1-6}$ alkyl; and k is 2. In certain embodiments, one instance of $R^A$ is halogen; another instance of $R^A$ is methyl; and k is 2. In certain embodiments, one instance of $R^A$ is F; another instance of $R^A$ is methyl; and k is 2. In certain embodiments, one instance of $R^A$ is Cl; another instance of $R^A$ is methyl; and k is 2. In certain embodiments, one instance of $R^A$ is halogen; another instance of $R^A$ is —CF$_3$; and k is 2. In certain embodiments, one instance of $R^A$ is F; another instance of $R^A$ is —CF$_3$; and k is 2. In certain embodiments, one instance of $R^A$ is Cl; another instance of $R^A$ is —CF$_3$; and k is 2.

In certain embodiments, at least one $R^{A1}$ is H. In certain embodiments, at least one $R^{A1}$ is substituted acyl. In certain embodiments, at least one $R^{A1}$ is unsubstituted acyl. In certain embodiments, at least one $R^{A1}$ is acetyl. In certain embodiments, at least one $R^{A1}$ is substituted alkyl. In certain embodiments, at least one $R^{A1}$ is unsubstituted alkyl. In certain embodiments, at least one $R^{A1}$ is C$_{1-6}$ alkyl. In certain embodiments, at least one $R^{A1}$ is methyl. In certain embodiments, at least one $R^{A1}$ is ethyl. In certain embodiments, at least one $R^{A1}$ is propyl. In certain embodiments, at least one $R^{A1}$ is butyl. In certain embodiments, at least one $R^{A1}$ is substituted alkenyl. In certain embodiments, at least one $R^{A1}$ is unsubstituted alkenyl. In certain embodiments, at least one $R^{A1}$ is substituted alkynyl. In certain embodiments, at least one $R^{A1}$ is unsubstituted alkynyl. In certain embodiments, at least one $R^{A1}$ is substituted carbocyclyl. In certain embodiments, at least one $R^{A1}$ is unsubstituted carbocyclyl. In certain embodiments, at least one $R^{A1}$ is substituted heterocyclyl. In certain embodiments, at least one $R^{A1}$ is unsubstituted heterocyclyl. In certain embodiments, at least one $R^{A1}$ is substituted aryl. In certain embodiments, at least one $R^{A1}$ is unsubstituted aryl. In certain embodiments, at least one $R^{A1}$ is substituted phenyl. In certain embodiments, at least one $R^{A1}$ is unsubstituted phenyl. In certain embodiments, at least one $R^{A1}$ is substituted heteroaryl. In certain embodiments, at least one $R^{A1}$ is unsubstituted heteroaryl. In certain embodiments, at least one $R^{A1}$ is substituted pyridyl. In certain embodiments, at least one $R^{A1}$ is unsubstituted pyridyl. In certain embodiments, at least one $R^{A1}$ is a nitrogen protecting group when attached to a nitrogen atom. In certain embodiments, at least one $R^{A1}$ is Bn, BOC, Cbz, Fmoc, trifluoroacetyl, triphenylmethyl, or Ts when attached to a nitrogen atom. In certain embodiments, $R^{A1}$ is an oxygen protecting group when attached to an oxygen atom. In certain embodiments, $R^{A1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{A1}$ is a sulfur protecting group when attached to a sulfur atom. In certain embodiments, $R^{A1}$ is acetamidomethyl, t-Bu, 3-nitro-2-pyridine sulfenyl, 2-pyridine-sulfenyl, or triphenylmethyl when attached to a sulfur atom.

In compounds of Formula (A), two $R^{A1}$ groups may be joined to form an optionally substituted carbocyclic, optionally substituted heterocyclic, optionally substituted aryl, or optionally substituted heteroaryl ring. In certain embodiments, two $R^{A1}$ groups are joined to form a substituted carbocyclic ring. In certain embodiments, two $R^{A1}$ groups are joined to form an unsubstituted carbocyclic ring. In certain embodiments, two $R^{A1}$ groups are joined to form a substituted heterocyclic ring. In certain embodiments, two $R^{A1}$ groups are joined to form an unsubstituted heterocyclic ring. In certain embodiments, two $R^{A1}$ groups are joined to form a substituted aryl ring. In certain embodiments, two $R^{A1}$ groups are joined to form an unsubstituted aryl ring. In certain embodiments, two $R^{A1}$ groups are joined to form a substituted phenyl ring. In certain embodiments, two $R^{A1}$ groups are joined to form an unsubstituted phenyl ring. In certain embodiments, two $R^{A1}$ groups are joined to form a substituted heteroaryl ring. In certain embodiments, two $R^{A1}$ groups are joined to form an unsubstituted heteroaryl ring.

Compounds of Formula (A) include a phenyl Ring C optionally substituted with one or more $R^B$ groups. In certain embodiments, l is 1. In certain embodiments, Ring C is of the formula:

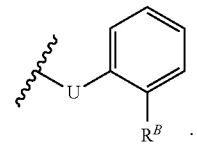

In certain embodiments, Ring C is of the formula:

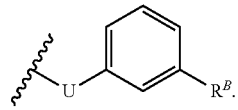

In certain embodiments, Ring C is of the formula:

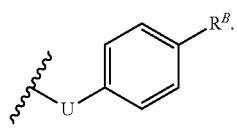

certain embodiments, l is 2. In certain embodiments, Ring C is of the formula:

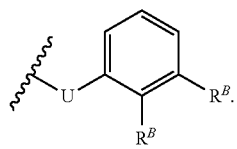

In certain embodiments, l is 2. In certain embodiments, Ring C is of the formula:

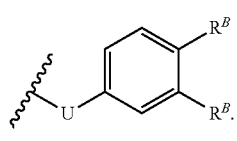

In certain embodiments, Ring C is of the formula:

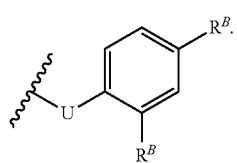

In certain embodiments, Ring C is of the formula:

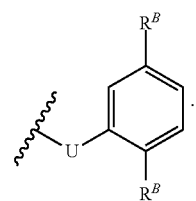

In certain embodiments, Ring C is of the formula:

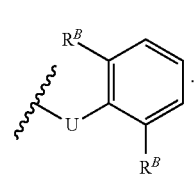

In certain embodiments, Ring C is of the formula:

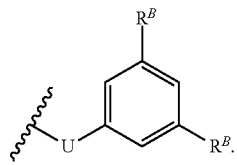

In certain embodiments, 1 is 3. In certain embodiments, Ring C is of the formula:

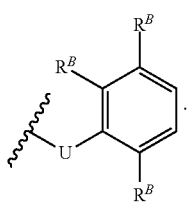

In certain embodiments, Ring C is of the formula:

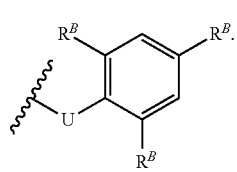

In certain embodiments, Ring C is of the formula:

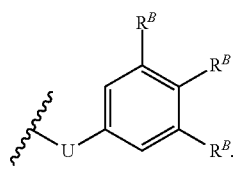

In certain embodiments, Ring C is of the formula:

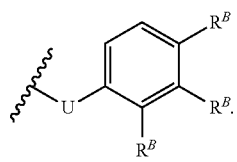

In certain embodiments, 1 is 4. In certain embodiments, Ring C is of the formula:

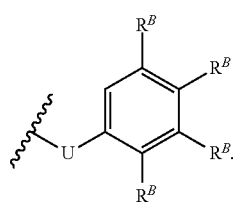

In certain embodiments, Ring C is of the formula:

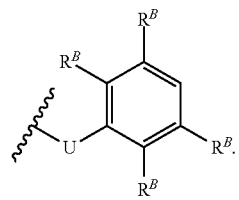

In certain embodiments, Ring C is of the formula:

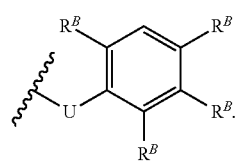

In certain embodiments, 1 is 5. In certain embodiments, Ring C is of the formula:

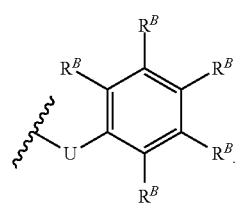

In compounds of Formula (A), Ring C may be substituted with one or more $R^B$ groups. In certain embodiments, at least one $R^B$ is H. In certain embodiments, at least two $R^B$ groups are H. In certain embodiments, at least three $R^B$ groups are H. In certain embodiments, at least four $R^B$ groups are H. In certain embodiments, at least one $R^B$ is not H. In certain embodiments, at least two $R^B$ groups are not H. In certain embodiments, at least three $R^B$ groups are not H. In certain embodiments, at least one $R^B$ is halogen. In certain embodiments, at least one $R^B$ is F. In certain embodiments, at least one $R^B$ is Cl. In certain embodiments, at least one $R^B$ is Br. In certain embodiments, at least one $R^B$ is I (iodine). In certain embodiments, one $R^B$ is F. In certain embodiments, one $R^B$ is Cl. In certain embodiments, at least one $R^B$ is substituted alkyl. In certain embodiments, at least one $R^B$ is unsubstituted alkyl. In certain embodiments, at least one $R^B$ is substituted $C_{1-6}$ alkyl. In certain embodiments, at least one $R^B$ is unsubstituted $C_{1-6}$ alkyl. In certain embodiments, at least one $R^B$ is methyl. In certain embodiments, at least one $R^B$ is ethyl. In certain embodiments, at least one $R^B$ is propyl. In certain embodiments, at least one $R^B$ is

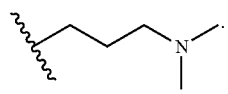

In certain embodiments, at least one $R^B$ is

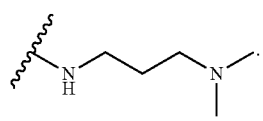 [SMILES: *NCCCN(C)C]

In certain embodiments, at least one $R^B$ is

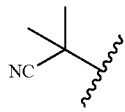

In certain embodiments, at least one $R^B$ is butyl. In certain embodiments, at least one $R^B$ is substituted carbocyclyl. In certain embodiments, at least one $R^B$ is unsubstituted carbocyclyl. In certain embodiments, at least one $R^B$ is substituted heterocyclyl. In certain embodiments, at least one $R^B$ is unsubstituted heterocyclyl. In certain embodiments, at least one $R^B$ is substituted piperidine. In certain embodiments, at least one $R^B$ is unsubstituted piperidine. In certain embodiments, at least one $R^B$ substituted piperizine. In certain embodiments, at least one $R^B$ unsubstituted piperizine. In certain embodiments, at least one $R^B$ substituted pyrrolidine. In certain embodiments, at least one $R^B$ unsubstituted pyrrolidine. In certain embodiments, at least one $R^B$ is substituted morpholine. In certain embodiments, at least one $R^B$ is unsubstituted morpholine. In certain embodiments, at least one $R^B$ is substituted diazepane. In certain embodiments, at least one $R^B$ is unsubstituted diazepane. In certain embodiments, at least one $R^B$ is

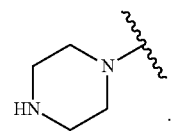

In certain embodiments, at least one $R^B$ is

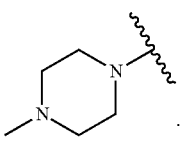 [SMILES: *N1CCN(C)CC1]

In certain embodiments, at least one $R^B$ is

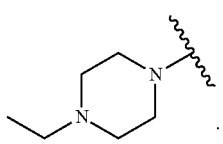 [SMILES: *N1CCN(CC)CC1]

In certain embodiments, at least one $R^B$ is

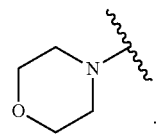 [SMILES: *N1CCOCC1]

In certain embodiments, at least one $R^B$ is substituted —(CH$_2$)(heterocyclyl). In certain embodiments, at least one $R^B$ is unsubstituted —(CH$_2$)(heterocyclyl). In certain embodiments, at least one $R^B$ is

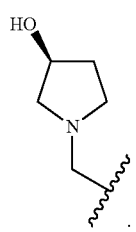

In certain embodiments, at least one $R^B$ is

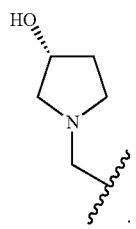

In certain embodiments, at least one $R^B$ is

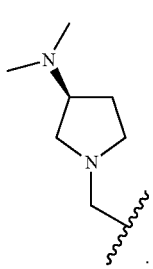 [SMILES: *CN1CC[C@H](N(C)C)C1]

In certain embodiments, at least one $R^B$ is

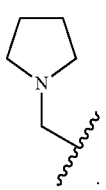

In certain embodiments, at least one $R^B$ is

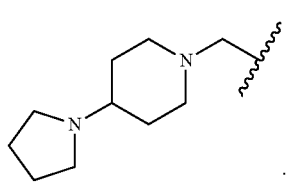 [SMILES: *CN1CCC(N2CCCC2)CC1]

In certain embodiments, at least one $R^B$ is

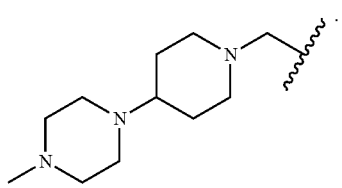 [SMILES: *CN1CCC(N2CCN(C)CC2)CC1]

In certain embodiments, at least one $R^B$ is

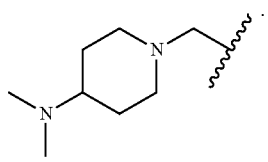 [SMILES: *CN1CCC(N(C)C)CC1]

In certain embodiments, at least one $R^B$ is

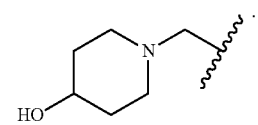

In certain embodiments, at least one $R^B$ is

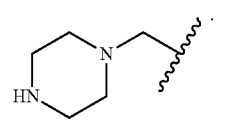

In certain embodiments, at least one $R^B$ is

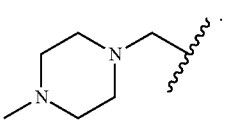

In certain embodiments, at least one $R^B$ is

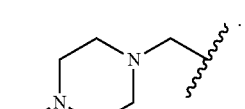

In certain embodiments, at least one $R^B$ is

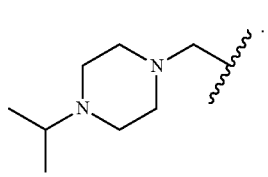 [SMILES: *CN1CCN(C(C)C)CC1]

In certain embodiments, at least one $R^B$ is

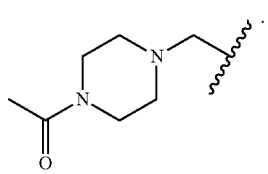 [SMILES: *CN1CCN(C(C)=O)CC1]

In certain embodiments, at least one $R^B$ is

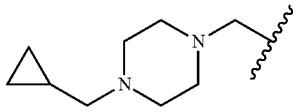

In certain embodiments, at least one $R^B$ is

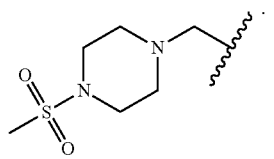 [SMILES: *CN1CCN(S(C)(=O)=O)CC1]

In certain embodiments, at least one $R^B$ is

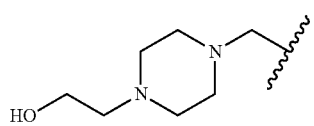

In certain embodiments, at least one $R^B$ is

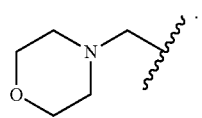 [SMILES: *CN1CCOCC1]

In certain embodiments, at least one $R^B$ is

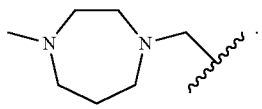 [SMILES: *CN1CCCN(C)CC1]

In certain embodiments, at least one $R^B$ is substituted —$(CH_2)_2$(heterocyclyl). In certain embodiments, at least one $R^B$ is unsubstituted —$(CH_2)_2$(heterocyclyl). In certain embodiments, at least one $R^B$ is

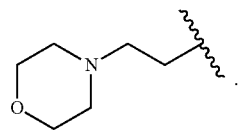 [SMILES: *CCN1CCOCC1]

In certain embodiments, at least one $R^B$ is substituted —$(CH_2)_3$(heterocyclyl). In certain embodiments, at least one $R^B$ is unsubstituted —$(CH_2)_3$(heterocyclyl). In certain embodiments, at least one $R^B$ is

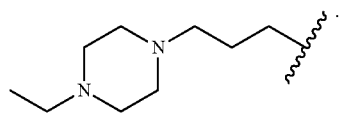 [SMILES: *CCCN1CCN(CC)CC1]

In certain embodiments, at least one $R^B$ is substituted aryl. In certain embodiments, at least one $R^B$ is unsubstituted aryl. In certain embodiments, at least one $R^B$ is substituted phenyl. In certain embodiments, at least one $R^B$ is unsubstituted phenyl. In certain embodiments, at least one $R^B$ is substituted heteroaryl. In certain embodiments, at least one $R^B$ is unsubstituted heteroaryl. In certain embodiments, at least one $R^B$ is substituted pyridyl. In certain embodiments, at least one $R^B$ is unsubstituted pyridyl. In certain embodiments, at least one $R^B$ is substituted imidazole. In certain embodiments, at least one $R^B$ is unsubstituted imidazole. In certain embodiments, at least one $R^B$ is

In certain embodiments, at least one $R^B$ is

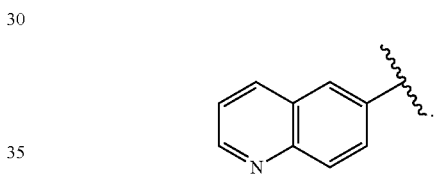

In certain embodiments, at least one $R^B$ is —$OR^{A1}$. In certain embodiments, at least one $R^B$ is —$O(C_{1-6}$ alkyl) where the alkyl is substituted or unsubstituted. In certain embodiments, at least one $R^B$ is —OMe. In certain embodiments, at least one $R^B$ is —OPh. In certain embodiments, at least one $R^B$ is

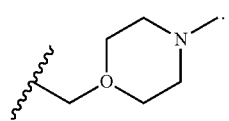

In certain embodiments, at least one $R^B$ is

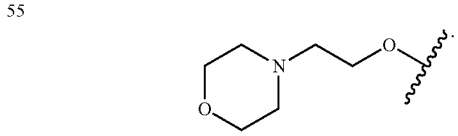

In certain embodiments, at least one $R^B$ is —OH. In certain embodiments, at least one $R^B$ is —$N(R^{A1})_2$. In certain embodiments, at least one $R^B$ is —$NEt_2$. In certain embodiments, at least one $R^B$ is —$NMe_2$. In certain embodiments, at least one $R^B$ is —NHtBu. In certain embodiments, at least one $R^B$ is In certain embodiments, at least one $R^B$ is

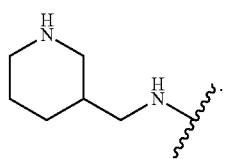 [SMILES: *NCC1CCCNC1]

In certain embodiments, at least one $R^B$ is

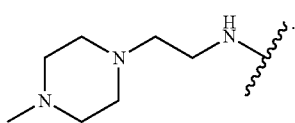 [SMILES: *NCCN1CCN(C)CC1]

In certain embodiments, at least one $R^B$ is —NH$_2$. In certain embodiments, at least one $R^B$ certain embodiments, at least one $R^B$ is —NH$_2$. In certain embodiments, at least one R is —CN. In certain embodiments, at least one $R^B$ is —C(=O)R$^{41}$. In certain embodiments, at least one $R^B$ is acetyl. In certain embodiments, at least one $R^B$ is —C(=O)OR$^{41}$. In certain embodiments, at least one $R^B$ is —C(=O)N(R$^{41}$)$_2$. In certain embodiments, at least one $R^B$ is —C(=O)NHR$^{41}$. In certain embodiments, at least one $R^B$ is —C(=O)NH(C$_{1-6}$ alkyl) where the alkyl is substituted or unsubstituted. In certain embodiments, at least one $R^B$ is —C(=O)NHMe. In certain embodiments, at least one $R^B$ is —C(=O)NH$_2$. In certain embodiments, at least one $R^B$ is

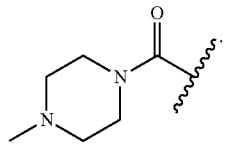 [SMILES: *C(=O)N1CCN(C)CC1]

In certain embodiments, at least one $R^B$ is

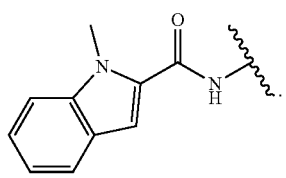 [SMILES: *NC(=O)c1cc2ccccc2n1C]

In certain embodiments, at least one $R^B$ is —NO$_2$. In certain embodiments, at least one $R^B$ is —NR$^{41}$C(=O)R$^{41}$. In certain embodiments, at least one $R^B$ is —NR$^{41}$C(=O)OR$^{41}$. In certain embodiments, at least one $R^B$ is —NR$^{41}$S(=O)$_2$R$^{41}$. In certain embodiments, at least one $R^B$ is —NHS(=O)$_2$R$^{41}$. In certain embodiments, at least one $R^B$ is —NHS(=O)$_2$(C$_{1-6}$ alkyl) where the alkyl is substituted or unsubstituted. In certain embodiments, at least one $R^B$ is —NHS(=O)$_2$Me. In certain embodiments, at least one $R^B$ is —S(=O)$_2$R$^{41}$. In certain embodiments, at least one $R^B$ is —S(=O)$_2$N(R$^{41}$)$_2$. In certain embodiments, at least one $R^B$ is —S(=O)$_2$N(R$^{41}$)$_2$. In certain embodiments, at least one $R^B$ is —S(=O)$_2$N(C$_{1-6}$ alkyl)$_2$. In certain embodiments, at least one $R^B$ is —S(=O)$_2$NH(C$_{1-6}$ alkyl). In certain embodiments, at least one $R^B$ is —S(=O)$_2$NH(t-Bu). In certain embodiments, at least one $R^B$ is —S(=O)$_2$NH$_2$.

In certain embodiments, $R^B$ is substituted or unsubstituted C$_{1-6}$alkyl; and l is 1. In certain embodiments, $R^B$ is substituted or unsubstituted C$_{1-6}$alkyl; l is 1; and $R^B$ is meta to the point of attachment of U. In certain embodiments, $R^B$ is substituted or unsubstituted C$_{1-6}$alkyl; l is 1; and $R^B$ is para to the point of attachment of U. In certain embodiments, $R^B$ is C$_{1-6}$alkyl substituted with one —CN group; and l is 1. In certain embodiments, $R^B$ is C$_{1-6}$alkyl substituted with one —CN group; l is 1; and $R^B$ is meta to the point of attachment of U. In certain embodiments, $R^B$ is C$_{1-6}$alkyl substituted with one —CN group; l is 1; and $R^B$ is para to the point of attachment of U. In certain embodiments, $R^B$ is

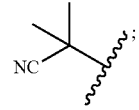

and l is 1. In certain embodiments, $R^B$ is

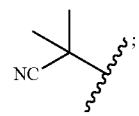

l is 1; and $R^B$ is meta to the point of attachment of U. In certain embodiments, $R^B$ is

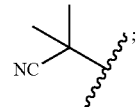

l is 1; and $R^B$ is para to the point of attachment of U. In certain embodiments, $R^B$ is substituted or unsubstituted —CH$_2$-(piperazinyl); and l is 1. In certain embodiments, $R^B$ is substituted or unsubstituted —CH$_2$-(piperazinyl); l is 1; and $R^B$ is meta to the point of attachment of U. In certain embodiments, $R^B$ is substituted or unsubstituted —CH$_2$-(piperazinyl); l is 1; and $R^B$ is para to the point of attachment of U. In certain embodiments, $R^B$ is

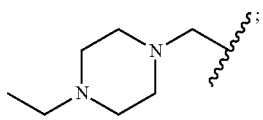 [SMILES: *CN1CCN(CC)CC1]

and l is 1. In certain embodiments, $R^B$ is

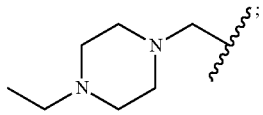

l is 1; and $R^B$ is meta to the point of attachment of U. In certain embodiments, $R^B$ is

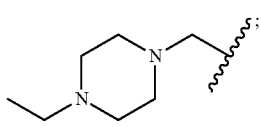 [SMILES: *CN1CCN(CC)CC1]

l is 1; and $R^B$ is para to the point of attachment of U. In certain embodiments, $R^B$ is haloalkyl; and l is 1. In certain embodiments, $R^B$ is haloalkyl; l is 1; and $R^B$ is meta to the point of attachment of U. In certain embodiments, $R^B$ is haloalkyl; l is 1; and $R^B$ is para to the point of attachment of U. In certain embodiments, $R^B$ is —$CF_3$; and l is 1. In certain embodiments, $R^B$ is —$CF_3$; l is 1; and $R^B$ is meta to the point of attachment of U. In certain embodiments, $R^B$ is —$CF_3$; l is 1; and $R^B$ is para to the point of attachment of U. In certain embodiments, $R^B$ is substituted or unsubstituted imidazoyl and l is 1. In certain embodiments, $R^B$ is substituted or unsubstituted imidazoyl l is 1; and $R^B$ is meta to the point of attachment of U. In certain embodiments, $R^B$ is substituted or unsubstituted imidazoyl; l is 1; and $R^B$ is para to the point of attachment of U. In certain embodiments, $R^B$ is

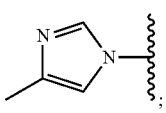

and l is 1. In certain embodiments, $R^B$ is

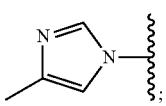

is 1; and $R^B$ is meta to the point of attachment of U. In certain embodiments, $R^B$ is

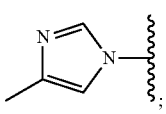 [SMILES: *n1cnc(C)c1]

l is 1; and $R^B$ is meta to the point of attachment of U. In certain embodiments, $R^B$ is 1; and $R^B$ is para to the point of attachment of U. In certain embodiments, $R^B$ is substituted or unsubstituted piperazinyl; and l is 1. In certain embodiments, $R^B$ is substituted or unsubstituted piperazinyl; l is 1; and $R^B$ is meta to the point of attachment of U. In certain embodiments, $R^B$ is substituted or unsubstituted piperazinyl; l is 1; and $R^B$ is para to the point of attachment of U. In certain embodiments, $R^B$ is

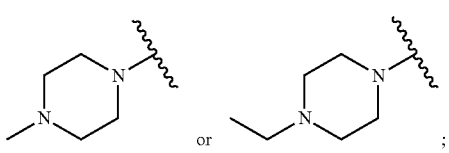

and l is 1. In certain embodiments, $R^B$ is

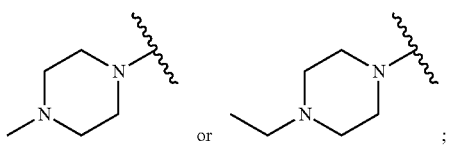

l is 1; and $R^B$ is meta to the point of attachment of U. In certain embodiments, $R^B$ is

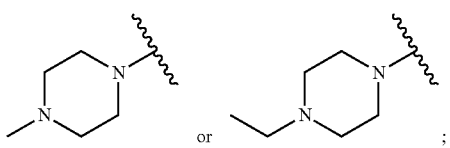

l is 1; and $R^B$ is para to the point of attachment of U. In certain embodiments, $R^B$ is substituted or unsubstituted morpholine; and l is 1. In certain embodiments, $R^B$ is substituted or unsubstituted morpholine; l is 1; and $R^B$ is meta to the point of attachment of U. In certain embodiments, $R^B$ is substituted or unsubstituted morpholine; l is 1; and $R^B$ is para to the point of attachment of U.

In certain embodiments, at least one $R^B$ group is substituted or unsubstituted $C_{1-6}$alkyl; and l is 2. In certain embodiments, at least one $R^B$ group is substituted or unsubstituted $C_{1-6}$alkyl; l is 2; and at least one $R^B$ is meta to the point of attachment of U. In certain embodiments, at least one $R^B$ group is substituted or unsubstituted $C_{1-6}$alkyl; l is 2; and one $R^B$ is para to the point of attachment of U. In certain embodiments, at least one $R^B$ group is $C_{1-6}$alkyl substituted with one —CN group; and l is 2. In certain embodiments, at least one $R^B$ group is $C_{1-6}$alkyl substituted with one —CN group; l is 2; and at least one $R^B$ is meta to the point of attachment of U. In certain embodiments, at least one $R^B$ group is $C_{1-6}$alkyl substituted with one —CN group; l is 2; and one $R^B$ is para to the point of attachment of U. In certain embodiments, at least one $R^B$ group is

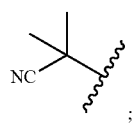

and l is 2. In certain embodiments, at least one $R^B$ group is

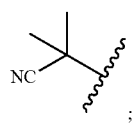

l is 2; and at least one $R^B$ is meta to the point of attachment of U. In certain embodiments, at least one $R^B$ group is

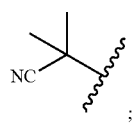 [SMILES: *C(C)(C)C#N]

l is 2; and one $R^B$ is para to the point of attachment of U. In certain embodiments, at least one $R^B$ group is substituted or unsubstituted —CH$_2$-(piperazinyl); and l is 2. In certain embodiments, at least one $R^B$ group is substituted or unsubstituted —CH$_2$-(piperazinyl); l is 2; and at least one $R^B$ is meta to the point of attachment of U. In certain embodiments, at least one $R^B$ group is substituted or unsubstituted —CH$_2$-(piperazinyl); l is 2; and one $R^B$ is para to the point of attachment of U. In certain embodiments, at least one $R^B$ group is

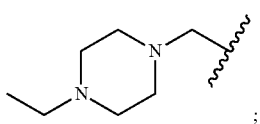 [SMILES: *CN1CCN(CC)CC1]

and l is 2. In certain embodiments, at least one $R^B$ group is

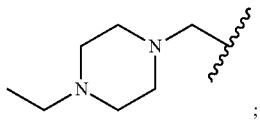 [SMILES: *CN1CCN(CC)CC1]

l is 2; and at least one $R^B$ is meta to the point of attachment of U. In certain embodiments, at least one $R^B$ group is

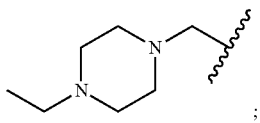

l is 2; and one $R^B$ is para to the point of attachment of U. In certain embodiments, at least one $R^B$ group is haloalkyl; and l is 2. In certain embodiments, at least one $R^B$ group is haloalkyl; l is 2; and at least one $R^B$ is meta to the point of attachment of U. In certain embodiments, at least one $R^B$ group is haloalkyl; l is 2; and one $R^B$ is para to the point of attachment of U. In certain embodiments, at least one $R^B$ group is —CF$_3$; and l is 2. In certain embodiments, at least one $R^B$ group is —CF$_3$; l is 2; and at least one $R^B$ is meta to the point of attachment of U. In certain embodiments, at least one $R^B$ group is —CF$_3$; l is 2; and one $R^B$ is para to the point of attachment of U. In certain embodiments, at least one $R^B$ group is substituted or unsubstituted imidazoyl; and l is 2. In certain embodiments, at least one $R^B$ group is substituted or unsubstituted imidazoyl; l is 2; and at least one $R^B$ is meta to the point of attachment of U. In certain embodiments, at least one $R^B$ group is substituted or unsubstituted imidazoyl; l is 2; and one $R^B$ is para to the point of attachment of U. In certain embodiments, at least one $R^B$ group is

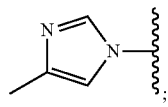 [SMILES: *n1cnc(C)c1]

and l is 2. In certain embodiments, at least one $R^B$ group is

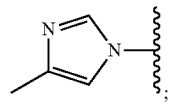

l is 2; and at least one $R^B$ is meta to the point of attachment of U. In certain embodiments, at least one $R^B$ group is

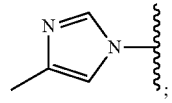

l is 2; and one $R^B$ is para to the point of attachment of U. In certain embodiments, at least one $R^B$ group is substituted or unsubstituted piperazinyl; and l is 2. In certain embodiments, at least one $R^B$ group is substituted or unsubstituted piperazinyl; l is 2; and at least one $R^B$ is meta to the point of attachment of U. In certain embodiments, at least one $R^B$ group is substituted or unsubstituted piperazinyl; l is 2; and one $R^B$ is para to the point of attachment of U. In certain embodiments, at least one $R^B$ group is

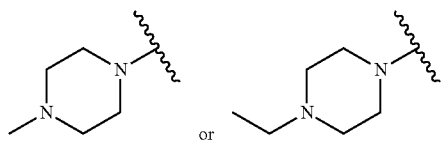

and l is 2. In certain embodiments, at least one $R^B$ group is

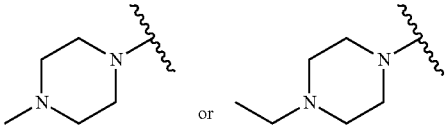

l is 2; and at least one $R^B$ is meta to the point of attachment of U. In certain embodiments, at least one $R^B$ group is

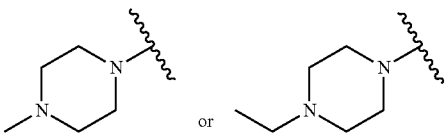

l is 2; and one $R^B$ is para to the point of attachment of U. In certain embodiments, at least one $R^B$ group is substituted or unsubstituted morpholine; and l is 2. In certain embodiments, at least one $R^B$ group is substituted or unsubstituted morpholine; l is 2; and at least one $R^B$ is meta to the point of attachment of U. In certain embodiments, at least one $R^B$ group is substituted or unsubstituted morpholine; l is 2; and one $R^B$ is para to the point of attachment of U. In certain embodiments, two $R^B$ groups are substituted or unsubstituted morpholine; l is 2; and both $R^B$ groups are meta to the point of attachment of U.

In compounds of Formula (A), Q and U are taken together to represent a divalent linker moiety. In certain embodiments, Q and U are taken together to represent

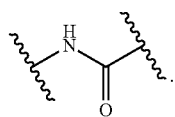 [SMILES: *NC(*)=O]

In certain embodiments, Q and U are taken together to represent

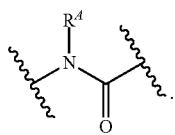

In certain embodiments, Q and U are taken together to represent

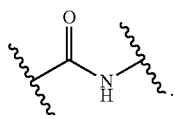

In certain embodiments, Q and U are taken together to represent

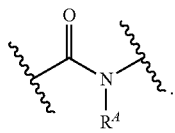

Formula (A) includes a pyridine or pyrimidine ring as Ring B. In certain embodiments, each instance of A included in Ring B is carbon. In certain embodiments, one instance of A included in Ring B is carbon, and the other instance of A included in Ring B is nitrogen. In certain embodiments, Ring B is of the formula:

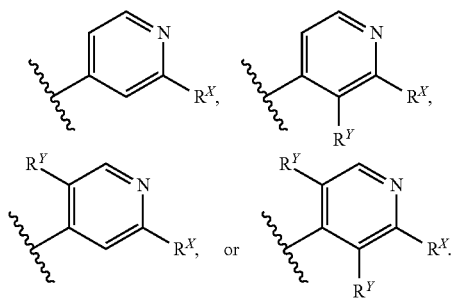

In certain embodiments, Ring B is of the formula:

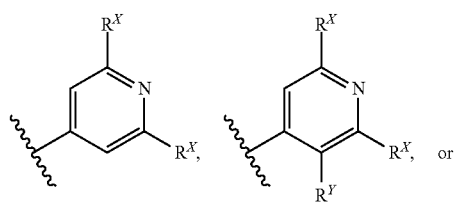

In certain embodiments, Ring B is of the formula:

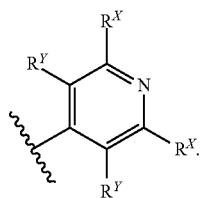

In certain embodiments, Ring B is of the formula:

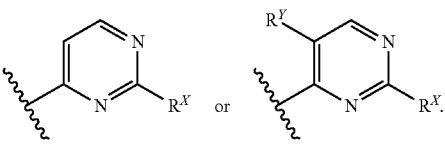

In certain embodiments, Ring B is of the formula:

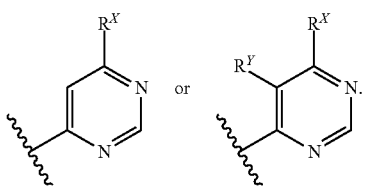

In certain embodiments, Ring B is of the formula:

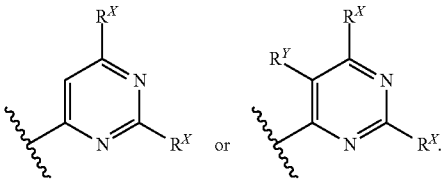

Formula (A) may include one or more $R^Y$ groups. When Formula (A) includes two instances of $R^Y$, the two instances of $R^Y$ may be the same or different from each other. In certain embodiments, at least one instance of $R^Y$ is H. In certain embodiments, each instance of $R^Y$ is H. In certain embodiments, at least one instance of $R^Y$ is halogen (e.g., F, Cl, Br, or I). In certain embodiments, at least one instance of $R^Y$ is substituted or unsubstituted $C_{1-6}$ alkyl. In certain embodiments, at least one instance of $R^Y$ is Me. In certain embodiments, at least one instance of $R^Y$ is substituted methyl (e.g., —CF$_3$ or Bn). In certain embodiments, at least one instance of $R^Y$ is Et, substituted ethyl (e.g., perfluoroethyl), Pr, substituted propyl (e.g., perfluoropropyl), Bu, or substituted butyl (e.g., perfluorobutyl).

In compounds of Formula (A), the pyridine or pyrimidine ring may be substituted with one or more $R^X$ groups. When Formula (A) includes two instances of $R^X$, the two instances of $R^X$ may be the same or different from each other. In certain embodiments, at least one $R^X$ is substituted carbocyclyl. In certain embodiments, at least one $R^X$ is unsubstituted carbocyclyl. In certain embodiments, at least one $R^X$ is

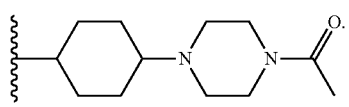

In certain embodiments, at least one $R^X$ is

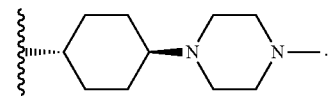

In certain embodiments, at least one $R^X$ is

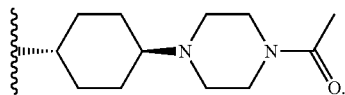 [SMILES: *[C@H]1CC[C@H](N2CCN(C(C)=O)CC2)CC1]

In certain embodiments, at least one $R^X$ is substituted heterocyclyl. In certain embodiments, at least one $R^X$ is unsubstituted heterocyclyl. In certain embodiments, at least one $R^X$ is

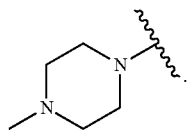 [SMILES: *N1CCN(C)CC1]

In certain embodiments, at least one $R^X$ is

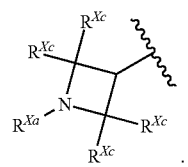

In certain embodiments, at least one $R^X$ is

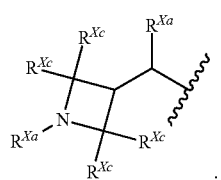

In certain embodiments, at least one $R^X$ is

In certain embodiments, at least one $R^X$ is

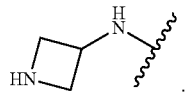

In certain embodiments, at least one $R^X$ is

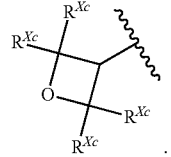

In certain embodiments, at least one $R^X$ is

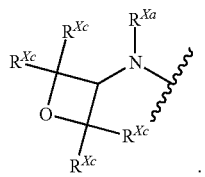

In certain embodiments, at least one $R^X$ is

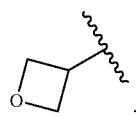

In certain embodiments, at least one $R^X$ is

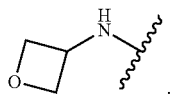

In certain embodiments, at least one $R^X$ is substituted aryl. In certain embodiments, at least one $R^X$ is unsubstituted aryl. In certain embodiments, at least one $R^X$ is substituted phenyl. In certain embodiments, at least one $R^X$ is unsubstituted phenyl. In certain embodiments, at least one $R^X$ is

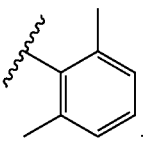 [SMILES: *c1c(C)cccc1C]

In certain embodiments, at least one $R^X$ is

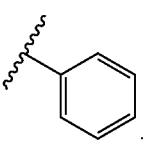 [SMILES: *c1ccccc1]

In certain embodiments, at least one $R^X$ is

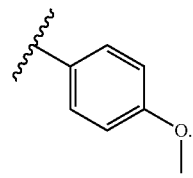 [SMILES: *c1ccc(OC)cc1]

In certain embodiments, at least one $R^X$ is

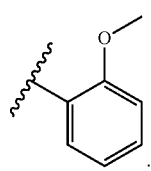 [SMILES: *c1ccccc1OC]

In certain embodiments, at least one $R^X$ is

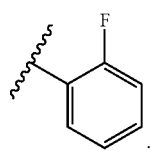 [SMILES: *c1ccccc1F]

In certain embodiments, at least one $R^X$ is

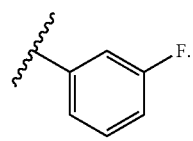 [SMILES: *c1cccc(F)c1]

In certain embodiments, at least one $R^X$ is

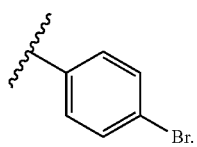 [SMILES: *c1ccc(Br)cc1]

In certain embodiments, at least one $R^X$ is

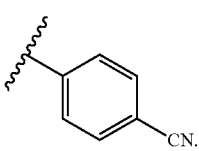 [SMILES: *c1ccc(C#N)cc1]

In certain embodiments, at least one $R^X$ is substituted heteroaryl. In certain embodiments, at least one $R^X$ is unsubstituted heteroaryl. In certain embodiments, at least one $R^X$ is

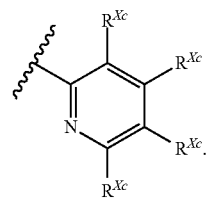

In certain embodiments, at least one $R^X$ is

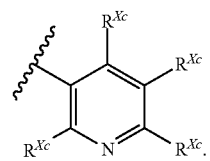

In certain embodiments, at least one $R^X$ is

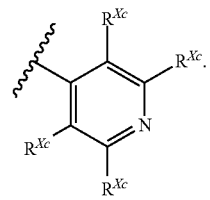

In certain embodiments, at least one $R^X$ is

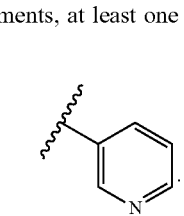

In certain embodiments, at least one $R^X$ is

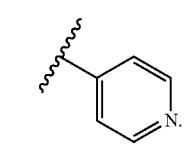 [SMILES: *c1ccncc1]

In certain embodiments, at least one $R^X$ is

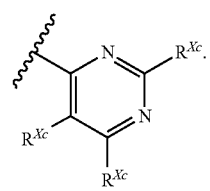

In certain embodiments, at least one $R^X$ is

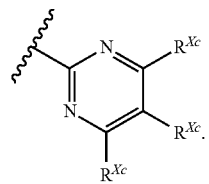

In certain embodiments, at least one $R^X$ is

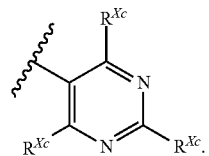

In certain embodiments, at least one $R^X$ is

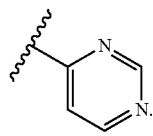

In certain embodiments, at least one $R^X$ is

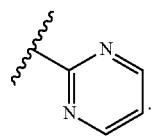

In certain embodiments, at least one $R^X$ is

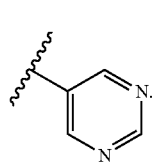

In certain embodiments, at least one R is

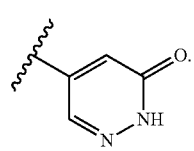

In certain embodiments, at least one $R^X$ is

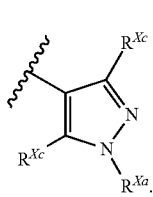

In certain embodiments, at least one $R^X$ is

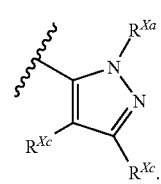

In certain embodiments, at least one $R^X$ is

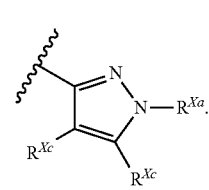

In certain embodiments, at least one $R^X$ is

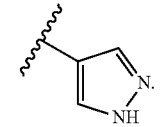 [SMILES: *c1cn[nH]c1]

In certain embodiments, at least one $R^X$ is

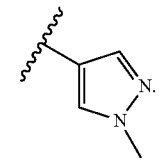 [SMILES: *c1cnn(C)c1]

In certain embodiments, at least one $R^X$ is

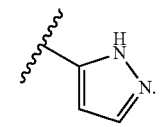

In certain embodiments, at least one $R^X$ is

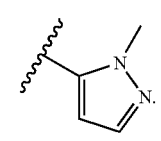 [SMILES: *c1ccnn1C]

In certain embodiments, at least one $R^X$ is

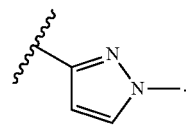

In certain embodiments, at least one $R^X$ is

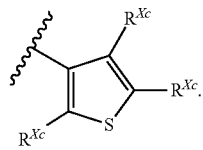

In certain embodiments, at least one $R^X$ is

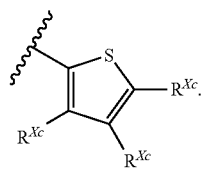

In certain embodiments, at least one $R^X$ is

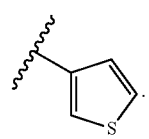 [SMILES: *c1ccsc1]

In certain embodiments, at least one $R^X$ is

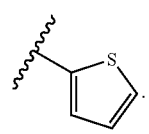

In certain embodiments, at least one $R^X$ is

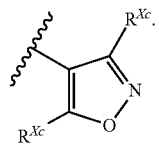

In certain embodiments, at least one $R^X$ is

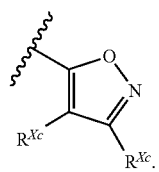

In certain embodiments, at least one $R^X$ is

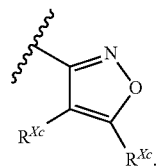

In certain embodiments, at least one $R^X$ is

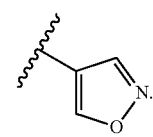 [SMILES: *c1cnoc1]

In certain embodiments, at least one $R^X$ is

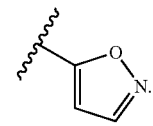 [SMILES: *c1ccno1]

In certain embodiments, at least one $R^X$ is

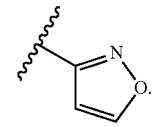 [SMILES: *c1ccon1]

In certain embodiments, at least one $R^X$ is —N($R^{A1}$)($R^{Xa}$). In certain embodiments, at least one $R^X$ is —NH$_2$. In certain embodiments, at least one $R^X$ is —NH (3-6 membered cycloalkyl) where the cycloalkyl is substituted or unsubstituted. In certain embodiments, at least one $R^X$ is

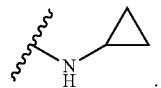

In certain embodiments, at least one $R^X$ is —NH(C$_{1-6}$alkyl) where the alkyl is substituted or unsubstituted. In certain embodiments, at least one $R^X$ is —N(C$_{1-6}$alkyl)$_2$ where the alkyl is substituted or unsubstituted. In certain embodiments, at least one $R^X$ is

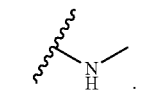

In certain embodiments, at least one $R^X$ is —NH(acyl). In certain embodiments, at least one $R^X$ is

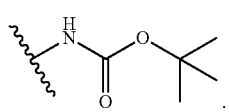 [SMILES: *NC(=O)OC(C)(C)C]

In certain embodiments, at least one $R^X$ is

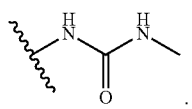

In certain embodiments, at least one $R^X$ is

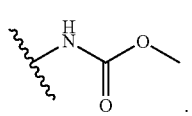

In certain embodiments, at least one $R^X$ is

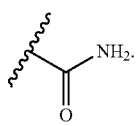

In certain embodiments, at least one $R^X$ is —NHC(=O)(3-6 membered cycloalkyl) where the cycloalkyl is substituted or unsubstituted. In certain embodiments, at least one $R^X$ is

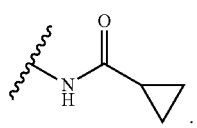

In certain embodiments, at least one $R^X$ is —NHC(=O)(C$_{1-6}$alkyl) where the alkyl is substituted or unsubstituted. In certain embodiments, at least one $R^X$ is

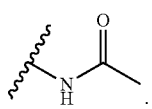 [SMILES: *NC(C)=O]

In certain embodiments, at least one $R^X$ is

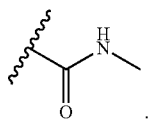

In certain embodiments, at least one $R^X$ is

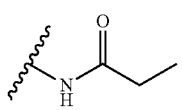

In certain embodiments, at least one $R^X$ is

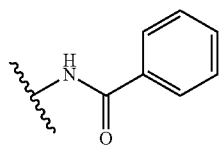

In certain embodiments, at least one $R^X$ is

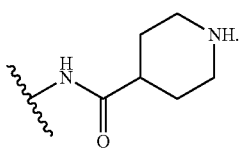 [SMILES: *NC(=O)C1CCNCC1]

In certain embodiments, at least one $R^X$ is

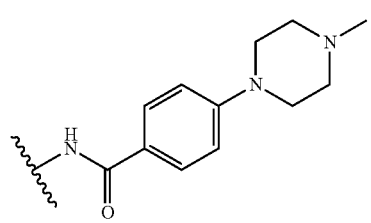

In certain embodiments, at least one $R^X$ is

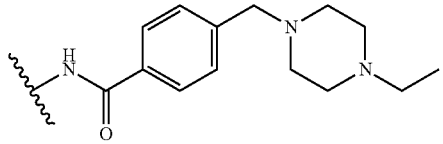

In certain embodiments, at least one $R^X$ is

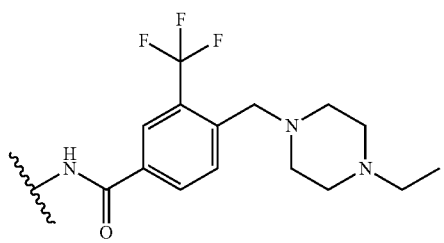

In certain embodiments, at least one $R^X$ is

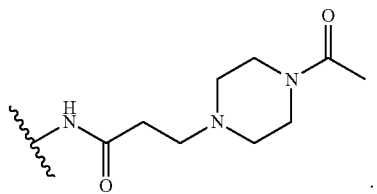 [SMILES: *NC(=O)CCN1CCN(C(C)=O)CC1]

In certain embodiments, at least one $R^X$ is

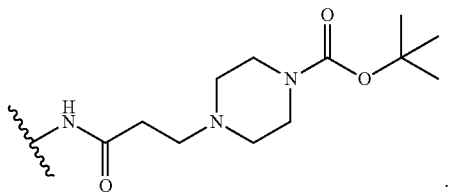 [SMILES: *NC(=O)CCN1CCN(C(=O)OC(C)(C)C)CC1]

In certain embodiments, at least one $R^X$ is

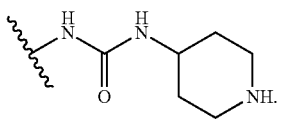 [SMILES: *NC(=O)NC1CCNCC1]

In certain embodiments, at least one $R^X$ is

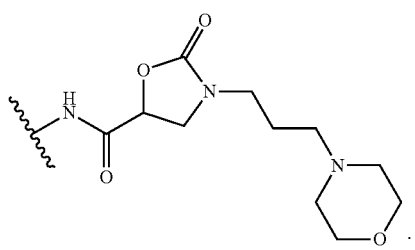 [SMILES: *NC(=O)C1CN(CCCN2CCOCC2)C(=O)O1]

In certain embodiments, at least one $R^X$ is

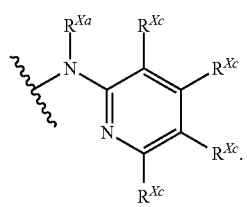

In certain embodiments, at least one $R^X$ is

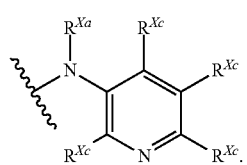

In certain embodiments, at least one $R^X$ is

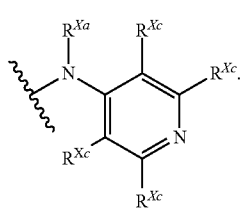

In certain embodiments, at least one $R^X$ is

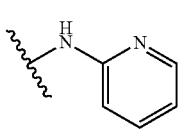

In certain embodiments, at least one $R^X$ is

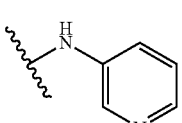

In certain embodiments, at least one $R^X$ is

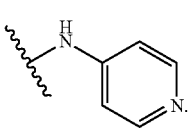

In certain embodiments, at least one $R^X$ is

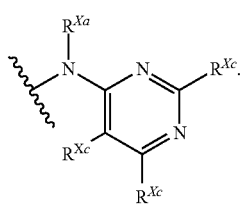

In certain embodiments, at least one $R^X$ is

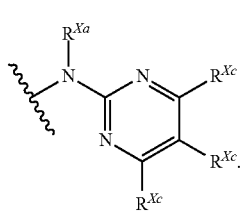

In certain embodiments, at least one $R^X$ is

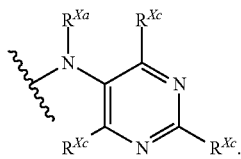

In certain embodiments, at least one $R^X$ is

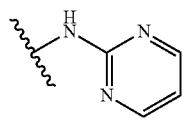

In certain embodiments, at least one $R^X$ is

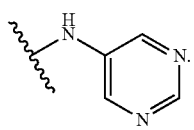

In certain embodiments, at least one $R^X$ is

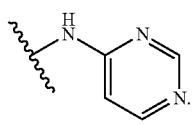 [SMILES: *Nc1ccncn1]

In certain embodiments, at least one $R^X$ is

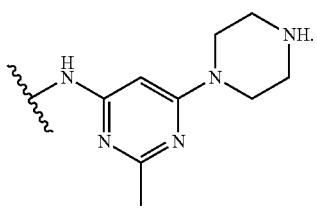 [SMILES: *Nc1cc(N2CCNCC2)nc(C)n1]

In certain embodiments, at least one $R^X$ is

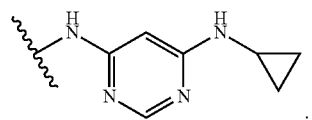 [SMILES: *Nc1cc(NC2CC2)ncn1]

In certain embodiments, at least one $R^X$ is

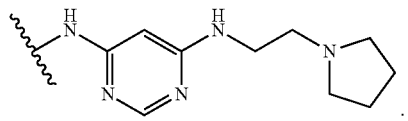 [SMILES: *Nc1cc(NCCN2CCCC2)ncn1]

In certain embodiments, at least one $R^X$ is

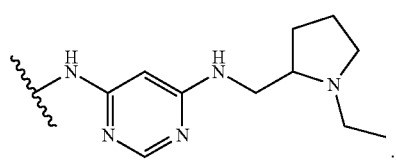 [SMILES: *Nc1cc(NCC2CCCN2CC)ncn1]

In certain embodiments, at least one $R^X$ is

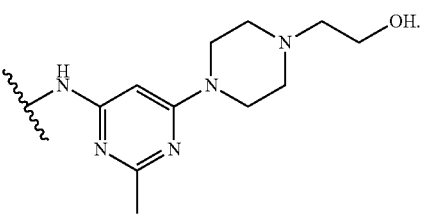 [SMILES: *Nc1cc(N2CCN(CCO)CC2)nc(C)n1]

In certain embodiments, at least one $R^X$ is

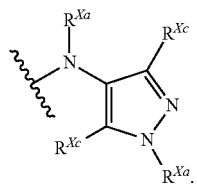

In certain embodiments, at least one $R^X$ is

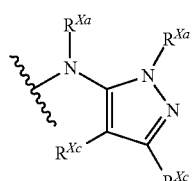

In certain embodiments, at least one $R^X$ is

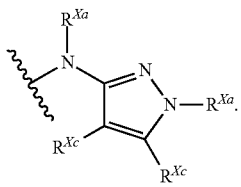

In certain embodiments, at least one $R^X$ is

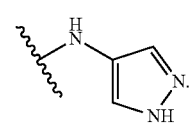 [SMILES: *Nc1cn[nH]c1]

In certain embodiments, at least one $R^X$ is

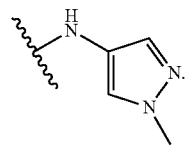 [SMILES: *Nc1cnn(C)c1]

In certain embodiments, at least one $R^X$ is

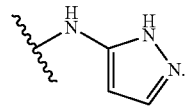

In certain embodiments, at least one $R^X$ is

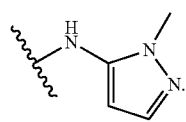 [SMILES: *Nc1ccnn1C]

In certain embodiments, at least one $R^X$ is

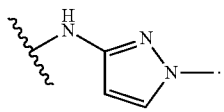 [SMILES: *Nc1ccn(C)n1]

In certain embodiments, at least one $R^X$ is

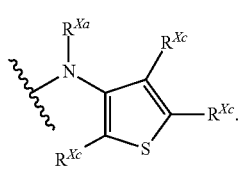

In certain embodiments, at least one $R^X$ is

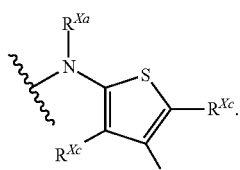

In certain embodiments, at least one $R^X$ is

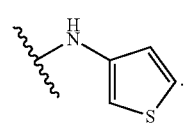 [SMILES: *Nc1ccsc1]

In certain embodiments, at least one $R^X$ is

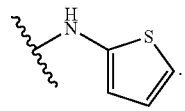 [SMILES: *Nc1cccs1]

In certain embodiments, at least one $R^X$ is

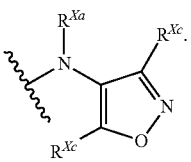

In certain embodiments, at least one $R^X$ is

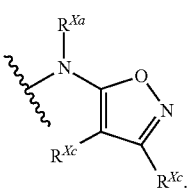

In certain embodiments, at least one $R^X$ is

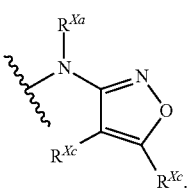

In certain embodiments, at least one $R^X$ is

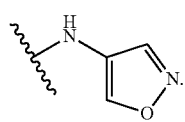 [SMILES: *Nc1cnoc1]

In certain embodiments, at least one $R^X$ is

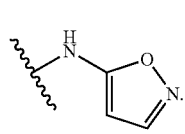 [SMILES: *Nc1ccno1]

In certain embodiments, at least one $R^X$ is

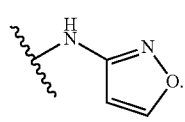

In certain embodiments, at least one $R^X$ is

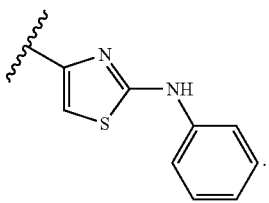 [SMILES: *c1csc(Nc2ccccc2)n1]

In certain embodiments, at least one $R^X$ is

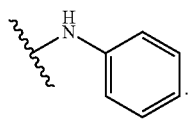

In certain embodiments, at least one $R^X$ is

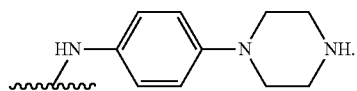

In certain embodiments, at least one $R^X$ is

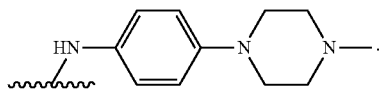

In certain embodiments, at least one $R^X$ is

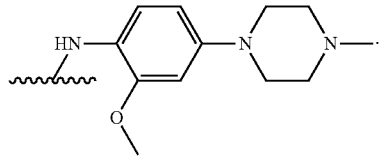

In certain embodiments, at least one $R^X$ is

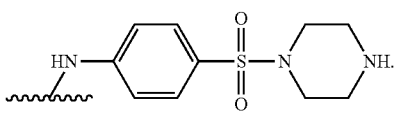

In certain embodiments, at least one $R^X$ is —N($R^{41}$)N($R^{41}$)$_2$. In certain embodiments, at least one $R^X$ is —NHN($R^{41}$)$_2$. In certain embodiments, at least one $R^X$ is —NHNH(acyl). In certain embodiments, at least one $R^X$ is —NHNHC(=O)Me. In certain embodiments, at least one $R^X$ is —NHN($C_{1-6}$alkyl)$_2$ where the alkyl is substituted or unsubstituted. In certain embodiments, at least one $R^X$ is —NHNMe$_2$.

In compounds of Formula (A), $R^X$ may be substituted with one or more $R^{Xa}$ groups. Each instance of $R^{Xa}$ is selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)$R^{41}$, —C(=O)O$R^{41}$, —C(=O)N($R^{41}$)$_2$, —S(=O)$R^{41}$, —S(=O)N($R^{41}$)$_2$, —S(=O)$_2R^{41}$S(=O)$_2$O$R^{4}$, —S(=O)$_2R^{41}$, —S(=O)$_2$N($R^{41}$)$_2$, —N($R^{41}$)$_2$, and a nitrogen protecting group; wherein each occurrence of $R^{41}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two $R^{41}$ groups are joined to form an optionally substituted heterocyclic ring.

In certain embodiments, at least one $R^{Xa}$ is H. In certain embodiments, all $R^{Xa}$ groups are H. In certain embodiments, at least one $R^{Xa}$ is substituted alkyl. In certain embodiments, at least one $R^{Xa}$ is substituted $C_{1-6}$ alkyl. In certain embodiments, at least one $R^{Xa}$ is substituted methyl. In certain embodiments, at least one $R^{Xa}$ is unsubstituted alkyl. In certain embodiments, at least one $R^{Xa}$ is unsubstituted $C_{1-6}$ alkyl. In certain embodiments, at least one $R^{Xa}$ is methyl. In certain embodiments, at least one $R^{Xa}$ is ethyl. In certain embodiments, at least one $R^{Xa}$ is propyl. In certain embodiments, at least one $R^{Xa}$ is butyl. In certain embodiments, at least one $R^{Xa}$ is substituted alkenyl. In certain embodiments, at least one $R^{Xa}$ is unsubstituted alkenyl. In certain embodiments, at least one $R^{Xa}$ is substituted alkynyl. In certain embodiments, at least one $R^{Xa}$ is unsubstituted alkynyl. In certain embodiments, at least one $R^{Xa}$ is substituted carbocyclyl. In certain embodiments, at least one $R^{Xa}$ is unsubstituted carbocyclyl. In certain embodiments, at least one $R^{Xa}$ is substituted heterocyclyl. In certain embodiments, at least one $R^{Xa}$ is unsubstituted heterocyclyl. In certain embodiments, at least one $R^{Xa}$ is substituted aryl. In certain embodiments, at least one $R^{Xa}$ is unsubstituted aryl. In certain embodiments, at least one $R^{Xa}$ is substituted phenyl. In certain embodiments, at least one $R^{Xa}$ is unsubstituted phenyl. In certain embodiments, at least one $R^{Xa}$ is substituted heteroaryl. In certain embodiments, at least one $R^{Xa}$ is unsubstituted heteroaryl. In certain embodiments, at least one $R^{Xa}$ is —C(=O)$R^{41}$. In certain embodiments, at least one $R^{Xa}$ is —C(=O)H. In certain embodiments, at least one $R^{Xa}$ is acetyl. In certain embodiments, at least one $R^{Xa}$ is —C(=O)($C_{1-6}$alkyl). In certain embodiments, at least one $R^{Xa}$ is —C(=O)O$R^{41}$. In certain embodiments, at least one $R^{Xa}$ is —C(=O)OH. In certain embodiments, at least one $R^{Xa}$ is —C(=O)O($C_{1-6}$alkyl). In certain embodiments, at least one $R^{Xa}$ is —C(=O)N($R^{41}$)$_2$. In certain embodiments, at least one $R^{Xa}$ is —C(=O)NH$R^{41}$. In certain embodiments, at least one $R^{Xa}$ is —C(=O)N($C_{1-6}$ alkyl)$_2$. In certain embodiments, at least one $R^{Xa}$ is —C(=O)NH($C_{1-6}$ alkyl). In certain embodiments, at least one $R^{Xa}$ is —C(=O)NH$_2$. In certain embodiments, at least one $R^{Xa}$ is —S(=O)$R^{41}$. In certain embodiments, at least one $R^{Xa}$ is —S(=O)($C_{1-6}$ alkyl). In certain embodiments, at least one $R^{Xa}$ is —S(=O)N($R^{41}$)$_2$. In certain embodiments, at least one $R^{Xa}$ is —S(=O)NH($R^{41}$). In certain embodiments, at least one $R^{Xa}$ is —S(=O)NH$_2$. In certain embodiments, at least one $R^{Xa}$ is —S(=O)N($C_{1-6}$alkyl)$_2$. In certain embodiments, at least one $R^{Xa}$ is —S(=O)NH($C_{1-6}$alkyl). In certain embodiments, at least one $R^{Xa}$ is —S(=O)$_2R^{41}$. In certain embodiments, at least one $R^{Xa}$ is —S(=O)$_2$($C_{1-6}$alkyl). In certain embodiments, at least one $R^{Xa}$ is —S(=O)$_2$O$R^{41}$. In certain embodiments, at least one $R^{Xa}$ is —S(=O)$_2$OH. In certain embodiments, at least one $R^{Xa}$ is —S(=O)$_2$N($R^{41}$)$_2$. In certain embodiments, at least one $R^{Xa}$ is —S(=O)$_2$NH ($R^{A1}$). In certain embodiments, at least one $R^{Xa}$ is —S(=O)$_2$NH$_2$. In certain embodiments, at least one $R^{Xa}$ is —S(=O)$_2$N(C$_{1-6}$alkyl)$_2$. In certain embodiments, at least one $R^{Xa}$ is —S(=O)$_2$NH(C$_{1-6}$alkyl). In certain embodiments, at least one $R^{Xa}$ is —N(R$^{A1}$)$_2$. In certain embodiments, at least one $R^{Xa}$ is —NH(R$^{A1}$). In certain embodiments, at least one $R^{Xa}$ is —NH(acyl). In certain embodiments, at least one $R^{Xa}$ is —NHC(=O)Me. In certain embodiments, at least one $R^{Xa}$ is —N(C$_{1-6}$alkyl)$_2$ where the alkyl is substituted or unsubstituted. In certain embodiments, at least one $R^{Xa}$ is —NMe$_2$.

In compounds of Formula (A), $R^X$ may be substituted with one or more $R^{Xc}$ groups. Each instance of $R^{Xc}$ is selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{A1}$, —N(R$^{A1}$)$_2$, —SR$^{A1}$, —CN, —C(=O)R$^{A1}$, —C(=O)OR$^{A1}$, —C(=O)N(R$^{A1}$)$_2$, —NO$_2$, —N$_3$, —NR$^{A1}$C(=O)R$^{A1}$, —NR$^{A1}$C(=O)OR$^{A1}$, —NR$^{A1}$C(=O)N(R$^{A1}$)$_2$, —NR$^{A1}$S(=O)$_2$R$^{A1}$, —NR$^{A1}$S(=O)R$^{A1}$, —OC(=O)R$^{A1}$, —OC(=O)OR$^{A1}$, —OC(=O)N(R$^{A1}$)$_2$, —S(=O)R$^{A1}$, —S(=O)N(R$^{A1}$)$_2$, —S(=O)$_2$R$^{A1}$, —S(=O)$_2$N(R$^{A1}$)$_2$; wherein each occurrence of $R^{A1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two $R^{A1}$ groups are joined to form an optionally substituted heterocyclic ring.

In certain embodiments, at least one $R^{Xc}$ is H. In certain embodiments, all $R^{Xc}$ groups are H. In certain embodiments, at least one $R^{Xc}$ is substituted alkyl. In certain embodiments, at least one $R^{Xc}$ is substituted C$_{1-6}$ alkyl. In certain embodiments, at least one $R^{Xc}$ is substituted methyl. In certain embodiments, at least one $R^{Xc}$ is unsubstituted alkyl. In certain embodiments, at least one $R^{Xc}$ is unsubstituted C$_{1-6}$ alkyl. In certain embodiments, at least one $R^{Xc}$ is methyl. In certain embodiments, at least one $R^{Xc}$ is ethyl. In certain embodiments, at least one $R^{Xc}$ is propyl. In certain embodiments, at least one $R^{Xc}$ is butyl. In certain embodiments, at least one $R^{Xc}$ is substituted alkenyl. In certain embodiments, at least one $R^{Xc}$ is unsubstituted alkenyl. In certain embodiments, at least one $R^{Xc}$ is substituted alkynyl. In certain embodiments, at least one $R^{Xc}$ is unsubstituted alkynyl. In certain embodiments, at least one $R^{Xc}$ is substituted carbocyclyl. In certain embodiments, at least one $R^{Xc}$ is unsubstituted carbocyclyl. In certain embodiments, at least one $R^{Xc}$ is substituted heterocyclyl. In certain embodiments, at least one $R^{Xc}$ is unsubstituted heterocyclyl. In certain embodiments, at least one $R^{Xc}$ is substituted aryl. In certain embodiments, at least one $R^{Xc}$ is unsubstituted aryl. In certain embodiments, at least one $R^{Xc}$ is substituted phenyl. In certain embodiments, at least one $R^{Xc}$ is unsubstituted phenyl. In certain embodiments, at least one $R^{Xc}$ is substituted heteroaryl. In certain embodiments, at least one $R^{Xc}$ is unsubstituted heteroaryl. In certain embodiments, at least one $R^{Xc}$ is —OR$^{A1}$. In certain embodiments, at least one $R^{Xc}$ is —OH. In certain embodiments, at least one $R^{Xc}$ is —O(C$_{1-6}$alkyl). In certain embodiments, at least one $R^{Xc}$ is —N(R$^{A1}$)$_2$. In certain embodiments, at least one $R^{Xc}$ is —NH(R$^{A1}$). In certain embodiments, at least one $R^{Xc}$ is —N(C$_{1-6}$alkyl)$_2$. In certain embodiments, at least one $R^{Xc}$ is —NH(C$_{1-6}$alkyl). In certain embodiments, at least one $R^{Xc}$ is —NH$_2$. In certain embodiments, at least one $R^{Xc}$ is —SR$^{A1}$. In certain embodiments, at least one $R^{Xc}$ is —SH. In certain embodiments, at least one $R^{Xc}$ is —S(C$_{1-6}$alkyl). In certain embodiments, at least one $R^{Xc}$ is —CN. In certain embodiments, at least one $R^{Xc}$ is —NO$_2$. In certain embodiments, at least one $R^{Xc}$ is —N$_3$. In certain embodiments, at least one $R^{Xc}$ is —NR$^{A1}$C(=O)R$^{A1}$. In certain embodiments, at least one $R^{Xc}$ is —NHC(=O)R$^{A1}$. In certain embodiments, at least one $R^{Xc}$ is —NHC(=O)(C$_{1-6}$alkyl). In certain embodiments, at least one $R^{Xc}$ is —NR$^{A1}$C(=O)OR$^{A1}$. In certain embodiments, at least one $R^{Xc}$ is —NHC(=O)OR$^{A1}$. In certain embodiments, at least one $R^{Xc}$ is —NR$^{A1}$C(=O)O(C$_{1-6}$alkyl). In certain embodiments, at least one $R^{Xc}$ is —NR$^{A1}$C(=O)N(R$^{A1}$)$_2$. In certain embodiments, at least one $R^{Xc}$ is —NHC(=O)N(C$_{1-6}$alkyl)$_2$. In certain embodiments, at least one $R^{Xc}$ is —NHC(=O)NH$_2$. In certain embodiments, at least one $R^{Xc}$ is —NR$^{A1}$S(=O)$_2$R$^{A1}$. In certain embodiments, at least one $R^{Xc}$ is —NHS(=O)$_2$R$^{A1}$. In certain embodiments, at least one $R^{Xc}$ is —NHS(=O)$_2$(C$_{1-6}$alkyl). In certain embodiments, at least one $R^{Xc}$ is —NR$^{A1}$S(=O)R$^{A1}$. In certain embodiments, at least one $R^{Xc}$ is —NR$^{A1}$S(=O)(C$_{1-6}$alkyl). In certain embodiments, at least one $R^{Xc}$ is —NHS(=O)(C$_{1-6}$alkyl). In certain embodiments, at least one $R^{Xc}$ is —OC(=O)R$^{A1}$. In certain embodiments, at least one $R^{Xc}$ is —OC(=O)(C$_{1-6}$alkyl). In certain embodiments, at least one $R^{Xc}$ is —OC(=O)OR$^{A1}$ In certain embodiments, at least one $R^{Xc}$ is —OC(=O)O(C$_{1-6}$alkyl). In certain embodiments, at least one $R^{Xc}$ is —OC(=O)N(R$^{A1}$)$_2$. In certain embodiments, at least one $R^{Xc}$ is —OC(=O)NH(R$^{A1}$). In certain embodiments, at least one $R^{Xc}$ is —OC(=O)N(C$_{1-6}$alkyl)$_2$. In certain embodiments, at least one $R^{Xc}$ is —C(=O)R$^{A1}$. In certain embodiments, at least one $R^{Xc}$ is —C(=O)H. In certain embodiments, at least one $R^{Xc}$ is acetyl. In certain embodiments, at least one $R^{Xc}$ is —C(=O)(C$_{1-6}$alkyl). In certain embodiments, at least one $R^{Xc}$ is —C(=O)OR$^{A1}$ In certain embodiments, at least one $R^{Xc}$ is —C(=O)OH. In certain embodiments, at least one $R^{Xc}$ is —C(=O)O(C$_{1-6}$alkyl). In certain embodiments, at least one $R^{Xc}$ is —C(=O)N(R$^{A1}$)$_2$. In certain embodiments, at least one $R^{Xc}$ is —C(=O)NHR$^{A1}$. In certain embodiments, at least one $R^{Xc}$ is —C(=O)N(C$_{1-6}$ alkyl)$_2$. In certain embodiments, at least one $R^{Xc}$ is —C(=O)NH(C$_{1-6}$ alkyl). In certain embodiments, at least one $R^{Xc}$ is —C(=O)NH$_2$. In certain embodiments, at least one $R^{Xc}$ is —S(=O)R$^{A1}$. In certain embodiments, at least one $R^{Xc}$ is —S(=O)(C$_{1-6}$alkyl). In certain embodiments, at least one $R^{Xc}$ is —S(=O)N(R$^{A1}$)$_2$. In certain embodiments, at least one $R^{Xc}$ is —S(=O)NH(R$^{A1}$). In certain embodiments, at least one $R^{Xc}$ is —S(=O)NH$_2$. In certain embodiments, at least one $R^{Xc}$ is —S(=O)N(C$_{1-6}$alkyl)$_2$. In certain embodiments, at least one $R^{Xc}$ is —S(=O)NH(C$_{1-6}$alkyl). In certain embodiments, at least one $R^{Xc}$ is —S(=O)$_2$R$^{A1}$. In certain embodiments, at least one $R^{Xc}$ is —S(=O)$_2$(C$_{1-6}$alkyl). In certain embodiments, at least one $R^{Xc}$ is —S(=O)$_2$OR$^{A1}$. In certain embodiments, at least one $R^{Xc}$ is —S(=O)$_2$OH. In certain embodiments, at least one $R^{Xc}$ is —S(=O)$_2$N(R$^{A1}$)$_2$. In certain embodiments, at least one $R^{Xc}$ is —S(=O)$_2$NH(R$^{A1}$). In certain embodiments, at least one $R^{Xc}$ is —S(=O)$_2$NH$_2$. In certain embodiments, at least one $R^{Xc}$ is —S(=O)$_2$N(C$_{1-6}$alkyl)$_2$. In certain embodiments, at least one $R^{Xc}$ is —S(=O)$_2$NH(C$_{1-6}$alkyl).

In compounds of Formula (A), $R^D$ is an optional electrophilic moiety that is attached to the pyridyl ring. In certain embodiments, $R^D$ is any one of Formulae (i-1)-(i-18):

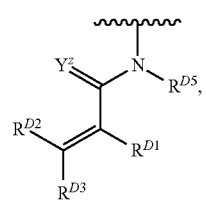 (i-1)
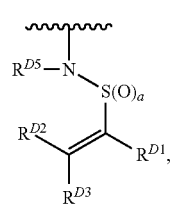 (i-2)
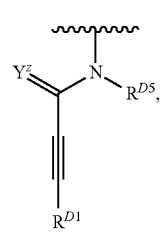 (i-3)
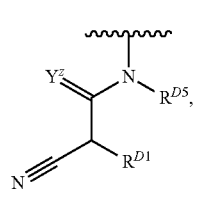 (i-4)
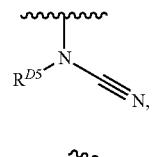 (i-5)
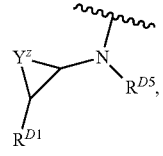 (i-6)
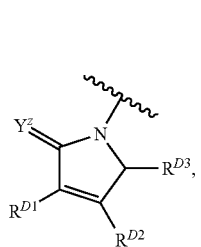 (i-7)
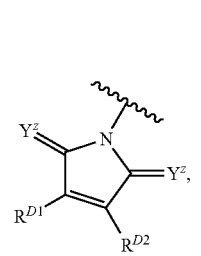 (i-8)
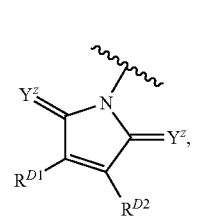 (i-9)
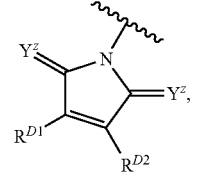 (i-10)
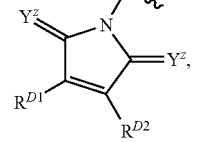 (i-11)
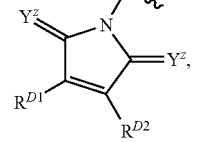 (i-12)
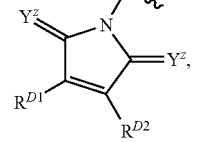 (i-13)
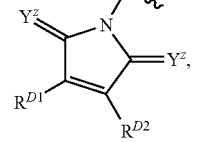 (i-14)
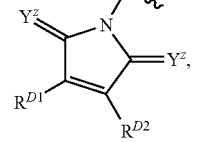 (i-15)
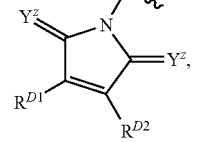 (i-16)

-continued

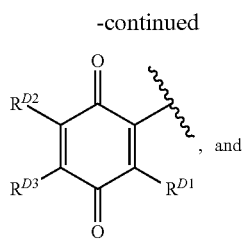
(i-17)

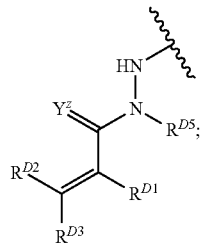
(i-18)

$R^{D1}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —NO$_2$, —OR$^{D1a}$, —N(R$^{D1a}$)$_2$, —SR$^{D1a}$, —CH$_2$OR$^{D1a}$, —CH$_2$N(R$^{D1a}$)$_2$, —CH$_2$SR$^{D1a}$, —C(=O)R$^{D1a}$, —C(=O)OR$^{D1a}$, —C(=O)SR$^{D1a}$, —C(=O)N(R$^{D1a}$)$_2$, —C(=S)R$^{D1a}$, —C(=S)OR$^{D1a}$, —C(=S)SR$^{D1a}$, —C(=S)N(R$^{D1a}$)$_2$, —C(=NR$^{D1a}$)R$^{D1a}$, —C(=NR$^{D1a}$)OR$^{D1a}$, —C(=NR$^{D1a}$)SR$^{D1a}$, and —C(=NR$^{D1a}$)N(R$^{D1a}$)$_2$ wherein each occurrence of R$^{D1a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{D1a}$ groups are joined to form an optionally substituted heterocyclic ring;

$R^{D2}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —NO$_2$, —OR$^{D2a}$, —N(R$^{D2a}$)$_2$, —SR$^{D2a}$, —CH$_2$OR$^{D2a}$, —CH$_2$N(R$^{D2a}$)$_2$, —CH$_2$SR$^{D2a}$, —C(=O)R$^{D2a}$, —C(=O)OR$^{D2a}$, —C(=O)SR$^{D2a}$, —C(=O)N(R$^{D2a}$)$_2$, —C(=S)R$^{D2a}$, —C(=S)OR$^{D2a}$, —C(=S)SR$^{D2a}$, —C(=S)N(R$^{D2a}$)$_2$, —C(=NR$^{D2a}$)R$^{D2a}$, —C(=NR$^{D2a}$)OR$^{D2a}$, —C(=NR$^{D2a}$)SR$^{D2a}$, and —C(=NR$^{D2a}$)N(R$^{D2a}$)$_2$, wherein each occurrence of R$^{D2a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{D2a}$ groups are joined to form an optionally substituted heterocyclic ring;

$R^{D3}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —NO$_2$, —OR$^{D3a}$, —N(R$^{D3a}$)$_2$, —SR$^{D3a}$, —CH$_2$OR$^{D3a}$, —CH$_2$N(R$^{D3a}$)$_2$, —CH$_2$SR$^{D3a}$, —C(=O)R$^{D3a}$, —C(=O)OR$^{D3a}$, —C(=O)SR$^{D3a}$, —C(=O)N(R$^{D3a}$)$_2$, —C(=S)R$^{D3a}$, —C(=S)OR$^{D3a}$, —C(=S)SR$^{D3a}$, —C(=S)N(R$^{D3a}$)$_2$, —C(=NR$^{D3a}$)R$^{D3a}$, —C(=NR$^{D3a}$)OR$^{D3a}$, —C(=NR$^{D3a}$)SR$^{D3a}$, and —C(=NR$^{D3a}$)N(R$^{D3a}$)$_2$, wherein each occurrence of R$^{D3a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{D3a}$ groups are joined to form an optionally substituted heterocyclic ring;

optionally R$^{D1}$ and R$^{D3}$, or R$^{D2}$ and R$^{D3}$, or R$^{D1}$ and R$^{D2}$ are joined to form an optionally substituted carbocyclic or optionally substituted heterocyclic ring;

R$^{D4}$ is a leaving group;

R$^{D5}$ is hydrogen, C$_{1-6}$ alkyl, or a nitrogen protecting group;

Y$^Z$ is —O—, —S—, or —NR$^{D6}$—, wherein R$^{D6}$ is hydrogen, C$_{1-6}$ alkyl, or a nitrogen protecting group;

a is 1 or 2;

z is 0, 1, 2, 3, 4, 5, or 6; and optionally R$^{D5}$ and one R$^C$ are joined to form an optionally substituted heterocyclic ring.

In certain embodiments, R$^D$ comprises a Michael acceptor moiety. This Michael acceptor moiety may react with a cysteine or other nucleophilic residue to allow covalent attachment of the compound to the target. In certain embodiments, the covalent attachment is irreversible. In other embodiments, the covalent attachment is reversible. In certain embodiments, R$^D$ is of Formula (i-1). In certain embodiments, R$^D$ is of Formula (i-2). In certain embodiments, R$^D$ is of Formula (i-3). In certain embodiments, R$^D$ is of Formula (i-4). In certain embodiments, R$^D$ is of Formula (i-5). In certain embodiments, R$^D$ is of Formula (i-6). In certain embodiments, R$^D$ is of Formula (i-7). In certain embodiments, R$^D$ is of Formula (i-8). In certain embodiments, R$^D$ is of Formula (i-9). In certain embodiments, R$^D$ is of Formula (i-10). In certain embodiments, R$^D$ is of Formula (i-11). In certain embodiments, R$^D$ is of Formula (i-12). In certain embodiments, R$^D$ is of Formula (i-13). In certain embodiments, R$^D$ is of Formula (i-14). In certain embodiments, R$^D$ is of Formula (i-15). In certain embodiments, R$^D$ is of Formula (i-16). In certain embodiments, R$^D$ is of Formula (i-17).

In compounds of Formula (A), R$^D$ may include a substituent R$^{D1}$. In certain embodiments, R$^{D1}$ is H. In certain embodiments, R$^{D1}$ is halogen. In certain embodiments, R$^{D1}$ is F. In certain embodiments, R$^{D1}$ is Cl. In certain embodiments, R$^{D1}$ is Br. In certain embodiments, R$^{D1}$ is I (iodine). In certain embodiments, R$^{D1}$ is substituted acyl. In certain embodiments, R$^{D1}$ is unsubstituted acyl. In certain embodiments, R$^{D1}$ is acetyl. In certain embodiments, R$^{D1}$ is substituted alkyl. In certain embodiments, R$^{D1}$ is unsubstituted alkyl. In certain embodiments, R$^{D1}$ is C$_{1-6}$ alkyl. In certain embodiments, R$^{D1}$ is methyl. In certain embodiments, R$^{D1}$ is ethyl. In certain embodiments, R$^{D1}$ is propyl. In certain embodiments, R$^{D1}$ is butyl. In certain embodiments, R$^{D1}$ is substituted alkenyl. In certain embodiments, R$^{D1}$ is unsubstituted alkenyl. In certain embodiments, R$^{D1}$ is substituted alkynyl. In certain embodiments, R$^{D1}$ is unsubstituted alkynyl. In certain embodiments, R$^{D1}$ is substituted carbocyclyl. In certain embodiments, R$^{D1}$ is unsubstituted carbocyclyl. In certain embodiments, R$^{D1}$ is substituted heterocyclyl. In certain embodiments, R$^{D1}$ is unsubstituted heterocyclyl. In certain embodiments, R$^{D1}$ is substituted aryl. In certain embodiments, R$^{D1}$ is unsubstituted aryl. In certain embodiments, R$^{D1}$ is substituted phenyl. In certain embodiments, $R^{D1}$ is unsubstituted phenyl. In certain embodiments, $R^{D1}$ is substituted heteroaryl. In certain embodiments, $R^{D1}$ is unsubstituted heteroaryl. In certain embodiments, $R^{D1}$ is substituted pyridyl. In certain embodiments, $R^{D1}$ is unsubstituted pyridyl. In certain embodiments, $R^{D1}$ is —CN. In certain embodiments, $R^{D1}$ is —NO$_2$. In certain embodiments, $R^{D1}$ is —OR$^{D1a}$. In certain embodiments, $R^{D1}$ is —N(R$^{D1a}$)$_2$. In certain embodiments, $R^{D1}$ is —SR$^{D1a}$. In certain embodiments, $R^{D1}$ is —CH$_2$OR$^{D1a}$. In certain embodiments, $R^{D1}$ is —CH$_2$N(R$^{D1a}$)$_2$. In certain embodiments, $R^{D1}$ is —CH$_2$SR$^{D1a}$.

In certain embodiments, at least one $R^{D1a}$ is H. In certain embodiments, at least one $R^{D1a}$ is substituted acyl. In certain embodiments, at least one $R^{D1a}$ is unsubstituted acyl. In certain embodiments, at least one $R^{D1a}$ is acetyl. In certain embodiments, at least one $R^{D1a}$ is substituted alkyl. In certain embodiments, at least one $R^{D1a}$ is unsubstituted alkyl. In certain embodiments, at least one $R^{D1a}$ is $C_{1-6}$ alkyl. In certain embodiments, at least one $R^{D1a}$ is methyl. In certain embodiments, at least one $R^{D1a}$ is ethyl. In certain embodiments, at least one $R^{D1a}$ is propyl. In certain embodiments, at least one $R^{D1a}$ is butyl. In certain embodiments, at least one $R^{D1a}$ is substituted alkenyl. In certain embodiments, at least one $R^{D1a}$ is unsubstituted alkenyl. In certain embodiments, at least one $R^{D1a}$ is substituted alkynyl. In certain embodiments, at least one $R^{D1a}$ is unsubstituted alkynyl. In certain embodiments, at least one $R^{D1a}$ is substituted carbocyclyl. In certain embodiments, at least one $R^{D1a}$ is unsubstituted carbocyclyl. In certain embodiments, at least one $R^{D1a}$ is substituted heterocyclyl. In certain embodiments, at least one $R^{D1a}$ is unsubstituted heterocyclyl. In certain embodiments, at least one $R^{D1a}$ is substituted aryl. In certain embodiments, at least one $R^{D1a}$ is unsubstituted aryl. In certain embodiments, at least one $R^{D1a}$ is substituted phenyl. In certain embodiments, at least one $R^{D1a}$ is unsubstituted phenyl. In certain embodiments, at least one $R^{D1a}$ is substituted heteroaryl. In certain embodiments, at least one $R^{D1a}$ is unsubstituted heteroaryl. In certain embodiments, at least one $R^{D1a}$ is substituted pyridyl. In certain embodiments, at least one $R^{D1a}$ is unsubstituted pyridyl. In certain embodiments, at least one $R^{D1a}$ is a nitrogen protecting group when attached to a nitrogen atom. In certain embodiments, at least one $R^{D1a}$ is Bn, BOC, Cbz, Fmoc, trifluoroacetyl, triphenylmethyl, or Ts when attached to a nitrogen atom. In certain embodiments, $R^{D1a}$ is an oxygen protecting group when attached to an oxygen atom. In certain embodiments, $R^{D1a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{D1a}$ is a sulfur protecting group when attached to a sulfur atom. In certain embodiments, $R^{D1a}$ is acetamidomethyl, t-Bu, 3-nitro-2-pyridine sulfenyl, 2-pyridine-sulfenyl, or triphenylmethyl when attached to a sulfur atom. In certain embodiments, two $R^{D1a}$ groups are joined to form a substituted heterocyclic ring. In certain embodiments, two $R^{D1a}$ groups are joined to form an unsubstituted heterocyclic ring.

In compounds of Formula (A), $R^D$ may include a substituent $R^{D2}$. In certain embodiments, $R^{D2}$ is H. In certain embodiments, $R^{D2}$ is halogen. In certain embodiments, $R^{D2}$ is F. In certain embodiments, $R^{D2}$ is Cl. In certain embodiments, $R^{D2}$ is Br. In certain embodiments, $R^{D2}$ is I (iodine). In certain embodiments, $R^{D2}$ is substituted acyl. In certain embodiments, $R^{D2}$ is unsubstituted acyl. In certain embodiments, $R^{D2}$ is acetyl. In certain embodiments, $R^{D2}$ is substituted alkyl. In certain embodiments, $R^{D2}$ is unsubstituted alkyl. In certain embodiments, $R^{D2}$ is $C_{1-6}$ alkyl. In certain embodiments, $R^{D2}$ is methyl. In certain embodiments, $R^{D2}$ is ethyl. In certain embodiments, $R^{D2}$ is propyl. In certain embodiments, $R^{D2}$ is butyl. In certain embodiments, $R^{D2}$ is substituted alkenyl. In certain embodiments, $R^{D2}$ is unsubstituted alkenyl. In certain embodiments, $R^{D2}$ is substituted alkynyl. In certain embodiments, $R^{D2}$ is unsubstituted alkynyl. In certain embodiments, $R^{D2}$ is substituted carbocyclyl. In certain embodiments, $R^{D2}$ is unsubstituted carbocyclyl. In certain embodiments, $R^{D2}$ is substituted heterocyclyl. In certain embodiments, $R^{D2}$ is unsubstituted heterocyclyl. In certain embodiments, $R^{D2}$ is substituted aryl. In certain embodiments, $R^{D2}$ is unsubstituted aryl. In certain embodiments, $R^{D2}$ is substituted phenyl. In certain embodiments, $R^{D2}$ is unsubstituted phenyl. In certain embodiments, $R^{D2}$ is substituted heteroaryl. In certain embodiments, $R^{D2}$ is unsubstituted heteroaryl. In certain embodiments, $R^{D2}$ is substituted pyridyl. In certain embodiments, $R^{D2}$ is unsubstituted pyridyl. In certain embodiments, $R^{D2}$ is —CN. In certain embodiments, $R^{D2}$ is —NO$_2$. In certain embodiments, $R^{D2}$ is —OR$^{D2a}$. In certain embodiments, $R^{D2}$ is —N(R$^{D2a}$)$_2$. In certain embodiments, $R^{D2}$ is —SR$^{D2a}$. In certain embodiments, $R^{D2}$ is —CH$_2$OR$^{D2a}$. In certain embodiments, $R^{D2}$ is —CH$_2$N(R$^{D2a}$)$_2$. In certain embodiments, $R^{D2}$ is —CH$_2$SR$^{D2a}$.

In certain embodiments, at least one $R^{D2a}$ is H. In certain embodiments, at least one $R^{D2a}$ is substituted acyl. In certain embodiments, at least one $R^{D2a}$ is unsubstituted acyl. In certain embodiments, at least one $R^{D2a}$ is acetyl. In certain embodiments, at least one $R^{D2a}$ is substituted alkyl. In certain embodiments, at least one $R^{D2a}$ is unsubstituted alkyl. In certain embodiments, at least one $R^{D2a}$ is $C_{1-6}$ alkyl. In certain embodiments, at least one $R^{D2a}$ is methyl. In certain embodiments, at least one $R^{D2a}$ is ethyl. In certain embodiments, at least one $R^{D2a}$ is propyl. In certain embodiments, at least one $R^{D2a}$ is butyl. In certain embodiments, at least one $R^{D2a}$ is substituted alkenyl. In certain embodiments, at least one $R^{D2a}$ is unsubstituted alkenyl. In certain embodiments, at least one $R^{D2a}$ is substituted alkynyl. In certain embodiments, at least one $R^{D2a}$ is unsubstituted alkynyl. In certain embodiments, at least one $R^{D2a}$ is substituted carbocyclyl. In certain embodiments, at least one $R^{D2a}$ is unsubstituted carbocyclyl. In certain embodiments, at least one $R^{D2a}$ is substituted heterocyclyl. In certain embodiments, at least one $R^{D2a}$ is unsubstituted heterocyclyl. In certain embodiments, at least one $R^{D2a}$ is substituted aryl. In certain embodiments, at least one $R^{D2a}$ is unsubstituted aryl. In certain embodiments, at least one $R^{D2a}$ is substituted phenyl. In certain embodiments, at least one $R^{D2a}$ is unsubstituted phenyl. In certain embodiments, at least one $R^{D2a}$ is substituted heteroaryl. In certain embodiments, at least one $R^{D2a}$ is unsubstituted heteroaryl. In certain embodiments, at least one $R^{D2a}$ is substituted pyridyl. In certain embodiments, at least one $R^{D2a}$ is unsubstituted pyridyl. In certain embodiments, at least one $R^{D2a}$ is a nitrogen protecting group when attached to a nitrogen atom. In certain embodiments, at least one $R^{D2a}$ is Bn, BOC, Cbz, Fmoc, trifluoroacetyl, triphenylmethyl, or Ts when attached to a nitrogen atom. In certain embodiments, $R^{D2a}$ is an oxygen protecting group when attached to an oxygen atom. In certain embodiments, $R^{D2a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{D2a}$ is a sulfur protecting group when attached to a sulfur atom. In certain embodiments, $R^{D2a}$ is acetamidomethyl, t-Bu, 3-nitro-2-pyridine sulfenyl, 2-pyridine-sulfenyl, or triphenylmethyl when attached to a sulfur atom. In certain embodiments, two $R^{D2a}$ groups are joined to form a substituted heterocyclic ring. In certain embodiments, two $R^{D2a}$ groups are joined to form an unsubstituted heterocyclic ring.

In compounds of Formula (A), $R^D$ may include a substituent $R^{D3}$. In certain embodiments, $R^{D3}$ is H. In certain embodiments, $R^{D3}$ is halogen. In certain embodiments, $R^{D3}$ is F. In certain embodiments, $R^{D3}$ is Cl. In certain embodiments, $R^{D3}$ is Br. In certain embodiments, $R^{D3}$ is I (iodine). In certain embodiments, $R^{D3}$ is substituted acyl. In certain embodiments, $R^{D3}$ is unsubstituted acyl. In certain embodiments, $R^{D3}$ is acetyl. In certain embodiments, $R^{D3}$ is substituted alkyl. In certain embodiments, $R^{D3}$ is unsubstituted alkyl. In certain embodiments, $R^{D3}$ is $C_{1-6}$ alkyl. In certain embodiments, $R^{D3}$ is methyl. In certain embodiments, $R^{D3}$ is ethyl. In certain embodiments, $R^{D3}$ is propyl. In certain embodiments, $R^{D3}$ is butyl. In certain embodiments, $R^{D3}$ is substituted alkenyl. In certain embodiments, $R^{D3}$ is unsubstituted alkenyl. In certain embodiments, $R^{D3}$ is substituted alkynyl. In certain embodiments, $R^{D3}$ is unsubstituted alkynyl. In certain embodiments, $R^{D3}$ is substituted carbocyclyl. In certain embodiments, $R^{D3}$ is unsubstituted carbocyclyl. In certain embodiments, $R^{D3}$ is substituted heterocyclyl. In certain embodiments, $R^{D3}$ is unsubstituted heterocyclyl. In certain embodiments, $R^{D3}$ is substituted aryl. In certain embodiments, $R^{D3}$ is unsubstituted aryl. In certain embodiments, $R^{D3}$ is substituted phenyl. In certain embodiments, $R^{D3}$ is unsubstituted phenyl. In certain embodiments, $R^{D3}$ is substituted heteroaryl. In certain embodiments, $R^{D3}$ is unsubstituted heteroaryl. In certain embodiments, $R^{D3}$ is substituted pyridyl. In certain embodiments, $R^{D3}$ is unsubstituted pyridyl. In certain embodiments, $R^{D3}$ is —CN. In certain embodiments, $R^{D3}$ is —$NO_2$. In certain embodiments, $R^{D3}$ is —$OR^{D3a}$. In certain embodiments, $R^{D3}$ is —$N(R^{D3a})_2$. In certain embodiments, $R^{D3}$ is —$SR^{D3a}$. In certain embodiments, $R^{D3}$ is —$CH_2OR^{D3a}$. In certain embodiments, $R^{D3}$ is —$CH_2N(R^{D3a})_2$. In certain embodiments, $R^{D3}$ is —$CH_2SR^{D3a}$.

In certain embodiments, at least one $R^{D3a}$ is H. In certain embodiments, at least one $R^{D3a}$ is substituted acyl. In certain embodiments, at least one $R^{D3a}$ is unsubstituted acyl. In certain embodiments, at least one $R^{D3a}$ is acetyl. In certain embodiments, at least one $R^{D3a}$ is substituted alkyl. In certain embodiments, at least one $R^{D3a}$ is unsubstituted alkyl. In certain embodiments, at least one $R^{D3a}$ is $C_{1-6}$ alkyl. In certain embodiments, at least one $R^{D3a}$ is methyl. In certain embodiments, at least one $R^{D3a}$ is ethyl. In certain embodiments, at least one $R^{D3a}$ is propyl. In certain embodiments, at least one $R^{D3a}$ is butyl. In certain embodiments, at least one $R^{D3a}$ is substituted alkenyl. In certain embodiments, at least one $R^{D3a}$ is unsubstituted alkenyl. In certain embodiments, at least one $R^{D3a}$ is substituted alkynyl. In certain embodiments, at least one $R^{D3a}$ is unsubstituted alkynyl. In certain embodiments, at least one $R^{D3a}$ is substituted carbocyclyl. In certain embodiments, at least one $R^{D3a}$ is unsubstituted carbocyclyl. In certain embodiments, at least one $R^{D3a}$ is substituted heterocyclyl. In certain embodiments, at least one $R^{D3a}$ is unsubstituted heterocyclyl. In certain embodiments, at least one $R^{D3a}$ is substituted aryl. In certain embodiments, at least one $R^{D3a}$ is unsubstituted aryl. In certain embodiments, at least one $R^{D3a}$ is substituted phenyl. In certain embodiments, at least one $R^{D3a}$ is unsubstituted phenyl. In certain embodiments, at least one $R^{D3a}$ is substituted heteroaryl. In certain embodiments, at least one $R^{D3a}$ is unsubstituted heteroaryl. In certain embodiments, at least one $R^{D3a}$ is substituted pyridyl. In certain embodiments, at least one $R^{D3a}$ is unsubstituted pyridyl. In certain embodiments, at least one $R^{D3a}$ is a nitrogen protecting group when attached to a nitrogen atom. In certain embodiments, at least one $R^{D3a}$ is Bn, BOC, Cbz, Fmoc, trifluoroacetyl, triphenylmethyl, or Ts when attached to a nitrogen atom. In certain embodiments, $R^{D3a}$ is an oxygen protecting group when attached to an oxygen atom. In certain embodiments, $R^{D3a}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{D3a}$ is a sulfur protecting group when attached to a sulfur atom. In certain embodiments, $R^{D3a}$ is acetamidomethyl, t-Bu, 3-nitro-2-pyridine sulfenyl, 2-pyridine-sulfenyl, or triphenylmethyl when attached to a sulfur atom. In certain embodiments, two $R^{D3a}$ groups are joined to form a substituted heterocyclic ring. In certain embodiments, two $R^{D3a}$ groups are joined to form an unsubstituted heterocyclic ring.

In compounds of Formula (A), $R^D$ may include a substituent $R^{D4}$. In certain embodiments, $R^{D4}$ is a leaving group. In certain embodiments, $R^{D4}$ is halogen. In certain embodiments, $R^{D4}$ is F. In certain embodiments, $R^{D4}$ is Cl. In certain embodiments, $R^{D4}$ is Br. In certain embodiments, $R^{D4}$ is I (iodine). In certain embodiments, $R^{D4}$ is —$OS(=O)_w R^{D4a}$. In certain embodiments, w is 1. In certain embodiments, w is 2. In certain embodiments, $R^{D4}$ is —OMs. In certain embodiments, $R^{D4}$ is —OTf. In certain embodiments, $R^{D4}$ is —OTs. In certain embodiments, $R^{D4}$ is —OBs. In certain embodiments, $R^{D4}$ is 2-nitrobenzenesulfonyloxy. In certain embodiments, $R^{D4}$ is —$OR^{D4a}$. In certain embodiments, $R^{D4}$ is —OMe. In certain embodiments, $R^{D4}$ is —$OCF_3$. In certain embodiments, $R^{D4}$ is —OPh. In certain embodiments, $R^{D4}$ is —$OC(=O)R^{D4a}$. In certain embodiments, $R^{D4}$ is —$OC(=O)Me$. In certain embodiments, $R^{D4}$ is —$OC(=O)CF_3$. In certain embodiments, $R^{D4}$ is —$OC(=O)Ph$. In certain embodiments, $R^{D4}$ is —$OC(=O)Cl$. In certain embodiments, $R^{D4}$ is —$OC(=O)OR^{D4a}$. In certain embodiments, $R^{D4}$ is —$OC(=O)OMe$. In certain embodiments, $R^{D4}$ is —$OC(=O)O(t-Bu)$.

In certain embodiments, $R^{D4a}$ is substituted alkyl. In certain embodiments, $R^{D4a}$ is unsubstituted alkyl. In certain embodiments, $R^{D4a}$ is $C_{1-6}$ alkyl. In certain embodiments, $R^{D4a}$ is methyl. In certain embodiments, $R^{D4a}$ is ethyl. In certain embodiments, $R^{D4a}$ is propyl. In certain embodiments, $R^{D4a}$ is butyl. In certain embodiments, $R^{D4a}$ is substituted alkenyl. In certain embodiments, $R^{D4a}$ is unsubstituted alkenyl. In certain embodiments, $R^{D4a}$ is vinyl. In certain embodiments, $R^{D4a}$ is substituted alkynyl. In certain embodiments, $R^{D4a}$ is unsubstituted alkynyl. In certain embodiments, $R^{D4a}$ is ethynyl. In certain embodiments, $R^{D4a}$ is substituted carbocyclyl. In certain embodiments, $R^{D4a}$ is unsubstituted carbocyclyl. In certain embodiments, $R^{D4a}$ is substituted heterocyclyl. In certain embodiments, $R^{D4a}$ is unsubstituted heterocyclyl. In certain embodiments, $R^{D4a}$ is substituted aryl. In certain embodiments, $R^{D4a}$ is unsubstituted aryl. In certain embodiments, $R^{D4a}$ is substituted phenyl. In certain embodiments, $R^{D4a}$ is unsubstituted phenyl. In certain embodiments, $R^{D4a}$ is substituted heteroaryl. In certain embodiments, $R^{D4a}$ is unsubstituted heteroaryl. In certain embodiments, $R^{D4a}$ is substituted pyridyl. In certain embodiments, $R^{D4a}$ is unsubstituted pyridyl.

In compounds of Formula (A), $R^D$ may include a substituent $R^{D5}$. In certain embodiments, $R^{D5}$ is H. In certain embodiments, $R^{D5}$ is substituted alkyl. In certain embodiments, $R^{D5}$ is unsubstituted alkyl. In certain embodiments, $R^{D5}$ is $C_{1-6}$ alkyl. In certain embodiments, $R^{D5}$ is methyl. In certain embodiments, $R^{D5}$ is ethyl. In certain embodiments, $R^{D5}$ is propyl. In certain embodiments, $R^{D5}$ is butyl. In certain embodiments, $R^{D5}$ is a nitrogen protecting group. In certain embodiments, $R^{D5}$ is Bn, BOC, Cbz, Fmoc, trifluoroacetyl, triphenylmethyl, or Ts.

In certain embodiments, $R^{D1}$ and $R^{D2}$ are each hydrogen. In certain embodiments, $R^{D1}$ and $R^{D3}$ are each hydrogen. In certain embodiments, $R^{D2}$ and $R^{D3}$ are each hydrogen. In certain embodiments, $R^{D1}$, $R^{D2}$, and $R^{D3}$ are each hydrogen. In certain embodiments, $R^{D1}$, $R^{D2}$, and $R^{D3}$, and $R^{D5}$ are each hydrogen.

In certain embodiments, a is 1. In certain embodiments, a is 2.

In certain embodiments, z is 0. In certain embodiments, z is 1. In certain embodiments, z is 2. In certain embodiments, z is 3. In certain embodiments, z is 4. In certain embodiments, z is 5. In certain embodiments, z is 6.

In certain embodiments, Y is —O—. In certain embodiments, Y is —C(=O)—. In certain embodiments, Y is —S—. In certain embodiments, Y is —C(=S)—. In certain embodiments, Y is —NR$^{D6}$—, wherein $R^{D6}$ is hydrogen, $C_{1-6}$ alkyl, or a nitrogen protecting group. In certain embodiments, Y is —NH—. In certain embodiments, Y is —NCH$_3$—. In certain embodiments, Y is —N(BOC)—. In certain embodiments, Y is —N(Fmoc)-. In certain embodiments, Y is —N(Cbz)-. In certain embodiments, Y is —N(Bn)-. In certain embodiments, Y is —C(=NR$^{D6}$)—, wherein $R^{D6}$ is hydrogen, $C_{1-6}$ alkyl, or a nitrogen protecting group. In certain embodiments, Y is —C(=NH)—. In certain embodiments, Y is —C(=NCH$_3$)—. In certain embodiments, Y is —C(=NTs)-. In certain embodiments, Y is —C(=NBn)-. In certain embodiments, Y is —C(=NCH(Ph)$_2$)-.

In certain embodiments, $R^D$ is of the formula:

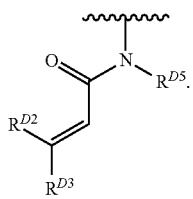

In certain embodiments, $R^D$ is of the formula:

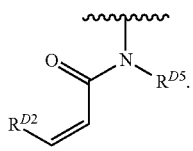

In certain embodiments, $R^D$ is of the formula:

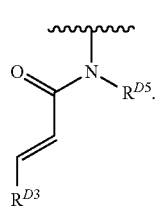

In certain embodiments, $R^D$ is of the formula:

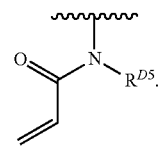

In certain embodiments, $R^D$ is of the formula:

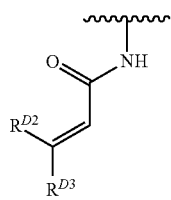

In certain embodiments, $R^D$ is of the formula:

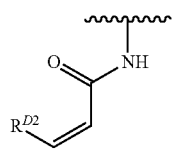

In certain embodiments, $R^D$ is of the formula:

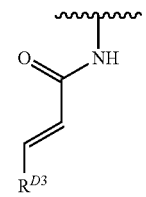

In certain embodiments, $R^D$ is of the formula:

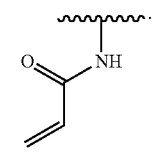 [SMILES: *NC(=O)C=C]

In certain embodiments, $R^D$ is of the formula:

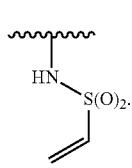

In certain embodiments, $R^D$ is of the formula:

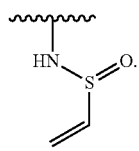 [SMILES: *NS(=O)C=C]

In certain embodiments, $R^D$ is of the formula:

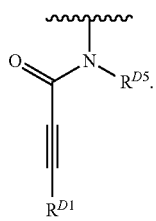

In certain embodiments, $R^D$ is of the formula:

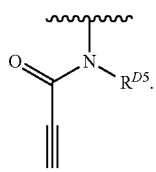

In certain embodiments, $R^D$ is of the formula:

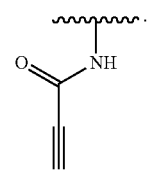 [SMILES: *NC(=O)C#C]

In certain embodiments, $R^D$ is of the formula:

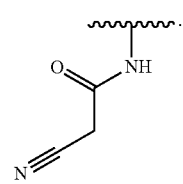 [SMILES: *NC(=O)CC#N]

In certain embodiments, $R^D$ is of the formula:

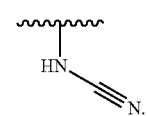

In certain embodiments, $R^D$ is of the formula:

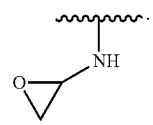

In certain embodiments, $R^D$ is of the formula:

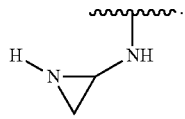

In certain embodiments, $R^D$ is of the formula:

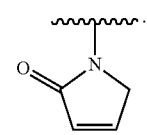

In certain embodiments, $R^D$ is of the formula:

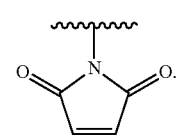

In certain embodiments, $R^D$ is of the formula:

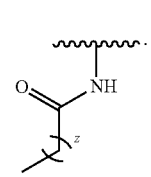

In certain embodiments, $R^D$ is of the formula:

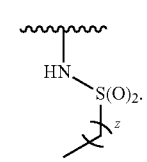

In certain embodiments, $R^D$ is of the formula:

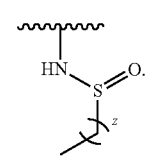

In certain embodiments, $R^D$ is of the formula:

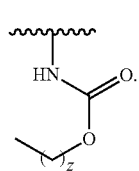

In certain embodiments, $R^D$ is of the formula:

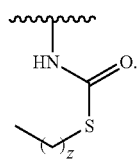

In certain embodiments, $R^D$ is of the formula:

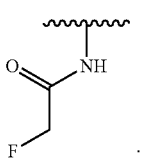

In certain embodiments, $R^D$ is of the formula:

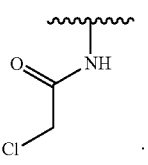

In certain embodiments, $R^D$ is of the formula:

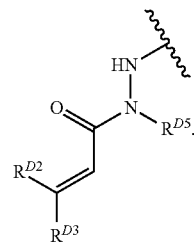

In certain embodiments, $R^D$ is of the formula:

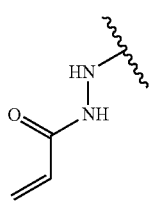

Various combinations of certain embodiments of Formula (A) are further contemplated herein.

For example, in certain embodiments, a compound of Formula (A) is a compound of Formula (A1) or (A2):

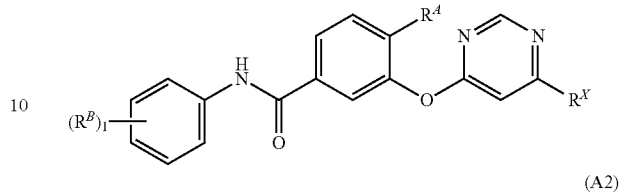

(A1)

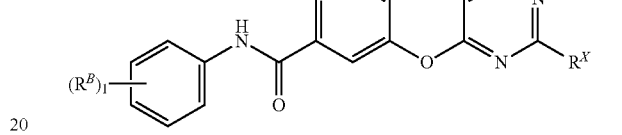

(A2)

wherein $R^X$, $R^A$, $R^B$, and l are defined herein. In certain embodiments $R^A$ is substituted or unsubstituted $C_{1-6}$ alkyl. In certain embodiments, $R^A$ is methyl. In certain embodiments, l is 1. In certain embodiments, l is 1; and $R^B$ is meta to the point of attachment of the amide linker. In certain embodiments, l is 2. In certain embodiments, l is 2; and the two $R^B$ groups are meta to the point of attachment of the amide linker. In certain embodiments, l is 2; one $R^B$ group is meta to the point of attachment of the amide linker; and the second $R^B$ group is para to the point of attachment of the amide linker. In certain embodiments, one $R^B$ group is substituted or unsubstituted $C_{1-6}$alkyl. In certain embodiments, one $R^B$ group is $C_{1-6}$alkyl substituted with one —CN group. In certain embodiments, one $R^B$ group is

In certain embodiments, one $R^B$ group is substituted or unsubstituted —CH$_2$-(piperazinyl). In certain embodiments, one $R^B$ group is

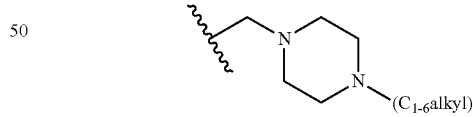

where the alkyl is optionally substituted. In certain embodiments, one $R^B$ group is

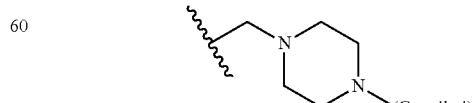

where the alkyl is unsubstituted. In certain embodiments, one $R^B$ group is

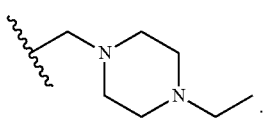 [SMILES: *CN1CCN(CC)CC1]

In certain embodiments, one $R^B$ group is haloalkyl. In certain embodiments, one $R^B$ group is —CF$_3$. In certain embodiments, one $R^B$ group is substituted or unsubstituted imidazoyl. In certain embodiments, one $R^B$ group is

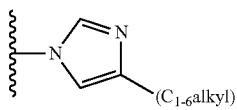

where the alkyl is optionally substituted. In certain embodiments, one $R^B$ group is

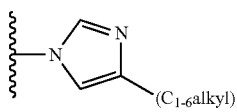

where the alkyl is unsubstituted. In certain embodiments, one $R^B$ group is

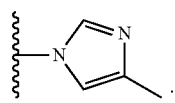

In certain embodiments, one $R^B$ group is substituted or unsubstituted piperazinyl. In certain embodiments, one $R^B$ group is

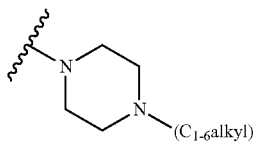

where there alkyl is optionally substituted. In certain embodiments, one $R^B$ group is

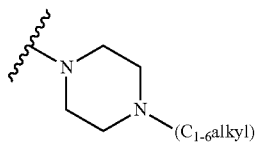

where there alkyl is unsubstituted. In certain embodiments, one $R^B$ group is

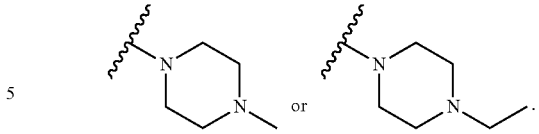

In certain embodiments, one $R^B$ group is substituted or unsubstituted morpholine. In certain embodiments, two $R^B$ groups are substituted or unsubstituted morpholine. In certain embodiments, $R^X$ is —N(R$^{A1}$)N(R$^{A1}$)$_2$. In certain embodiments, $R^X$ is —N(R$^{A1}$)N(R$^{A1}$)$_2$; and each instance of $R^A$ is hydrogen, methyl, or acetyl. In certain embodiments, $R^X$ is —NHNMe$_2$ or —NHNHAc. In certain embodiments, Rx is —NH$_2$. In certain embodiments, $R^X$ is —NH(R$^{A1}$). In certain embodiments, $R^X$ is —NH(R$^{A1}$); and R$^{A1}$ is substituted or unsubstituted C$_{1-6}$alkyl. In certain embodiments, $R^X$ is —NH(R$^{A1}$); and R$^{A1}$ is substituted or unsubstituted methyl. In certain embodiments, $R^X$ is —NH(R$^{A1}$); and R$^{A1}$ is acyl. In certain embodiments, $R^X$ is —NH(R$^{A1}$); and R$^{A1}$ is substituted or unsubstituted —C(=O)—(C$_{1-6}$alkyl). In certain embodiments, $R^X$ is —NH(R$^{A1}$); and R$^{A1}$ is acetyl or propionyl. In certain embodiments, $R^X$ is —NH(R$^{A1}$); and R$^{A1}$ is substituted or unsubstituted —C(=O)-(carbocyclyl). In certain embodiments, $R^X$ is —NH(R$^A$); and R$^{A1}$ is substituted or unsubstituted —C(=O)-(cyclopropyl). In certain embodiments, $R^X$ is —NH(R$^{A1}$); and R$^{A1}$ is substituted or unsubstituted heteroaryl. In certain embodiments, $R^X$ is —NH(R$^{A1}$); and R$^{A1}$ is substituted or unsubstituted pyrazole. In certain embodiments, $R^X$ is —NH(R$^{A1}$); and R$^{A1}$ is substituted or unsubstituted isoxazole. In certain embodiments, $R^X$ is —NH(R$^A$); and R$^{A1}$ is substituted or unsubstituted pyrimidine. In certain embodiments, $R^X$ is —NH(R$^{A1}$); and R$^{A1}$ is substituted or unsubstituted heterocyclyl. In certain embodiments, $R^X$ is —NH(R$^{A1}$); and R$^{A1}$ is substituted or unsubstituted azetidine. In certain embodiments, $R^X$ is —NH(R$^{A1}$); and R$^{A1}$ is substituted or unsubstituted oxetane.

In certain embodiments, a compound of Formula (A1) is a compound of Formula (A1-a), (A1-b), (A1-c), or (A1-d):

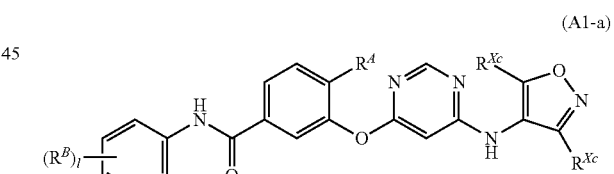

(A1-a)

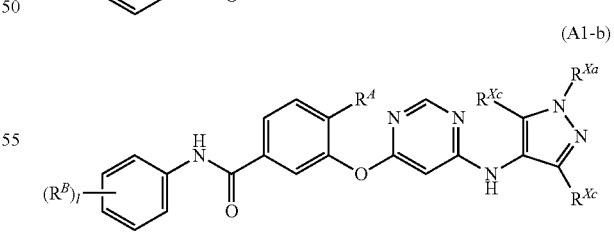

(A1-b)

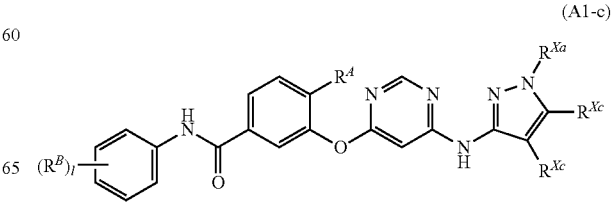

(A1-c)

(A1-d)

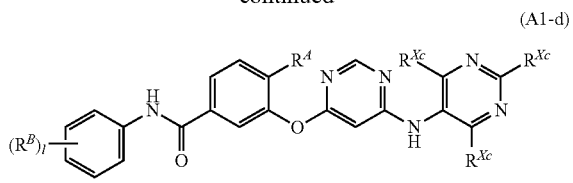

wherein $R^{Xa}$, $R^{Xc}$, $R^A$, $R^B$, and l are defined herein. In certain embodiments $R^A$ is substituted or unsubstituted $C_{1-6}$ alkyl. In certain embodiments, $R^A$ is methyl. In certain embodiments, l is 1. In certain embodiments, l is 1; and $R^B$ is meta to the point of attachment of the amide linker. In certain embodiments, l is 2. In certain embodiments, l is 2; and the two $R^B$ groups are meta to the point of attachment of the amide linker. In certain embodiments, l is 2; one $R^B$ group is meta to the point of attachment of the amide linker; and the second $R^B$ group is para to the point of attachment of the amide linker. In certain embodiments, one $R^B$ group is substituted or unsubstituted $C_{1-6}$alkyl. In certain embodiments, one $R^B$ group is $C_{1-6}$alkyl substituted with one —CN group. In certain embodiments, one $R^B$ group is

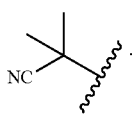

In certain embodiments, one $R^B$ group is substituted or unsubstituted —CH$_2$-(piperazinyl). In certain embodiments, one $R^B$ group is

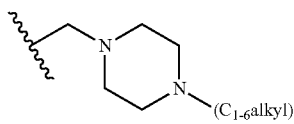

where the alkyl is optionally substituted. In certain embodiments, one $R^B$ group is

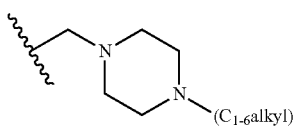

where the alkyl is unsubstituted. In certain embodiments, one $R^B$ group is

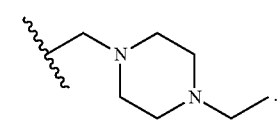

In certain embodiments, one $R^B$ group is haloalkyl. In certain embodiments, one $R^B$ group is —CF$_3$. In certain embodiments, one $R^B$ group is substituted or unsubstituted imidazoyl. In certain embodiments, one $R^B$ group is

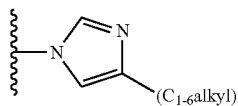

where the alkyl is optionally substituted. In certain embodiments, one $R^B$ group is

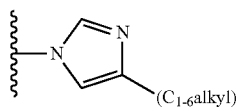

where the alkyl is unsubstituted. In certain embodiments, one $R^B$ group is

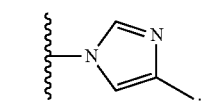

In certain embodiments, one $R^B$ group is substituted or unsubstituted piperazinyl. In certain embodiments, one $R^B$ group is

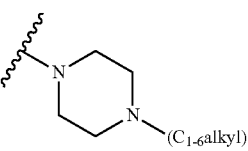

where there alkyl is optionally substituted. In certain embodiments, one $R^B$ group is

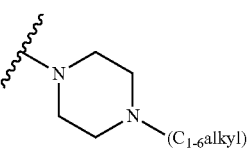

where there alkyl is unsubstituted. In certain embodiments, one $R^B$ group is

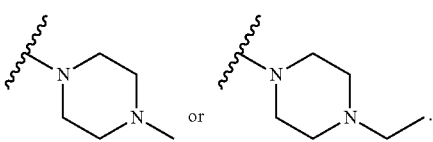

In certain embodiments, one $R^B$ group is substituted or unsubstituted morpholine. In certain embodiments, two $R^B$ groups are substituted or unsubstituted morpholine. In certain embodiments, all instances of $R^{Xc}$ are hydrogen. In certain embodiments, $R^{Xa}$ is substituted or unsubstituted $C_{1-6}$alkyl. In certain embodiments, $R^{Xa}$ is methyl or ethyl.

In certain embodiments, a compound of Formula (A2) is a compound of Formula (A2-a), (A2-b), (A2-c), or (A2-d):

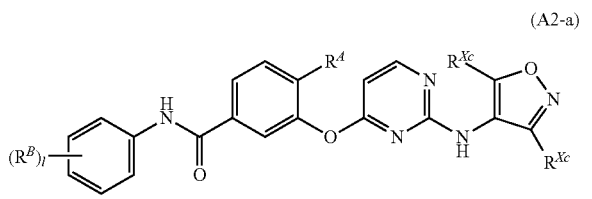
(A2-a)

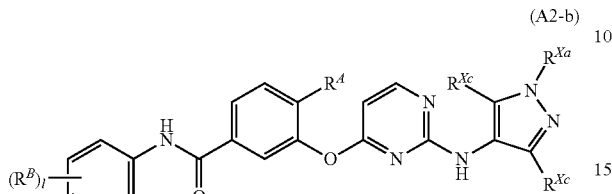
(A2-b)

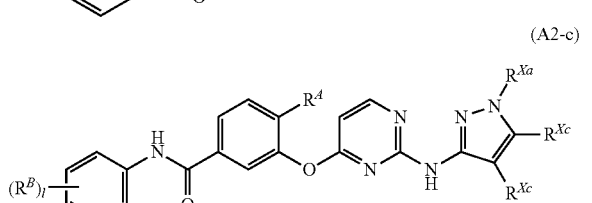
(A2-c)

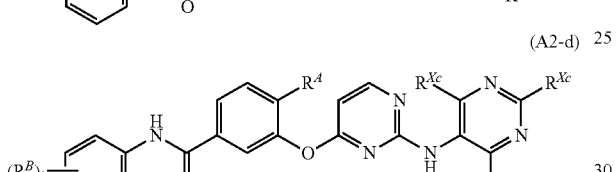
(A2-d)

wherein $R^{Xa}$, $R^{Xc}$, $R^A$, $R^B$, and l are defined herein. In certain embodiments $R^A$ is substituted or unsubstituted $C_{1-6}$ alkyl. In certain embodiments, $R^A$ is methyl. In certain embodiments, l is 1. In certain embodiments, l is 1; and $R^B$ is meta to the point of attachment of the amide linker. In certain embodiments, l is 2. In certain embodiments, l is 2; and the two $R^B$ groups are meta to the point of attachment of the amide linker. In certain embodiments, l is 2; one $R^B$ group is meta to the point of attachment of the amide linker; and the second $R^B$ group is para to the point of attachment of the amide linker. In certain embodiments, one $R^B$ group is substituted or unsubstituted $C_{1-6}$alkyl. In certain embodiments, one $R^B$ group is $C_{1-6}$alkyl substituted with one —CN group. In certain embodiments, one $R^B$ group is

In certain embodiments, one $R^B$ group is substituted or unsubstituted —CH$_2$-(piperazinyl). In certain embodiments, one $R^B$ group is

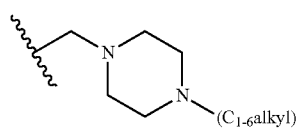

where the alkyl is optionally substituted. In certain embodiments, one $R^B$ group is

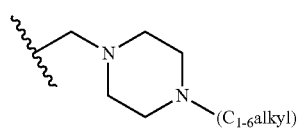

where the alkyl is unsubstituted. In certain embodiments, one $R^B$ group is

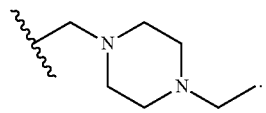 [SMILES: *CN1CCN(CC)CC1]

In certain embodiments, one $R^B$ group is haloalkyl. In certain embodiments, one $R^B$ group is —CF$_3$. In certain embodiments, one $R^B$ group is substituted or unsubstituted imidazoyl. In certain embodiments, one $R^B$ group is

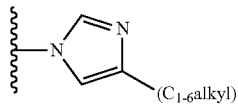

where the alkyl is optionally substituted. In certain embodiments, one $R^B$ group is

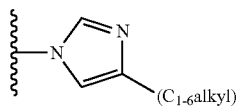

where the alkyl is unsubstituted. In certain embodiments, one $R^B$ group is

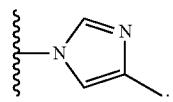

In certain embodiments, one $R^B$ group is substituted or unsubstituted piperazinyl. In certain embodiments, one $R^B$ group is

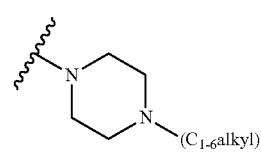

where there alkyl is optionally substituted. In certain embodiments, one $R^B$ group is

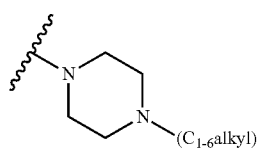

where there alkyl is unsubstituted. In certain embodiments, one $R^B$ group is

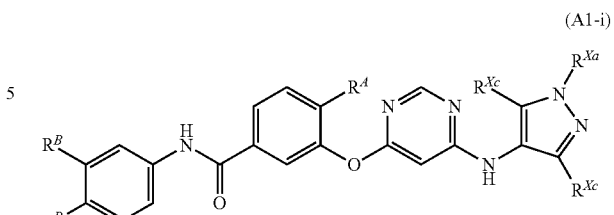

In certain embodiments, one $R^B$ group is substituted or unsubstituted morpholine. In certain embodiments, two $R^B$ groups are substituted or unsubstituted morpholine. In certain embodiments, all instances of $R^{Xc}$ are hydrogen. In certain embodiments, $R^{Xa}$ is substituted or unsubstituted $C_{1-6}$alkyl. In certain embodiments, $R^{Xa}$ is methyl or ethyl.

In certain embodiments, a compound of Formula (A1) is a compound of Formula (A1-e)-(A1-p):

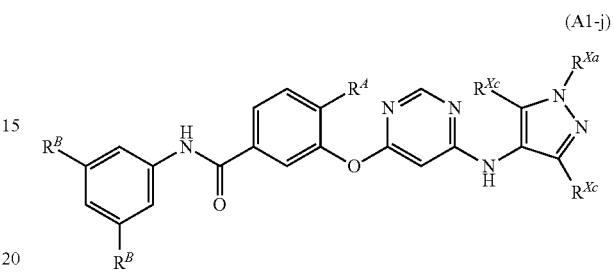

(A1-e)

(A1-f)

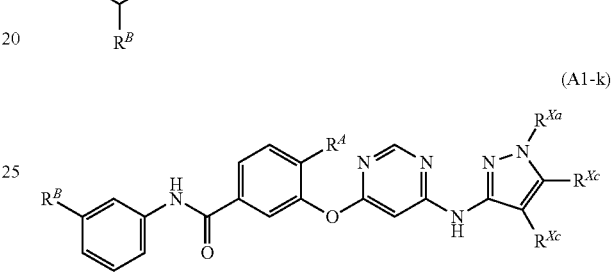

(A1-g)

(A1-h)

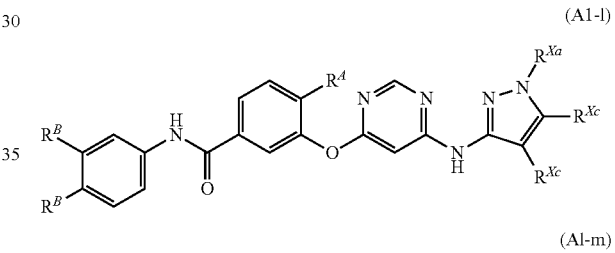

(A1-i)

(A1-j)

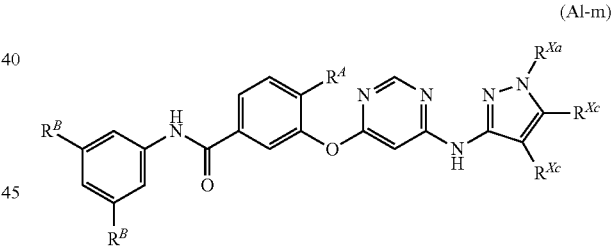

(A1-k)

(A1-l)

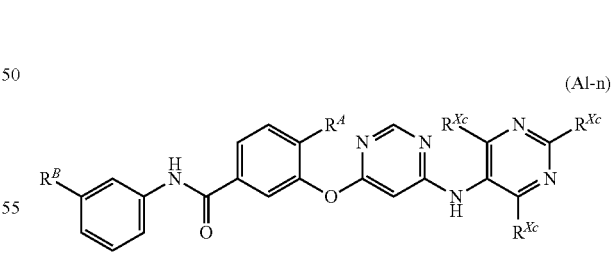

(A1-m)

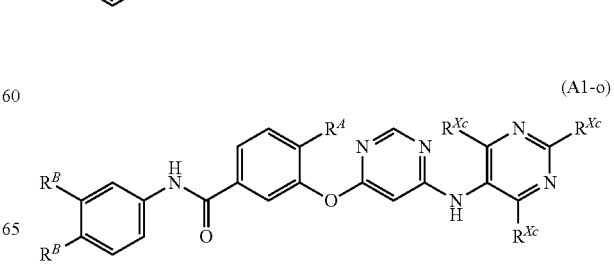

(A1-n)

(A1-o)

-continued

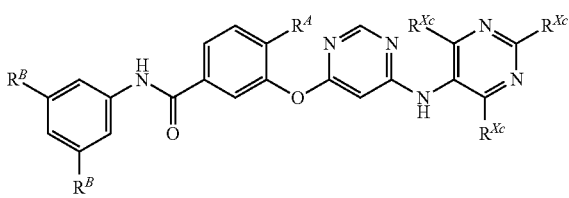
(A1-p)

wherein $R^{Xa}$, $R^{Xc}$, $R^A$, and $R^B$ are defined herein. In certain embodiments $R^A$ is substituted or unsubstituted $C_{1-6}$ alkyl. In certain embodiments, $R^A$ is methyl. In certain embodiments, one $R^B$ group is substituted or unsubstituted $C_{1-6}$alkyl. In certain embodiments, one $R^B$ group is $C_{1-6}$alkyl substituted with one —CN group. In certain embodiments, one $R^B$ group is

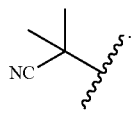

In certain embodiments, one $R^B$ group is substituted or unsubstituted —$CH_2$-(piperazinyl). In certain embodiments, one $R^B$ group is

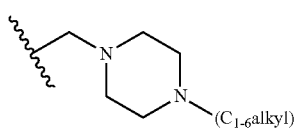

where the alkyl is optionally substituted. In certain embodiments, one $R^B$ group is

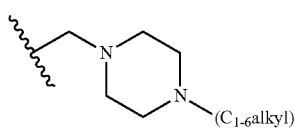

where the alkyl is unsubstituted. In certain embodiments, one $R^B$ group is

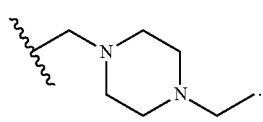 [SMILES: *CN1CCN(CC)CC1]

In certain embodiments, one $R^B$ group is haloalkyl. In certain embodiments, one $R^B$ group is —$CF_3$. In certain embodiments, one $R^B$ group is substituted or unsubstituted imidazoyl. In certain embodiments, one $R^B$ group is

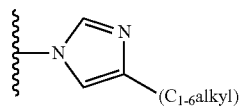

where the alkyl is optionally substituted. In certain embodiments, one $R^B$ group is

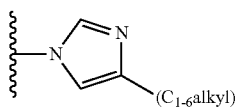

where the alkyl is unsubstituted. In certain embodiments, one $R^B$ group is

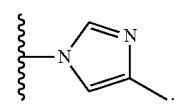

In certain embodiments, one $R^B$ group is substituted or unsubstituted piperazinyl. In certain embodiments, one $R^B$ group is

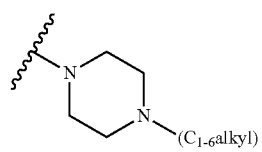

where there alkyl is optionally substituted. In certain embodiments, one $R^B$ group is

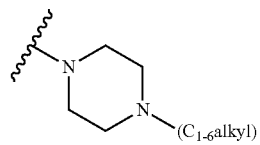

where there alkyl is unsubstituted. In certain embodiments, one $R^B$ group is

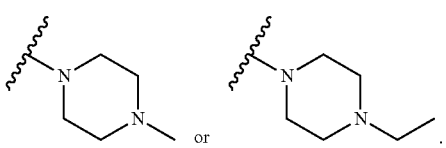

In certain embodiments, one $R^B$ group is substituted or unsubstituted morpholine. In certain embodiments, two $R^B$ groups are substituted or unsubstituted morpholine. In certain embodiments, all instances of $R^{Xc}$ are hydrogen. In certain embodiments, $R^{Xa}$ is substituted or unsubstituted $C_{1-6}$alkyl. In certain embodiments, $R^{Xa}$ is methyl or ethyl.

In certain embodiments, a compound of Formula (A2) is a compound of Formula (A2-e)-(A2-p):

(A2-e) 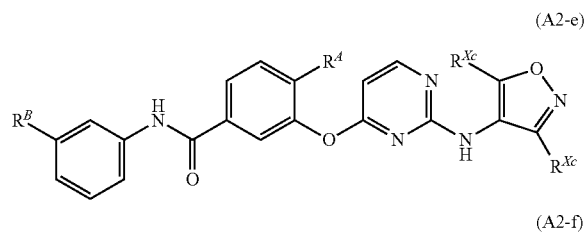
(A2-f) 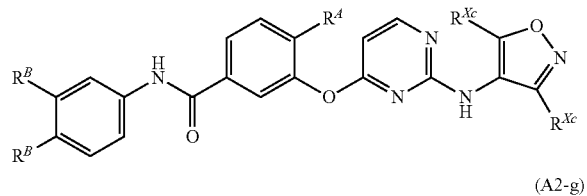
(A2-g) 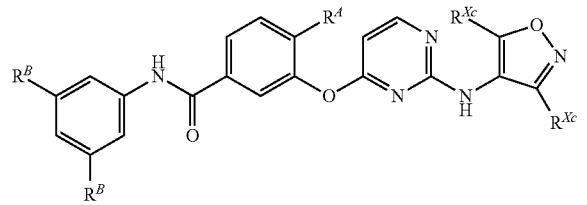
(A2-h) 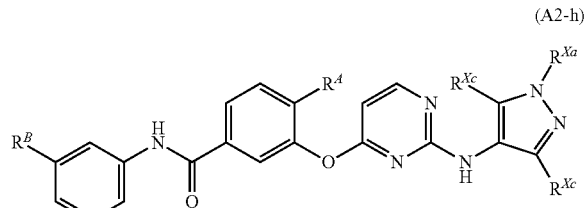
(A2-i) 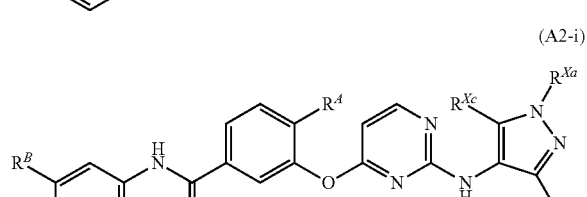
(A2-j) 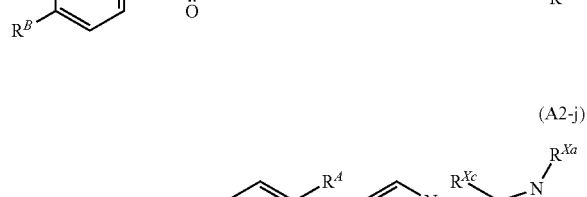
(A2-k) 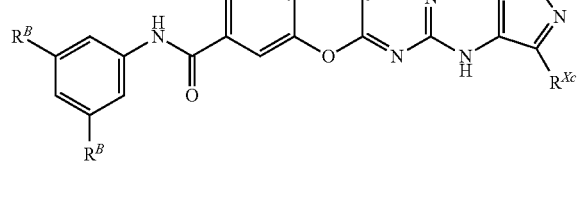

(A2-l) 
(A2-m) 
(A2-n) 
(A2-o) 
(A2-p) 

wherein $R^{Xa}$, $R^{Xc}$, $R^A$, and $R^B$ are defined herein. In certain embodiments $R^A$ is substituted or unsubstituted $C_{1-6}$ alkyl. In certain embodiments, $R^A$ is methyl. In certain embodiments, one $R^B$ group is substituted or unsubstituted $C_{1-6}$alkyl. In certain embodiments, one $R^B$ group is

$C_{1-6}$alkyl substituted with one —CN group. In certain embodiments, one $R^B$ group is NC In certain embodiments, one $R^B$ group is substituted or unsubstituted —CH$_2$-(piperazinyl). In certain embodiments, one $R^B$ group is

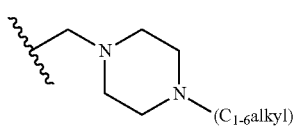

where the alkyl is optionally substituted. In certain embodiments, one $R^B$ group is

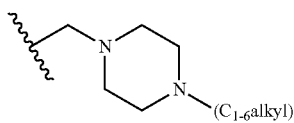

where the alkyl is unsubstituted. In certain embodiments, one $R^B$ group is

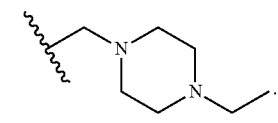 [SMILES: *CN1CCN(CC)CC1]

In certain embodiments, one $R^B$ group is haloalkyl. In certain embodiments, one $R^B$ group is —CF$_3$. In certain embodiments, one $R^B$ group is substituted or unsubstituted imidazoyl. In certain embodiments, one $R^B$ group is

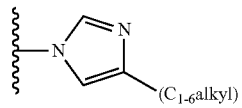

where the alkyl is optionally substituted. In certain embodiments, one $R^B$ group is

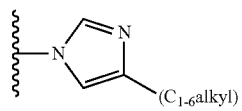

where the alkyl is unsubstituted. In certain embodiments, one $R^B$ group is

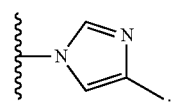 [SMILES: *n1cnc(C)c1]

In certain embodiments, one $R^B$ group is substituted or unsubstituted piperazinyl. In certain embodiments, one $R^B$ group is

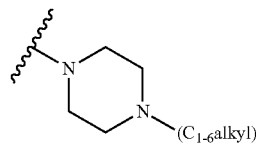

where there alkyl is optionally substituted. In certain embodiments, one $R^B$ group is

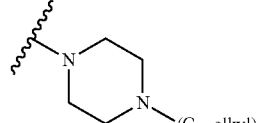

where there alkyl is unsubstituted. In certain embodiments, one $R^B$ group is

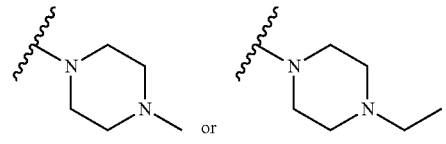

In certain embodiments, one $R^B$ group is substituted or unsubstituted morpholine. In certain embodiments, two $R^B$ groups are substituted or unsubstituted morpholine. In certain embodiments, all instances of $R^{Xc}$ are hydrogen. In certain embodiments, $R^{Xa}$ is substituted or unsubstituted C$_{1-6}$alkyl. In certain embodiments, $R^{Xa}$ is methyl or ethyl.

In certain embodiments, a compound of Formula (A) is a compound of Formula (A3) or (A4):

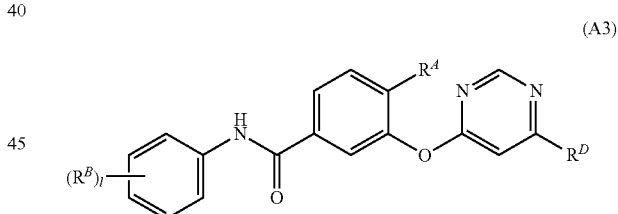

(A3)

(A4)

wherein $R^D$, $R^A$, $R^B$, and l are defined herein. In certain embodiments $R^A$ is substituted or unsubstituted C$_{1-6}$ alkyl. In certain embodiments, $R^A$ is methyl. In certain embodiments, l is 1. In certain embodiments, l is 1; and $R^B$ is meta to the point of attachment of the amide linker. In certain embodiments, l is 2. In certain embodiments, l is 2; and the two $R^B$ groups are meta to the point of attachment of the amide linker. In certain embodiments, l is 2; one $R^B$ group is meta to the point of attachment of the amide linker; and the second $R^B$ group is para to the point of attachment of the amide linker. In certain embodiments, one $R^B$ group is substituted or unsubstituted $C_{1-6}$alkyl. In certain embodiments, one $R^B$ group is $C_{1-6}$alkyl substituted with one —CN group. In certain embodiments, one $R^B$ group is

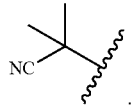

In certain embodiments, one $R^B$ group is substituted or unsubstituted —$CH_2$-(piperazinyl). In certain embodiments, one $R^B$ group is

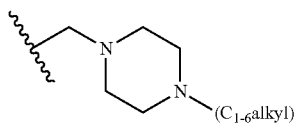

where the alkyl is optionally substituted. In certain embodiments, one $R^B$ group is

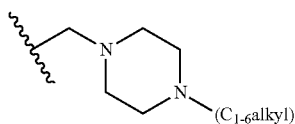

where the alkyl is unsubstituted. In certain embodiments, one $R^B$ group is

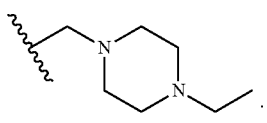 [SMILES: *CN1CCN(CC)CC1]

In certain embodiments, one $R^B$ group is haloalkyl. In certain embodiments, one $R^B$ group is —$CF_3$. In certain embodiments, one $R^B$ group is substituted or unsubstituted imidazoyl. In certain embodiments, one $R^B$ group is

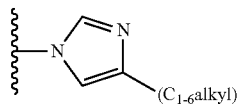

where the alkyl is optionally substituted. In certain embodiments, one $R^B$ group is

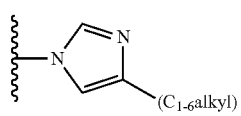

where the alkyl is unsubstituted. In certain embodiments, one $R^B$ group is

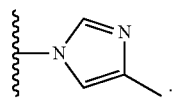

In certain embodiments, one $R^B$ group is substituted or unsubstituted piperazinyl. In certain embodiments, one $R^B$ group is

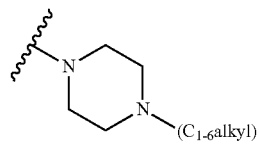

where there alkyl is optionally substituted. In certain embodiments, one $R^B$ group is

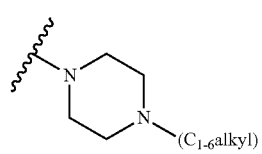

alkyl where there alkyl is unsubstituted. In certain embodiments, one $R^B$ group is

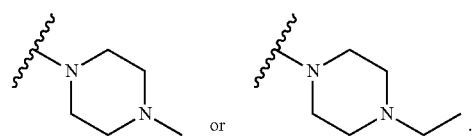

In certain embodiments, one $R^B$ group is substituted or unsubstituted morpholine. In certain embodiments, two $R^B$ groups are substituted or unsubstituted morpholine. In certain embodiments, $R^D$ is $R^D$ is

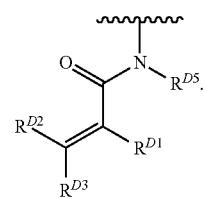

In certain embodiments, $R^D$ is

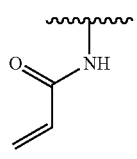

In certain embodiments, $R^D$ is

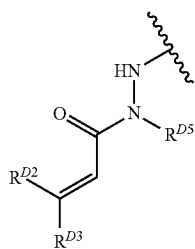

In certain embodiments, $R^D$ is

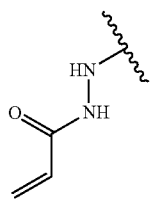

In certain embodiments, a compound of Formula (A3) is a compound of Formula (A3-a), (A3-b), or (A3-c):

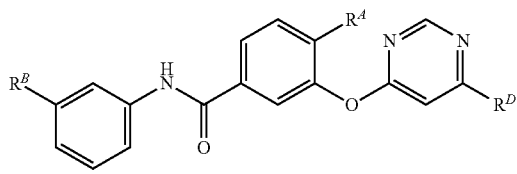
(A3-a)

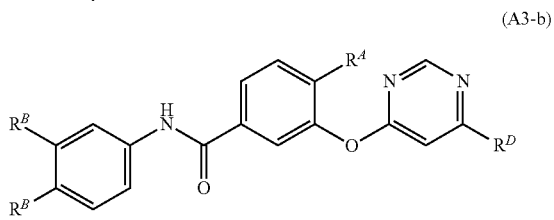
(A3-b)

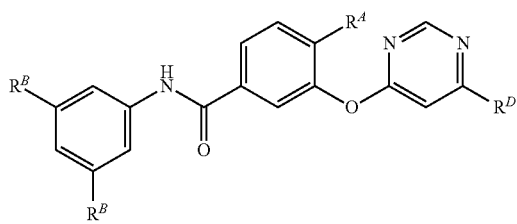
(A3-c)

wherein $R^D$, $R^A$, $R^B$, and l are defined herein. In certain embodiments $R^A$ is substituted or unsubstituted $C_{1-6}$ alkyl. In certain embodiments, $R^A$ is methyl. In certain embodiments, l is 1. In certain embodiments, l is 1; and $R^B$ is meta to the point of attachment of the amide linker. In certain embodiments, l is 2. In certain embodiments, l is 2; and the two $R^B$ groups are meta to the point of attachment of the amide linker. In certain embodiments, l is 2; one $R^B$ group is meta to the point of attachment of the amide linker; and the second $R^B$ group is para to the point of attachment of the amide linker. In certain embodiments, one $R^B$ group is substituted or unsubstituted $C_{1-6}$alkyl. In certain embodiments, one $R^B$ group is $C_{1-6}$alkyl substituted with one —CN group. In certain embodiments, one $R^B$ group is

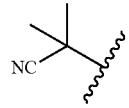

In certain embodiments, one $R^B$ group is substituted or unsubstituted —CH$_2$-(piperazinyl). In certain embodiments, one $R^B$ group is

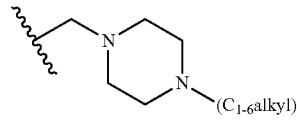

where the alkyl is optionally substituted. In certain embodiments, one $R^B$ group is

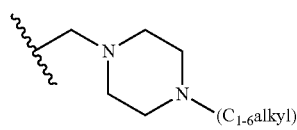

where the alkyl is unsubstituted. In certain embodiments, one $R^B$ group is

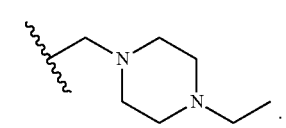 [SMILES: *CN1CCN(CC)CC1]

In certain embodiments, one $R^B$ group is haloalkyl. In certain embodiments, one $R^B$ group is —CF$_3$. In certain embodiments, one $R^B$ group is substituted or unsubstituted imidazoyl. In certain embodiments, one $R^B$ group is

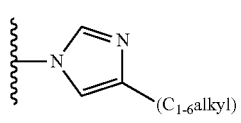

where the alkyl is optionally substituted. In certain embodiments, one $R^B$ group is where the alkyl where the alkyl is unsubstituted. In certain embodiments, one $R^B$ group is

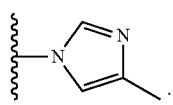

In certain embodiments, one $R^B$ group is substituted or unsubstituted piperazinyl. In certain embodiments, one $R^B$ group is

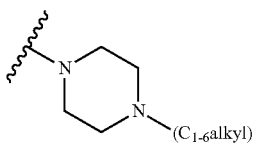

where there alkyl is optionally substituted. In certain embodiments, one $R^B$ group is

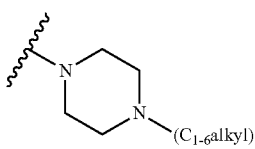

where there alkyl is unsubstituted. In certain embodiments, one $R^B$ group is

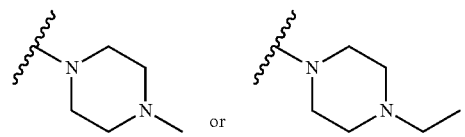

In certain embodiments, one $R^B$ group is substituted or unsubstituted morpholine. In certain embodiments, two $R^B$ groups are substituted or unsubstituted morpholine. In certain embodiments, $R^D$ is

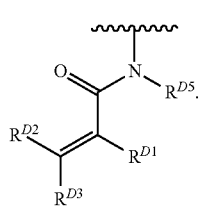

In certain embodiments, $R^D$ is

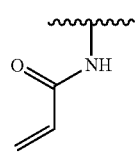

In certain embodiments, $R^D$ is

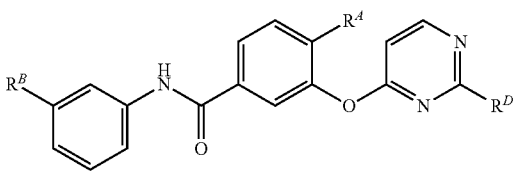

In certain embodiments, $R^D$ is

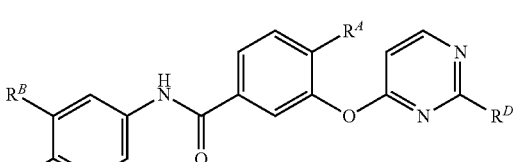

In certain embodiments, a compound of Formula (A4) is a compound of Formula (A4-a), (A4-b), or (A4-c):

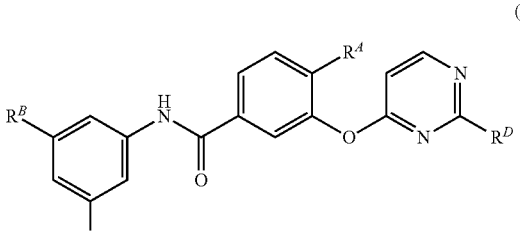

wherein $R^D$, $R^A$, $R^B$, and l are defined herein. In certain embodiments $R^A$ is substituted or unsubstituted $C_{1-6}$ alkyl. In certain embodiments, $R^A$ is methyl. In certain embodiments, l is 1. In certain embodiments, l is 1; and $R^B$ is meta to the point of attachment of the amide linker. In certain embodiments, l is 2. In certain embodiments, l is 2; and the two $R^B$ groups are meta to the point of attachment of the amide linker. In certain embodiments, l is 2; one $R^B$ group is meta to the point of attachment of the amide linker; and the second $R^B$ group is para to the point of attachment of the amide linker. In certain embodiments, one $R^B$ group is substituted or unsubstituted $C_{1-6}$alkyl. In certain embodiments, one $R^B$ group is $C_{1-6}$alkyl substituted with one —CN group. In certain embodiments, one $R^B$ group is

In certain embodiments, one $R^B$ group is substituted or unsubstituted —CH$_2$-(piperazinyl). In certain embodiments, one $R^B$ group is

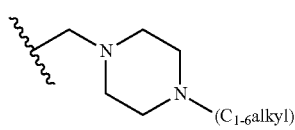

where the alkyl is optionally substituted. In certain embodiments, one $R^B$ group is

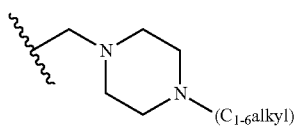

where the alkyl is unsubstituted. In certain embodiments, one $R^B$ group is

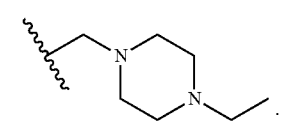 [SMILES: *CN1CCN(CC)CC1]

In certain embodiments, one $R^B$ group is haloalkyl. In certain embodiments, one $R^B$ group is —CF$_3$. In certain embodiments, one $R^B$ group is substituted or unsubstituted imidazoyl. In certain embodiments, one $R^B$ group is

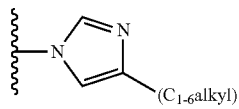

where the alkyl is optionally substituted. In certain embodiments, one $R^B$ group is

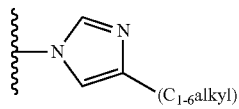

where the alkyl is unsubstituted. In certain embodiments, one $R^B$ group is

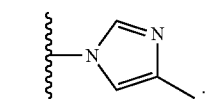 [SMILES: *n1cnc(C)c1]

In certain embodiments, one $R^B$ group is substituted or unsubstituted piperazinyl. In certain embodiments, one $R^B$ group is

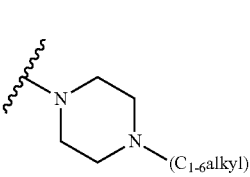

where there alkyl is optionally substituted. In certain embodiments, one $R^B$ group is

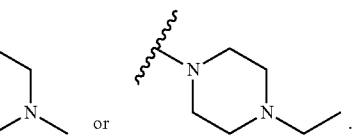

where there alkyl is unsubstituted. In certain embodiments, one $R^B$ group is

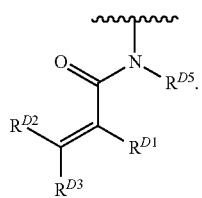

In certain embodiments, one $R^B$ group is substituted or unsubstituted morpholine. In certain embodiments, two $R^B$ groups are substituted or unsubstituted morpholine. In certain embodiments, $R^D$ is

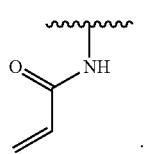

In certain embodiments, $R^D$ is

In certain embodiments, $R^D$ is

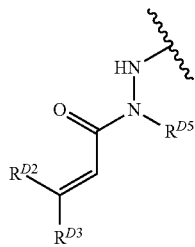

In certain embodiments, $R^D$ is

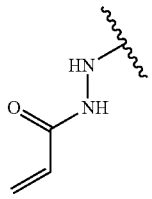

Another aspect of the invention relates to the compound of Formula (I-11):

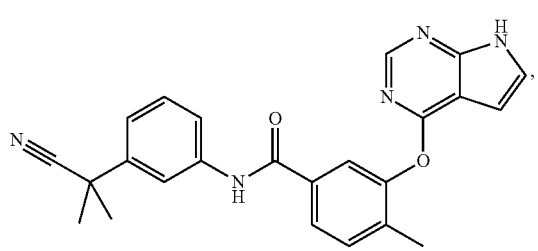

(I-11)

and pharmaceutically acceptable salts, solvates, hydrates, polymorphs, co-crystals, tautomers, stereoisomers, isotopically labeled derivatives, and prodrugs thereof.

In another aspect, provided are compounds of Formula (V):

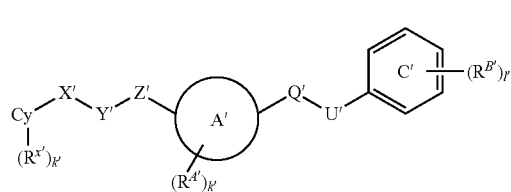

(V)

and pharmaceutically acceptable salts, solvates, hydrates, polymorphs, co-crystals, tautomers, stereoisomers, isotopically labeled derivatives, and prodrugs thereof; wherein:

each instance of each instance of $R^{A\prime}$, $R^{B\prime}$, and $R^{X\prime}$ are independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{41\prime}$, —N(R$^{41\prime}$)$_2$, —SR$^{41\prime}$, —CN, —C(=O)R$^{41\prime}$, —C(=O)OR$^{41\prime}$, —C(=O)SR$^{41\prime}$, —C(=O)N(R$^{41\prime}$)$_2$, —C(=S)R$^{41\prime}$, —C(=S)OR$^{41\prime}$, —C(=S)SR$^{41\prime}$, —C(=S)N(R$^{41\prime}$)$_2$, —C(=NR$^{41\prime}$)R$^{41\prime}$, —C(=NR$^{41\prime}$)OR$^{41\prime}$, —C(=NR$^{41\prime}$)SR$^{41\prime}$, —C(=NR$^{41\prime}$)N(R$^{41\prime}$)$_2$, —NO$_2$, —N$_3$, —N(R$^{41\prime}$)$_3^+$X$^{\prime-}$, wherein X$^{\prime-}$ is a counterion, —N(OR$^{41\prime}$)R$^{41\prime}$, —NR$^{41\prime}$C(=O)R$^{41\prime}$, —NR$^{41\prime}$C(=O)OR$^{41\prime}$, —NR$^{41\prime}$C(=O)SR$^{41\prime}$, —NR$^{41\prime}$C(=O)N(R$^{41\prime}$)$_2$, —NR$^{41\prime}$C(=S)R$^{41\prime}$, —NR$^{41\prime}$C(=S)OR$^{41\prime}$, —NR$^{41\prime}$C(=S)SR$^{41\prime}$, —NR$^{41\prime}$C(=S)N(R$^{41\prime}$)$_2$, —NR$^{41\prime}$C(=NR$^{41\prime}$)R$^{41\prime}$, —NR$^{41\prime}$C(=NR$^{41\prime}$)OR$^{41\prime}$, —NR$^{41\prime}$C(=NR$^{41\prime}$)SR$^{41\prime}$, —NR$^{41\prime}$C(=NR$^{41\prime}$)N(R$^{41\prime}$)$_2$, —NR$^{41\prime}$S(=O)$_2$R$^{41\prime}$, —NR$^{41\prime}$S(=O)$_2$OR$^{41\prime}$, —NR$^{41\prime}$S(=O)$_2$SR$^{41\prime}$, —NR$^{41\prime}$S(=O)$_2$N(R$^{41\prime}$)$_2$, —NR$^{41\prime}$S(=O)R$^{41\prime}$, —NR$^{41\prime}$S(=O)OR$^{41\prime}$, —NR$^{41\prime}$S(=O)SR$^{41\prime}$, —NR$^{41\prime}$S(=O)N(R$^{41\prime}$)$_2$, —NR$^{41\prime}$P(=O), —NR$^{41\prime}$P(=O)$_2$, —NR$^{41\prime}$P(=O)(R$^{41\prime}$)$_2$, —NR$^{41\prime}$P(=O)R$^{41\prime}$(OR$^{41\prime}$), —NR$^{41\prime}$P(=O)(OR$^{41\prime}$)$_2$, —OC(=O)R$^{41\prime}$, —OC(=O)OR$^{41\prime}$, —OC(=O)SR$^{41\prime}$, —OC(=O)N(R$^{41\prime}$)$_2$, —OC(=NR$^{41\prime}$)R$^{41\prime}$, —OC(=NR$^{41\prime}$)OR$^{41\prime}$, —OC(=NR$^{41\prime}$)N(R$^{41\prime}$)$_2$, —OC(=S)R$^{41\prime}$, —OC(=S)OR$^{41\prime}$, —OC(=S)SR$^{41\prime}$, —OC(=S)N(R$^{41\prime}$)$_2$, —ON(R$^{41\prime}$)$_2$, —OS(=O)R$^{41\prime}$, —OS(=O)OR$^{41\prime}$, —OS(=O)SR$^{41\prime}$, —OS(=O)N(R$^{41\prime}$)$_2$, —OS(=O)$_2$R$^{41\prime}$, —OS(=O)$_2$OR$^{41\prime}$, —OS(=O)$_2$SR$^{41\prime}$, —OS(=O)$_2$N(R$^{41\prime}$)$_2$, —OP(=O)$_2$, —OP(=O)(R$^{41\prime}$)$_2$, —OP(=O)R$^{41\prime}$(OR$^{41\prime}$), —OP(=O)(OR$^{41\prime}$)$_2$, —OP(=O), —OP(R$^{41\prime}$)$_2$, —OPR$^{41\prime}$(OR$^{41\prime}$), —OP(OR$^{41\prime}$)$_2$, —OSi(R$^{41\prime}$)$_3$, —OSi(R$^{41\prime}$)$_2$OR$^{41\prime}$, —OSi(R$^{41\prime}$)(OR$^{41\prime}$)$_2$, —OSi(OR$^{41\prime}$)$_3$, —SSR$^{41\prime}$, —S(=O)R$^{41\prime}$, —S(=O)OR$^{41\prime}$, —S(=O)N(R$^{41\prime}$)$_2$, —S(=O)$_2$R$^{41\prime}$, —S(=O)$_2$OR$^{41\prime}$, —S(=O)$_2$N(R$^{41\prime}$)$_2$, —SC(=O)R$^{41\prime}$, —SC(=O)OR$^{41\prime}$, —SC(=O)SR$^{41\prime}$, —SC(=O)N(R$^{41\prime}$)$_2$, —SC(=S)R$^{41\prime}$, —SC(=S)OR$^{41\prime}$, —SC(=S)SR$^{41\prime}$, —SC(=S)N(R$^{41\prime}$)$_2$, —P(R$^{41\prime}$)$_2$, —PR$^{41\prime}$(OR$^{41\prime}$), —P(OR$^{41\prime}$)$_2$, —P(=O), —P(=O)(R$^{41\prime}$)$_2$, —P(=O)(OR$^{41\prime}$)$_2$, —P(=O)R$^{41\prime}$(OR$^{41\prime}$), —P(=O)$_2$, —B(R$^{41\prime}$)$_2$, —B(OR$^{41\prime}$)$_2$, —BR$^{41\prime}$(OR$^{41\prime}$), —Si(R$^{41\prime}$)$_3$, —Si(R$^{41\prime}$)$_2$OR$^{41\prime}$, —SiR$^{41\prime}$(OR$^{41\prime}$)$_2$, and —Si(OR$^{41\prime}$)$_3$, two R$^{A\prime}$ or R$^{B\prime}$ groups are joined to form an optionally substituted carbocyclic, optionally substituted heterocyclic, optionally substituted aryl, or optionally substituted heteroaryl ring, or R$^{A\prime}$ or R$^{B\prime}$ forms an optional 5 to 8 membered ring with any one of X', Y', Z', Q', U', or Cy; wherein each occurrence of R$^{41\prime}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two R$^{41\prime}$ groups are joined to form an optionally substituted heterocyclic ring;

k' and l' are each independently 0, 1, 2, 3, 4, or 5;

X', Y', Z' are each independently —CH$_2$, —CHR$^{A\prime}$, —CH, —C(R$^{A\prime}$)$_2$, —C, —N, —NR$^{A\prime}$, —O, —S or —C=O, or bond and may optionally form a 5 to 8 membered ring with R$^{A\prime}$ or R$^{B\prime}$;

Q' and U' are each independently —NR$^{A\prime}$, —O, —C=O, —NR$^{A\prime}$CO, or bond;

Ring A' is an optionally substituted aryl, or optionally substituted heteroaryl ring Ring C' is an optionally substituted aryl ring; and Cy is an optionally substituted aryl ring, optionally substituted heteroaryl ring, bond, or hydrogen.

Compounds of Formula (V) include an aryl group for Ring A' optionally substituted with one or more R$^{A\prime}$ groups. In certain embodiments, when Ring A' is naphthyl, the invention provides compounds of Formula (V-a):

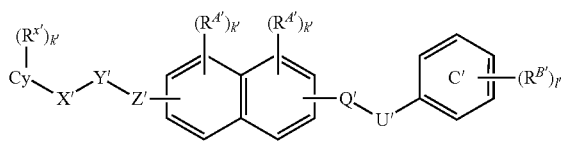

(V-a)

wherein Ring C', Cy, Q', U', X', Y', Z', $R^{A'}$, $R^{B'}$, $R^{X'}$, k', and l' are as defined herein.

Compounds of Formula (V) include an aryl group for Ring A' optionally substituted with one or more $R^{A'}$ groups. In certain embodiments, Ring A' is naphthyl, the invention provides compounds of Formula (V-b):

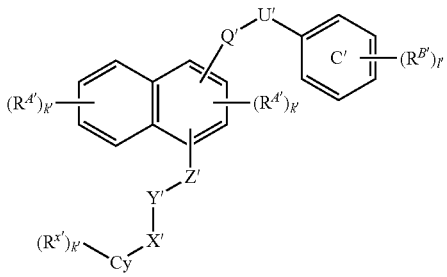

(V-b)

wherein Ring C', Cy, Q', U', X', Y', Z', $R^{A'}$, $R^{B'}$, $R^{X'}$, k', and l' are as defined herein.

Compounds of Formula (V) include an aryl group for Ring A' optionally substituted with one or more $R^{A'}$ groups. In certain embodiments, when Ring A' is phenyl, the invention provides compounds of Formula (V-c):

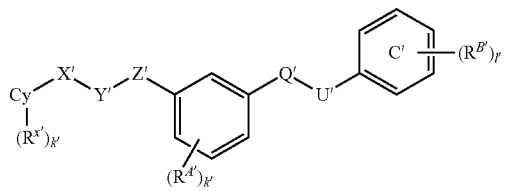

(V-c)

wherein Ring C', Cy, Q', U', X', Y', Z', $R^{A'}$, $R^{B'}$, $R^{X'}$, k', and l' are as defined herein.

Compounds of Formula (V) include an aryl group for Ring A' optionally substituted with one or more $R^{A'}$ groups. In certain embodiments, when Ring A' is phenyl, the invention provides compounds of Formula (V-d):

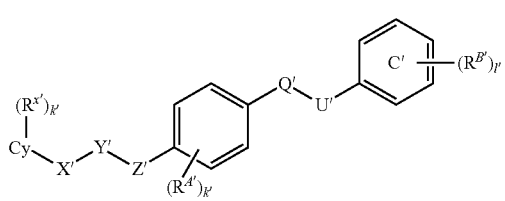

(V-d)

wherein Ring C', Cy, Q', U', X', Y', Z', $R^{A'}$, $R^{B'}$, $R^{X'}$, k', and l' are as defined herein.

Compounds of Formula (V) include an heteroaryl group for Ring A' optionally substituted with one or more $R^{A'}$ groups. In certain embodiments, when Ring A' is pyrrolopyrimidine, the invention provides compounds of Formula (V-e):

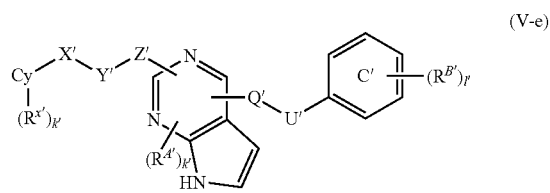

(V-e)

wherein Ring C', Cy, Q', U', X', Y', Z', $R^{A'}$, $R^{B'}$, $R^{X'}$, k', and l' are as defined herein.

Compounds of Formula (V) include an heteroaryl group for Ring A' optionally substituted with one or more $R^{A'}$ groups. In certain embodiments, when Ring A' is a pyrimidine, the invention provides compounds of Formula (V-e$^A$):

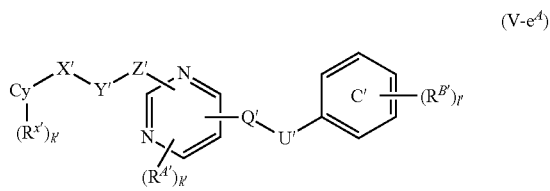

(V-e$^A$)

wherein Ring C', Cy, Q', U', X', Y', Z', $R^{A'}$, $R^{B'}$, $R^{X'}$, k', and l' are as defined herein.

Compounds of Formula (V) include an heteroaryl group for Ring A' optionally substituted with one or more $R^{A'}$ groups. In certain embodiments, when Ring A' is a 1H-pyrazolo[3,4-d]pyrimidin-4-amine, the invention provides compounds of Formula (V-e$^B$):

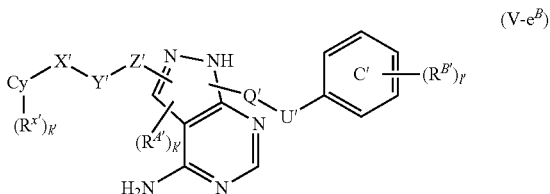

(V-e$^B$)

wherein Ring C', Cy, Q', U', X', Y', Z', $R^{A'}$, $R^{B'}$, $R^{X'}$, k', and l' are as defined herein.

Compounds of Formula (V) include an heteroaryl group for Ring A' optionally substituted with one or more $R^{A'}$ groups. In certain embodiments, when Ring A' is a furo[2,3-c]pyridin-7-amine, the invention provides compounds of Formula (V-e$^C$):

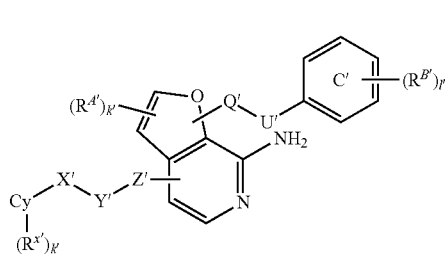

(V-e^C)

wherein Ring C', Cy, Q', U', X', Y', Z', $R^{A'}$, $R^{B'}$, $R^{X'}$, k', and l' are as defined herein.

Compounds of Formula (V) include an heteroaryl group for Ring A' optionally substituted with one or more $R^{A'}$ groups. In certain embodiments, when Ring A' is a quinazoline, the invention provides compounds of Formula (V-e^D):

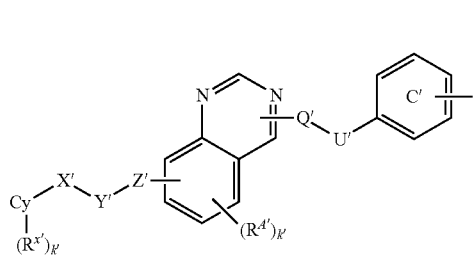

(V-e^D)

wherein Ring C', Cy, Q', U', X', Y', Z', $R^{A'}$, $R^{B'}$, $R^{X'}$, k', and l' are as defined herein.

Compounds of Formula (V) include an heteroaryl group for Ring A' optionally substituted with one or more $R^{A'}$ groups. In certain embodiments, when Ring A' is phenyl, and at least one $R^{A'}$ group links to Cy forming an optional 5 to 8 membered ring, the invention provides compounds of Formula (V-f):

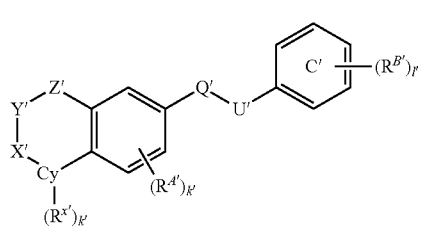

(V-f)

wherein Ring C', Cy, Q', U', X', Y', Z', $R^{A'}$, $R^{B'}$, $R^{X'}$, k', and l' are as defined herein.

Compounds of Formula (V) include an heteroaryl group for Ring A' optionally substituted with one or more $R^{A'}$ groups. In certain embodiments, when Ring A' is phenyl, and at least one $R^{A'}$ group links to Cy forming an optional 5 to 8 membered ring, the invention provides compounds of Formula (V-g):

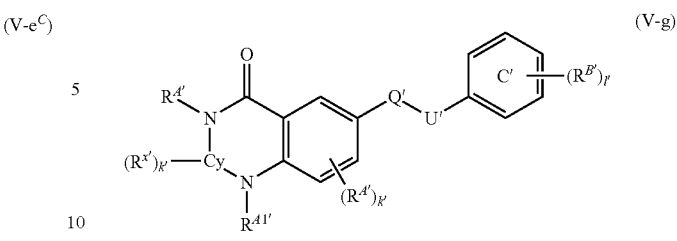

(V-g)

wherein Ring C', Cy, Q', U', X', Y', Z', $R^{A'}$, $R^{B'}$, $R^{X'}$, k', and l' are as defined herein.

In another aspect, provided herein are compounds of Formula (II):

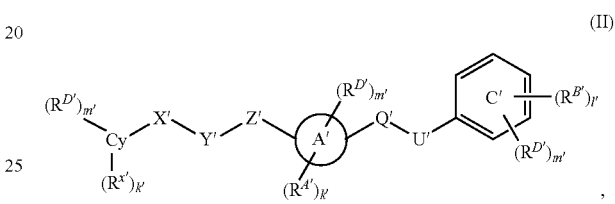

(II)

and pharmaceutically acceptable salts, solvates, hydrates, polymorphs, co-crystals, tautomers, stereoisomers, isotopically labeled derivatives, and prodrugs thereof; wherein:

each instance of $R^{D'}$ is independently an optional electrophilic moiety that can be attached to Cy, Ring A', or Ring C';

each instance of m' is independently 0 or 1; and

Ring A', Ring C', Cy, Q', U', X', Y', Z', $R^{A'}$, $R^{B'}$, $R^{X'}$, k', and l' are as defined herein.

In certain embodiments, $R^{D'}$ is an optional electrophilic moiety that can be attached to Cy, Ring A', or Ring C'; and m' is 0 or 1. In compounds of Formula (II), $R^{D'}$ is an optional electrophilic moiety that can be attached to Cy, Ring A', or Ring C'. In certain embodiments, $R^{D'}$ is any one of Formulae (i-1)-(i-17):

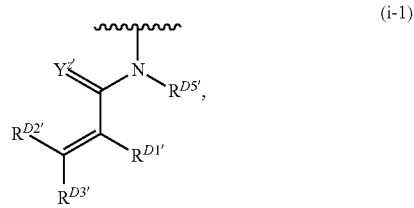

(i-1)

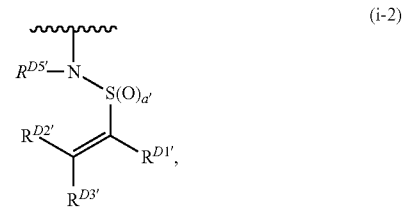

(i-2)

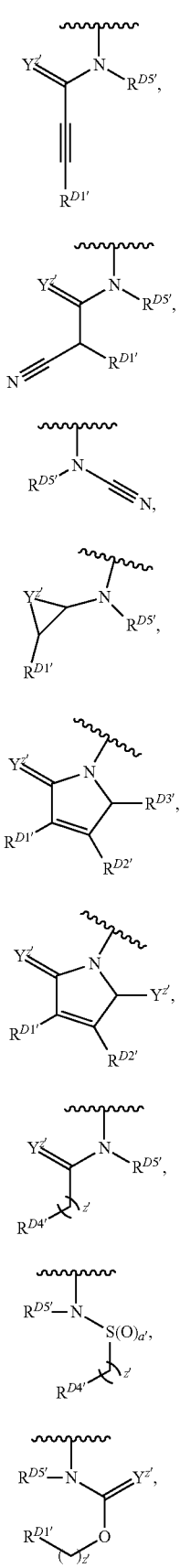
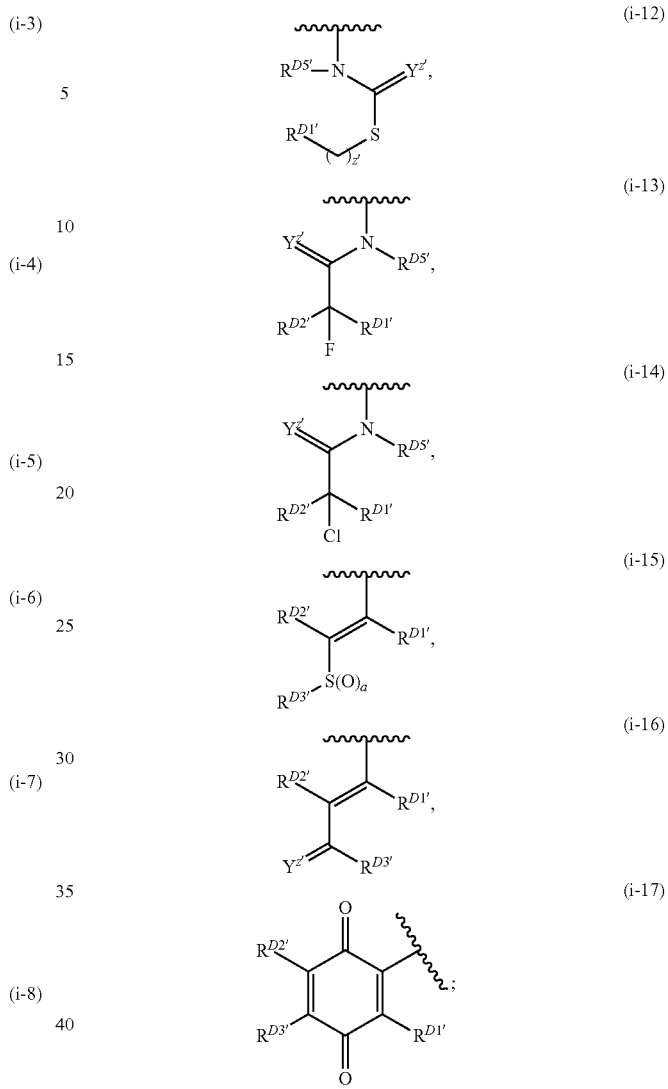

wherein:
R$^{D1'}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —NO$_2$, —OR$^{D1a'}$, —N(R$^{D1a'}$)$_2$, —SR$^{D1a'}$, —CH$_2$OR$^{D1a'}$, —CH$_2$N(R$^{D1a'}$)$_2$, —CH$_2$SR$^{D1a'}$, —C(=O)R$^{D1a'}$, —C(=O)OR$^{D1a'}$, —C(=O)SR$^{D1a'}$, C(=O)N(R$^{D1a'}$)$_2$, —C(=S)R$^{D1a'}$, —C(=S)OR$^{D1a'}$, —C(=S)SR$^{D1a'}$, —C(=S)N(R$^{D1a'}$)$_2$, —C(=NR$^{D1a'}$)R$^{D1a'}$, —C(=NR$^{D1a'}$)OR$^{D1a'}$, —C(=NR$^{D1a'}$)SR$^{D1a'}$, and —C(=NR$^{D1a'}$)N(R$^{D1a'}$)$_2$, wherein each occurrence of R$^{D1a'}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{D1a'}$ groups are joined to form an optionally substituted heterocyclic ring;

R$^{D2'}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —NO$_2$, —OR$^{D2a'}$, —N(R$^{D2a'}$)$_2$, —SR$^{D2a'}$, —CH$_2$OR$^{D2a'}$, —CH$_2$N(R$^{D2a'}$)$_2$, —CH$_2$SR$^{D2a'}$, —C(=O)R$^{D2a'}$, —C(=O)OR$^{D2a'}$, —C(=O)SR$^{D2a'}$, —C(=O)N(R$^{D2a'}$)$_2$, —C(=S)R$^{D2a'}$, —C(=S)OR$^{D2a'}$, —C(=S)SR$^{D2a'}$, —C(=S)N(R$^{D2a'}$)$_2$, —C(=NR$^{D2a'}$)R$^{D2a'}$, —C(=NR$^{D2a'}$)OR$^{D2a'}$, —C(=NR$^{D2a'}$)SR$^{D2a'}$, and —C(=NR$^{D2a'}$)N(R$^{D2a'}$)$_2$, wherein each occurrence of R$^{D2a'}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{D2a'}$ groups are joined to form an optionally substituted heterocyclic ring;

R$^{D3'}$ is selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —NO$_2$, —OR$^{D3a'}$, —N(R$^{D3a'}$)$_2$, —SR$^{D3a'}$, —CH$_2$OR$^{D3a'}$, —CH$_2$N(R$^{D3a'}$)$_2$, —CH$_2$SR$^{D3a'}$, —C(=O)R$^{D3a'}$, —C(=O)OR$^{D3a'}$, —C(=O)SR$^{D3a'}$, —C(=O)N(R$^{D3a'}$)$_2$, —C(=S)R$^{D3a'}$, —C(=S)OR$^{D3a'}$, —C(=S)SR$^{D3a'}$, —C(=S)N(R$^{D3a'}$)$_2$, —C(=NR$^{D3a'}$)R$^{D3a'}$, —C(=NR$^{D3a'}$)OR$^{D3a'}$, —C(=NR$^{D3a'}$)SR$^{D3a'}$, and —C(=NR$^{D3a'}$)N(R$^{D3a'}$)$_2$, wherein each occurrence of R$^{D3a'}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{D3a'}$ groups are joined to form an optionally substituted heterocyclic ring;

optionally R$^{D1'}$, and R$^{D3'}$, or R$^{D2'}$ and R$^{D3'}$, or R$^{D1'}$ and R$^{D2'}$ are joined to form an optionally substituted carbocyclic or optionally substituted heterocyclic ring;

R$^{D4'}$ is a leaving group;

R$^{D5'}$ is hydrogen, C$_{1-6}$ alkyl, or a nitrogen protecting group;

Y$^{Z'}$ is —O, —S, or —NR$^{D6'}$, wherein R$^{D6'}$ is hydrogen, C$_{1-6}$ alkyl, or a nitrogen protecting group;

a' is 1 or 2; and z' is 0, 1, 2, 3, 4, 5, or 6.

Compounds of Formula (II) include an aryl group for Ring A' optionally substituted with one or more R$^{A'}$ groups. In certain embodiments, when Ring A' is naphthyl, the invention provides compounds of Formula (II-a):

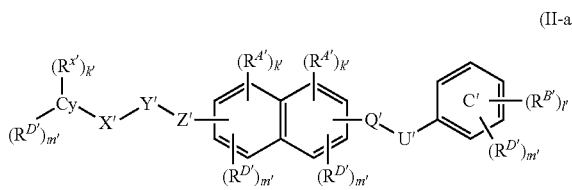

(II-a)

wherein Ring C', Cy, Q', U', X', Y', Z', R$^{A'}$, R$^{B'}$, R$^{D'}$, R$^{X'}$, k', l', and m' are as defined herein.

Compounds of Formula (II) include an aryl group for Ring A' optionally substituted with one or more R$^{A'}$ groups. In certain embodiments, when Ring A' is naphthyl, the invention provides compounds of Formula (II-b):

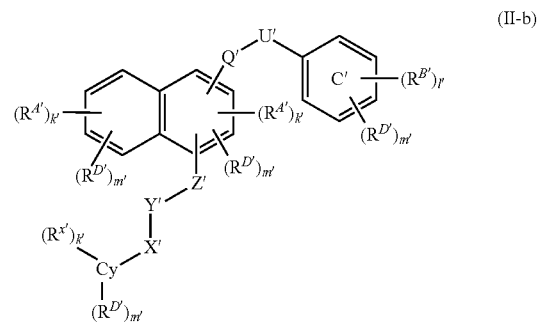

(II-b)

wherein Ring C', Cy, Q', U', X', Y', Z', R$^{A'}$, R$^{B'}$, R$^{D'}$, R$^{X'}$, k', l', and m' are as defined herein.

Compounds of Formula (II) include an aryl group for Ring A' optionally substituted with one or more R$^{A'}$ groups. In certain embodiments, when Ring A' is phenyl, the invention provides compounds of Formula (II-c):

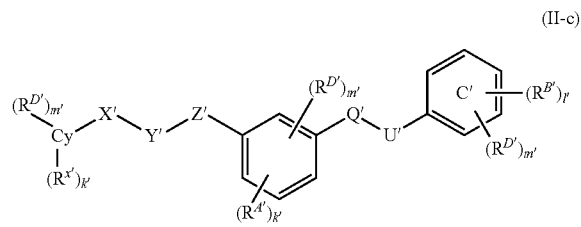

(II-c)

wherein Ring C', Cy, Q', U', X', Y', Z', R$^{A'}$, R$^{B'}$, R$^{D'}$, R$^{X'}$, k', l', and m' are as defined herein.

Compounds of Formula (II) include an aryl group for Ring A' optionally substituted with one or more R$^{A'}$ groups. In certain embodiments, when Ring A' is phenyl, the invention provides compounds of Formula (II-d):

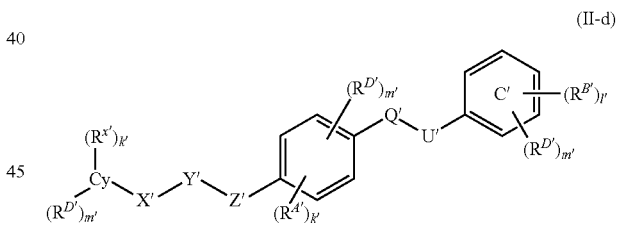

(II-d)

wherein Ring C', Cy, Q', U', X', Y', Z', R$^{A'}$, R$^{B'}$, R$^{D'}$, R$^{X'}$, k', l', and m' are as defined herein.

Compounds of Formula (II) include an heteroaryl group for Ring A' optionally substituted with one or more R$^{A'}$ groups. In certain embodiments, when Ring A' is pyrrolopyrimidine, the invention provides compounds of Formula (II-e):

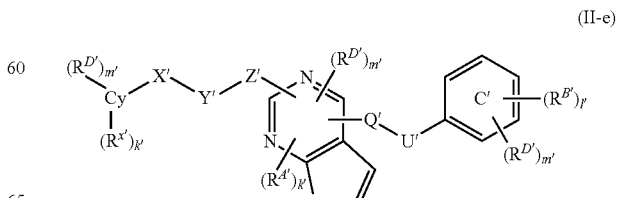

(II-e)

wherein Ring C', Cy, Q', U', X', Y', Z', $R^{A'}$, $R^{B'}$, $R^{D'}$, $R^{X'}$, k', l', and m' are as defined herein.

Compounds of Formula (II) include an heteroaryl group for Ring A' optionally substituted with one or more $R^{A'}$ groups. In certain embodiments, when Ring A' is pyrimidine, the invention provides compounds of Formula (II-e$^A$):

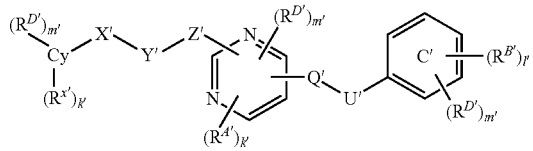

(II-e$^A$)

wherein Ring C', Cy, Q', U', X', Y', Z', $R^{A'}$, $R^{B'}$, $R^{D'}$, $R^{X'}$, k', l', and m' are as defined herein.

Compounds of Formula (II) include an heteroaryl group for Ring A' optionally substituted with one or more $R^{A'}$ groups. In certain embodiments, when Ring A' is pyrimidine, the invention provides compounds of Formula (II-e$^B$):

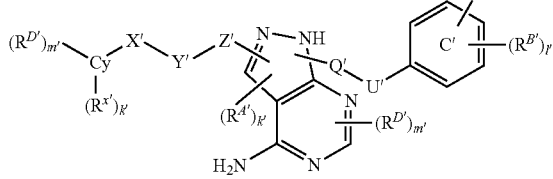

(II-e$^B$)

wherein Ring C', Cy, Q', U', X', Y', Z', $R^{A'}$, $R^{B'}$, $R^{D'}$, $R^{X'}$, k', l', and m' are as defined herein.

Compounds of Formula (II) include an heteroaryl group for Ring A' optionally substituted with one or more $R^{A'}$ groups. In certain embodiments, when Ring A' is a furo[2,3-c]pyridin-7-amine, the invention provides compounds of Formula (II-e$^C$):

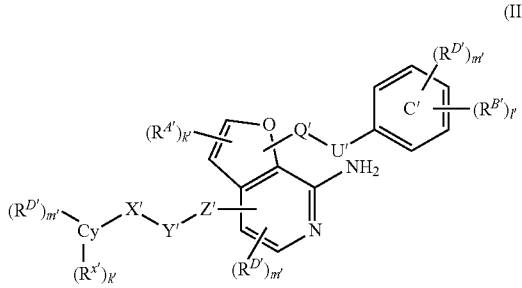

(II-e$^C$)

wherein Ring C', Cy, Q', U', X', Y', Z', $R^{A'}$, $R^{B'}$, $R^{D'}$, $R^{X'}$, k', and l' are as defined herein.

Compounds of Formula (II) include an heteroaryl group for Ring A' optionally substituted with one or more $R^{A'}$ groups. In certain embodiments, when Ring A' is a quinazoline, the invention provides compounds of Formula (II-e$^D$):

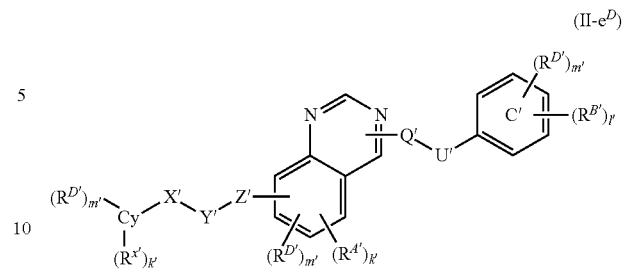

(II-e$^D$)

wherein Ring C', Cy, Q', U', X', Y', Z', $R^{A'}$, $R^{B'}$, $R^{X'}$, k', and l' are as defined herein.

Compounds of Formula (II) include an heteroaryl group for Ring A' optionally substituted with one or more $R^{A'}$ groups. In certain embodiments, when Ring A' is phenyl, and at least one $R^{A'}$ group links to Cy forming an optional 5 to 8 membered ring, the invention provides compounds of Formula (II-f):

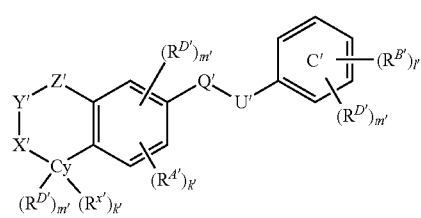

(II-f)

wherein Ring C', Cy, Q', U', X', Y', Z', $R^{A'}$, $R^{B'}$, $R^{D'}$, $R^{X'}$, k', l', and m' are as defined herein.

Compounds of Formula (II) include an heteroaryl group for Ring A' optionally substituted with one or more $R^{A'}$ groups. In certain embodiments, when Ring A' is phenyl, and at least one $R^{A'}$ group links to Cy forming an optional 5 to 8 membered ring, the invention provides compounds of Formula (II-g):

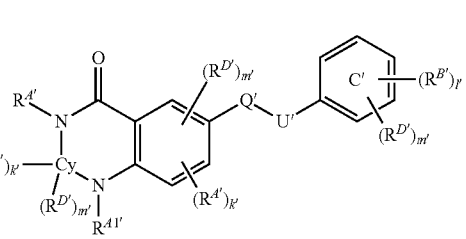

(II-g)

wherein Ring C', Cy, Q', U', X', Y', Z', $R^{A'}$, $R^{B'}$, $R^{D'}$, $R^{X'}$, k', l', and m' are as defined herein.

In compounds of Formula (II), $R^{D'}$ is a substituent on Ring A', Ring C', or Cy. In certain embodiments, $R^{D'}$ comprises a Michael acceptor moiety. This Michael acceptor moiety may react with a cysteine or other nucleophilic residue to allow covalent attachment of the compound to the target. In certain embodiments, the covalent attachment is irreversible. In other embodiments, the covalent attachment is reversible. In certain embodiments, $R^{D'}$ is of Formula (i-1). In certain embodiments, $R^{D'}$ is of Formula (i-2). In certain embodiments, $R^{D'}$ is of Formula (i-3). In certain embodiments, $R^{D'}$ is of Formula (i-4). In certain embodiments, $R^{D'}$ is of Formula (i-5). In certain embodiments, $R^{D'}$ is of Formula (i-6). In certain embodiments, $R^{D'}$ is of Formula (i-7). In certain embodiments, $R^{D'}$ is of Formula (i-8). In certain embodiments, $R^{D'}$ is of Formula (i-9). In certain embodiments, $R^{D'}$ is of Formula (i-10). In certain embodiments, $R^{D'}$ is of Formula (i-11). In certain embodiments, $R^{D'}$ is of Formula (i-12). In certain embodiments, $R^{D'}$ is of Formula (i-13). In certain embodiments, $R^{D'}$ is of Formula (i-14). In certain embodiments, $R^{D'}$ is of Formula (i-15). In certain embodiments, $R^{D'}$ is of Formula (i-16). In certain embodiments, $R^{D'}$ is of Formula (i-17).

In compounds of Formula (II), $R^{D'}$ may include a substituent $R^{D1'}$. In certain embodiments, $R^{D1'}$ is H. In certain embodiments, $R^{D1'}$ is halogen. In certain embodiments, $R^{D1'}$ is F. In certain embodiments, $R^{D1'}$ is Cl. In certain embodiments, $R^{D'}$, is Br. In certain embodiments, $R^{D1'}$ is I (iodine). In certain embodiments, $R^{D1}$, is substituted acyl. In certain embodiments, $R^{D1'}$ is unsubstituted acyl. In certain embodiments, $R^{D1}$, is acetyl. In certain embodiments, $R^{D1'}$ is substituted alkyl. In certain embodiments, $R^{D1}$, is unsubstituted alkyl. In certain embodiments, $R^{D1'}$ is $C_{1-6}$ alkyl. In certain embodiments, $R^{D1'}$ is methyl. In certain embodiments, $R^{D1'}$ is ethyl. In certain embodiments, $R^{D1'}$ is propyl. In certain embodiments, $R^{D1'}$ is butyl. In certain embodiments, $R^{D1'}$ is substituted alkenyl. In certain embodiments, $R^{D1'}$ is unsubstituted alkenyl. In certain embodiments, $R^{D1'}$ is substituted alkynyl. In certain embodiments, $R^{D1'}$ is unsubstituted alkynyl. In certain embodiments, $R^{D1'}$ is substituted carbocyclyl. In certain embodiments, $R^{D1'}$ is unsubstituted carbocyclyl. In certain embodiments, $R^{D1'}$ is substituted heterocyclyl. In certain embodiments, $R^{D1'}$ is unsubstituted heterocyclyl. In certain embodiments, $R^{D1'}$ is substituted aryl. In certain embodiments, $R^{D1'}$ is unsubstituted aryl. In certain embodiments, $R^{D1'}$ is substituted phenyl. In certain embodiments, $R^{D1'}$ is unsubstituted phenyl. In certain embodiments, $R^{D1'}$ is substituted heteroaryl. In certain embodiments, $R^{D1'}$ is unsubstituted heteroaryl. In certain embodiments, $R^{D1'}$ is substituted pyridyl. In certain embodiments, $R^{D1'}$ is unsubstituted pyridyl. In certain embodiments, $R^{D1'}$ is —CN. In certain embodiments, $R^{D1'}$ is —NO$_2$. In certain embodiments, $R^{D1'}$ is —OR$^{D1a'}$. In certain embodiments, $R^{D1'}$ is —N(R$^{D1a'}$)$_2$. In certain embodiments, $R^{D1'}$ is —SR$^{D1a'}$. In certain embodiments, $R^{D1'}$, is —CH$_2$OR$^{D1a'}$. In certain embodiments, $R^{D1'}$ is —CH$_2$N(R$^{D1a'}$)$_2$. In certain embodiments, $R^{D1'}$ is —CH$_2$SR$^{D1a'}$.

In certain embodiments, at least one $R^{D1a'}$ is H. In certain embodiments, at least one $R^{D1a'}$ is substituted acyl. In certain embodiments, at least one $R^{D1a'}$ is unsubstituted acyl. In certain embodiments, at least one $R^{D1a'}$ is acetyl. In certain embodiments, at least one $R^{D1a}$, is substituted alkyl. In certain embodiments, at least one $R^{D1a'}$ is unsubstituted alkyl. In certain embodiments, at least one $R^{D1a'}$ is $C_{1-6}$ alkyl. In certain embodiments, at least one $R^{D1a'}$ is methyl. In certain embodiments, at least one $R^{D1a'}$ is ethyl. In certain embodiments, at least one $R^{D1a'}$ is propyl. In certain embodiments, at least one $R^{D1a'}$ is butyl. In certain embodiments, at least one $R^{D1a'}$ is substituted alkenyl. In certain embodiments, at least one $R^{D1a'}$ is unsubstituted alkenyl. In certain embodiments, at least one $R^{D1a'}$ is substituted alkynyl. In certain embodiments, at least one $R^{D1a'}$ is unsubstituted alkynyl. In certain embodiments, at least one $R^{D1a'}$ is substituted carbocyclyl. In certain embodiments, at least one $R^{D1a'}$ is unsubstituted carbocyclyl. In certain embodiments, at least one $R^{D1a'}$ is substituted heterocyclyl. In certain embodiments, at least one $R^{D1a'}$ is unsubstituted heterocyclyl. In certain embodiments, at least one $R^{D1a'}$ is substituted aryl. In certain embodiments, at least one $R^{D1a'}$ is unsubstituted aryl. In certain embodiments, at least one $R^{D1a'}$ is substituted phenyl. In certain embodiments, at least one $R^{D1a'}$ is unsubstituted phenyl. In certain embodiments, at least one $R^{D1a'}$ is substituted heteroaryl. In certain embodiments, at least one $R^{D1a'}$ is unsubstituted heteroaryl. In certain embodiments, at least one $R^{D1a'}$ is substituted pyridyl. In certain embodiments, at least one $R^{D1a'}$ is unsubstituted pyridyl. In certain embodiments, at least one $R^{D1a'}$ is a nitrogen protecting group when attached to a nitrogen atom. In certain embodiments, at least one $R^{D1a'}$ is Bn, BOC, Cbz, Fmoc, trifluoroacetyl, triphenylmethyl, or Ts when attached to a nitrogen atom. In certain embodiments, $R^{D1a'}$ is an oxygen protecting group when attached to an oxygen atom. In certain embodiments, $R^{D1a'}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{D1a'}$ is a sulfur protecting group when attached to a sulfur atom. In certain embodiments, $R^{D1a'}$ is acetamidomethyl, t-Bu, 3-nitro-2-pyridine sulfenyl, 2-pyridine-sulfenyl, or triphenylmethyl when attached to a sulfur atom. In certain embodiments, two $R^{D1a'}$ groups are joined to form a substituted heterocyclic ring. In certain embodiments, two $R^{D1a'}$ groups are joined to form an unsubstituted heterocyclic ring.

In compounds of Formula (II), $R^{D'}$ may include a substituent $R^{D2'}$. In certain embodiments, $R^{D2'}$ is H. In certain embodiments, $R^{D2'}$ is halogen. In certain embodiments, $R^{D2}$, is F. In certain embodiments, $R^{D2'}$ is Cl. In certain embodiments, $R^{D2'}$ is Br. In certain embodiments, $R^{D2'}$ is I (iodine). In certain embodiments, $R^{D2'}$ is substituted acyl. In certain embodiments, $R^{D2'}$ is unsubstituted acyl. In certain embodiments, $R^{D2'}$ is acetyl. In certain embodiments, $R^{D2'}$ is substituted alkyl. In certain embodiments, $R^{D2'}$ is unsubstituted alkyl. In certain embodiments, $R^{D2'}$ is $C_{1-6}$ alkyl. In certain embodiments, $R^{D2'}$ is methyl. In certain embodiments, $R^{D2'}$ is ethyl. In certain embodiments, $R^{D2'}$ is propyl. In certain embodiments, $R^{D2'}$ is butyl. In certain embodiments, $R^{D2'}$ is substituted alkenyl. In certain embodiments, $R^{D2'}$ is unsubstituted alkenyl. In certain embodiments, $R^{D2'}$ is substituted alkynyl. In certain embodiments, $R^{D2'}$ is unsubstituted alkynyl. In certain embodiments, $R^{D2'}$ is substituted carbocyclyl. In certain embodiments, $R^{D2'}$ is unsubstituted carbocyclyl. In certain embodiments, $R^{D2'}$ is substituted heterocyclyl. In certain embodiments, $R^{D2'}$ is unsubstituted heterocyclyl. In certain embodiments, $R^{D2'}$ is substituted aryl. In certain embodiments, $R^{D2'}$ is unsubstituted aryl. In certain embodiments, $R^{D2'}$ is substituted phenyl. In certain embodiments, $R^{D2'}$ is unsubstituted phenyl. In certain embodiments, $R^{D2'}$ is substituted heteroaryl. In certain embodiments, $R^{D2'}$ is unsubstituted heteroaryl. In certain embodiments, $R^{D2}$, is substituted pyridyl. In certain embodiments, $R^{D2'}$ is unsubstituted pyridyl. In certain embodiments, $R^{D2'}$ is —CN. In certain embodiments, $R^{D2'}$ is —NO$_2$. In certain embodiments, $R^{D2'}$ is —OR$^{D2a'}$. In certain embodiments, $R^{D2'}$ is —N(R$^{D2a'}$)$_2$. In certain embodiments, $R^{D2'}$ is —SR$^{D2a'}$. In certain embodiments, $R^{D2'}$ is —CH$_2$OR$^{D2a'}$. In certain embodiments, $R^{D2'}$ is —CH$_2$N(R$^{D2a'}$)$_2$. In certain embodiments, $R^{D2'}$ is —CH$_2$SR$^{D2a'}$.

In certain embodiments, at least one $R^{D2a'}$ is H. In certain embodiments, at least one $R^{D2a'}$ is substituted acyl. In certain embodiments, at least one $R^{D2a'}$ is unsubstituted acyl. In certain embodiments, at least one $R^{D2a'}$ is acetyl. In certain embodiments, at least one $R^{D2a'}$ is substituted alkyl. In certain embodiments, at least one $R^{D2a'}$ is unsubstituted alkyl. In certain embodiments, at least one $R^{D2a'}$ is $C_{1-6}$ alkyl. In certain embodiments, at least one $R^{D2a'}$ is methyl. In certain embodiments, at least one $R^{D2a'}$ is ethyl. In certain embodiments, at least one $R^{D2a'}$ is propyl. In certain embodiments, at least one $R^{D2a'}$ is butyl. In certain embodiments, at least one $R^{D2a'}$ is substituted alkenyl. In certain embodiments, at least one $R^{D2a'}$ is unsubstituted alkenyl. In certain embodiments, at least one $R^{D2a'}$ is substituted alkynyl. In certain embodiments, at least one $R^{D2a'}$ is unsubstituted alkynyl. In certain embodiments, at least one $R^{D2a'}$ is substituted carbocyclyl. In certain embodiments, at least one $R^{D2a'}$ is unsubstituted carbocyclyl. In certain embodiments, at least one $R^{D2a'}$ is substituted heterocyclyl. In certain embodiments, at least one $R^{D2a'}$ is unsubstituted heterocyclyl. In certain embodiments, at least one $R^{D2a'}$ is substituted aryl. In certain embodiments, at least one $R^{D2a'}$ is unsubstituted aryl. In certain embodiments, at least one $R^{D2a'}$ is substituted phenyl. In certain embodiments, at least one $R^{D2a'}$ is unsubstituted phenyl. In certain embodiments, at least one $R^{D2a'}$ is substituted heteroaryl. In certain embodiments, at least one $R^{D2a'}$ is unsubstituted heteroaryl. In certain embodiments, at least one $R^{D2a'}$ is substituted pyridyl. In certain embodiments, at least one $R^{D2a'}$ is unsubstituted pyridyl. In certain embodiments, at least one $R^{D2a'}$ is a nitrogen protecting group when attached to a nitrogen atom. In certain embodiments, at least one $R^{D2a'}$ is Bn, BOC, Cbz, Fmoc, trifluoroacetyl, triphenylmethyl, or Ts when attached to a nitrogen atom. In certain embodiments, $R^{D2a'}$ is an oxygen protecting group when attached to an oxygen atom. In certain embodiments, $R^{D2a'}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{D2a'}$ is a sulfur protecting group when attached to a sulfur atom. In certain embodiments, $R^{D2a'}$ is acetamidomethyl, t-Bu, 3-nitro-2-pyridine sulfenyl, 2-pyridine-sulfenyl, or triphenylmethyl when attached to a sulfur atom. In certain embodiments, two $R^{D2a'}$ groups are joined to form a substituted heterocyclic ring. In certain embodiments, two $R^{D2a'}$ groups are joined to form an unsubstituted heterocyclic ring.

In compounds of Formula (II), $R^{D'}$ may include a substituent $R^{D3'}$. In certain embodiments, $R^{D3'}$ is H. In certain embodiments, $R^{D3'}$ is halogen. In certain embodiments, $R^{D3'}$ is F. In certain embodiments, $R^{D3'}$ is Cl. In certain embodiments, $R^{D3'}$ is Br. In certain embodiments, $R^{D3'}$ is I (iodine). In certain embodiments, $R^{D3'}$ is substituted acyl. In certain embodiments, $R^{D3'}$ is unsubstituted acyl. In certain embodiments, $R^{D3'}$ is acetyl. In certain embodiments, $R^{D3'}$ is substituted alkyl. In certain embodiments, $R^{D3'}$ is unsubstituted alkyl. In certain embodiments, $R^{D3'}$ is $C_{1-6}$ alkyl. In certain embodiments, $R^{D3'}$ is methyl. In certain embodiments, $R^{D3'}$ is ethyl. In certain embodiments, $R^{D3'}$ is propyl. In certain embodiments, $R^{D3'}$ is butyl. In certain embodiments, $R^{D3'}$ is substituted alkenyl. In certain embodiments, $R^{D3'}$ is unsubstituted alkenyl. In certain embodiments, $R^{D3'}$ is substituted alkynyl. In certain embodiments, $R^{D3'}$ is unsubstituted alkynyl. In certain embodiments, $R^{D3'}$ is substituted carbocyclyl. In certain embodiments, $R^{D3'}$ is unsubstituted carbocyclyl. In certain embodiments, $R^{D3'}$ is substituted heterocyclyl. In certain embodiments, $R^{D3'}$ is unsubstituted heterocyclyl. In certain embodiments, $R^{D3'}$ is substituted aryl. In certain embodiments, $R^{D3'}$ is unsubstituted aryl. In certain embodiments, $R^{D3'}$ is substituted phenyl. In certain embodiments, $R^{D3'}$ is unsubstituted phenyl. In certain embodiments, $R^{D3'}$ is substituted heteroaryl. In certain embodiments, $R^{D3'}$ is unsubstituted heteroaryl. In certain embodiments, $R^{D3'}$ is substituted pyridyl. In certain embodiments, $R^{D3'}$ is unsubstituted pyridyl. In certain embodiments, $R^{D3'}$ is —CN. In certain embodiments, $R^{D3'}$ is —NO$_2$. In certain embodiments, $R^{D3'}$ is —OR$^{D3a'}$. In certain embodiments, $R^{D3'}$ is —N(R$^{D3a'}$)$_2$. In certain embodiments, $R^{D3'}$ is —SR$^{D3a'}$. In certain embodiments, $R^{D3'}$ is —CH$_2$OR$^{D3a'}$. In certain embodiments, $R^{D3'}$ is —CH$_2$N(R$^{D3a'}$)$_2$. In certain embodiments, $R^{D3'}$ is —CH$_2$SR$^{D3a'}$.

In certain embodiments, at least one $R^{D3a'}$ is H. In certain embodiments, at least one $R^{D3a'}$ is substituted acyl. In certain embodiments, at least one $R^{D3a'}$ is unsubstituted acyl. In certain embodiments, at least one $R^{D3a'}$ is acetyl. In certain embodiments, at least one $R^{D3a'}$ is substituted alkyl. In certain embodiments, at least one $R^{D3a'}$ is unsubstituted alkyl. In certain embodiments, at least one $R^{D3a'}$ is $C_{1-6}$ alkyl. In certain embodiments, at least one $R^{D3a'}$ is methyl. In certain embodiments, at least one $R^{D3a'}$ is ethyl. In certain embodiments, at least one $R^{D3a'}$ is propyl. In certain embodiments, at least one $R^{D3a'}$ is butyl. In certain embodiments, at least one $R^{D3a'}$ is substituted alkenyl. In certain embodiments, at least one $R^{D3a'}$ is unsubstituted alkenyl. In certain embodiments, at least one $R^{D3a'}$ is substituted alkynyl. In certain embodiments, at least one $R^{D3a'}$ is unsubstituted alkynyl. In certain embodiments, at least one $R^{D3a'}$ is substituted carbocyclyl. In certain embodiments, at least one $R^{D3a'}$ is unsubstituted carbocyclyl. In certain embodiments, at least one $R^{D3a'}$ is substituted heterocyclyl. In certain embodiments, at least one $R^{D3a'}$ is unsubstituted heterocyclyl. In certain embodiments, at least one $R^{D3a'}$ is substituted aryl. In certain embodiments, at least one $R^{D3a'}$ is unsubstituted aryl. In certain embodiments, at least one $R^{D3a'}$ is substituted phenyl. In certain embodiments, at least one $R^{D3a'}$ is unsubstituted phenyl. In certain embodiments, at least one $R^{D3a}$, is substituted heteroaryl. In certain embodiments, at least one $R^{D3a'}$ is unsubstituted heteroaryl. In certain embodiments, at least one $R^{D3a'}$ is substituted pyridyl. In certain embodiments, at least one $R^{D3a'}$ is unsubstituted pyridyl. In certain embodiments, at least one $R^{D3a'}$ is a nitrogen protecting group when attached to a nitrogen atom. In certain embodiments, at least one $R^{D3a'}$ is Bn, BOC, Cbz, Fmoc, trifluoroacetyl, triphenylmethyl, or Ts when attached to a nitrogen atom. In certain embodiments, $R^{D3a'}$ is an oxygen protecting group when attached to an oxygen atom. In certain embodiments, $R^{D3a'}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{D3a'}$ is a sulfur protecting group when attached to a sulfur atom. In certain embodiments, $R^{D3a'}$ is acetamidomethyl, t-Bu, 3-nitro-2-pyridine sulfenyl, 2-pyridine-sulfenyl, or triphenylmethyl when attached to a sulfur atom. In certain embodiments, two $R^{D3a'}$ groups are joined to form a substituted heterocyclic ring. In certain embodiments, two $R^{D3a'}$ groups are joined to form an unsubstituted heterocyclic ring.

In compounds of Formula (II), $R^{D'}$ may include a substituent $R^{D4'}$. In certain embodiments, $R^{D4'}$ is a leaving group. In certain embodiments, $R^{D4'}$ is halogen. In certain embodiments, $R^{D4'}$ is F. In certain embodiments, $R^{D4'}$ is Cl. In certain embodiments, $R^{D4'}$ is Br. In certain embodiments, $R^{D4'}$ is I (iodine). In certain embodiments, $R^{D4'}$ is —OS(=O)$_{w'}$R$^{D4a'}$. In certain embodiments, w' is 1. In certain embodiments, w' is 2. In certain embodiments, $R^{D4'}$ is —OMs. In certain embodiments, $R^{D4'}$ is —OTf. In certain embodiments, $R^{D4'}$ is —OTs. In certain embodiments, $R^{D4'}$ is —OBs. In certain embodiments, $R^{D4'}$ is 2-nitrobenzene-sulfonyloxy. In certain embodiments, $R^{D4'}$ is —OR$^{D4a'}$. In certain embodiments, $R^{D4'}$ is —OMe. In certain embodiments, $R^{D4'}$ is —OCF$_3$. In certain embodiments, $R^{D4'}$ is —OPh. In certain embodiments, $R^{D4'}$ is —OC(=O)$R^{D4a'}$. In certain embodiments, $R^{D4'}$ is —OC(=O)Me. In certain embodiments, $R^{D4'}$ is —OC(=O)CF$_3$. In certain embodiments, $R^{D4'}$ is —OC(=O)Ph. In certain embodiments, $R^{D4'}$ is —OC(=O)Cl. In certain embodiments, $R^{D4'}$ is —OC(=O)O$R^{D4a'}$. In certain embodiments, $R^{D4'}$ is —OC(=O)OMe. In certain embodiments, $R^{D4'}$ is —OC(=O)O(t-Bu).

In certain embodiments, $R^{D4a'}$ is substituted alkyl. In certain embodiments, $R^{D4a'}$ is unsubstituted alkyl. In certain embodiments, $R^{D4a'}$ is $C_{1-6}$ alkyl. In certain embodiments, $R^{D4a'}$ is methyl. In certain embodiments, $R^{D4a'}$ is ethyl. In certain embodiments, $R^{D4a'}$ is propyl. In certain embodiments, $R^{D4a'}$ is butyl. In certain embodiments, $R^{D4a'}$ is substituted alkenyl. In certain embodiments, $R^{D4a'}$ is unsubstituted alkenyl. In certain embodiments, $R^{D4a'}$ is vinyl. In certain embodiments, $R^{D4a'}$ is substituted alkynyl. In certain embodiments, $R^{D4a'}$ is unsubstituted alkynyl. In certain embodiments, $R^{D4a'}$ is ethynyl. In certain embodiments, $R^{D4a'}$ is substituted carbocyclyl. In certain embodiments, $R^{D4a'}$ is unsubstituted carbocyclyl. In certain embodiments, $R^{D4a'}$ is substituted heterocyclyl. In certain embodiments, $R^{D4a'}$ is unsubstituted heterocyclyl. In certain embodiments, $R^{D4a'}$ is substituted aryl. In certain embodiments, $R^{D4a'}$ is unsubstituted aryl. In certain embodiments, $R^{D4a'}$ is substituted phenyl. In certain embodiments, $R^{D4a'}$ is unsubstituted phenyl. In certain embodiments, $R^{D4a'}$ is substituted heteroaryl. In certain embodiments, $R^{D4a'}$ is unsubstituted heteroaryl. In certain embodiments, $R^{D4a'}$ is substituted pyridyl. In certain embodiments, $R^{D4a'}$ is unsubstituted pyridyl.

In compounds of Formula (II), $R^{D'}$ may include a substituent $R^{D5'}$. In certain embodiments, $R^{D5'}$ is H. In certain embodiments, $R^{D5'}$ is substituted alkyl. In certain embodiments, $R^{D5'}$ is unsubstituted alkyl. In certain embodiments, $R^{D5'}$ is $C_{1-6}$ alkyl. In certain embodiments, $R^{D5'}$ is methyl. In certain embodiments, $R^{D5'}$ is ethyl. In certain embodiments, $R^{D5'}$ is propyl. In certain embodiments, $R^{D5'}$ is butyl. In certain embodiments, $R^{D5'}$ is a nitrogen protecting group. In certain embodiments, $R^{D5'}$ is Bn, BOC, Cbz, Fmoc, trifluoroacetyl, triphenylmethyl, or Ts.

In certain embodiments, $R^{D1'}$ and $R^{D2'}$ are each hydrogen. In certain embodiments, $R^{D1'}$ and $R^{D3'}$ are each hydrogen. In certain embodiments, $R^{D2'}$ and $R^{D3'}$ are each hydrogen. In certain embodiments, $R^{D1'}$, $R^{D2'}$, and $R^{D3'}$ are each hydrogen. In certain embodiments, $R^{D1'}$, $R^{D2'}$, and $R^{D3'}$, and $R^{D5'}$ are each hydrogen.

In certain embodiments, A' is 1. In certain embodiments, A' is 2.

In certain embodiments, z' is 0. In certain embodiments, z' is 1. In certain embodiments, z' is 2. In certain embodiments, Z' is 3. In certain embodiments, z' is 4. In certain embodiments, z' is 5. In certain embodiments, z' is 6.

In certain embodiments, $Y^{Z'}$ is —O—. In certain embodiments, $Y^{Z'}$ is =O. In certain embodiments, $Y^{Z'}$ is —S—. In certain embodiments, $Y^{Z'}$ is =S. In certain embodiments, $Y^{Z'}$ is —$NR^{D6'}$—, wherein $R^{D6'}$ is hydrogen, $C_{1-6}$ alkyl, or a nitrogen protecting group. In certain embodiments, $Y^{Z'}$ is —NH—. In certain embodiments, $Y^{Z'}$ is —NCH$_3$—. In certain embodiments, $Y^{Z'}$ is —N(BOC)—. In certain embodiments, $Y^{Z'}$ is —N(Fmoc)-. In certain embodiments, $Y^{Z'}$ is —N(Cbz)-. In certain embodiments, $Y^{Z'}$ is —N(Bn)-. In certain embodiments, $Y^{Z'}$ is =$NR^{D6'}$, wherein $R^{D6'}$ is hydrogen, $C_{1-6}$ alkyl, or a nitrogen protecting group. In certain embodiments, $Y^{Z'}$ is =NH. In certain embodiments, $Y^{Z'}$ is =NCH$_3$. In certain embodiments, $Y^{Z'}$ is =NTs. In certain embodiments, $Y^{Z'}$ is =NBn. In certain embodiments, $Y^{Z'}$ is =NCH(Ph)$_2$.

In certain embodiments, $R^{D'}$ is of the formula:

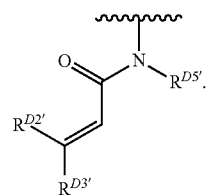

In certain embodiments, $R^{D'}$ is of the formula:

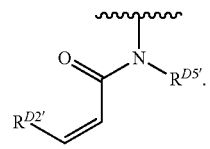

In certain embodiments, $R^{D'}$ is of the formula:

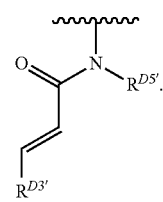

In certain embodiments, $R^{D'}$ is of the formula:

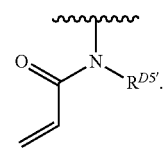

In certain embodiments, $R^{D'}$ is of the formula:

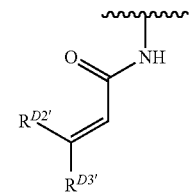

In certain embodiments, $R^{D'}$ is of the formula:

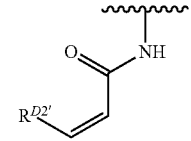

In certain embodiments, $R^{D'}$ is of the formula:

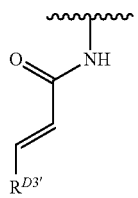

In certain embodiments, $R^{D'}$ is of the formula:

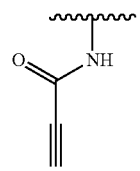

In certain embodiments, $R^{D'}$ is of the formula:

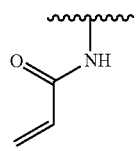

In certain embodiments, $R^{D'}$ is of the formula:

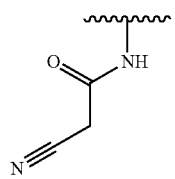

In certain embodiments, $R^{D'}$ is of the formula:

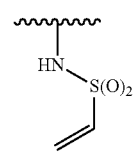

In certain embodiments, $R^{D'}$ is of the formula:

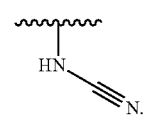

In certain embodiments, $R^{D'}$ is of the formula:

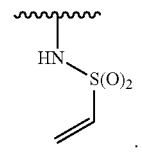

In certain embodiments, $R^{D'}$ is of the formula:

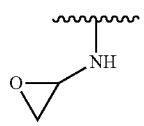

In certain embodiments, $R^{D'}$ is of the formula:

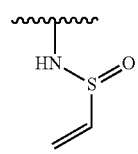

In certain embodiments, $R^{D'}$ is of the formula:

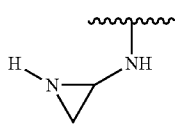

In certain embodiments, $R^{D'}$ is of the formula:

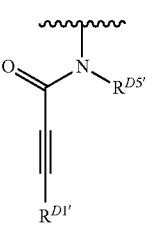

In certain embodiments, $R^{D'}$ is of the formula:

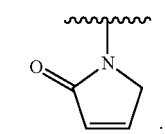

In certain embodiments, $R^{D'}$ is of the formula:

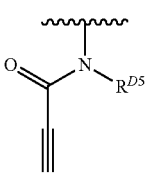

In certain embodiments, $R^{D'}$ is of the formula:

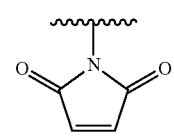

In certain embodiments, $R^{D'}$ is of the formula:

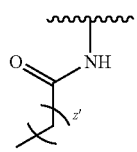

In certain embodiments, $R^{D'}$ is of the formula:

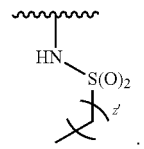

In certain embodiments, $R^{D'}$ is of the formula:

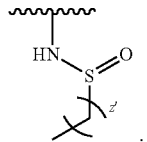

In certain embodiments, $R^{D'}$ is of the formula:

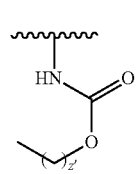

In certain embodiments, $R^{D'}$ is of the formula:

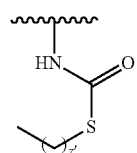

In certain embodiments, $R^{D'}$ is of the formula:

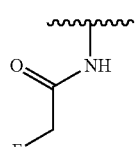

In certain embodiments, $R^{D'}$ is of the formula:

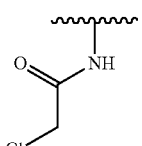

Compounds of Formula (II) or (V) include an aryl Ring A' optionally substituted with one or more $R^{A'}$ groups. In certain embodiments, k' is 0. In certain embodiments, Ring A' is of the formula:

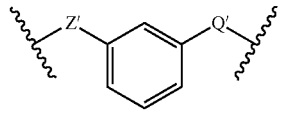

In certain embodiments, Ring A' is of the formula:

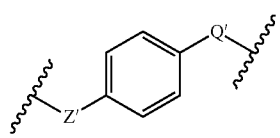

In certain embodiments, k' is 1. In certain embodiments, Ring A' is of the formula:

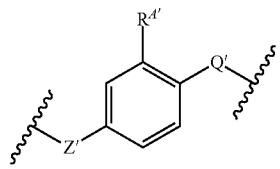

In certain embodiments, Ring A' is of the formula:

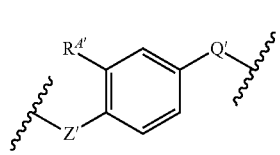

In certain embodiments, Ring A' is of the formula:

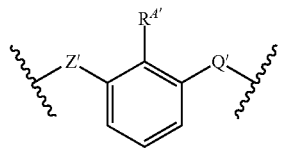

In certain embodiments, Ring A' is of the formula:

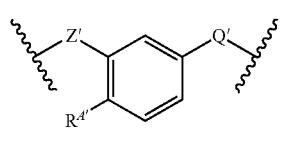

In certain embodiments, Ring A' is of the formula:

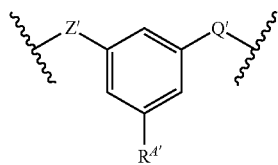

In certain embodiments, Ring A' is of the formula:

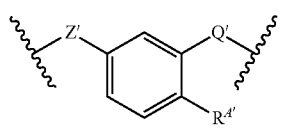

In certain embodiments, k' is 2. In certain embodiments, Ring A' is of the formula:

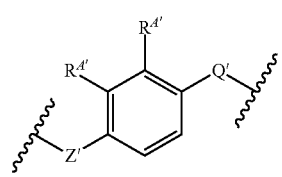

In certain embodiments, Ring A' is of the formula:

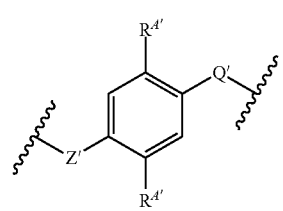

In certain embodiments, Ring A' is of the formula:

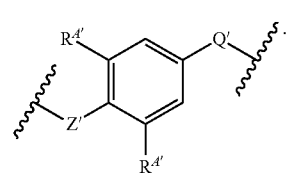

In certain embodiments, Ring A' is of the formula:

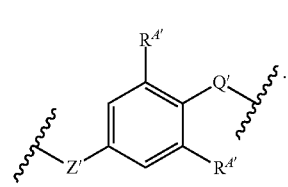

In certain embodiments, Ring A' is of the formula:

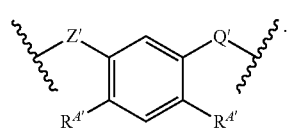

In certain embodiments, Ring A' is of the formula:

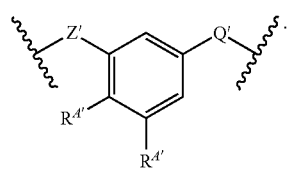

In certain embodiments, Ring A' is of the formula:

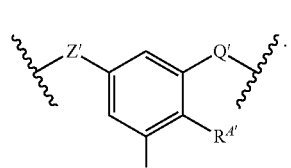

In certain embodiments, Ring A' is of the formula:

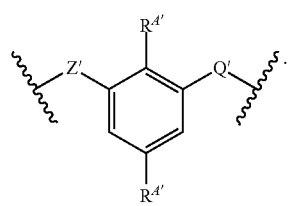

In certain embodiments, Ring A' is of the formula:

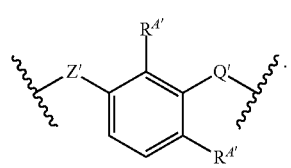

In certain embodiments, Ring A' is of the formula:

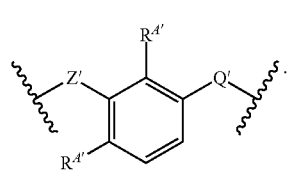

In certain embodiments, k' is 3. In certain embodiments, Ring A' is of the formula:

In certain embodiments, Ring A' is of the formula:

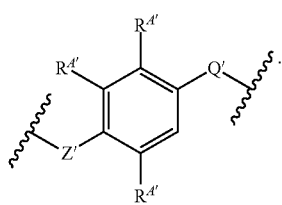

In certain embodiments, Ring A' is of the formula:

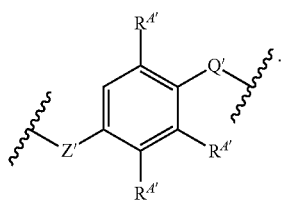

In certain embodiments, Ring A' is of the formula:

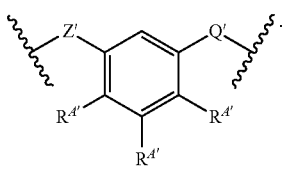

In certain embodiments, Ring A' is of the formula:

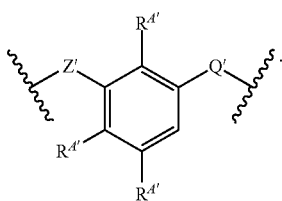

In certain embodiments, Ring A' is of the formula:

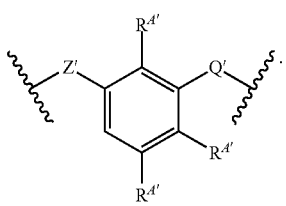

In certain embodiments, k' is 4. In certain embodiments, Ring A' is of the formula:

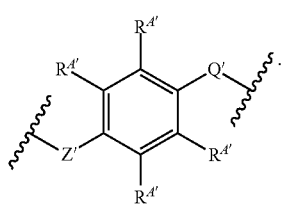

In certain embodiments, Ring A' is of the formula:

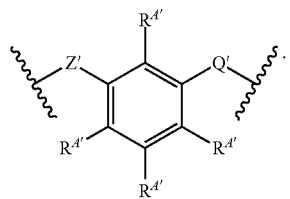

Compounds of Formula (II) or (V) include an aryl Ring A' optionally substituted with one or more $R^{A'}$ groups. In certain embodiments, X', Y', and Z' are bonds, and Cy is hydrogen. In certain embodiments, k' is 0. In certain embodiments, Ring A' is of the formula:

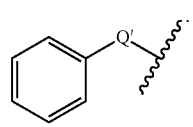

In certain embodiments, k' is 1. In certain embodiments, Ring A' is of the formula:

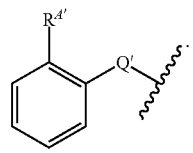

In certain embodiments, Ring A' is of the formula:

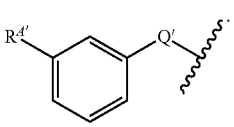

In certain embodiments, Ring A' is of the formula:

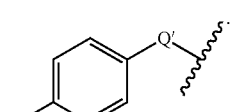

In certain embodiments, k' is 2. In certain embodiments, Ring A' is of the formula:

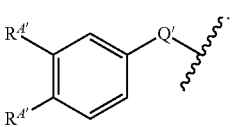

In certain embodiments, Ring A' is of the formula:

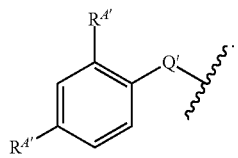

In certain embodiments, Ring A' is of the formula:

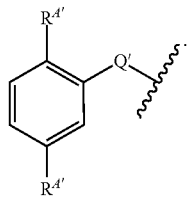

In certain embodiments, Ring A' is of the formula:

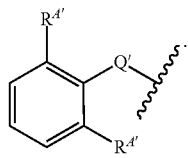

In certain embodiments, Ring A' is of the formula:

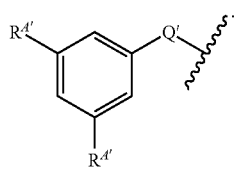

In certain embodiments, Ring A' is of the formula:

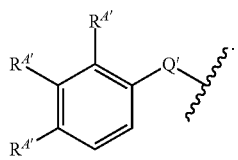

In certain embodiments, Ring A' is of the formula:

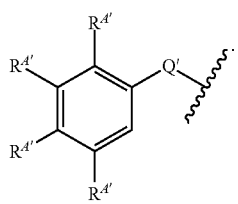

In certain embodiments, Ring A' is of the formula:

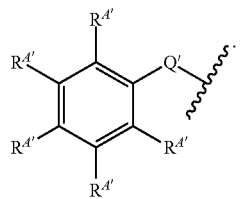

In compounds of Formula (II) or (V), Ring A' may be substituted with one or more $R^{A'}$ groups. In certain embodiments, at least one $R^{A'}$ is H. In certain embodiments, at least two $R^{A'}$ groups are H. In certain embodiments, at least three $R^{A'}$ groups are H. In certain embodiments, at least four $R^{A'}$ groups are H. In certain embodiments, at least one $R^{A'}$ is halogen. In certain embodiments, at least one $R^{A'}$ is F. In certain embodiments, at least one $R^{A'}$ is Cl. In certain embodiments, at least one $R^{A'}$ is Br. In certain embodiments, at least one $R^{A'}$ is I (iodine). In certain embodiments, at least one $R^{A'}$ is substituted acyl. In certain embodiments, at least one $R^{A'}$ is —C(=O)N($R^{A1'}$)$_2$. In certain embodiments, at least one $R^{A'}$ is —C(=O)NH$R^{A1'}$. In certain embodiments, at least one $R^{A'}$ is —C(=O)NH(C$_{1-6}$ alkyl). In certain embodiments, at least one $R^{A'}$ is —C(=O)NHMe. In certain embodiments, at least one $R^{A'}$ is —C(=O)NH$_2$. In certain embodiments, at least one $R^{A'}$ is unsubstituted acyl. In certain embodiments, at least one $R^{A'}$ is acetyl. In certain embodiments, at least one $R^{A'}$ is substituted alkyl. In certain embodiments, at least one $R^{A'}$ is substituted methyl. In certain embodiments, at least one $R^{A'}$ is unsubstituted alkyl. In certain embodiments, at least one $R^{A'}$ is C$_{1-6}$ alkyl. In certain embodiments, at least one $R^{A'}$ is methyl. In certain embodiments, at least one $R^{A'}$ is ethyl. In certain embodiments, at least one $R^{A'}$ is propyl. In certain embodiments, at least one $R^{A'}$ is butyl. In certain embodiments, at least one $R^{A'}$ is substituted alkenyl. In certain embodiments, at least one $R^{A'}$ is unsubstituted alkenyl. In certain embodiments, at least one $R^{A'}$ is substituted alkynyl. In certain embodiments, at least one $R^{A'}$ is unsubstituted alkynyl. In certain embodiments, at least one $R^{A'}$ is substituted carbocyclyl. In certain embodiments, at least one $R^{A'}$ is unsubstituted carbocyclyl. In certain embodiments, at least one $R^{A'}$ is substituted heterocyclyl. In certain embodiments, at least one $R^{A'}$ is unsubstituted heterocyclyl. In certain embodiments, at least one $R^{A'}$ is

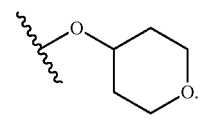

In certain embodiments, at least one $R^{A'}$ is substituted aryl. In certain embodiments, at least one $R^{A'}$ is unsubstituted aryl. In certain embodiments, at least one $R^{A'}$ is substituted phenyl. In certain embodiments, at least one $R^{A'}$ is unsubstituted phenyl. In certain embodiments, at least one $R^{A'}$ is substituted heteroaryl. In certain embodiments, at least one $R^{A'}$ is unsubstituted heteroaryl. In certain embodiments, at least one $R^{A'}$ is substituted pyridyl. In certain embodiments, at least one $R^{A'}$ is unsubstituted pyridyl. In certain embodiments, at least one $R^{A'}$ is —O$R^{A1'}$. In certain embodiments, at least one $R^{A'}$ is —O(C$_{1-6}$ alkyl). In certain embodiments, at least one $R^{A'}$ is —OMe. In certain embodiments, at least one $R^{A'}$ is —OH. In certain embodiments, at least one $R^{A'}$ is —N($R^{A1'}$)$_2$. In certain embodiments, at least one $R^{A'}$ is —NH$_2$. In certain embodiments, at least one $R^{A'}$ is —S$R^{A1'}$. In certain embodiments, at least one $R^{A'}$ is —SH. In certain embodiments, at least one $R^{A'}$ is —N$R^{A1'}$C(=O)N($R^{A1'}$)$_2$. In certain embodiments, at least one $R^{A'}$ is —NHC(=O)N($R^{A1'}$)$_2$. In certain embodiments, at least one $R^{A'}$ is —NHC(=O)NH$R^{A1'}$. In certain embodiments, at least one $R^{A'}$ is —NHC(=O)NH(C$_{1-6}$ alkyl). In certain embodiments, at least one $R^{A'}$ is —NHC(=O)NHMe. In certain embodiments, at least one $R^{A'}$ is —NHC(=O)NH$_2$. In certain embodiments, at least one $R^{A'}$ is —N$R^{A1'}$C(=O)NH$R^{A1'}$. In certain embodiments, at least one $R^{A'}$ is —N$R^{A1'}$C(=O)NH$_2$. In certain embodiments, at least one $R^{A'}$ is —N$R^{A1'}$S(=O)$_2$$R^{A1'}$. In certain embodiments, at least one $R^{A'}$ is —NHS(=O)$_2$$R^{A1'}$. In certain embodiments, at least one $R^{A'}$ is —NHS(=O)$_2$(C$_{1-6}$ alkyl). In certain embodiments, at least one $R^{A'}$ is —NHS(=O)$_2$Me. In certain embodiments, at least one $R^{A'}$ is —S(=O)$_2$N($R^{A1'}$)$_2$. In certain embodiments, at least one $R^{A'}$ is —S(=O)$_2$N($R^{A1'}$)$_2$. In certain embodiments, at least one $R^{A'}$ is —S(=O)$_2$N(C$_{1-6}$ alkyl)$_2$. In certain embodiments, at least one $R^{A'}$ is —S(=O)$_2$NH(C$_{1-6}$ alkyl). In certain embodiments, at least one $R^{A'}$ is —S(=O)$_2$NH(t-Bu). In certain embodiments, at least one $R^{A'}$ is —S(=O)$_2$NH$_2$.

In compounds of Formula (II) or (V), Ring C' may be substituted with one or more $R^{B'}$ groups. In certain embodiments, at least one $R^{B'}$ is H. In certain embodiments, at least two $R^{B'}$ groups are H. In certain embodiments, at least three $R^{B'}$ groups are H. In certain embodiments, at least four $R^{B'}$ groups are H. In certain embodiments, at least one $R^{B'}$ is halogen. In certain embodiments, at least one $R^{B'}$ is F. In certain embodiments, at least one $R^{B'}$ is Cl. In certain embodiments, at least one $R^{B'}$ is Br. In certain embodiments, at least one $R^{B'}$ is I (iodine). In certain embodiments, at least one $R^{B'}$ is substituted acyl. In certain embodiments, at least one $R^{B'}$ is —C(=O)N($R^{A1'}$)$_2$. In certain embodiments, at least one $R^{B'}$ is —C(=O)NH$R^{A1'}$. In certain embodiments, at least one $R^{B'}$ is —C(=O)NH(C$_{1-6}$ alkyl). In certain embodiments, at least one $R^{B'}$ is —C(=O)NHMe. In certain embodiments, at least one $R^{B'}$ is —C(=O)NH$_2$. In certain embodiments, at least one $R^{B'}$ is unsubstituted acyl. In certain embodiments, at least one $R^{B'}$ is acetyl. In certain embodiments, at least one $R^{B'}$ is substituted alkyl. In certain embodiments, at least one $R^{B'}$ is substituted methyl. In certain embodiments, at least one $R^{B'}$ is unsubstituted alkyl. In certain embodiments, at least one $R^{B'}$ is C$_{1-6}$ alkyl. In certain embodiments, at least one $R^{B'}$ is methyl. In certain embodiments, at least one $R^{B'}$ is ethyl. In certain embodiments, at least one $R^{B'}$ is propyl. In certain embodiments, at least one $R^{B'}$ is butyl. In certain embodiments, at least one $R^{B'}$ is —CF$_3$. In certain embodiments, at least one $R^{B'}$ is substituted alkenyl. In certain embodiments, at least one $R^{B'}$ is unsubstituted alkenyl. In certain embodiments, at least one $R^{B'}$ is substituted alkynyl. In certain embodiments, at least one $R^{B'}$ is unsubstituted alkynyl. In certain embodiments, at least one $R^{B'}$ is substituted carbocyclyl. In certain embodiments, at least one $R^{B'}$ is unsubstituted carbocyclyl. In certain embodiments, at least one $R^{B'}$ is substituted heterocyclyl. In certain embodiments, at least one $R^{B'}$ is unsubstituted heterocyclyl. In certain embodiments, at least one $R^{B'}$ is substituted aryl. In certain embodiments, at least one $R^{B'}$ is unsubstituted aryl. In certain embodiments, at least one $R^{B'}$ is substituted phenyl. In certain embodiments, at least one $R^{B'}$ is unsubstituted phenyl. In certain embodiments, at least one $R^{B'}$ is substituted heteroaryl. In certain embodiments, at least one $R^{B'}$ is unsubstituted heteroaryl. In certain embodiments, at least one $R^{B'}$ is substituted pyridyl. In certain embodiments, at least one $R^{B'}$ is unsubstituted pyridyl. In certain embodiments, at least one $R^{B'}$ is —O$^{A1}$. In certain embodiments, at least one $R^{B'}$ is —O(C$_{1-6}$ alkyl). In certain embodiments, at least one $R^{B'}$ is —OMe. In certain embodiments, at least one $R^{B'}$ is —OH. In certain embodiments, at least one $R^{B'}$ is —N($R^{A1'}$)$_2$. In certain embodiments, at least one $R^{B'}$ is —NH$_2$. In certain embodiments, at least one $R^{B'}$ is —S$R^{A1'}$. In certain embodiments, at least one $R^{B'}$ is —SH. In certain embodiments, at least one $R^{B'}$ is —N$R^{A1'}$C(=O)N($R^{A1'}$)$_2$. In certain embodiments, at least one $R^{B'}$ is —NHC(=O)N($R^{A1'}$)$_2$. In certain embodiments, at least one $R^{B'}$ is —NHC(=O)NH$R^{A1'}$. In certain embodiments, at least one $R^{B'}$ is —NHC(=O)NH(C$_{1-6}$ alkyl). In certain embodiments, at least one $R^{B'}$ is —NHC(=O)NHMe. In certain embodiments, at least one $R^{B'}$ is —NHC(=O)NH$_2$. In certain embodiments, at least one $R^{B'}$ is —N$R^{A1'}$C(=O)NH$R^{A1'}$. In certain embodiments, at least one $R^{B'}$ is —N$R^{A1'}$C(=O)NH$_2$. In certain embodiments, at least one $R^{B'}$ is —N$R^{A1'}$S(=O)$_2$$R^{A1'}$. In certain embodiments, at least one $R^{B'}$ is —NHS(=O)$_2$$R^{A1'}$. In certain embodiments, at least one $R^{B'}$ is —NHS(=O)$_2$(C$_{1-6}$ alkyl). In certain embodiments, at least one $R^{B'}$ is —NHS(=O)$_2$Me. In certain embodiments, at least one $R^{B'}$ is —S(=O)$_2$N($R^{A1'}$)$_2$. In certain embodiments, at least one $R^{B'}$ is —S(=O)$_2$N($R^{A1'}$)$_2$. In certain embodiments, at least one $R^{B'}$ is —S(=O)$_2$N(C$_{1-6}$ alkyl)$_2$. In certain embodiments, at least one $R^{B'}$ is —S(=O)$_2$NH(C$_{1-6}$ alkyl). In certain embodiments, at least one $R^{B'}$ is —S(=O)$_2$NH(t-Bu). In certain embodiments, at least one $R^{B'}$ is —S(=O)$_2$NH$_2$. In certain embodiments, at least one $R^{B'}$ is substituted imidazole. In certain embodiments, at least one $R^{B'}$ is substituted piperidine. In certain embodiments, at least one $R^{B'}$ substituted piperizine. In certain embodiments, at least one $R^{B'}$ substituted pyrrolidine. In certain embodiments, at least one $R^{B'}$ is substituted morpholine. In certain embodiments, at least one $R^{B'}$ is substituted diazepane. In certain embodiments, at least one $R^{B'}$ is

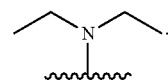

In certain embodiments, at least one $R^{B'}$ is

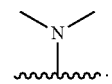

In certain embodiments, at least one $R^{B'}$ is

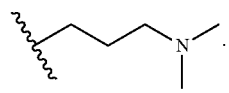 [SMILES: *CCCN(C)C]

In certain embodiments, at least one $R^{B'}$ is

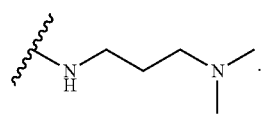 [SMILES: *NCCCN(C)C]

In certain embodiments, at least one $R^{B'}$ is

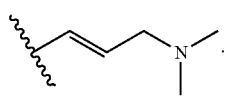 [SMILES: */C=C/CN(C)C]

In certain embodiments, at least one $R^{B'}$ is

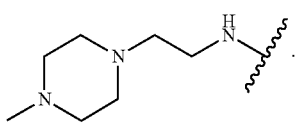 [SMILES: *NCCN1CCN(C)CC1]

In certain embodiments, at least one $R^{B'}$ is

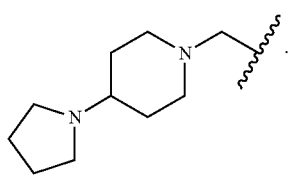 [SMILES: *CN1CCC(N2CCCC2)CC1]

In certain embodiments, at least one $R^{B'}$ is

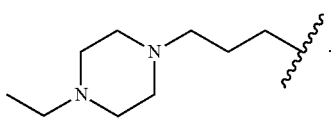 [SMILES: *CCCN1CCN(CC)CC1]

In certain embodiments, at least one $R^{B'}$ is

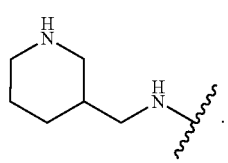 [SMILES: *NCC1CCCNC1]

In certain embodiments, at least one $R^{B'}$ is

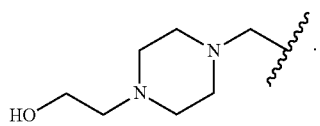 [SMILES: *CN1CCN(CCO)CC1]

In certain embodiments, at least one $R^{B'}$ is

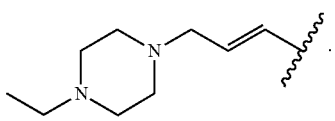 [SMILES: */C=C/CN1CCN(CC)CC1]

In certain embodiments, at least one $R^{B'}$ is

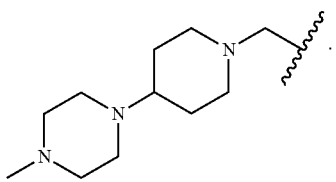 [SMILES: *CN1CCC(N2CCN(C)CC2)CC1]

In certain embodiments, at least one $R^{B'}$ is

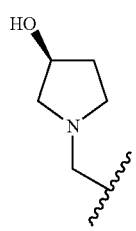

In certain embodiments, at least one $R^{B'}$ is

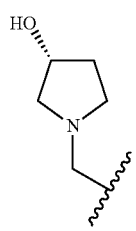

In certain embodiments, at least one $R^{B'}$ is

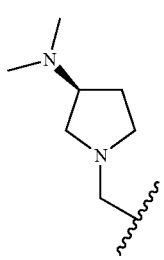

In certain embodiments, at least one $R^{B'}$ is

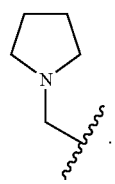 [SMILES: *CN1CCCC1]

In certain embodiments, at least one $R^{B'}$ is

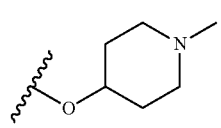

In certain embodiments, at least one $R^{B'}$ is

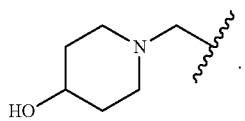

In certain embodiments, at least one $R^{B'}$ is

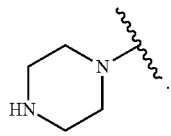

In certain embodiments, at least one $R^{B'}$ is

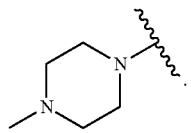 [SMILES: *N1CCN(C)CC1]

In certain embodiments, at least one $R^{B'}$ is

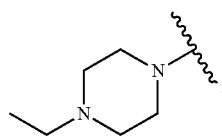

In certain embodiments, at least one $R^{B'}$ is

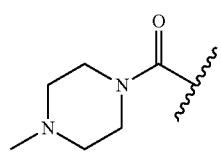

In certain embodiments, at least one $R^{B'}$ is

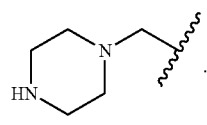

In certain embodiments, at least one $R^{B'}$ is

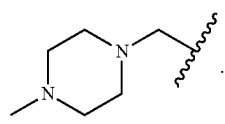 [SMILES: *CN1CCN(C)CC1]

In certain embodiments, at least one $R^{B'}$ is

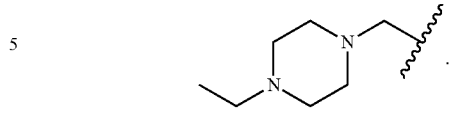

In certain embodiments, at least one $R^{B'}$ is

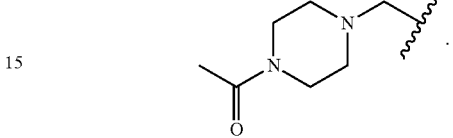

In certain embodiments, at least one $R^{B'}$ is

In certain embodiments, at least one $R^{B'}$ is

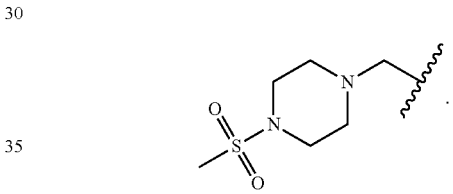

In certain embodiments, at least one $R^{B'}$ is

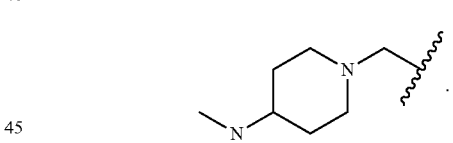

In certain embodiments at least one $R^{B'}$ is

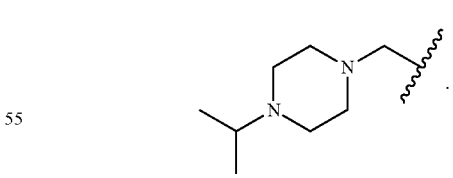

In certain embodiments, at least one $R^{B'}$ is

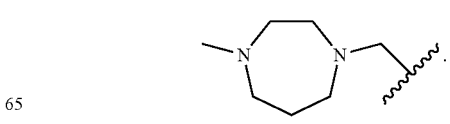

In certain embodiments, at least one $R^{B'}$ is

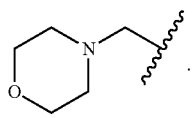

In certain embodiments, at least one $R^{B'}$ is

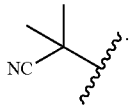

In certain embodiments, at least one $R^{B'}$ is

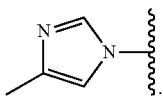

In certain embodiments, at least one $R^{B'}$ is

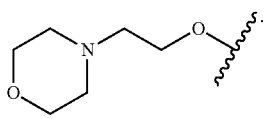 [SMILES: *OCCN1CCOCC1]

In certain embodiments, at least one $R^{B'}$ is

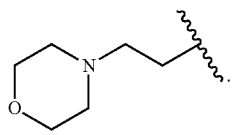 [SMILES: *CCN1CCOCC1]

In certain embodiments, at least one $R^{B'}$ is

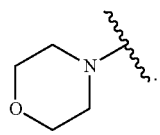

In certain embodiments, at least one $R^{B'}$ is

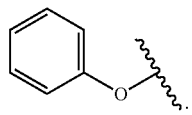 [SMILES: *Oc1ccccc1]

In certain embodiments, at least one $R^{B'}$ is

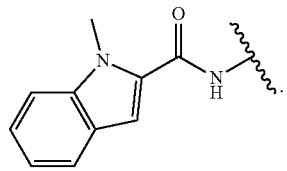 [SMILES: *NC(=O)c1cc2ccccc2n1C]

In certain embodiments, at least one $R^{B'}$ is

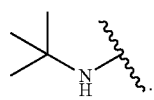

In certain embodiments, at least one $R^{B'}$ is

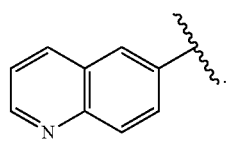 [SMILES: *c1ccc2ncccc2c1]

In certain embodiments, two $R^{B'}$ groups are joined to form a 1,3 dioxolane. In certain embodiments, two $R^{B'}$ groups are joined to form a 1,3 dioxolane which is fused to aryl Ring C', together comprising an optionally substituted benzodioxolane. In certain embodiments, two $R^{B'}$ groups are joined to form a 1,2,3-thiadiazole. In certain embodiments, two $R^{B'}$ groups are joined to form a 1,2,3-thiadiazole which is fused to aryl Ring C', together comprising an optionally substituted. benzo[d][1,2,3]thiadiazole.

In certain embodiments, at least one $R^{A1'}$ is H. In certain embodiments, at least one $R^{A1'}$ is substituted acyl. In certain embodiments, at least one $R^{A1'}$ is unsubstituted acyl. In certain embodiments, at least one $R^{A1'}$ is acetyl. In certain embodiments, at least one $R^{A1'}$ is substituted alkyl. In certain embodiments, at least one $R^{A1'}$ is unsubstituted alkyl. In certain embodiments, at least one $R^{A1'}$ is $C_{1-6}$ alkyl. In certain embodiments, at least one $R^{A1'}$ is methyl. In certain embodiments, at least one $R^{A1'}$ is ethyl. In certain embodiments, at least one $R^{A1'}$ is propyl. In certain embodiments, at least one $R^{A1'}$ is butyl. In certain embodiments, at least one $R^{A1'}$ is substituted alkenyl. In certain embodiments, at least one $R^{A1'}$ is unsubstituted alkenyl. In certain embodiments, at least one $R^{A1'}$ is substituted alkynyl. In certain embodiments, at least one $R^{A1'}$ is unsubstituted alkynyl. In certain embodiments, at least one $R^{A1'}$ is substituted carbocyclyl. In certain embodiments, at least one $R^{A1'}$ is unsubstituted carbocyclyl. In certain embodiments, at least one $R^{A1'}$ is substituted heterocyclyl. In certain embodiments, at least one $R^{A1'}$ is unsubstituted heterocyclyl. In certain embodiments, at least one $R^{A1'}$ is substituted aryl. In certain embodiments, at least one $R^{A1'}$ is unsubstituted aryl. In certain embodiments, at least one $R^{A1'}$ is substituted phenyl. In certain embodiments, at least one $R^{A1'}$ is unsubstituted phenyl. In certain embodiments, at least one $R^{A1'}$ is substituted heteroaryl. In certain embodiments, at least one $R^{A1'}$ is unsubstituted heteroaryl. In certain embodiments, at least one $R^{A1'}$ is substituted pyridyl. In certain embodiments, at least one $R^{A1'}$ is unsubstituted pyridyl. In certain embodiments, at least one $R^{A1'}$ is a nitrogen protecting group when attached to a nitrogen atom. In certain embodiments, at least one $R^{41'}$ is Bn, BOC, Cbz, Fmoc, trifluoroacetyl, triphenylmethyl, or Ts when attached to a nitrogen atom. In certain embodiments, $R^{41'}$ is an oxygen protecting group when attached to an oxygen atom. In certain embodiments, $R^{41'}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{41'}$ is a sulfur protecting group when attached to a sulfur atom. In certain embodiments, $R^{41'}$ is acetamidomethyl, t-Bu, 3-nitro-2-pyridine sulfenyl, 2-pyridine-sulfenyl, or triphenylmethyl when attached to a sulfur atom.

In compounds of Formula (II) or (V), two $R^{41'}$ groups may be joined to form an optionally substituted carbocyclic, optionally substituted heterocyclic, optionally substituted aryl, or optionally substituted heteroaryl ring. In certain embodiments, two $R^{41'}$ groups are joined to form a substituted carbocyclic ring. In certain embodiments, two $R^{41'}$ groups are joined to form an unsubstituted carbocyclic ring. In certain embodiments, two $R^{41'}$ groups are joined to form a substituted heterocyclic ring. In certain embodiments, two $R^{41'}$ groups are joined to form an unsubstituted heterocyclic ring. In certain embodiments, two $R^{41'}$ groups are joined to form a substituted aryl ring. In certain embodiments, two $R^{41'}$ groups are joined to form an unsubstituted aryl ring. In certain embodiments, two $R^{41'}$ groups are joined to form a substituted phenyl ring. In certain embodiments, two $R^{41'}$ groups are joined to form an unsubstituted phenyl ring. In certain embodiments, two $R^{41'}$ groups are joined to form a substituted heteroaryl ring. In certain embodiments, two $R^{41'}$ groups are joined to form an unsubstituted heteroaryl ring.

In certain embodiments, $R^{4'}$ is $-OR^{41'}$ and k' is 1. In certain embodiments, $R^{4'}$ is $-O(C_{1-6}$ alkyl) and k' is 1. In certain embodiments, $R^{4'}$ is $-OMe$ and k' is 1. In certain embodiments, $R^{4'}$ is $-OH$ and k' is 1.

In certain embodiments, $R^{4'}$ is substituted $C_{1-6}$ alkyl; and k' is 1. In certain embodiments, $R^{4'}$ is unsubstituted $C_{1-6}$ alkyl; and k' is 1. In certain embodiments, $R^{4'}$ is methyl; and k' is 1. In certain embodiments, $R^{4'}$ is $-CF_3$; and k' is 1. In certain embodiments, $R^{4}$, is ethyl; and k' is 1. In certain embodiments, $R^{4'}$ is propyl; and k' is 1. In certain embodiments, $R^{4'}$ is butyl; and k' is 1. In certain embodiments, $R^{4'}$ is propyl; and k' is 1. In certain embodiments, $R^{4'}$ is butyl; and k' is 1.

In certain embodiments, $R^{4'}$ is halogen; and k' is 1. In certain embodiments, $R^{4'}$ is F; and k' is 1. In certain embodiments, $R^{4'}$ is Cl; and k' is 1. In certain embodiments, $R^{4'}$ is Br; and k' is 1. In certain embodiments, $R^{4'}$ is I (iodine); and k' is 1.

In certain embodiments, one instance of $R^{4'}$ is halogen, another instance of $R^{4'}$ is substituted $C_{1-6}$ alkyl; and k' is 2. In certain embodiments, one instance of $R^{4'}$ is F, another instance of $R^{4'}$ is substituted $C_{1-6}$ alkyl; and k' is 2. In certain embodiments, one instance of $R^{4'}$ is Cl, another instance of $R^{4'}$ is substituted $C_{1-6}$ alkyl; and k' is 2. In certain embodiments, one instance of $R^{4'}$ is halogen, another instance of $R^{4'}$ is unsubstituted $C_{1-6}$ alkyl; and k' is 2. In certain embodiments, one instance of $R^{4'}$ is F, another instance of $R^{4'}$ is unsubstituted $C_{1-6}$ alkyl; and k' is 2. In certain embodiments, one instance of $R^{4'}$ is Cl, another instance of $R^{4'}$ is unsubstituted $C_{1-6}$ alkyl; and k' is 2. In certain embodiments, one instance of $R^{4'}$ is halogen, another instance of $R^{4'}$ is methyl; and k' is 2. In certain embodiments, one instance of $R^{4'}$ is F, another instance of $R^{4'}$ is methyl; and k' is 2. In certain embodiments, one instance of $R^{4'}$ is Cl, another instance of $R^{4'}$ is methyl; and k' is 2. In certain embodiments, one instance of $R^{4'}$ is halogen, another instance of $R^{4'}$ is $-CF_3$; and k' is 2. In certain embodiments, one instance of $R^{4'}$ is F, another instance of $R^{4'}$ is $-CF_3$; and k' is 2. In certain embodiments, one instance of $R^{4'}$ is Cl, another instance of $R^{4'}$ is $-CF_3$; and k' is 2.

In compounds of Formula (II) or (V), linker X', Y', and Z' are divalent linker moieties. In certain embodiments, X' is a bond. In certain embodiments, X' is a single bond. In certain embodiments, X' is $-CH_2$. In certain embodiments, X' is $-CHR^{4'}$. In certain embodiments, X' is $-CH$. In certain embodiments, X' is $-C(R^{4'})_2$. In certain embodiments, X' is $-C$. In certain embodiments, X' is $-N$. In certain embodiments, X' is $-NR^{4'}$. In certain embodiments, X' is $-O$. In certain embodiments, X' is $-C=O$. In certain embodiments, X' is $-O$. In certain embodiments, X' is $-S$. In certain embodiments, X' may optionally form a 5 to 8 membered ring with $R^{A'}$ or $R^{B'}$. In certain embodiments, Y' is a bond. In certain embodiments, Y' is a single bond. In certain embodiments, Y' is $-CH_2$. In certain embodiments, Y' is $-CHR^{4'}$. In certain embodiments, Y' is $-CH$. In certain embodiments, Y' is $-C(R^{4'})_2$. In certain embodiments, Y' is $-C$. In certain embodiments, Y' is $-N$. In certain embodiments, Y' is $-NR^{4'}$. In certain embodiments, Y' is $-O$. In certain embodiments, Y' is $-C=O$. In certain embodiments, Y' is $-S$. In certain embodiments, Y' may optionally form a 5 to 8 membered ring with $R^{A'}$ or $R^{B'}$. In certain embodiments, Z' is a bond. In certain embodiments, Z' is a single bond. In certain embodiments, Z' is $-CH_2$. In certain embodiments, Z' is $-CHR^{4'}$. In certain embodiments, Z' is $-CH$. In certain embodiments, Z' is $-C(R^{4'})_2$. In certain embodiments, Z' is $-C$. In certain embodiments, Z' is $-N$. In certain embodiments, Z' is $-NR^{4'}$. In certain embodiments, Z' is $-O$. In certain embodiments, Z' is $-C=O$. In certain embodiments, Z' is $-S$. In certain embodiments, Z' may optionally form a 5 to 8 membered ring with $R^{A'}$ or $R^{B'}$.

In compounds of Formula (II) or (V), linker X', Y', and Z' can be taken together to represent specific linking groups. In certain embodiments, X', Y', and Z' together represent

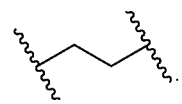 [SMILES: *CC*]

In certain embodiments, X', Y', and Z' together represent

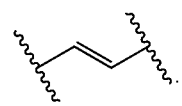

In certain embodiments, X', Y', and Z' together represent

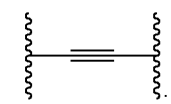

In certain embodiments, X', Y', and Z' together represent

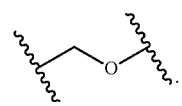 [SMILES: *CO*]

In certain embodiments, X', Y', and Z' together represent

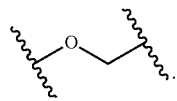

In certain embodiments, X', Y', and Z' together represent

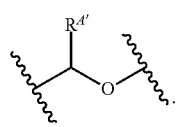

In certain embodiments, X', Y', and Z' together represent

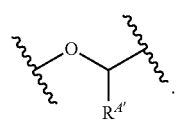

In certain embodiments, X', Y', and Z' together represent

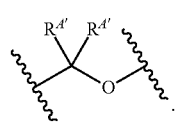

In certain embodiments, X', Y', and Z' together represent

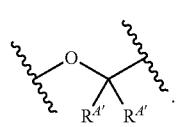

In certain embodiments, X', Y', and Z' together represent

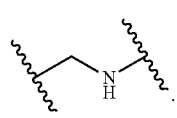

In certain embodiments, X', Y', and Z' together represent

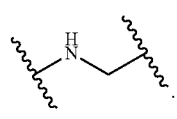 [SMILES: *CN*]

In certain embodiments, X', Y', and Z' together represent

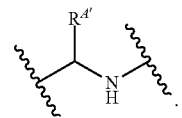

In certain embodiments, X', Y', and Z' together represent

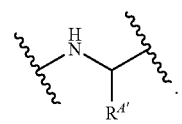

In certain embodiments, X', Y', and Z' together represent

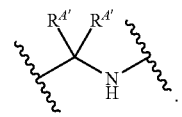

In certain embodiments, X', Y', and Z' together represent

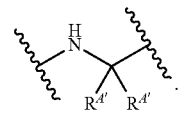

In certain embodiments, X', Y', and Z' together represent

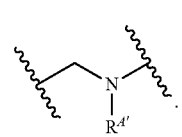

In certain embodiments, X', Y', and Z' together represent

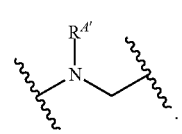

In certain embodiments, X', Y', and Z' together represent

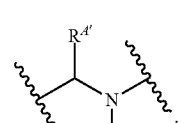
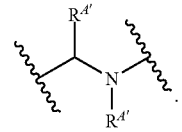

In certain embodiments, X', Y', and Z' together represent

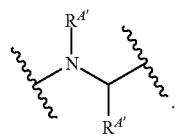

In certain embodiments, X', Y', and Z' together represent

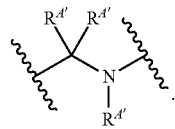

In certain embodiments, X', Y', and Z' together represent

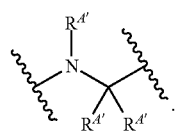

In certain embodiments, X', Y', and Z' together represent

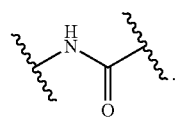 [SMILES: *NC(*)=O]

In certain embodiments, X', Y', and Z' together represent

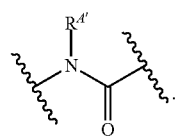

In certain embodiments, X', Y', and Z' together represent

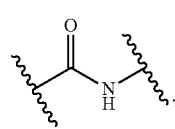 [SMILES: *NC(*)=O]

In certain embodiments, X', Y', and Z' together represent

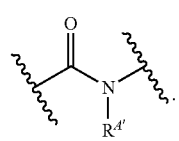

In certain embodiments, X', Y', and Z' together represent

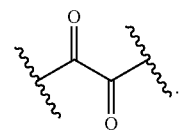 [SMILES: *C(=O)C(*)=O]

In certain embodiments, X', Y', and Z' together represent

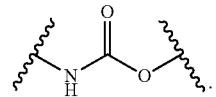 [SMILES: *NC(=O)O*]

In certain embodiments, X', Y', and Z' together represent

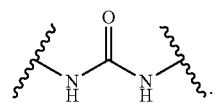

In certain embodiments, X', Y', and Z' together represent

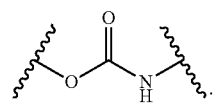 [SMILES: *NC(=O)O*]

In certain embodiments, X', Y', and Z' together represent

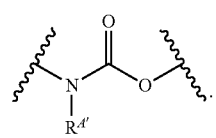

In certain embodiments, X', Y', and Z' together represent

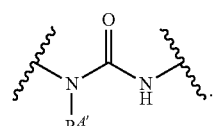

In certain embodiments, X', Y', and Z' together represent

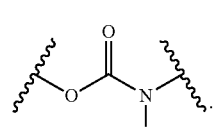

In certain embodiments, X', Y', and Z' together represent

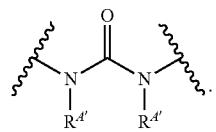

In certain embodiments, X', Y', and Z' together represent

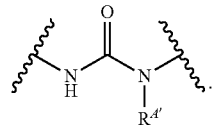

In certain embodiments, X', Y', and Z' together represent

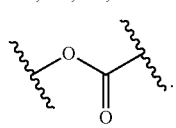

In certain embodiments, X', Y', and Z' together represent

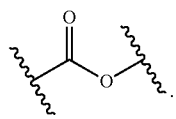

In certain embodiments, X', Y', and Z' together represent a single bond.

In compounds of Formula (II) or (V), linker Q' and U' are divalent linker moieties. In certain embodiments, Q' is —$NR^{A'}$. In certain embodiments, Q' is —NH. In certain embodiments, Q' is —C=O. In certain embodiments, Q' is —$NR^{A'}$CO. In certain embodiments, Q' is a bond. In certain embodiments, X' may optionally form a 5 to 8 membered ring with $R^{A'}$ or $R^{B'}$. In certain embodiments, U' is —$NR^{A'}$. In certain embodiments, U' is —NH. In certain embodiments, U' is —C=O. In certain embodiments, U' is —$NR^{A'}$CO. In certain embodiments, U' is a bond. In certain embodiments, U' may optionally form a 5 to 8 membered ring with $R^{A'}$ or $R^B$.

In compounds of Formula (II) or (V), linker Q' and U' can be taken together to represent specific linking groups. In certain embodiments, Q' and U' together represent

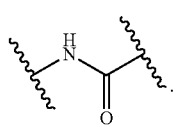

In certain embodiments, Q' and U' together represent

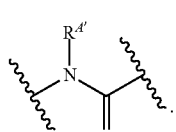

In certain embodiments, Q' and U' together represent

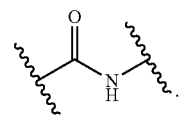 [SMILES: *NC(*)=O]

In certain embodiments, Q' and U' together represent

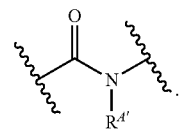

In certain embodiments, Q' and U' together represent

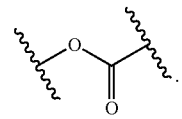 [SMILES: *OC(*)=O]

In certain embodiments, Q' and U' together represent

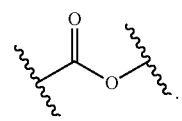 [SMILES: *OC(*)=O]

In certain embodiments, Q' and U' together represent

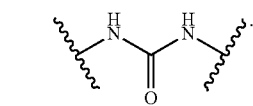

In certain embodiments, Q' and U' together represent

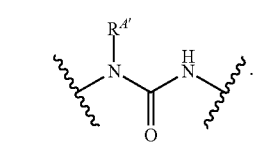

In certain embodiments, Q' and U' together represent

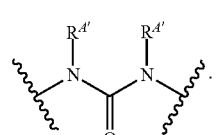

In certain embodiments, Q' and U' together represent

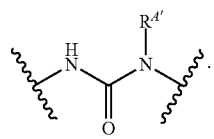

In certain embodiments, Q' and U' together represent

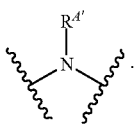

In certain embodiments, Q' and U' together represent

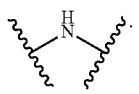 [SMILES: *N*]

Cy of Formula (II) or (V) may be an optionally substituted aryl ring. In certain embodiments, Ring Cy is a substituted aryl ring. In certain embodiments, Cy is an unsubstituted aryl ring. In certain embodiments, Cy is a monocyclic aryl ring. In certain embodiments, Cy is substituted phenyl. In certain embodiments, Cy is unsubstituted phenyl. In certain embodiments, Cy is a bicyclic aryl ring. In certain embodiments, Cy is substituted naphthyl. In certain embodiments, Cy is unsubstituted naphthyl. In certain embodiments, Cy is an optionally substituted aryl ring fused with one or more optionally substituted carbocyclic, optionally substituted heterocyclic, optionally substituted aryl, or optionally substituted heteroaryl groups wherein the point of attachment is on the aryl ring.

Cy of Formula (II) or (V) may also be an optionally substituted heteroaryl ring. In certain embodiments, Cy is a substituted heteroaryl ring. In certain embodiments, Cy is an unsubstituted heteroaryl ring. In certain embodiments, Cy is a monocyclic heteroaryl ring. In certain embodiments, Cy is a 5-membered monocyclic heteroaryl ring. In certain embodiments, Cy is a 5-membered monocyclic heteroaryl ring with one heteroatom selected from the group consisting of S, N, and O. In certain embodiments, Cy is a 5-membered monocyclic heteroaryl ring with two heteroatoms selected from the group consisting of S, N, and O. In certain embodiments, Cy is a 5-membered monocyclic heteroaryl ring with three heteroatoms selected from the group consisting of S, N, and O. In certain embodiments, Cy is substituted pyrrolyl. In certain embodiments, Cy is unsubstituted pyrrolyl. In certain embodiments, Cy is substituted furanyl. In certain embodiments, Cy is unsubstituted furanyl. In certain embodiments, Cy is substituted thienyl. In certain embodiments, Cy is unsubstituted thienyl. In certain embodiments, Cy is substituted pyrazolyl. In certain embodiments, Cy is unsubstituted pyrazolyl. In certain embodiments, Cy is substituted imidazolyl. In certain embodiments, Cy is unsubstituted imidazolyl. In certain embodiments, Cy is substituted oxazolyl. In certain embodiments, Cy is unsubstituted oxazolyl. In certain embodiments, Cy is substituted isoxazolyl. In certain embodiments, Cy is unsubstituted isoxazolyl. In certain embodiments, Cy is substituted thiazolyl. In certain embodiments, Cy is unsubstituted thiazolyl. In certain embodiments, Cy is substituted isothiazolyl. In certain embodiments, Cy is unsubstituted isothiazolyl. In certain embodiments, Cy is substituted triazolyl. In certain embodiments, Cy is unsubstituted triazolyl. In certain embodiments, Cy is substituted oxadiazolyl. In certain embodiments, Cy is unsubstituted oxadiazolyl. In certain embodiments, Cy is substituted thiadiazolyl. In certain embodiments, Cy is unsubstituted thiadiazolyl. In certain embodiments, Cy is a 6-membered monocyclic heteroaryl ring. In certain embodiments, Cy is a 6-membered monocyclic heteroaryl ring with one heteroatom selected from the group consisting of S, N, and O. In certain embodiments, Cy is a 6-membered monocyclic heteroaryl ring with two heteroatoms selected from the group consisting of S, N, and O. In certain embodiments, Cy is a 6-membered monocyclic heteroaryl ring with three heteroatoms selected from the group consisting of S, N, and O. In certain embodiments, Cy is substituted pyridyl. In certain embodiments, Cy is unsubstituted pyridyl. In certain embodiments, Cy is substituted pyridazinyl. In certain embodiments, Cy is unsubstituted pyridazinyl. In certain embodiments, Cy is substituted pyrimidinyl. In certain embodiments, Cy is unsubstituted pyrimidinyl. In certain embodiments, Cy is substituted pyrazinyl. In certain embodiments, Cy is unsubstituted pyrazinyl. In certain embodiments, Cy is substituted triazinyl. In certain embodiments, Cy is unsubstituted triazinyl. In certain embodiments, Cy is an optionally substituted heteroaryl ring fused with one or more optionally substituted carbocyclic, optionally substituted heterocyclic, optionally substituted aryl, or optionally substituted heteroaryl groups wherein the point of attachment is on any one of the heteroaryl ring, or carbocyclic, heterocyclic, aryl, or heteroaryl groups, as valency permits. In certain embodiments, Cy is a bicyclic heteroaryl ring. In certain embodiments, Cy is an optionally substituted heteroaryl ring fused with an optionally substituted phenyl ring. In certain embodiments, Cy is substituted indolyl. In certain embodiments, Cy is unsubstituted indolyl. In certain embodiments, Cy is substituted isoindolyl. In certain embodiments, Cy is unsubstituted isoindolyl. In certain embodiments, Cy is substituted indazolyl. In certain embodiments, Cy is unsubstituted indazolyl. In certain embodiments, Cy is substituted benzothienyl. In certain embodiments, Cy is unsubstituted benzothienyl. In certain embodiments, Cy is substituted isobenzothienyl. In certain embodiments, Cy is unsubstituted isobenzothienyl. In certain embodiments, Cy is substituted benzofuranyl. In certain embodiments, Cy is unsubstituted benzofuranyl. In certain embodiments, Cy is substituted benzoisofuranyl. In certain embodiments, Cy is unsubstituted benzoisofuranyl. In certain embodiments, Cy is substituted benzimidazolyl. In certain embodiments, Cy is unsubstituted benzimidazolyl. In certain embodiments, Cy is substituted benzoxazolyl. In certain embodiments, Cy is unsubstituted benzoxazolyl. In certain embodiments, Cy is substituted benzisoxazolyl. In certain embodiments, Cy is unsubstituted benzisoxazolyl. In certain embodiments, Cy is substituted benzothiazolyl. In certain embodiments, Cy is unsubstituted benzothiazolyl. In certain embodiments, Cy is substituted benzisothiazolyl. In certain embodiments, Cy is unsubstituted benzisothiazolyl. In certain embodiments, Cy is substituted benzotriazolyl. In certain embodiments, Cy is unsubstituted benzotriazolyl. In certain embodiments, Cy is substituted benzoxadiazolyl. In certain embodiments, Cy is unsubstituted benzoxadiazolyl. In certain embodiments, Cy is substituted quinolinyl. In certain embodiments, Cy is unsubstituted quinolinyl. In certain embodiments, Cy is substituted isoquinolinyl. In certain embodiments, Cy is unsubstituted isoquinolinyl. In certain embodiments, Cy is substituted cinnolinyl. In certain embodiments, Cy is unsubstituted cinnolinyl. In certain embodiments, Cy is substituted quinoxalinyl. In certain embodiments, Cy is unsubstituted quinoxalinyl. In certain embodiments, Cy is substituted phthalazinyl. In certain embodiments, Cy is unsubstituted phthalazinyl. In certain embodiments, Cy is substituted quinazolinyl. In certain embodiments, Cy is unsubstituted quinazolinyl. In certain embodiments, Cy is

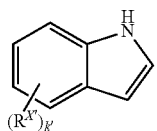

wherein X' may link to any freely valent position. In certain embodiments, Cy is

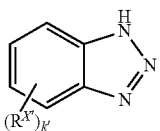

wherein X' may link to any freely valent position. In certain embodiments, Cy is

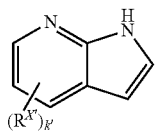

wherein X' may link to any freely valent position. In certain embodiments, Cy is

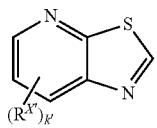

wherein X' may link to any freely valent position. In certain embodiments, Cy is

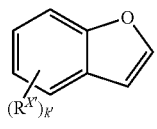

wherein X' may link to any freely valent position. In certain embodiments, Cy is

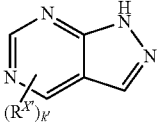

wherein X' may link to any freely valent position. In certain embodiments, Cy is

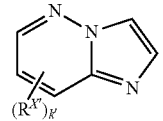

wherein X' may link to any freely valent position. In certain embodiments, Cy is

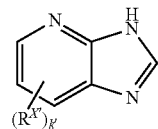

wherein X' may link to any freely valent position. In certain embodiments, Cy is

wherein X' may link to any freely valent position. In certain embodiments, Cy is

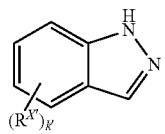

wherein X' may link to any freely valent position. In certain embodiments, Cy is

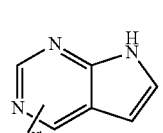

wherein X' may link to any freely valent position. In certain embodiments, Cy is

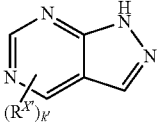

wherein X' may link to any freely valent position. In certain embodiments, Cy is

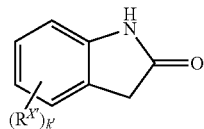

wherein X' may link to any freely valent position. In certain embodiments, Cy is

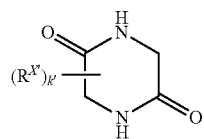

wherein X' may link to any freely valent position. In certain embodiments, Cy is

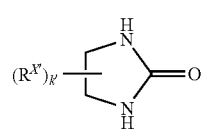

wherein X' may link to any freely valent position. In certain embodiments, Cy is

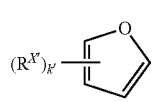

wherein X' may link to any freely valent position. In certain embodiments, Cy is

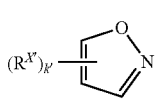

wherein X' may link to any freely valent position. In certain embodiments, Cy is

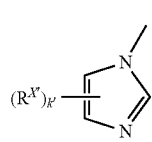

wherein X' may link to any freely valent position. In certain embodiments, Cy is

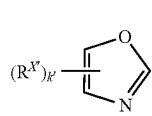

wherein X' may link to any freely valent position. In certain embodiments, Cy is

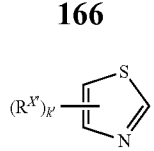

wherein X' may link to any freely valent position. In certain embodiments, Cy is

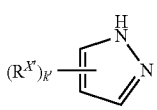

wherein X' may link to any freely valent position. In certain embodiments, Cy is

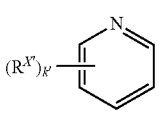

wherein X' may link to any freely valent position. In certain embodiments, Cy is

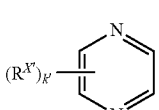

wherein X' may link to any freely valent position. In certain embodiments, Cy is

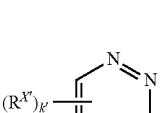

wherein X' may link to any freely valent position. In certain embodiments, Cy is

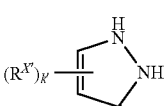

wherein X' may link to any freely valent position. In certain embodiments, Cy is

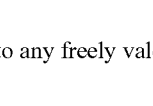

wherein X' may link to any freely valent position. In certain embodiments, Cy is

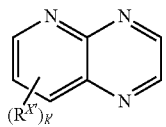

wherein X' may link to any freely valent position. In certain embodiments, Cy is

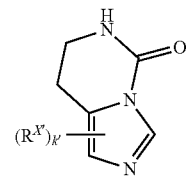

wherein X' may link to any freely valent position. In certain embodiments, Cy is

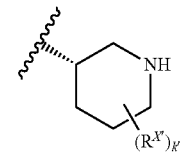

wherein X' may link to any freely valent position. In certain embodiments, Cy is

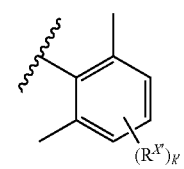

wherein X' may link to any freely valent position. In certain embodiments, Cy is

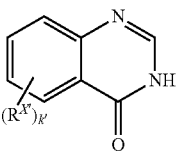

wherein X' may link to any freely valent position. In certain embodiments, Cy is

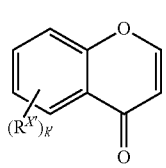

wherein X' may link to any freely valent position. In certain embodiments, Cy is wherein X' may link to any freely valent position.

In compounds of Formula (II) or (V), Cy may be substituted with one or more $R^{X'}$ groups. In certain embodiments, at least one $R^{X'}$ is H. In certain embodiments, at least two $R^{X'}$ groups are H. In certain embodiments, at least three $R^{X'}$ groups are H. In certain embodiments, at least four $R^{X'}$ groups are H. In certain embodiments, at least one $R^{X'}$ is halogen. In certain embodiments, at least one $R^{X'}$ is F. In certain embodiments, at least one $R^{X'}$ is Cl. In certain embodiments, at least one $R^{X'}$ is Br. In certain embodiments, at least one $R^{X'}$ is I (iodine). In certain embodiments, at least one $R^{X'}$ is substituted acyl. In certain embodiments, at least one $R^{X'}$ is —C(=O)N($R^{A1'}$)$_2$. In certain embodiments, at least one $R^{X'}$ is —C(=O)NH$R^{A1'}$. In certain embodiments, at least one $R^{X'}$ is —C(=O)NH(C$_{1-6}$ alkyl). In certain embodiments, at least one $R^{X'}$ is —C(=O)NHMe. In certain embodiments, at least one $R^{X'}$ is —C(=O)NH$_2$. In certain embodiments, at least one $R^{X'}$ is unsubstituted acyl. In certain embodiments, at least one $R^{X'}$ is acetyl. In certain embodiments, at least one $R^{X'}$ is substituted alkyl. In certain embodiments, at least one $R^{X'}$ is substituted methyl. In certain embodiments, at least one $R^{X'}$ is unsubstituted alkyl. In certain embodiments, at least one $R^{X'}$ is C$_{1-6}$ alkyl. In certain embodiments, at least one $R^{X'}$ is methyl. In certain embodiments, at least one $R^{X'}$ is ethyl. In certain embodiments, at least one $R^{X'}$ is propyl. In certain embodiments, at least one $R^{X'}$ is butyl. In certain embodiments, at least one $R^{X'}$ is substituted alkenyl. In certain embodiments, at least one $R^{X'}$ is unsubstituted alkenyl. In certain embodiments, at least one $R^{X'}$ is substituted alkynyl. In certain embodiments, at least one $R^{X'}$ is unsubstituted alkynyl. In certain embodiments, at least one $R^{X'}$ is substituted carbocyclyl. In certain embodiments, at least one $R^{X'}$ is unsubstituted carbocyclyl. In certain embodiments, at least one $R^{X'}$ is substituted heterocyclyl. In certain embodiments, at least one $R^{X'}$ is unsubstituted heterocyclyl. In certain embodiments, at least one $R^{X'}$ is substituted aryl. In certain embodiments, at least one $R^{Xt}$ is unsubstituted aryl. In certain embodiments, at least one $R^{Xt}$ is substituted phenyl. In certain embodiments, at least one $R^{Xt}$ is unsubstituted phenyl. In certain embodiments, at least one $R^{Xt}$ is substituted heteroaryl. In certain embodiments, at least one $R^{Xt}$ is unsubstituted heteroaryl. In certain embodiments, at least one $R^{Xt}$ is substituted pyridyl. In certain embodiments, at least one $R^{Xt}$ is unsubstituted pyridyl. In certain embodiments, at least one $R^{Xt}$ is —$OR^{A1t}$. In certain embodiments, at least one $R^{Xt}$ is —$O(C_{1-6}$ alkyl). In certain embodiments, at least one $R^{Xt}$ is —OMe. In certain embodiments, at least one $R^{Xt}$ is —OH. In certain embodiments, at least one $R^{Xt}$ is —$N(R^{A1t})_2$. In certain embodiments, at least one $R^{Xt}$ is —$NH_2$. In certain embodiments, at least one $R^{Xt}$ is —$SR^{A1t}$. In certain embodiments, at least one $R^{Xt}$ is —SH. In certain embodiments, at least one $R^{Xt}$ is —$NR^{A1t}C(=O)N(R^{A1t})_2$. In certain embodiments, at least one $R^{Xt}$ is —$NHC(=O)N(R^{A1t})_2$. In certain embodiments, at least one $R^{Xt}$ is —$NHC(=O)NHR^{A1t}$. In certain embodiments, at least one $R^{Xt}$ is —$NHC(=O)NH(C_{1-6}$ alkyl). In certain embodiments, at least one $R^{Xt}$ is —$NHC(=O)NHMe$. In certain embodiments, at least one $R^{Xt}$ is —$NHC(=O)NH_2$. In certain embodiments, at least one $R^{Xt}$ is —$NR^{A1t}C(=O)NHR^{A1t}$. In certain embodiments, at least one $R^{Xt}$ is —$NR^{A1t}C(=O)NH_2$. In certain embodiments, at least one $R^{Xt}$ is —$NR^{A1t}S(=O)_2R^{A1t}$. In certain embodiments, at least one $R^{Xt}$ is —$NHS(=O)_2R^{A1t}$. In certain embodiments, at least one $R^{Xt}$ is —$NHS(=O)_2(C_{1-6}$ alkyl). In certain embodiments, at least one $R^{Xt}$ is —$NHS(=O)_2Me$. In certain embodiments, at least one $R^{Xt}$ is —$S(=O)_2N(R^{A1t})_2$. In certain embodiments, at least one $R^{Xt}$ is —$S(=O)_2N(R^{A1t})_2$. In certain embodiments, at least one $R^{Xt}$ is —$S(=O)_2N(C_{1-6}$ alkyl)$_2$. In certain embodiments, at least one $R^{Xt}$ is —$S(=O)_2NH(C_{1-6}$ alkyl). In certain embodiments, at least one $R^{Xt}$ is —$S(=O)_2NH(t-Bu)$. In certain embodiments, at least one $R^{Xt}$ is —$S(=O)_2NH_2$. In certain embodiments, at least one $R^{Xt}$ is

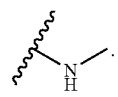

In certain embodiments, at least one $R^{Xt}$ is

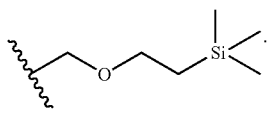 [SMILES: *COCC[Si](C)(C)C]

In certain embodiments, at least one $R^{Xt}$ is

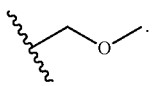

In certain embodiments, at least one $R^{Xt}$ is

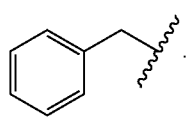 [SMILES: *Cc1ccccc1]

In certain embodiments, at least one $R^{Xt}$ is

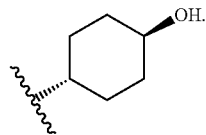 [SMILES: *[C@H]1CC[C@H](O)CC1]

In certain embodiments, at least one $R^{Xt}$ is

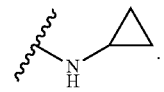

In certain embodiments, at least one $R^{Xt}$ is

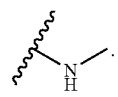

In certain embodiments, at least one $R^{Xt}$ is

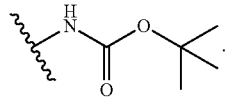 [SMILES: *NC(=O)OC(C)(C)C]

In certain embodiments, at least one $R^{Xt}$ is

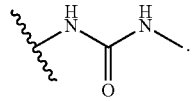

In certain embodiments, at least one $R^{Xt}$ is

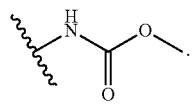

In certain embodiments, at least one $R^{Xt}$ is

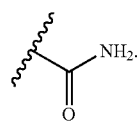

In certain embodiments, at least one $R^{Xt}$ is

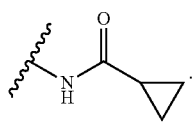 [SMILES: *NC(=O)C1CC1]

In certain embodiments, at least one $R^{X_1}$ is

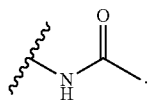 [SMILES: *NC(C)=O]

In certain embodiments, at least one $R^{X_1}$ is

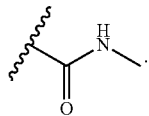

In certain embodiments, at least one $R^{X_1}$ is

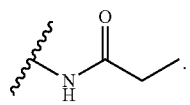 [SMILES: *NC(=O)CC]

In certain embodiments at least one $R^{X_1}$ is

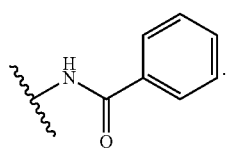 [SMILES: *NC(=O)c1ccccc1]

In certain embodiments, at least one $R^{X_1}$ is

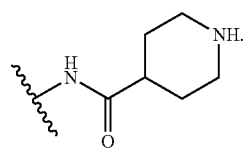 [SMILES: *NC(=O)C1CCNCC1]

In certain embodiments, at least one $R^{X_1}$ is

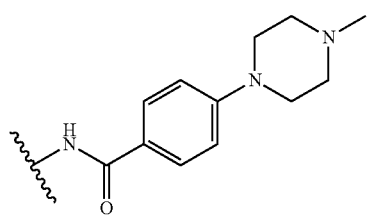

In certain embodiments, at least one $R^{X_1}$ is

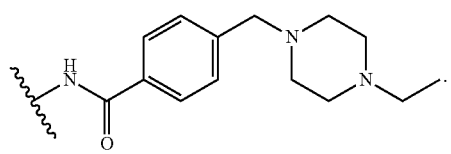 [SMILES: *NC(=O)c1ccc(CN2CCN(CC)CC2)cc1]

In certain embodiments, at least one $R^{X_1}$ is

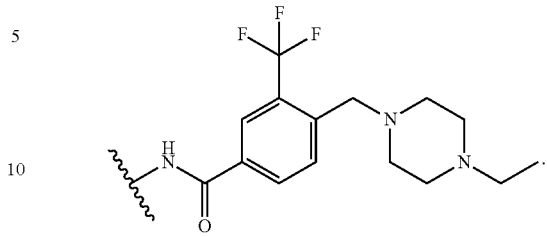

In certain embodiments, at least one $R^{X_1}$ is

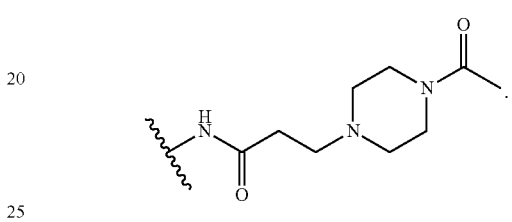

In certain embodiments, at least one $R^{X_1}$ is

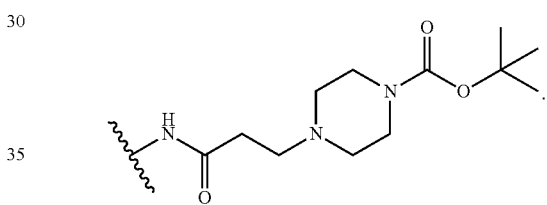

In certain embodiments, at least one $R^{X_1}$ is

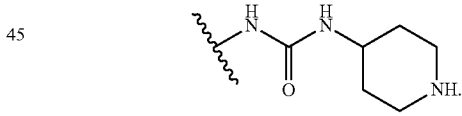

In certain embodiments, at least one $R^{X_1}$ is

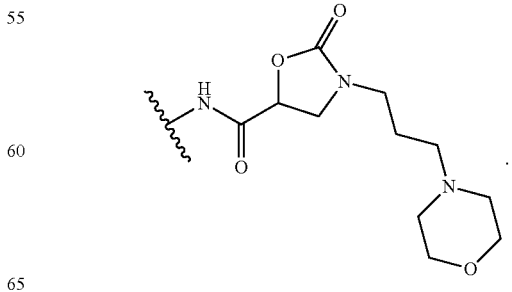

In certain embodiments, at least one $R^{X_1}$ is

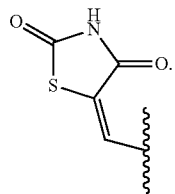

In certain embodiments, at least one $R^{X_1}$ is

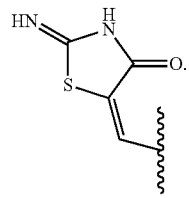

In certain embodiments, at least one $R^{X_1}$ is

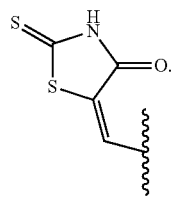 [SMILES: */C=C1/SC(=S)NC1=O]

In certain embodiments, at least one $R^{X_1}$ is

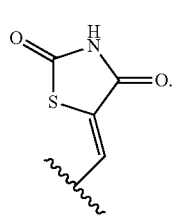 [SMILES: */C=C1\SC(=O)NC1=O]

In certain embodiments, at least one $R^{X_1}$ is

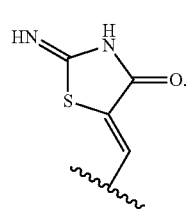

In certain embodiments, at least one $R^{X_1}$ is

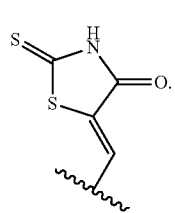 [SMILES: */C=C1\SC(=S)NC1=O]

In certain embodiments, at least one $R^{X_1}$ is

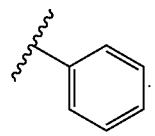 [SMILES: *c1ccccc1]

In certain embodiments, at least one $R^{X_1}$ is

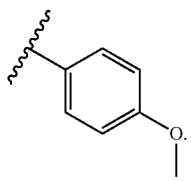 [SMILES: *c1ccc(OC)cc1]

In certain embodiments, at least one $R^{X_1}$ is

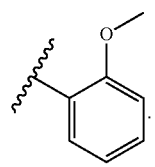 [SMILES: *c1ccccc1OC]

In certain embodiments, at least one $R^{X_1}$ is

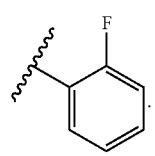 [SMILES: *c1ccccc1F]

In certain embodiments, at least one $R^{X_1}$ is

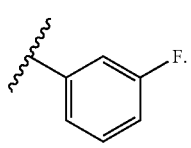 [SMILES: *c1cccc(F)c1]

In certain embodiments, at least one $R^{X_1}$ is

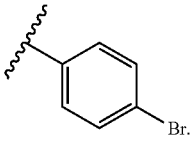

In certain embodiments, at least one $R^{X_1}$ is

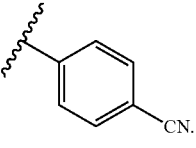

In certain embodiments, at least one $R^{X_1}$ is

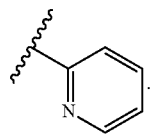

In certain embodiments, at least one $R^{X_1}$ is

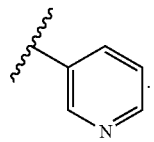

In certain embodiments, at least one $R^{X_1}$ is

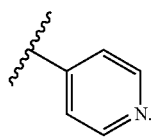

In certain embodiments, at least one $R^{X_1}$ is

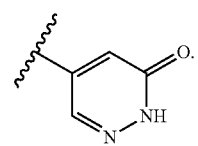 [SMILES: *c1cn[nH]c(=O)c1]

In certain embodiments, at least one $R^{X_1}$ is

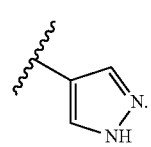

In certain embodiments, at least one $R^{X_1}$ is

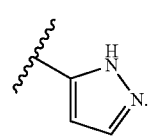

In certain embodiments, at least one $R^{X_1}$ is

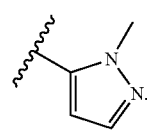 [SMILES: *c1ccnn1C]

In certain embodiments, at least one $R^{X_1}$ is

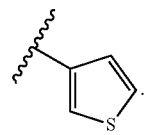

In certain embodiments, at least one $R^{X_1}$ is

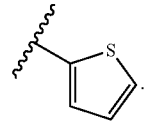

In certain embodiments, at least one $R^{X_1}$ is

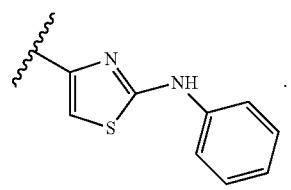 [SMILES: *c1csc(Nc2ccccc2)n1]

In certain embodiments, at least one $R^{X_1}$ is

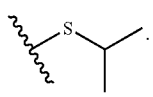

In certain embodiments, at least one $R^{X_1}$ is

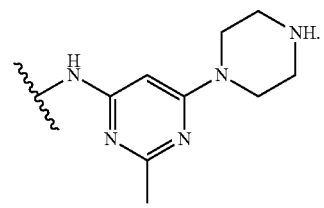 [SMILES: *Nc1cc(N2CCNCC2)nc(C)n1]

In certain embodiments, at least one $R^{X_1}$ is

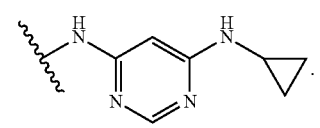 [SMILES: *Nc1cc(NC2CC2)ncn1]

In certain embodiments, at least one $R^{X_1}$ is

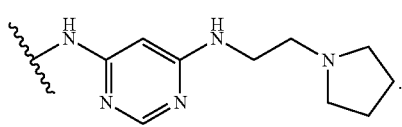 [SMILES: *Nc1cc(NCCN2CCCC2)ncn1]

In certain embodiments, at least one $R^{X_1}$ is

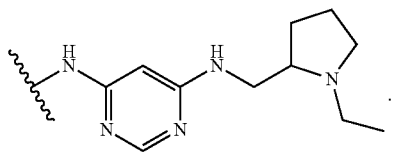 [SMILES: *Nc1cc(NCC2CCCN2CC)ncn1]

In certain embodiments, at least one $R^{X_1}$ is

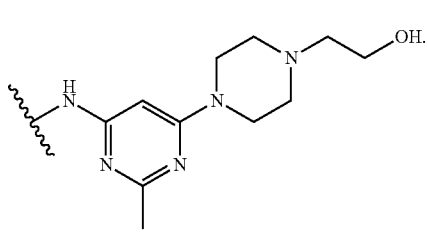 [SMILES: *Nc1cc(N2CCN(CCO)CC2)nc(C)n1]

In certain embodiments, at least one $R^{X_1}$ is

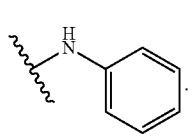

In certain embodiments, at least one $R^{X_1}$ is

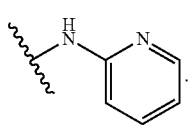

In certain embodiments, at least one $R^{X_1}$ is

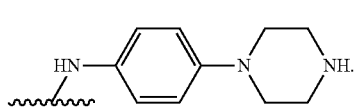

In certain embodiments, at least one $R^{X_1}$ is

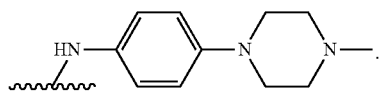

In certain embodiments, at least one $R^{X_1}$ is

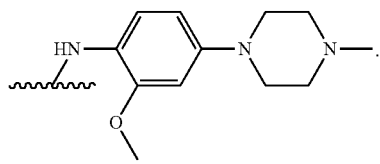 [SMILES: *Nc1ccc(N2CCN(C)CC2)cc1OC]

In certain embodiments, at least one $R^{X_1}$ is

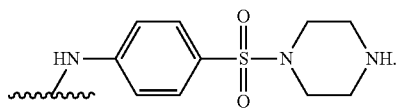

In certain embodiments, at least one $R^{X_1}$ is

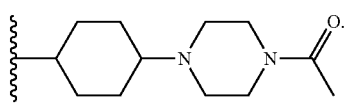

In certain embodiments, at least one $R^{X_1}$ is

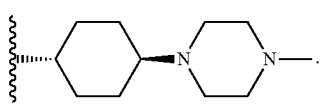

In certain embodiments, at least one $R^{X_1}$ is

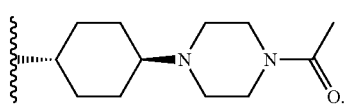

In certain embodiments, at least one $R^{X_1}$ is

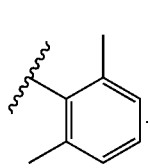 [SMILES: *c1c(C)cccc1C]

In certain embodiments, at least one $R^{X_1}$ is

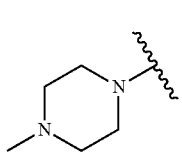

In certain embodiment, a compound of the invention is a compound of Formula (A), or a pharmaceutically acceptable salt, solvate, hydrate, polymorph, co-crystal, tautomer, stereoisomer, isotopically labeled derivative, or prodrug thereof. In certain embodiment, a compound of the invention is a compound of Formula (A), or a pharmaceutically acceptable salt thereof. In certain embodiment, a compound of the invention is a compound of Formula (I-11), or a pharmaceutically acceptable salt, solvate, hydrate, polymorph, co-crystal, tautomer, stereoisomer, isotopically labeled derivative, or prodrug thereof. In certain embodiment, a compound of the invention is a compound of Formula (I-11), or a pharmaceutically acceptable salt thereof. In certain embodiment, a compound of the invention is a compound of Formula (II), or a pharmaceutically acceptable salt, solvate, hydrate, polymorph, co-crystal, tautomer, stereoisomer, isotopically labeled derivative, or prodrug thereof. In certain embodiment, a compound of the invention is a compound of Formula (II), or a pharmaceutically acceptable salt thereof. In certain embodiment, a compound of the invention is a compound of Formula (V), or a pharmaceutically acceptable salt, solvate, hydrate, polymorph, co-crystal, tautomer, stereoisomer, isotopically labeled derivative, or prodrug thereof. In certain embodiment, a compound of the invention is a compound of Formula (V), or a pharmaceutically acceptable salt thereof.

In certain embodiments, compounds of the present invention include those which:
  exhibit kinase inhibitory activity,
  exhibit the ability to inhibit transforming growth factor b-activated kinase-1 (TAK1), hemopoietic cell kinase (HCK) or both TAK1 and HCK,
  exhibit the ability to inhibit hematopoietic progenitor kinase 1 (HPK1, also known as mitogen-activated protein kinase kinase kinase kinase 1 or MAP4K1),
  exhibit the ability to inhibit Bruton's tyrosine kinase (BTK), v-src sarcoma (Schmidt-Ruppin A-2) viral oncogene homolog (SRC) family of kinases or both BTK and SRC,
  exhibit cytotoxic or growth inhibitory effect on WM cell lines maintained in vitro or in animal studies using a scientifically acceptable cancer cell xenograft model; and/or
  exhibit a therapeutic profile (e.g., optimum safety and curative effect) that is superior to existing chemotherapeutic agents.

As used herein "kinase" refers to a large class of enzymes which catalyze the transfer of the γ-phosphate from ATP to the hydroxyl group on the side chain of Ser/Thr or Tyr in proteins and peptides and are intimately involved in the control of various important cell functions, perhaps most notably: signal transduction, differentiation and proliferation. There are estimated to be about 2,000 distinct protein kinases in the human body and although each of these phosphorylates particular protein/peptide substrates, they all bind the same second substrate ATP in a highly conserved pocket. About 50% of the known oncogene products are protein tyrosine kinases PTKs and their kinase activity has been shown to lead to cell transformation.

In certain embodiments, the kinase to be inhibited is involved in the myeloid differentiation primary response gene (88) (MYD88) signaling pathway. For example, the kinase is Transforming growth factor b-activated kinase-1 (TAK1) or Hemopoietic cell kinase (HCK). In certain embodiments, the compound of the invention inhibits TAK1, HCK, or both TAK1 and HCK.

Myeloid differentiation primary response gene (88) (MYD88) L265P is a widely expressed somatic mutation in WM patients that supports NF-NFκB signaling through stimulation of BTK, IRAK1/4, TAK1. MYD88 is an adaptor molecule for Toll-like receptors (TLR) with the exception of TLR-3 and interleukin-1 receptor (IL-1R) signaling. Following TLR or IL-1R stimulation, MYD88 is recruited to the activated receptor complex as a homodimer which then complexes with interleukin-1 receptor-associated kinase 4 (IRAK4) and activates IRAK1 and IRAK2. Tumor necrosis factor receptor associated factor 6 (TRAF6) is then activated by IRAK1 leading to NFκB activation via IκBα phosphorylation and TAK1 activation.

Transforming growth factor b-activated kinase-1 (TAK1; also known as MAP3K7) is a member of the serine/threonine protein kinase family. This kinase mediates the signaling transduction induced by TGF beta and morphogenetic protein (BMP), and controls a variety of cell functions including transcription regulation and apoptosis. TAK1 knockout is embryonic lethal to mice. Conditional knockdown of TAK1 in adult mice results in systemic inflammation, spenomegaly, degeneration in heart, kidneys and liver and increased proliferation and differentiation of myeloid progenitor cells. TAK1 is located downstream of Myd88, Bruton's tyrosine kinase (BTK), and interleukin-1 receptor-associated kinase (IRAK), and is being investigated for its role in innate immunity, inflammatory response, and Ras-dependent cancers.

Hemopoietic cell kinase (HCK) is a non-receptor tyrosine-protein kinase found in hematopoietic cells and is known to interact with Bruton's tyrosine kinase (BTK) upon activation by B cell receptors (Proc. Natl. Acad. Sci. USA. 1994, 91(17), 8152-55). HCK transmits signals from cell surface receptors and plays an important role in the regulation of innate immune responses, including neutrophil, monocyte, macrophage and mast cell functions, phagocytosis, cell survival and proliferation, cell adhesion and migration. It acts downstream of receptors that bind the Fc region of immunoglobulins, such as FCGR1A and FCGR2A, but also CSF3R, PLAUR, the receptors for IFNG, IL2, IL6 and IL8, and integrins, such as ITGB1 and ITGB2. During the phagocytic process, it mediates mobilization of secretory lysosomes, degranulation, and activation of NADPH oxidase to bring about the respiratory burst. It also plays a role in the release of inflammatory molecules, promotes reorganization of the actin cytoskeleton and actin polymerization, and formation of podosomes and cell protrusions.

Hematopoietic progenitor kinase 1 (HPK1) is a hematopoietic cell-restricted member of the Ste20 serine/threonine kinase super family. HPK1 is also known as mitogen-activated protein kinase kinase kinase kinase 1 (MAP4K1). HPK1 is a tissue-specific upstream activator of the MEKK/JNK/SAPK signaling pathway. HPK1 diminishes T cell receptor (TCR) signaling activity and T cell proliferation by phosphorylating the adaptor protein SLP-76. Cytosolic HPK1 is recruited to the TCR complex, and its kinase activity is induced upon the engagement of the TCR. Overexpression of HPK1 suppresses TCR-induced activation of AP-1-dependent gene transcription in a kinase-dependent manner, suggesting that the kinase activity of HPK1 is required to inhibit the Erk MAPK pathway. This blockage of the Erk MAPK pathway is thought to be the inhibitory mechanism that negatively regulates TCR-induced IL-2 gene transcription (Immunol. Res. 2012, 54(1-3), 262-65). In certain embodiments, the compounds of the invention, such as the compounds of Formula (A), (I-11), (II), or (V) (e.g., compounds of Formula (A-1)-(A-18)), inhibit HPK1.

In certain embodiments, the compounds of the invention are selective inhibitors of TAK1, HCK, or HPK1. The term "selective inhibitor" as used herein is understood to mean that in contrast to many kinase inhibitors of the prior art, the compounds do not act on a variety of kinases but act specifically on TAK1, HCK, or HPK1. In certain embodiments, the compounds of the invention inhibit one or more kinases in addition to TAK1, HCK, or HPK1 such as BTK or the SRC family of kinases. In certain embodiments of the invention, the specificity of the inhibitors is given by the $IC_{50}$ value. In some embodiments, the $IC_{50}$ value for a selective inhibitor is <100 μM for TAK1, HCK, or HPK1, but >100 μM for other kinases.

The $IC_{50}$ value is defined as the concentration of inhibitor required to inhibit 50% of the kinase activity. In certain embodiments, the compounds of the invention may exhibit $IC_{50}$ values<100 μM. In certain other embodiments, the compounds exhibit $IC_{50}$ values<50 µM. In certain other embodiments, the compounds exhibit $IC_{50}$ values<40 µM. In certain other embodiments, the compounds exhibit $IC_{50}$ values<30 µM. In certain other embodiments, the compounds exhibit $IC_{50}$ values<20 µM. In certain other embodiments, the compounds exhibit $IC_{50}$ values<10 µM. In certain other embodiments, the compounds exhibit $IC_{50}$ values<7.5 µM. In certain embodiments, the compounds exhibit $IC_{50}$ values<5 µM. In certain other embodiments, the compounds exhibit $IC_{50}$ values<2.5 µM. In certain embodiments, the compounds exhibit $IC_{50}$ values<1 µM. In certain embodiments, the compounds exhibit $IC_{50}$ values<0.75 µM. In certain embodiments, the compounds exhibit $IC_{50}$ values<0.5 µM. In certain embodiments, the compounds exhibit $IC_{50}$ values<0.25 µM. In certain embodiments, the compounds exhibit $IC_{50}$ values<0.1 µM. In certain other embodiments, the compounds exhibit $IC_{50}$ values<75 nM. In certain other embodiments, the compounds exhibit $IC_{50}$ values<50 nM. In certain other embodiments, the compounds exhibit $IC_{50}$ values<25 nM. In certain other embodiments, the compounds exhibit $IC_{50}$ values<10 nM. In other embodiments, the compounds exhibit $IC_{50}$ values<7.5 nM. In other embodiments, the compounds exhibit $IC_{50}$ values<5 nM.

In certain embodiments, the compounds of the invention (e.g., the compounds of Formula (A), (I-11), (II), or (V)) inhibit HCK selectively. In certain embodiments, the compounds of the invention (e.g., the compounds of Formula (A), (I-11), (II), or (V)) inhibit TAK1 selectively. A non-limiting example of a selective TAK1 inhibitor is:

(A-3)

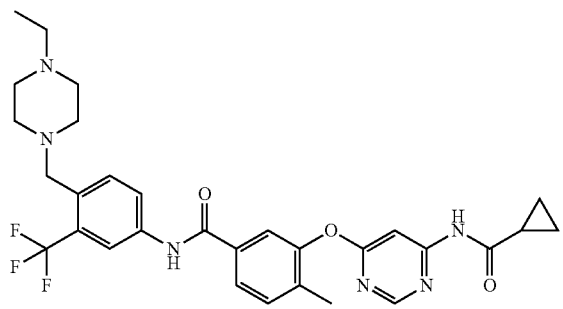

In certain embodiments, the compounds of the invention (e.g., the compounds of Formula (A), (I-11), (II), or (V)) inhibit both TAK1 and HCK. A non-limiting example of a dual TAK1/HCK inhibitor is:

(A-17)

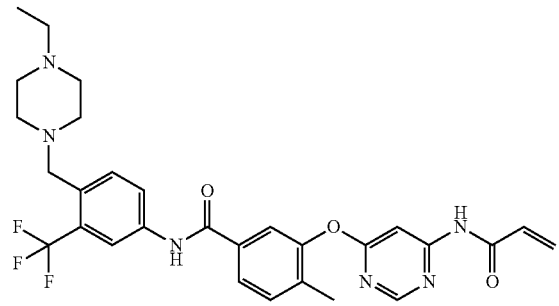

In certain embodiments, the compounds of the invention (e.g., the compounds of Formula (A), (I-11), (II), or (V)) inhibit HPK1 selectively. A non-limiting example of a selective HPK1 inhibitor is:

(A-14)

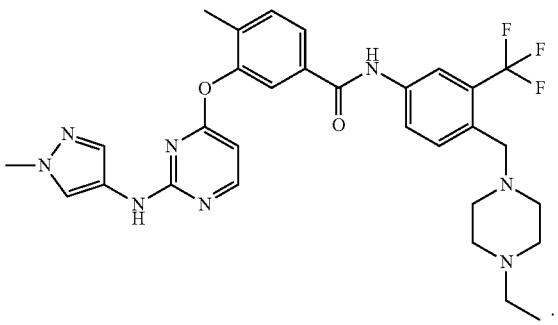

Also, provided are methods to treat B cell neoplasms using compounds of the invention in combination with inhibitors of Bruton's tyrosine kinase (BTK), interleukin-1 receptor-associated kinase 1 (IRAK1), interleukin-1 receptor-associated kinase 4 (IRAK4), bone marrow on X chromosome kinase (BMX), phosphoinositide 3-kinase (PI3K), transforming growth factor b-activated kinase-1 (TAK1), and/or a Src family kinase. In certain embodiments, one or more compounds of the invention are used in combination with an inhibitor of the phosphoinositide 3-kinase delta isoform (PI3Kδ). In certain embodiments, combinations of 2, 3, 4, 5, 6, 7, 8, 9, 10, or more of the agents described herein are used for treating WM. In certain embodiments, the agents described herein are used in combination with inhibitors of Bruton's tyrosine kinase (BTK), interleukin-1 receptor-associated kinase 1 (IRAK1), interleukin-1 receptor-associated kinase 4 (IRAK4), bone marrow on X chromosome kinase (BMX), phosphoinositide 3-kinase (PI3K), transforming growth factor b-activated kinase-1 (TAK1), and/or a Src family kinase.

Bruton's tyrosine kinase (BTK) is a key signaling enzyme expressed in all hematopoietic cells types except T lymphocytes and natural killer cells. BTK plays an essential role in the B cell signaling pathway linking cell surface B cell receptor BCR stimulation to downstream intracellular responses. BTK is a key regulator of B cell development activation signaling and survival (Kurosaki, *Curr. Op. Imm.*, 2000, 276-281; Schaeffer and Schwartzberg, *Curr. Op. Imm.*, 2000, 282-288). In addition BTK plays a role in a number of other hematopoietic cell signaling pathways, e.g., Toll like receptor (TLR) and cytokine receptor-mediated TNF-α production in macrophages, IgE receptor (FcepsilonRI) signaling in mast cells, inhibition of Fas/APO-1 apoptotic signaling in B-lineage lymphoid cells, and collagen stimulated platelet aggregation. See e.g., C. A. Jeffries, et al., *J. Biol. Chem.*, 2003, 278, 26258-26264; N. J. Horwood, et al., *J. Exp. Med.*, 2003, 197, 1603-1611; Iwaki et al., *J. Biol. Chem.*, 2005, 280(48), 40261-40270; Vassilev et al., *J. Biol. Chem.*, 1999, 274(3), 1646-1656; and Quek et al., *Curr. Biol.*, 1998, 8(20), 1137-1140. Activated Btk interacts with MyD88 and TRIF, promoting the activation of MyD88-dependent and TRIF-dependent pathways (*Nature Immunology*, 2011, 12, 416-424).

BTK inhibitors are well-known in the art, and include, for example, ibrutinib and benzonaphthyridinones (see U.S. provisional patent application U.S. Ser. No. 61/716,273, filed Oct. 19, 2012). Additional non-limiting examples of BTK inhibitors are disclosed in WO 1999/054286, WO 2013/010380, WO 2009/137596, WO 2011/029043, WO 2010/056875, WO 2000/056737, and WO 2013/067277.

IRAK1 and 4 are serine/threonine-protein kinases that play a critical role in initiating innate immune response against foreign pathogens. They are involved in Toll-like receptor (TLR) and IL-1R signaling pathways, and are rapidly recruited by MYD88 to the receptor-signaling complex upon TLR activation. Association with MYD88 leads to IRAK1 phosphorylation by IRAK4 and subsequent autophosphorylation and kinase activation of IRAK1 (*Immunity*, 1997, 7(6), 837-47). IRAK4−/− mice have abolished cellular responses to various IL-1 and TLR ligands and are severely impaired in their response to viral and bacterial challenges. IRAK1−/− mice show a similar but partial response.

IRAK1 and IRAK4 inhibitors are well-known in the art, and include, for example, those disclosed in WO 2003/030902, WO 2012/007375, G. M. Buckely et al., *Biorg. Med. Chem. Lett.*, 2008, 18, 3211-3214, and G. M. Buckely et al., *Biorg. Med. Chem. Lett.*, 2008, 18, 3656-3660, WO2013/074986, and U.S. provisional patent application, U.S. Ser. No. 61/727,640, filed Nov. 16, 2012.

In certain embodiments, the IRAK4 inhibitor is of formula:

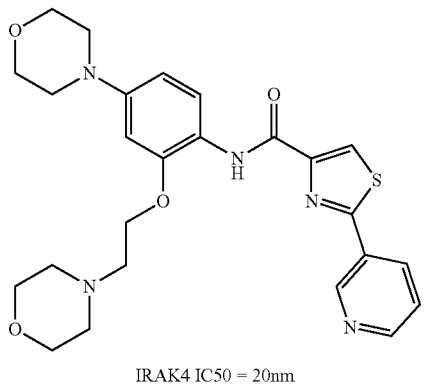

JH-IV-96-01

IRAK4 IC50 = 20nm or an analog thereof.

"Bone Marrow on X chromosome" kinase (BMX, also termed ETK) is a non-receptor tyrosine kinase and is activated downstream of phosphatidylinositol-3 kinase (PI-3K) and v-src sarcoma (Schmidt-Ruppin A-2) viral oncogene homolog (SRC), but its substrates are unknown. Positional scanning peptide library screening revealed a marked preference for a priming phosphotyrosine (pY) in the −1 position. Potential substrates include multiple tyrosine kinases with kinase domain pYpY sites required for full activity. BMX has been found to phosphorylate residue Y577 of focal adhesion kinase (FAK) subsequent to Y576 phosphorylation by SRC. In addition, BMX loss by RNA interference and mouse embryonic fibroblasts (MEFs) from Bmx negative (Bmx−) mice displayed impaired FAK signaling. Insulin receptor (IR) phosphorylation similarly was decreased by BMX loss, as was hepatic IR phosphorylation in Bmx− mice. However, glucose tolerance was increased, reflecting a marked compensatory decrease in the activity of the AKT phosphatase PHLPP. These findings reveal a mechanism through which BMX functions as a central regulator of multiple kinase pathways.

BMX inhibitors are well-known in the art, and include, for example, those disclosed in U.S. Ser. No. 61/716,273 and 61/717,345, the contents of both of which are incorporated herein by reference. In certain embodiments, the BMX inhibitor is of formula:

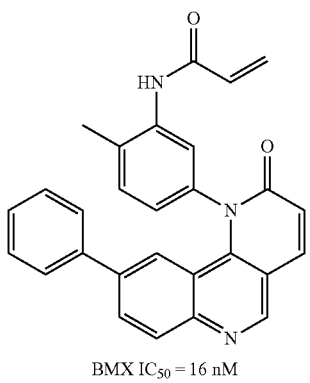 [SMILES: C=CC(=O)Nc1cc(-n2c(=O)ccc3cnc4ccc(-c5ccccc5)cc4c32)ccc1C]

BMX IC$_{50}$ = 16 nM or an analog thereof.

Phosphatidylinositol 3-kinases (PI3-kinases or PI3Ks) are a family of enzymes involved in cellular functions such as cell growth, proliferation, differentiation, motility, survival and intracellular trafficking, which in turn are involved in cancer. PI3Ks are a family of related intracellular signal transducer enzymes capable of phosphorylating the 3 position hydroxyl group of the inositol ring of phosphatidylinositol (PtdIns). Phosphatidylinositol 3-kinase is composed of an 85 kDa regulatory subunit and a 110 kDa catalytic subunit. The protein encoded by PI3KCA gene represents the catalytic subunit, which uses ATP to phosphorylate phosphatidylinositols (PtdIns), PtdIns4P and PtdIns(4,5)P2. Of particular interest is the PI3K delta isoform, which is expressed in white blood cells and is mainly involved in the signaling, development, and survival of B cells.

PI3K inhibitors are well-known in the art, and include, for example, those disclosed in International PCT Publications WO 2013/088404, WO 2012/068096, and WO 2013/052699, which are incorporated herein by reference.

In certain embodiments, the PI3K inhibitor is

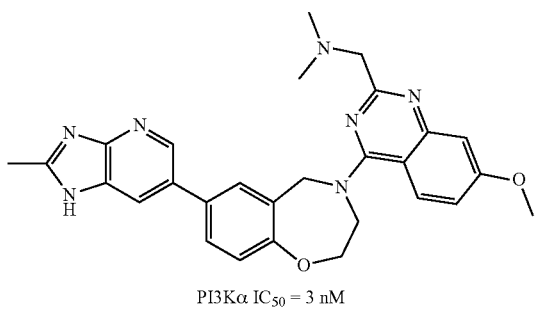

PI3Kα IC$_{50}$ = 3 nM or its analogs.

Compounds of the invention may be combined with other kinase inhibitors to treat WM or other B cell neoplasms. In certain embodiments, a compound of the invention is administered with an inhibitor of Bruton's tyrosine kinase (BTK) to treat WM or other B cell neoplasm. In certain embodiments, a compound of the invention is administered with an inhibitor of interleukin-1 receptor-associated kinase 1 (IRAK1) to treat WM or otherB cell neoplasm. In certain embodiments, a compound of the invention is administered with an inhibitor of phosphoinositide 3-kinase (PI3K) to treat WM or other B cell neoplasm. In certain embodiments, a compound of of the invention is administered with an inhibitor of the phosphoinositide 3-kinase delta isoform (PI3Kδ) to treat WM or other B cell neoplasm. In certain embodiments, a compound of of the invention is administered with two of any inhibitors of BTK, IRAK1, or PI3K to treat WM or other B cell neoplasm. In certain embodiments, a compound of the invention is administered with more than two of any inhibitors of BTK, IRAK1, or PI3K to treat WM or other B cell neoplasm.

The BTK inhibitors, the IRAK1 inhibitors, the IRAK4 inhibitors, and/or the PI3K inhibitors can be administered to the subject simultaneously or sequentially.

A "subject" or "patient" to which administration is contemplated includes, any animal. In some embodiments, a subject includes but is not limited to, humans, commercially relevant mammals such as cattle, pigs, horses, sheep, goats, cats, and/or dogs), birds (e.g., commercially relevant birds such as chickens, ducks, geese, and/or turkeys) and experimental animals (e.g., mice, rats, non-human primates). A subject in need of treatment is a subject identified as having a B cell neoplasm, i.e., the subject has been diagnosed by a physician (e.g., using methods well known in the art) as having a B cell neoplasm. In certain embodiments, the subject in need of treatment is a subject suspected of having or developing a B cell neoplasm, such as a subject presenting one or more symptoms indicative of a B cell neoplasm. The term "subject in need of treatment" further includes people who once had a B cell neoplasm but whose signs and/or symptoms have been ameliorated (i.e., their cancer is in remission). The one or more symptoms or clinical features of B cell neoplasms include, but are not limited to, asymptomatic localized or generalized peripheral lymphadenopathy, plasmacytic difference, bone marrow involvement, autoimmune thrombocytopenia, peripheral blood villous lymphocytes, end organ damage (hypercalcemia, renal insufficiency, bone lesions), recurrent infections, elevated creatine, hyperuricemia, and hypoalbunemia.

In certain embodiments, the subject is diagnosed as having Waldenström's macroglobulinemia (WM). The subject may present one or more signs, symptoms, or clinical features of WM including anemia, hyper-viscosity, neuropathy, coagulopathies, splenomegaly, hepatomegaly, adenopathy, and an IgM serum paraprotein. In certain embodiments, the subject is diagnosed as having WM on the basis that the subject has a mutation at position 38182641 of chromosome 3p22.2. In some embodiments, the mutation results in a single nucleotide change from T to C in the MYD88 gene. In some embodiments, the mutation results in an amino acid change from leucine to proline at position 265 in the MYD88 gene. The mutation may be detected in a biological sample obtained from the subject using any suitable method known in the art, including but not limited to, direct sequencing of nucleic acid molecules, HPLC analysis, DNA chip technologies, and mass spectroscopy. Non-limiting examples of the biological sample include bone marrow, lymph node, spleen, or blood.

The terms "administer," "administering," or "administration," as used he rein refers to implanting, absorbing, ingesting, injecting, or inhaling an inventive compound, or a pharmaceutical composition thereof.

As used herein, the terms "treatment," "treat," and "treating" refer to reversing, alleviating, delaying the onset of, or inhibiting the progress of a B cell neoplasm. In certain embodiments, treatment may be administered after one or more signs or symptoms have developed or have been observed. In other embodiments, treatment may be administered in the absence of signs or symptoms of the B cell neoplasm. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

An "effective amount" of compounds of the invention refers to an amount sufficient to elicit the desired biological response, i.e., treating the B cell neoplasm. As will be appreciated by those of ordinary skill in this art, the effective amount of compounds of the invention may vary depending on such factors as the desired biological endpoint, the pharmacokinetics of the compound, the condition being treated, the mode of administration, and the age and health of the subject. An effective amount includes, but is not limited to, that amount necessary to slow, reduce, inhibit, ameliorate or reverse one or more signs and/or symptoms associated with a B cell neoplasm. In the treatment of Waldenström's macroglobulinemia, this may refer to a reduction in the levels of IgM serum paraprotein, reduction in anemia, reduction in hyper-viscosity, reduction in neuropathy, reduction in coagulopathies, reduction in splenomegaly, reduction in hepatomegaly, and reduction in adenopathy.

An effective amount of a compound may vary from about 0.001 mg/kg to about 1000 mg/kg in one or more dose administrations, for one or several days (depending on the mode of administration). In certain embodiments, the effective amount varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, from about 1.0 mg/kg to about 100 mg/kg, and from about 10.0 mg/kg to about 150 mg/kg.

One or more additional pharmaceutical agents, such as anti-cancer agents (e.g., chemotherapeutics), anti-inflammatory agents, steroids, immunosuppressants, radiation therapy, or other agents, can be used in combination with the compounds of of the invention in the treatment of a B cell neoplasm. The one or more additional pharmaceutical agents can be administered to the subject simultaneously or sequentially.

Exemplary chemotherapeutic agents include alkylating agents such as nitrogen mustards, ethylenimines, methylmelamines, alkyl sulfonates, nitrosuoureas, and triazenes; antimetabolites such as folic acid analogs, pyrimidine analogs, in particular fluorouracil and cytosine arabinoside, and purine analogs; natural products such as vinca alkaloids epi-podophyllotoxins, antibiotics, enzymes, and biological response modifiers; and miscellaneous products such as platinum coordination complexes, anthracenedione, substituted urea such as hydroxyurea, methyl hydrazine derivatives, and adrenocorticoid suppressant.

Exemplary chemotherapeutic agents also include anthracycline antibiotics, actinomycin D, plicamycin, puromycin, gramicidin D, paclitaxel, colchicine, cytochalasin B, emetine, maytansine, amsacrine, cisplatin, carboplatin, mitomycin, altretamine, cyclophosphamide, lomustine, and carmustine.

In yet another aspect, the present invention provides pharmaceutical compositions comprising an effective amount of a compound of of the invention, and pharmaceutically acceptable salts, solvates, hydrates, polymorphs, co-crystals, tautomers, stereoisomers, isotopically labeled derivatives, and prodrugs, and optionally a pharmaceutically acceptable excipient, for use in the treatment of a B cell neoplasm. In certain embodiments, provided by the invention are the compounds of of the invention, and pharmaceutically acceptable salts and compositions thereof, for use in the treatment of a B cell neoplasm. In certain embodiments, the effective amount is a therapeutically effective amount. In certain embodiments, the therapeutically effective amount is an amount useful for the treatment and/or prevention of a B cell neoplasm. In certain embodiments, the B cell neoplasm is, but is not limited to, Hodgkin's lymphomas and most non-Hodgkins lymphomas, such as, diffuse large B cell lymphoma, Follicular lymphoma, Mucosa-Associated Lymphatic Tissue lymphoma (MALT), small cell lymphocytic lymphoma (overlaps with Chronic lymphocytic leukemia), Mantle cell lymphoma (MCL), Burkitt lymphoma, Mediastinal large B cell lymphoma, Waldenström's macroglobulinemia, Nodal marginal zone B cell lymphoma (NMZL), Splenic marginal zone lymphoma (SMZL), Intravascular large B-cell lymphoma, Primary effusion lymphoma and Lymphomatoid granulomatosis. An effective amount of a compound may vary from about 0.001 mg/kg to about 1000 mg/kg in one or more dose administrations, for one or several days (depending on the mode of administration). In certain embodiments, the effective amount varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

Pharmaceutical compositions described herein can be prepared by any method known in the art of pharmacology. In general, such preparatory methods include the steps of bringing a compound of of the invention (the "active ingredient") into association with a carrier or excipient, and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as, for example, one-half or one-third of such a dosage.

The pharmaceutical preparations of the present invention may include or be diluted into a pharmaceutically acceptable carrier. The term "pharmaceutically acceptable carrier" as used herein means one or more compatible fillers, diluents or other such substances, which are suitable for administration to a human or other mammal, such as a dog, cat, rat, mouse, or horse. The term "carrier" denotes an organic or inorganic ingredient, natural or synthetic, with which the active ingredient is combined to facilitate the application. The carriers are capable of being commingled with the preparations of the present invention, and with each other, in a manner such that there is no interaction which would substantially impair the desired pharmaceutical efficacy or stability. Carriers suitable for oral, subcutaneous, intravenous, intramuscular, etc. formulations can be found in *Remington's Pharmaceutical Sciences*, Mack Publishing Company, Easton, Pa.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, thR$^{ee}$, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compound of the invention is administered at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

The present invention is further illustrated by the following Example, which in no way should be construed as further limiting. The entire contents of all of the references (including literature references, issued patents, published patent applications, and co pending patent applications) cited throughout this application are hereby expressly incorporated by reference.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Example 1. Preparation of the Compounds Preparation of I-11

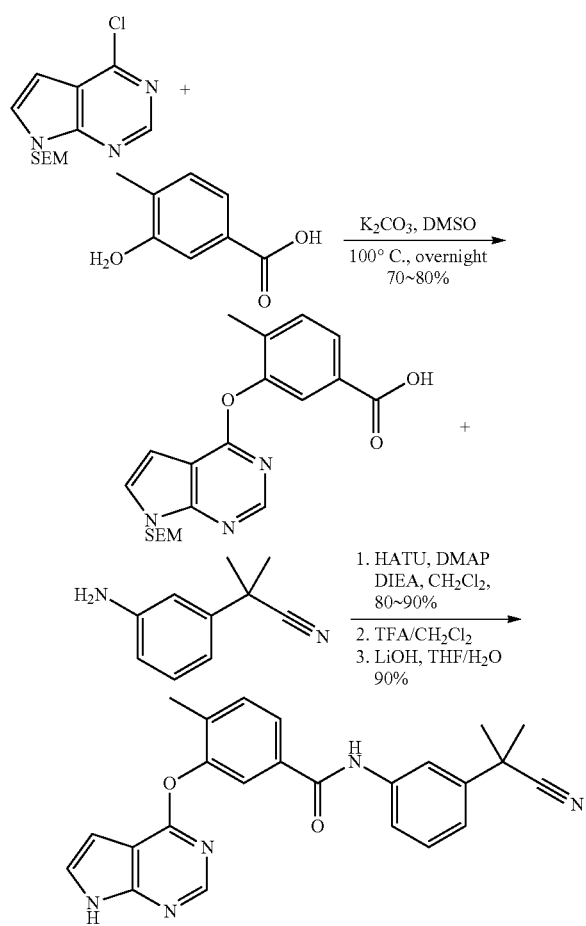

4-methyl-3-((7-((2-(trimethylsilyl)ethoxy)methyl)-7H-pyrrolo[2,3-d]pyrimidin-4-yl)oxy)benzoic acid 4-chloro-7-((2-(trimethylsilyl)ethoxy)methyl)-7H-pyrrolo[2,3-d]pyrimidine (284 mg, 1.0 mmol), 3-hydroxy-4-methylbenzoic acid (152 mg, 1.0 mmol) and $K_2CO_3$ (414 mg, 3.0 mmol) were combined in DMSO (5 mL) and stirred overnight at 100° C. The reaction mixture was then cooled to room temperature. The mixture was acidified with 1N HCl solution and extracted with ethyl acetate. The organic phase was washed with brine, dried over $Na_2SO_4$, filtered and concentrated. The crude product was purified by column chromatography to yield 296 mg of product as a colorless oil. MS (ESI) m/z 400 (M+H)$^+$.

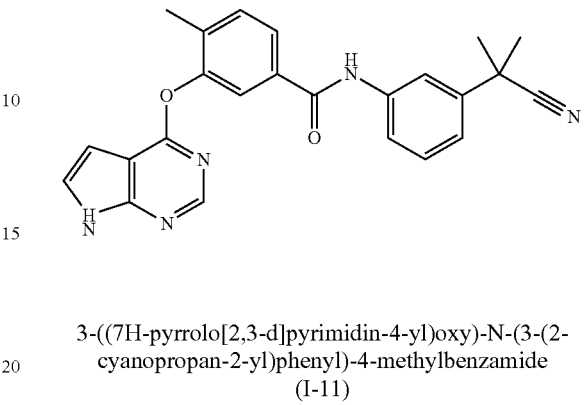

3-((7H-pyrrolo[2,3-d]pyrimidin-4-yl)oxy)-N-(3-(2-cyanopropan-2-yl)phenyl)-4-methylbenzamide
(I-11)

To a solution of 4-methyl-3-((7-((2-(trimethylsilyl)ethoxy)methyl)-7H-pyrrolo[2,3-d]pyrimidin-4-yl)oxy)benzoic acid (200 mg, 0.5 mmol), HATU (230 mg, 0.6 mmol), DMAP (73 mg, 0.6 mmol) and iPr$_2$NEt (220 uL, 1.25 mmol) in $CH_2Cl_2$ (3 mL) was added 2-(3-aminophenyl)-2-methylpropanenitrile (80 mg, 0.5 mmol) and the resulting mixture was stirred at room temperature for 24 hours. The solution was filtered to remove solids, concentrated and purified with column chromatography (dichloromethane:methanol=10:1) to afford 455 mg of product as a colorless oil. To the solution of the obtained oil in $CH_2Cl_2$ (5 mL) was added TFA (0.5 mL) and the resulting mixture was stirred at room temperature for 5 hours. The solution was concentrated and dried with vacuum, then dissolved in THF (4 mL) and 1 N NaOH solution (4 mL). The reaction mixture was stirred for 24 h and extracted with ethyl acetate. The combined organic phase was washed with brine and dried with $Na_2SO_4$, then filtered and concentrated, and purified by reverse phase HPLC to give 185 mg (90%) of title compound as a white solid.

Preparation of A-17

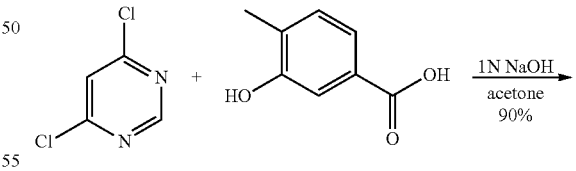

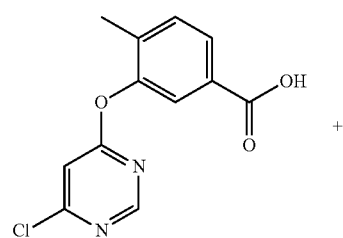

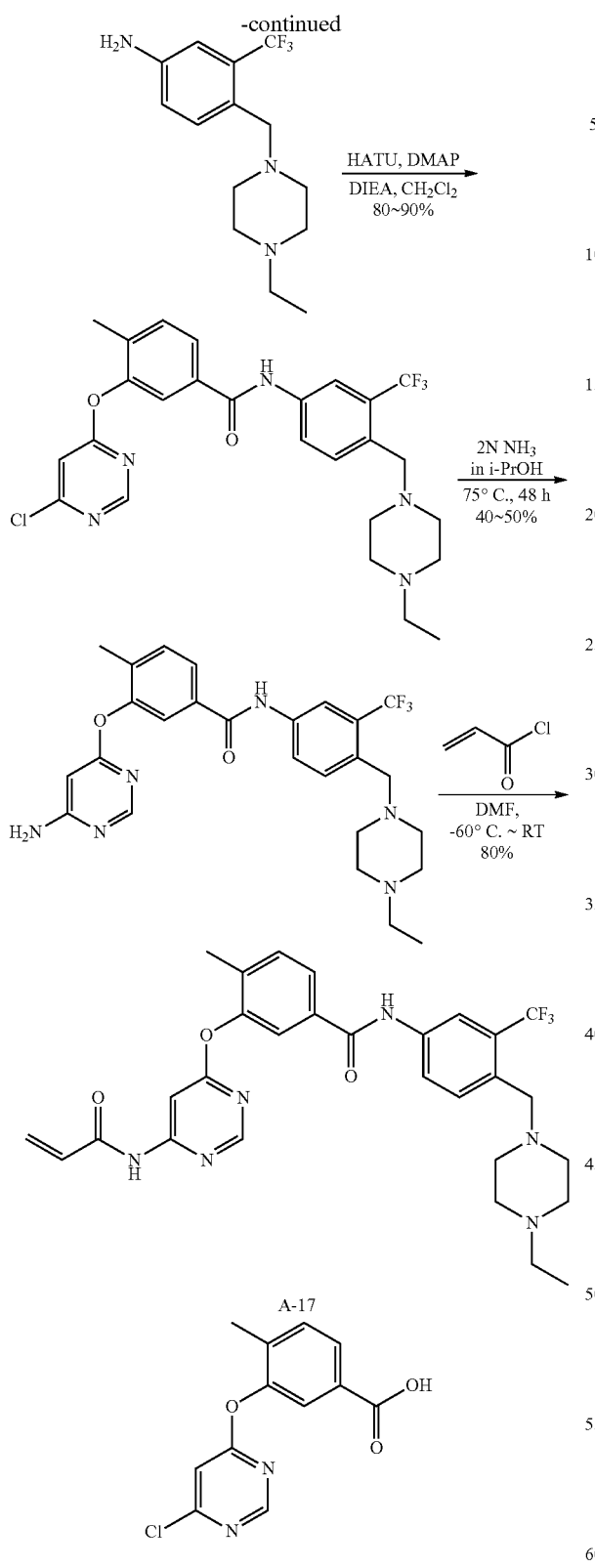

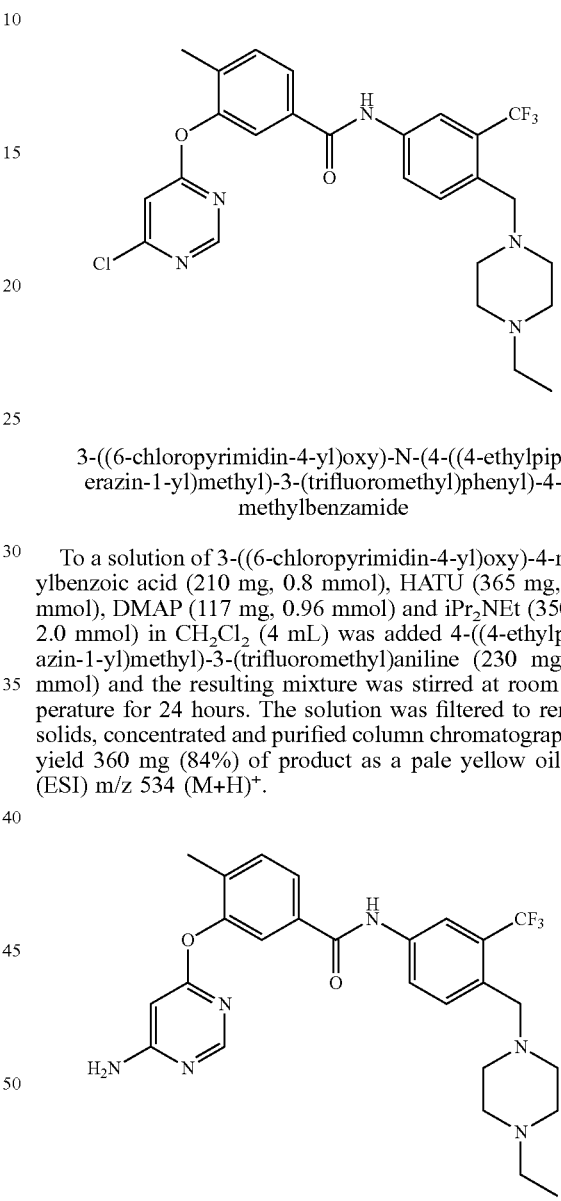

and 3-hydroxy-4-methylbenzoic acid (152 mg, 1.0 mmol) in acetone (2 mL) and the reaction mixture as stirred at room temperature for 1 hour at which point LC-MS analysis indicated complete consumption of starting material. The reaction mixture was extracted with ethyl acetate. The combined organic phase was washed with brine and dried with $Na_2SO_4$, then filtered and concentrated, and purified by column chromatography to yield 250 mg of product as a white solid. MS (ESI) m/z 265 (M+H)$^+$.

3-((6-chloropyrimidin-4-yl)oxy)-N-(4-((4-ethylpiperazin-1-yl)methyl)-3-(trifluoromethyl)phenyl)-4-methylbenzamide To a solution of 3-((6-chloropyrimidin-4-yl)oxy)-4-methylbenzoic acid (210 mg, 0.8 mmol), HATU (365 mg, 0.96 mmol), DMAP (117 mg, 0.96 mmol) and iPr$_2$NEt (350 uL, 2.0 mmol) in $CH_2Cl_2$ (4 mL) was added 4-((4-ethylpiperazin-1-yl)methyl)-3-(trifluoromethyl)aniline (230 mg, 0.8 mmol) and the resulting mixture was stirred at room temperature for 24 hours. The solution was filtered to remove solids, concentrated and purified column chromatography to yield 360 mg (84%) of product as a pale yellow oil. MS (ESI) m/z 534 (M+H)$^+$.

3-((6-aminopyrimidin-4-yl)oxy)-N-(4-((4-ethylpiperazin-1-yl)methyl)-3-(trifluoromethyl)phenyl)-4-methylbenzamide 10 mL of a 2N solution of $NH_3$ in i-PrOH was added to 3-((6-chloropyrimidin-4-yl)oxy)-N-(4-((4-ethylpiperazin-1-yl)methyl)-3-(trifluoromethyl)phenyl)-4-methylbenzamide (270 mg, 0.5 mmol) and the reaction mixture was stirred for 48 hours at 75° C. then cooled to room temperature and concentrated. The crude product was purified by column chromatography to yield 120 mg of product as a colorless oil. MS (ESI) m/z 515 (M+H)$^+$.

3-((6-chloropyrimidin-4-yl)oxy)-4-methylbenzoic acid

Sodium hydroxide (2 ml of a 1N solution) was added to a solution of 4,6-dichloropyrimidine (150 mg, 1.0 mmol)

A-17

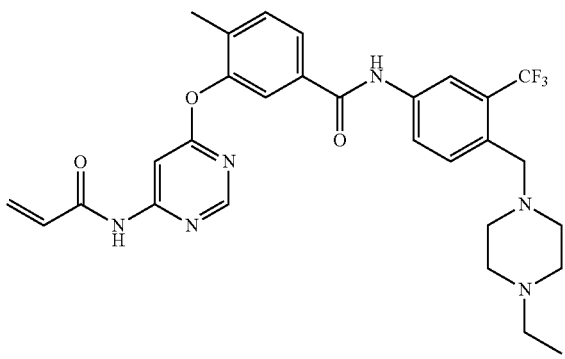

3-((6-acrylamidopyrimidin-4-yl)oxy)-N-(4-((4-ethyl-piperazin-1-yl)methyl)-3-(trifluoromethyl)phenyl)-4-methylbenzamide (A-17)

To a solution of 3-((6-aminopyrimidin-4-yl)oxy)-N-(4-((4-ethylpiperazin-1-yl)methyl)-3-(trifluoromethyl)phenyl)-4-methylbenzamide (51 mg, 0.1 mmol) in DMF cooled in a dry ice/SOLVENT bath was added acryloyl chloride (8.9 uL, 0.11 mmol). The cooling bath was removed allowing the mixture to warm to room temperature and continue stirring for an half hour. The solution was then diluted in DMSO and purified by reverse phase HPLC to afford 45 mg (80%) of A-17 as a white solid.

Compounds (A-1)-(A-16) and (A-18) were prepared similarly to A-17.

Characterization data for all final compounds is in the table below.

| ID # | Structure | Name | $^1$H NMR and or MS (m/z) |
|---|---|---|---|
| A-1 | 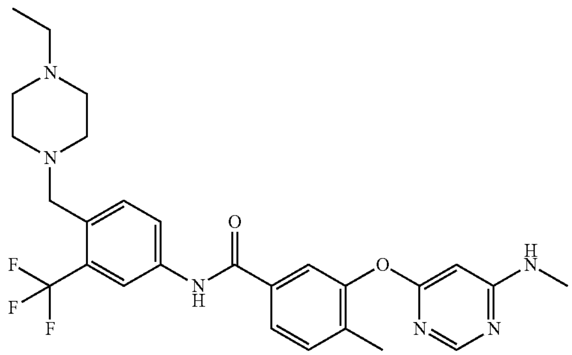 [SMILES: CCN1CCN(Cc2ccc(NC(=O)c3ccc(C)c(Oc4cc(NC)ncn4)c3)cc2C(F)(F)F)CC1] | N-(4-((4-ethylpiperazin-1-yl)methyl)-3-(trifluoromethyl)phenyl)-4-methyl-3-((6-(methylamino)pyrimidin-4-yl)oxy)benzamide | $^1$H NMR (400 MHz, DMSO) δ 10.39 (s, 1H), 8.11 (s, 1H), 9.00 (d, J = 8.4) Hz, 1H), 7.75 (d, J = 8.0 Hz, 1H), 7.64 (s, 1H), 7.62 (d, J = 8.8 Hz, 1H), 7.41 (d, J = 8.0 Hz, 1H), 7.33 (bs, 1H), 3.60 (s, 2H), 3.38 (m, 2H), 2.97-2.79 (m, 6H), 2.71 (bs, 3H), 2.37-2.22 (m, 2H), 2.09 (s, 3H), 1.12 (t, J = 6.8 Hz, 3H). MS (ESI) m/z 529 (M + H)$^+$. |
| A-2 | 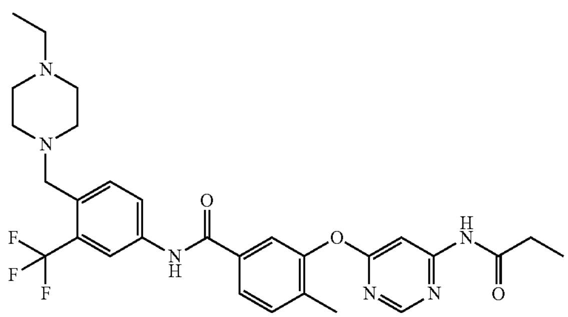 [SMILES: CCC(=O)Nc1cc(Oc2cc(C(=O)Nc3ccc(CN4CCN(CC)CC4)c(C(F)(F)F)c3)ccc2C)ncn1] | N-(4-((4-ethylpiperazin-1-yl)methyl)-3-(trifluoromethyl)phenyl)-4-methyl-3-((6-(propionamido-pyrimidin)-4-yl)oxy)benzamide | $^1$H NMR (600 MHz, TFA salt, DMSO) δ 10.89 (s, 1H), 10.42 (s, 1H), 9.36 (br, 1H), 8.42 (s, 1H), 8.13 (s, 1H), 8.02 (d, J = 8.4 Hz, 1H), 7.80 (d, J = 7.8 Hz, 1H), 7.71 (s, 1H), 7.64 (d, J = 9.0 Hz, 1H), 7.57 (s, 1H), 7.46 (d, J = 7.8 Hz, 1H), 3.61 (s, 2H), 3.38 (m, 2H), 3.07 (m, 2H), 2.92 (m, 2H), 2.85 (m, 2H), 2.37 (q, J = 7.2 Hz, 2H), 2.32 (m, 2H), 2.10 (s, 3H), 1.34 (t, J = 7.2 Hz, 3H), 0.98 (t, J = 7.2 Hz, 3H). MS (ESI) m/z 571 (M + H)$^+$. |
| A-3 | 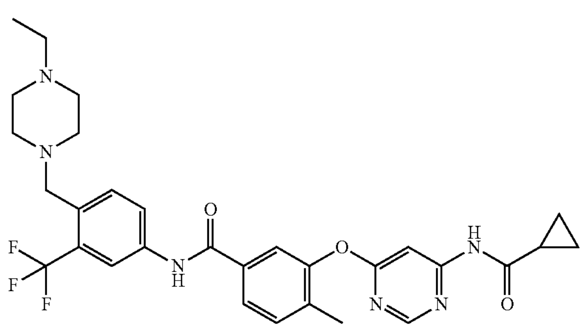 [SMILES: CCN1CCN(Cc2ccc(NC(=O)c3ccc(C)c(Oc4cc(NC(=O)C5CC5)ncn4)c3)cc2C(F)(F)F)CC1] | 3-((6-(cyclopropane-carboxamido)pyrimidin-4-yl)oxy)-N-(4-((4-ethylpiperazin-1-yl)methyl)-3-(trifluoromethyl)phenyl)-4-methyl-benzamide | $^1$H NMR (600 MHz, DMSO) δ 11.25 (s, 1H), 10.36 (s, 1H), 8.43 (s, 1H), 8.11 (s, 1H), 7.97 (d, J = 8.4 Hz, 1H), 7.79 (d, J = 7.8 Hz, 1H), 7.70 (s, 1H), 7.63 (d, J = 8.4 Hz, 1H), 7.54 (s, 1H), 7.45 (d, J = 8.4 Hz, 1H), 3.49 (s, 2H), 2.32 (m, 8H), 2.24 (m, 2H), 2.09 (s, 3H), 1.97 (m, 1H), 0.91 (t, J = 7.2 Hz, 3H), 0.79 (m, 4H). MS (ESI) m/z 583 (M + H)$^+$. |

| ID # | Structure | Name | ¹H NMR and or MS (m/z) |
|---|---|---|---|
| A-4 | 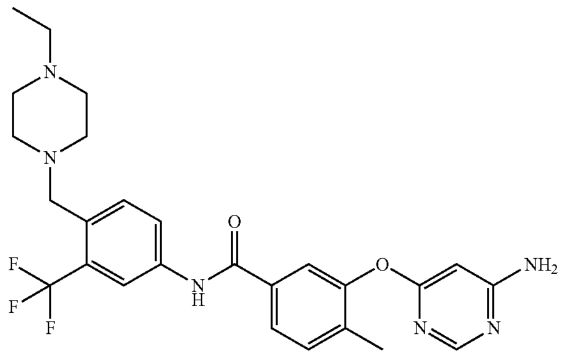 [SMILES: CCN1CCN(Cc2ccc(NC(=O)c3ccc(C)c(Oc4cc(N)ncn4)c3)cc2C(F)(F)F)CC1] | 3-((6-aminopyrimidin-4-yl)oxy)-N-(4-((4-ethylpiperazin-1-yl)methyl)-3-(trifluoromethyl)phenyl)-4-methyl-benzamide | ¹H NMR (600 MHz, TFA salt, DMSO) δ 8.06 (s, 1H), 8.03 (s, 1H), 7.92 (d, J = 8.4 Hz, 1H), 7.76 (d, J = 7.8 Hz, 1H), 7.69 (d, J = 8.4 Hz, 1H), 7.63 (s, 1H), 7.43 (d, J = 7.2 Hz, 1H), 5.78 (s, 1H), 3.70 (s, 2H), 3.47 (m, 2H), 3.15 (q, J = 7.2 Hz, 2H), 3.01 (m, 4H), 2.42 (m, 2H), 1.29 (t, J = 7.2 Hz, 3H). MS (ESI) m/z 515 (M + H)⁺. |
| A-5 | 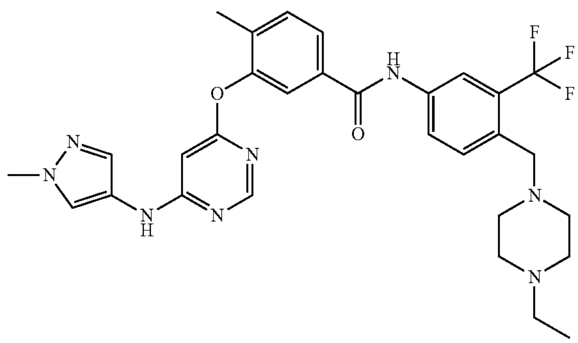 [SMILES: CCN1CCN(Cc2ccc(NC(=O)c3ccc(C)c(Oc4cc(Nc5cnn(C)c5)ncn4)c3)cc2C(F)(F)F)CC1] | N-(4-((4-ethylpiperazin-1-yl)methyl)-3-(trifluoromethyl)phenyl)-4-methyl-3-((6-((1-methyl-1H-pyrazol-4-yl)amino)pyrimidin-4-yl)oxy)benzamide | ¹H NMR (600 MHz, DMSO) δ 10.36 (s, 1H), 9.37 (br, 1H), 8.20 (s, 1H), 8.11 (s, 1H), 7.97 (d, J = 7.8 Hz, 1H), 7.84 (s, 1H), 7.78 (d, J = 8.4 Hz, 1H), 7.69 (s, 1H), 7.63 (d, J = 8.4 Hz, 1H), 7.44 (d, J = 8.4 Hz, 1H), 7.36 (s, 1H), 5.94 (s, 1H), 3.74 (s, 3H), 3.50 (s, 2H), 2.18-2.42 (m, 10H), 2.12 (s, 3H), 0.92 (m, 3H). MS (ESI) m/z 595 (M + H)⁺. |
| A-6 | 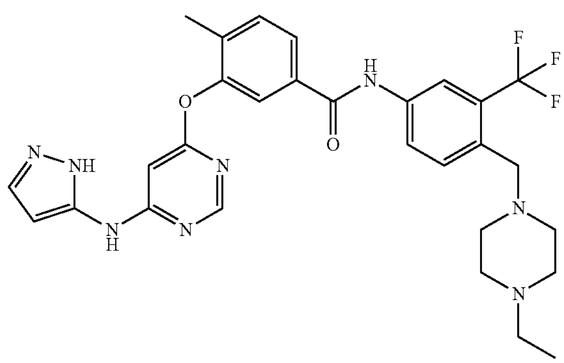 [SMILES: CCN1CCN(Cc2ccc(NC(=O)c3ccc(C)c(Oc4cc(Nc5ccn[nH]5)ncn4)c3)cc2C(F)(F)F)CC1] | 3-((6-((1H-pyrazol-5-yl)amino)pyrimidin-4-yl)oxy)-N-(4-((4-ethyl-piperazin-1-yl)methyl)-3-(trifluoromethyl)phenyl)-4-methyl-benzamide | ¹H NMR (600 MHz, TFA salt, DMSO) δ 10.45 (s, 1H), 9.92 (s, 1H), 9.33 (br, 1H), 8.24 (s, 1H), 8.18 (s, 1H), 8.08 (d, J = 8.4 Hz, 1H), 7.83 (d, J = 7.8 Hz, 1H), 7.74 (s, 1H), 7.69 (d, J = 8.4 Hz, 1H), 7.62 (s, 1H), 7.49 (d, J = 8.4 Hz, 1H), 3.66 (s, 2H), 3.44 (m, 2H), 3.12 (m, 2H), 2.97 (m, 2H), 2.91 (m, 2H), 2.37 (m, 2H), 2.17 (s, 3H), 1.19 (t, J = 7.2 Hz, 3H). MS (ESI) m/z 581 (M + H)⁺. |
| A-7 | 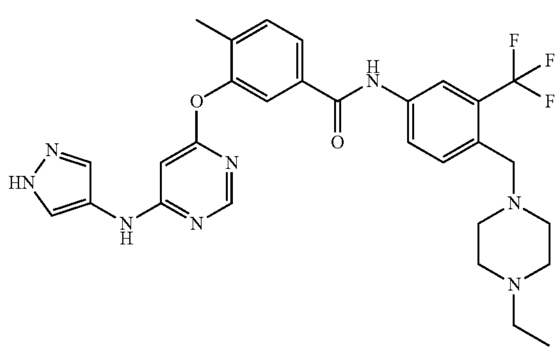 [SMILES: CCN1CCN(Cc2ccc(NC(=O)c3ccc(C)c(Oc4cc(Nc5cn[nH]c5)ncn4)c3)cc2C(F)(F)F)CC1] | 3-((6-((1H-pyrazol-4-yl)amino)pyrimidin-4-yl)oxy)-N-(4-((4-ethylpiperazin-1-yl)methyl)-3-(trifluoromethyl)phenyl)-4-methylbenzamide | ¹H NMR (600 MHz, DMSO) δ 12.63 (br, 1H), 10.44 (s, 1H), 9.42 (br, 1H), 8.26 (br, 1H), 8.19 (s, 1H), 8.06 (d, J = 9.0 Hz, 1H), 7.90 (br, 1H), 7.85 (d, J = 8.4 Hz, 1H), 7.76 (s, 1H), 7.70 (d, J = 9.0 Hz, 1H), 7.53 (br, 1H), 7.51 (d, J = 8.4 Hz, 1H), 6.00 (s, 1H), 3.60 (s, 2H), 2.25-2.86 (m, 10H), 2.19 (s, 3H), 1.05, (m, 3H). MS (ESI) m/z 581 (M + H)⁺. |

| ID # | Structure | Name | ¹H NMR and or MS (m/z) |
|------|-----------|------|------------------------|
| A-8 | 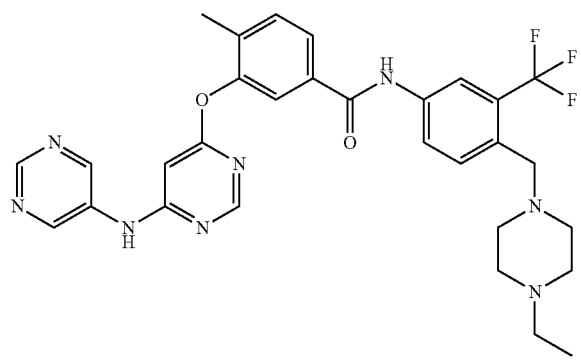 [SMILES: CCN1CCN(Cc2ccc(NC(=O)c3ccc(C)c(Oc4cc(Nc5cncnc5)ncn4)c3)cc2C(F)(F)F)CC1] | N-(4-((4-ethylpiperazin-1-yl)methyl)-3-(trifluoromethyl)phenyl)-4-methyl-3-((6-(pyrimidin-5-ylamino)pyrimidin-4-yl)oxy)benzamide | ¹H NMR (600 MHz, TFA salt, DMSO) δ 10.49 (s, 1H), 10.02 (s, 1H), 9.44 (br, 1H), 9.08 (s, 2H), 8.82 (s, 1H), 8.42 (s, 1H), 8.19 (s, 1H), 8.09 (d, J = 8.4 Hz, 1H), 7.88 (d, J = 7.8 Hz, 1H), 7.79 (s, 1H), 7.70 (d, J = 8.4 Hz, 1H), 7.54 (d, J = 8.4 Hz, 1H), 6.27 (s, 1H), 3.66 (s, 2H), 3.44 (m, 2H), 3.13 (m, 2H), 2.98 (m, 2H), 2.91 (m, 2H), 2.38 (m, 2H), 2.20 (s, 3H), 1.20 (t, J = 7.2 Hz, 3H). MS (ESI) m/z 593 (M + H)⁺. |
| A-9 | 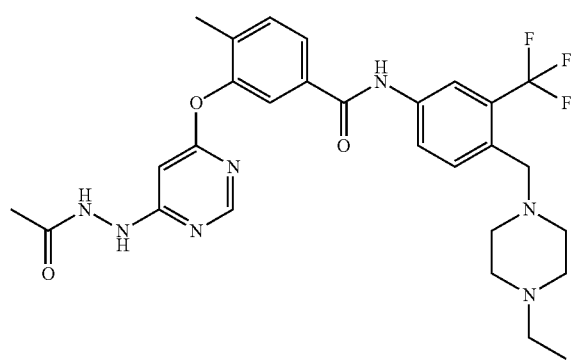 [SMILES: CCN1CCN(Cc2ccc(NC(=O)c3ccc(C)c(Oc4cc(NNC(C)=O)ncn4)c3)cc2C(F)(F)F)CC1] | 3-((6-(2-acetylhydrazinyl)pyrimidin-4-yl)oxy)-N-(4-((4-ethylpiperazin-1-yl)methyl)-3-(trifluoromethyl)phenyl)-4-methylbenzamide | ¹H NMR (600 MHz, DMSO) δ 10.43 (s, 1H), 9.88 (s, 1H), 9.20 (s, 1H), 8.19 (s, 1H), 8.17 (s, 1H), 8.04 (d, J = 8.4 Hz, 1H), 7.84 (d, J = 8.4 Hz, 1H), 7.73 (s, 1H), 7.70 (d, J = 8.4 Hz, 1H), 7.50 (d, J = 7.8 Hz, 1H), 5.99 (s, 1H), 3.56 (s, 2H), 3.32 (m, 4H), 2.29-2.48 (m, 4H), 2.32 (q, J = 7.2 Hz, 2H), 2.17 (s, 3H), 1.92 (s, 3H), 0.97 (J = 7.2 Hz, 3H). MS (ESI) m/z 572 (M + H)⁺. |
| A-10 | 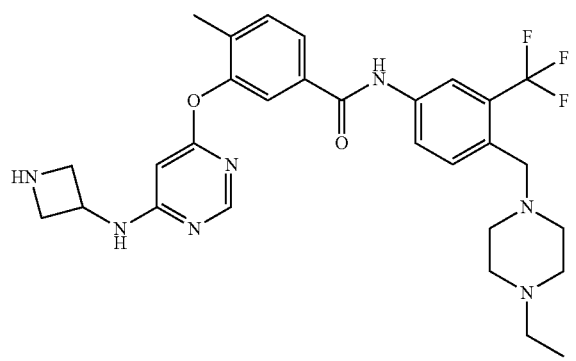 [SMILES: CCN1CCN(Cc2ccc(NC(=O)c3ccc(C)c(Oc4cc(NC5CNC5)ncn4)c3)cc2C(F)(F)F)CC1] | 3-((6-(azetidin-3-ylamino)pyrimidin-4-yl)oxy)-N-(4-((4-ethylpiperazin-1-yl)methyl)-3-(trifluoromethyl)phenyl)-4-methylbenzamide | ¹H NMR (600 MHz, TFA salt, DMSO) δ 10.56 (s, 1H), 10.05 (s, 1H), 9.47 (br, 1H), 8.76 (s, 1H), 8.20 (s, 1H), 8.08 (d, J = 8.4 Hz, 1H), 7.93 (d, J = 8.4 Hz, 1H), 7.77 (s, 1H), 7.72 (d, J = 9.0 Hz, 1H), 7.58 (d, J = 8.4 Hz, 1H), 6.35 (s, 1H), 4.60 (m, 1H), 4.38 (m, 2H), 3.68 (s, 2H), 3.57 (m, 2H), 3.46 (m, 2H), 3.12 (m, 2H), 2.98 (m, 2H), 2.92 (m, 2H), 2.39 (m, 2H), 2.21 (s, 3H), 1.21 (t, J = 7.2 Hz, 3H). MS (ESI) m/z 570 (M + H)⁺. |
| A-11 | 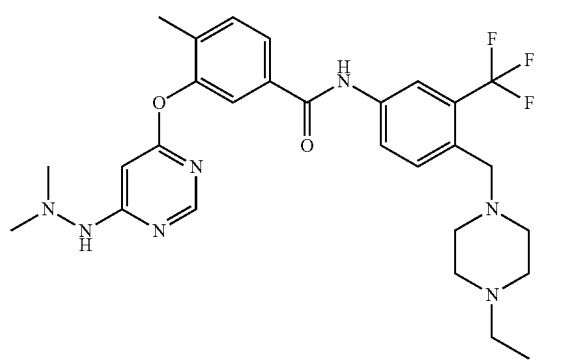 [SMILES: CCN1CCN(Cc2ccc(NC(=O)c3ccc(C)c(Oc4cc(NN(C)C)ncn4)c3)cc2C(F)(F)F)CC1] | 3-((6-(2,2-dimethylhydrazinyl)pyrimidin-4-yl)oxy)-N-(4-((4-ethylpiperazin-1-yl)methyl)-3-(trifluoromethyl)phenyl)-4-methylbenzamide | ¹H NMR (600 MHz, TFA salt, DMSO) δ 10.58 (s, 1H), 9.48 (br, 1H), 8.95 (s, 1H), 8.20 (s, 1H), 8.09 (d, J = 8.4 Hz, 1H), 7.98 (s, 1H), 7.95 (d, J = 7.2 Hz, 1H), 7.79 (s, 1H), 7.72 (d, J = 9.0 Hz, 1H), 7.60 (d, J = 8.4 Hz, 1H), 6.84 (br, 2H), 3.71 (s, 6H), 3.68 (s, 2H), 3.46 (m, 2H), 3.15 (m, 2H), 2.98 (m, 2H), 2.92 (m, 2H), 2.39 (m, 2H), 2.21 (s, 3H), 1.21 (t, J = 7.2 Hz, 3H). MS (ESI) m/z 558 (M + H)⁺. |

| ID # | Structure | Name | ¹H NMR and or MS (m/z) |
|---|---|---|---|
| A-12 | 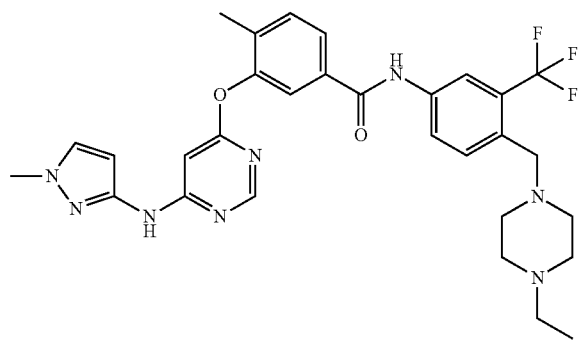 [SMILES: CCN1CCN(Cc2ccc(NC(=O)c3ccc(C)c(Oc4cc(Nc5ccn(C)n5)ncn4)c3)cc2C(F)(F)F)CC1] | N-(4-((4-ethylpiperazin-1-yl)methyl)-3-(trifluoromethyl)phenyl)-4-methyl-3-((6-((1-methyl-1H-pyrazol-3-yl)amino)pyrimidin-4-yl)oxy)benzamide | ¹H NMR (600 MHz, TFA salt, DMSO) δ 10.47 (s, 1H), 9.94 (s, 1H), 9.36 (br, 1H), 8.26 (s, 1H), 8.20 (s, 1H), 8.10 (d, J = 8.4 Hz, 1H), 7.85 (d, J = 7.8 Hz, 1H), 7.76 (s, 1H), 7.71 (d, J = 9.0 Hz, 1H), 7.58 (s, 1H), 7.52 (d, J = 8.4 Hz, 1H), 6.16 (br, 1H), 3.75 (s, 3H), 3.68 (s, 2H), 3.45 (m, 2H), 3.14 (m, 2H), 2.99 (m, 2H), 2.94 (m, 2H), 2.37 (m, 2H), 2.19 (s, 3H), 1.19 (t, J = 7.2 Hz, 3H). MS (ESI) m/z 595 (M + H)⁺. |
| A-13 | 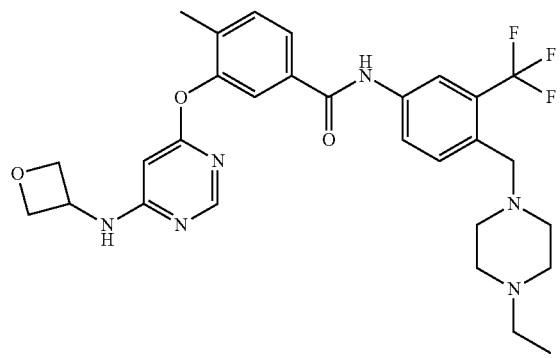 [SMILES: CCN1CCN(Cc2ccc(NC(=O)c3ccc(C)c(Oc4cc(NC5COC5)ncn4)c3)cc2C(F)(F)F)CC1] | N-(4-((4-ethylpiperazin-1-yl)methyl)-3-(trifluoromethyl)phenyl)-4-methyl-3-((6-(oxetan-3-ylamino)pyrimidin-4-yl)oxy)benzamide | ¹H NMR (600 MHz, TFA salt, DMSO) δ 10.46 (s, 1H), 9.32 (br, 1H), 8.24 (s, 1H), 8.19 (s, 1H), 8.15 (br, 1H), 8.09 (d, J = 8.4 Hz, 1H), 8.03 (d, J = 6.6 Hz, 1H), 7.84 (d, J = 8.4 Hz, 1H), 7.72 (s, 1H), 7.71 (d, J = 8.4 Hz, 1H), 7.51 (d, J = 7.2 Hz, 1H), 5.88 (br, 1H), 4.15 (m, 2H), 3.70 (m, 2H), 3.68 (s, 2H), 3.46 (m, 2H), 3.14 (m, 2H), 2.99 (m, 2H), 2.93 (m, 2H), 2.38 (m, 2H), 2.17 (s, 3H), 1.21 (t, J = 7.2 Hz, 3H). MS (ESI) m/z 571 (M + H)⁺. |
| A-14 | 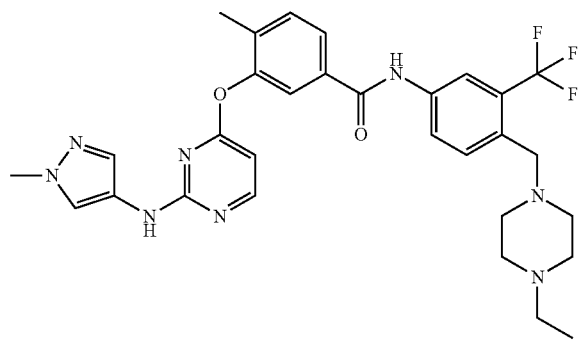 [SMILES: CCN1CCN(Cc2ccc(NC(=O)c3ccc(C)c(Oc4ccnc(Nc5cnn(C)c5)n4)c3)cc2C(F)(F)F)CC1] | N-(4-((4-ethylpiperazin-1-yl)methyl)-3-(trifluoromethyl)phenyl)-4-methyl-3-((2-((1-methyl-1H-pyrazol-4-yl)amino)pyrimidin-4-yl)oxy)benzamide | ¹H NMR (600 MHz, DMSO) δ 10.45 (s, 1H), 9.60 (br, 1H), 8.33 (s, 1H), 8.17 (s, 1H), 8.04 (d, J = 8.4 Hz, 1H), 7.98 (m, 1H), 7.88 (m, 1H), 7.69 (d, J = 9.0 Hz, 1H), 7.61 (m, 1H), 7.05 (m, 1H), 6.73 (m, 1H), 6.46 (m, 1H), 3.55 (s, 3H), 3.49 (br, 2H), 2.20-2.58 (m, 10H), 2.18 (s, 3H), 0.97 (t, J = 7.2 Hz, 3H), MS (ESI) m/z 595 (M + H)⁺. |
| A-15 | 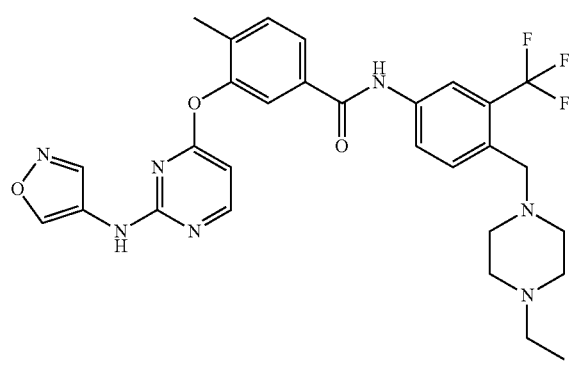 [SMILES: CCN1CCN(Cc2ccc(NC(=O)c3ccc(C)c(Oc4ccnc(Nc5cnoc5)n4)c3)cc2C(F)(F)F)CC1] | N-(4-((4-ethylpiperazin-1-yl)methyl)-3-(trifluoromethyl)phenyl)-3-((2-(isoxazol-4-ylamino)pyrimidin-4-yl)oxy)-4-methylbenzamide | ¹H NMR (600 MHz, TFA salt, DMSO) δ 10.51 (s,1H), 9.90 (m, 1H), 9.31 (br, 1H), 8.44 (d, J = 5.4 Hz, 1H), 8.32 (m, 1H), 8.20 (s, 1H), 8.11 (d, J = 8.4 Hz, 1H), 7.97 (m, 1H), 7.87 (s, 1H), 7.71 (d, J = 8.4 Hz, 1H), 7.61 (s, 1H), 6.62 (s, 1H), 3.69 (s, 2H), 3.46 (m, 2H), 3.15 (m, 2H), 2.99 (m, 2H), 2.94 (m, 2H), 2.39 (m, 2H), 2.19 (s, 3H), 1.21 (t, J = 7.2 Hz, 3H). MS (ESI) m/z 582 (M + H)⁺. |

-continued

| ID # | Structure | Name | ¹H NMR and or MS (m/z) |
|---|---|---|---|
| A-16 | 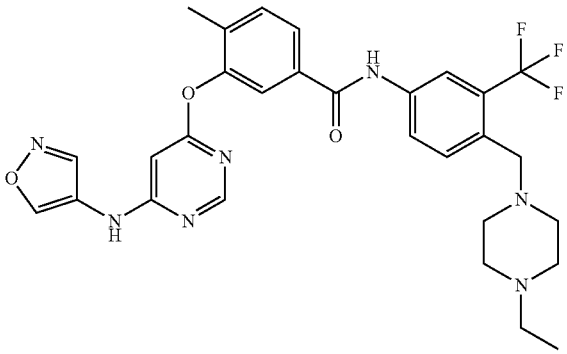 | N-(4-((4-ethylpiperazin-1-yl)methyl)-3-(trifluoromethyl)phenyl)-3-((6-(isoxazol-4-ylamino)pyrimidin-4-yl)oxy)-4-methylbenzamide | MS (ESI) m/z 582 (M + H)+. |
| A-17 | 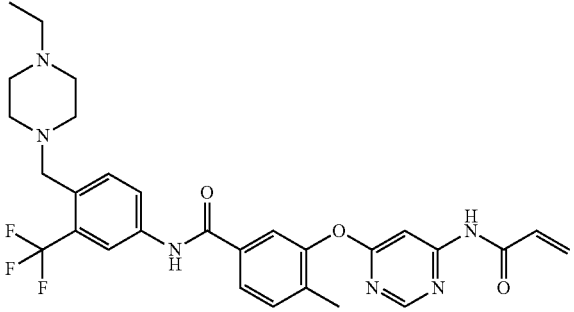 [SMILES: C=CC(=O)Nc1cc(Oc2cc(C(=O)Nc3ccc(CN4CCN(CC)CC4)c(C(F)(F)F)c3)ccc2C)ncn1] | 3-((6-acrylamido-pyrimidin-4-yl)oxy)-N-(4-((4-ethyl-piperazin-1-yl)methyl)-3-(tri-fluoromethyl)phenyl)-4-methylbenzamide | ¹H NMR (600 MHz, DMSO) δ 11.16 (s, 1H), 10.37 (s, 1H), 8.46 (s, 1H), 8.11 (s, 1H), 7.97 (d, J = 7.8 Hz, 1H), 7.81 (d, J = 8.4 Hz, 1H), 7.73 (s, 1H), 7.68 (s, 1H), 7.63 (d, J = 9.0 Hz, 1H), 7.47 (d, J = 7.8 Hz, 1H), 6.54 (dd, J = 16.8, 10.8 Hz, 1H), 6.30 (d, J = 16.8 Hz, 1H), 5.81 (d, J = 10.8 Hz, 1H), 3.49 (s, 2H), 2.32 (m, 8H), 2.23 (q, J = 7.2 Hz, 2H), 2.11 (s, 3H), 0.91 (t, J = 7.2 Hz, 3H). MS (ESI) m/z 569 (M + H)⁺. |
| I-11 | 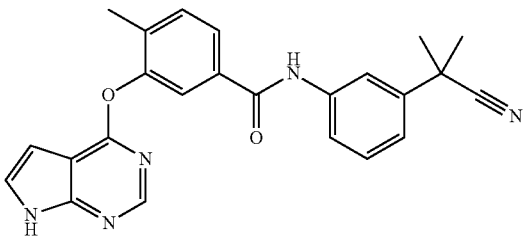 [SMILES: Cc1ccc(C(=O)Nc2cccc(C(C)(C)C#N)c2)cc1Oc1ncnc2[nH]ccc12] | 3-((7H-pyrrolo[2,3-d]pyrimidin-4-yl)oxy)-N-(3-(2-cyanopropan-2-yl)phenyl)-4-methyl-benzamide | ¹H NMR (400 MHz, DMSO) δ 10.23 (s, 1H), 8.22 (s, 1H), 7.86 (s, 1H), 7.82 (d, J = 8.0 Hz, 1H), 7.78 (s, 1H), 7.74 (d, J = 8.0 Hz, 1H), 7.46 (d, J = 8.0, 1H), 7.43 (d, J = 3.2 Hz, 1H), 7.33 (dd, J = 8.0, 8.0 Hz, 1H), 7.17 (d, J = 8.0 Hz, 1H), 6.48 (d, J = 3.2 Hz, 1H), 2.10 (s, 3H), 1.61 (s, 6H). MS (ESI) m/z 412 (M + H)⁺. |

Example 2. Biological Assays of the Compounds

In Vitro Activity Assays

The in vitro activity of the compounds described herein in inhibiting TAK1, HCK and other kinases were obtained using an Invitrogen Select Screening assay as known in the art. The IC50 values determined from this assay are shown below.

Cell Proliferation Analysis

CellTiter-Glo® Luminescent cell viability assay (Promega) was used to assess cell survival following treatment with the compounds described. Cells were seeded into 384 well plates with the EL406 Combination Washer Dispenser (BioTek Instruments, Inc.) and the compounds were injected into the cells culture media with the JANUS Automated Workstation (PerkinElmer Inc.). Cells were treated with a series diluted inhibitors (20~0.04 µM) for 72 hours at 37° C. Luminescent measurement is performed using the 2104 Envision® Multilabel Reader (PerkinElmer Inc.).

Apoptosis Analysis for Primary Patient Bone Marrow Tumor Cells

WM cells were treated with and without the compounds described herein. Cells were incubated at 37° C. with 0.01~4 uM of the compounds described herein. Apoptosis analysis was performed using Annexin V/Propidium iodide staining with the Apoptosis Detection Kit I (BD Pharmingen). 1×106/well cells were treated in 24 well plates for ~24 hours with inhibitors or corresponding controls. A minimum of 10,000 events were acquired using a BD™ FACSCanto II flow cytometer and analyzed with BD FACS DIVA Software.

Results

A number of compounds described herein show inhibitory activity against TAK1, HCK, BTK and other kinases. Shown in Table 1 and 1a are exemplary in vitro IC$_{50}$ data of these compounds. Table 2 and 2a shows the in vitro EC$_{50}$ values of these compounds.

TABLE 1

| Structure | Compound ID | BTK IC$_{50}$ (nM) | HCK IC$_{50}$ (nM) Inv | TAK1 IC$_{50}$ (nM) | GCK IC$_{50}$ (nM) |
|---|---|---|---|---|---|
| 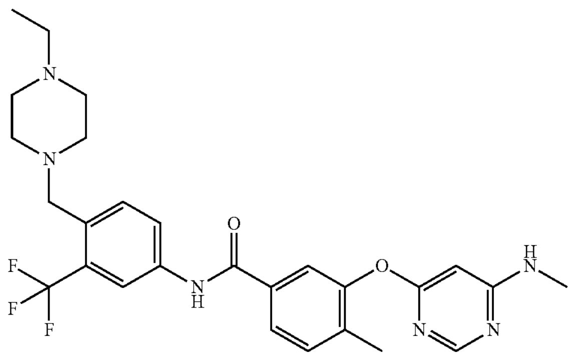 [SMILES: CCN1CCN(Cc2ccc(NC(=O)c3ccc(C)c(Oc4cc(NC)ncn4)c3)cc2C(F)(F)F)CC1] | (A-1) | — | 275 | 364 | 31 |
| 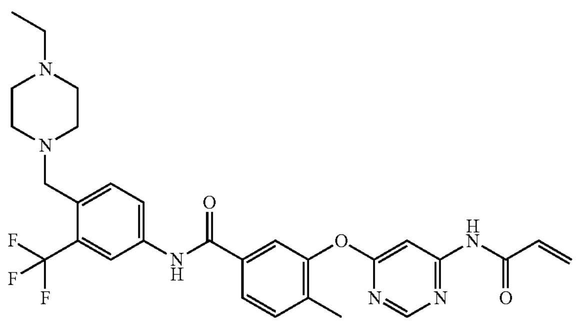 [SMILES: C=CC(=O)Nc1cc(Oc2cc(C(=O)Nc3ccc(CN4CCN(CC)CC4)c(C(F)(F)F)c3)ccc2C)ncn1] | (A-17) | 3380 | 28 | 45 | 17 |
| 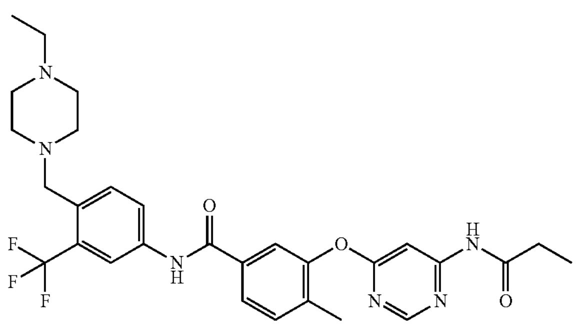 [SMILES: CCC(=O)Nc1cc(Oc2cc(C(=O)Nc3ccc(CN4CCN(CC)CC4)c(C(F)(F)F)c3)ccc2C)ncn1] | (A-2) | — | 253 | 100 | 28 |
| 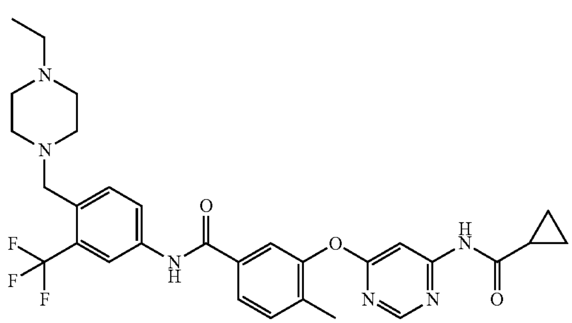 [SMILES: CCN1CCN(Cc2ccc(NC(=O)c3ccc(C)c(Oc4cc(NC(=O)C5CC5)ncn4)c3)cc2C(F)(F)F)CC1] | (A-3) | — | 185 | 92 | — |

TABLE 1-continued
| Structure | Compound ID | BTK IC$_{50}$ (nM) | HCK IC$_{50}$ (nM) Inv | TAK1 IC$_{50}$ (nM) | GCK IC$_{50}$ (nM) |
|---|---|---|---|---|---|
| 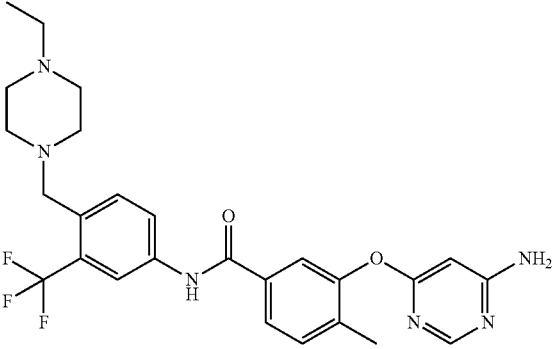 [SMILES: CCN1CCN(Cc2ccc(NC(=O)c3ccc(C)c(Oc4cc(N)ncn4)c3)cc2C(F)(F)F)CC1] | (A-4) | — | 382 | 591 | — |
| 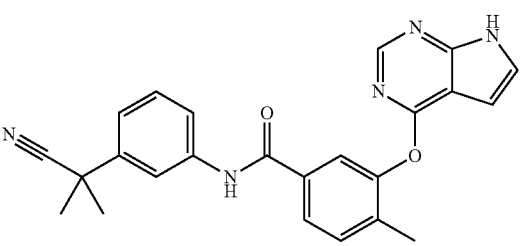 [SMILES: Cc1ccc(C(=O)Nc2cccc(C(C)(C)C#N)c2)cc1Oc1ncnc2[nH]ccc12] | (I-11) | — | — | — | — |
TABLE 1a
| Structure | Cpd. ID | BTK IC$_{50}$ (nM) | HCK IC$_{50}$ (nM) Inv | TAK1 IC$_{50}$ (nM) |
|---|---|---|---|---|
| 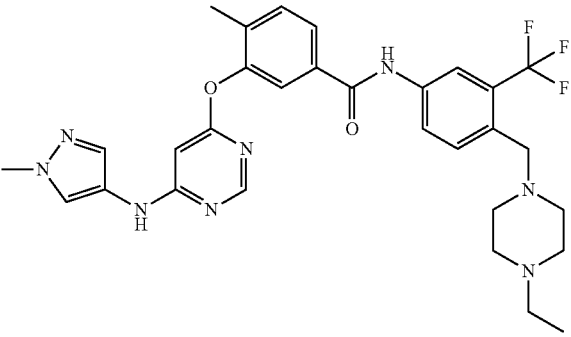 [SMILES: CCN1CCN(Cc2ccc(NC(=O)c3ccc(C)c(Oc4cc(Nc5cnn(C)c5)ncn4)c3)cc2C(F)(F)F)CC1] | (A-5) | >10000 | 61.8 | 100 |
| 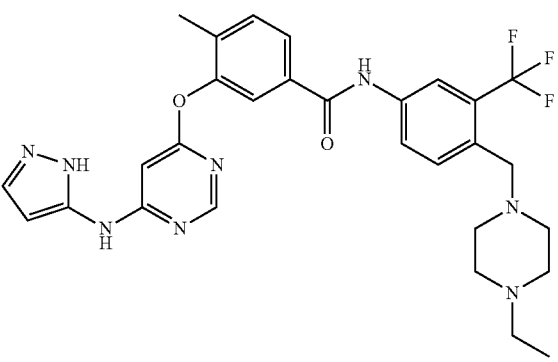 [SMILES: CCN1CCN(Cc2ccc(NC(=O)c3ccc(C)c(Oc4cc(Nc5ccn[nH]5)ncn4)c3)cc2C(F)(F)F)CC1] | (A-6) | — | 38.4 | 63.5 |

TABLE 1a-continued

| Structure | Cpd. ID | BTK IC$_{50}$ (nM) | HCK IC$_{50}$ (nM) Inv | TAK1 IC$_{50}$ (nM) |
|---|---|---|---|---|
| 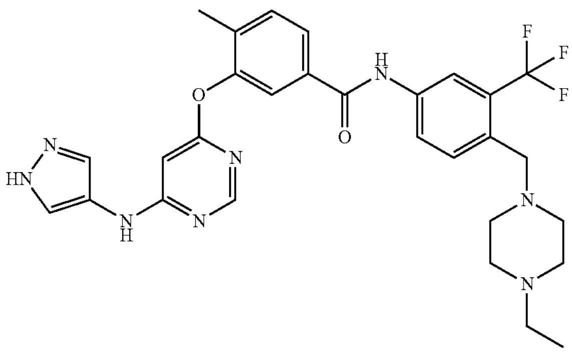 [SMILES: CCN1CCN(Cc2ccc(NC(=O)c3ccc(C)c(Oc4cc(Nc5cn[nH]c5)ncn4)c3)cc2C(F)(F)F)CC1] | (A-7) | — | 33.8 | 71.7 |
| 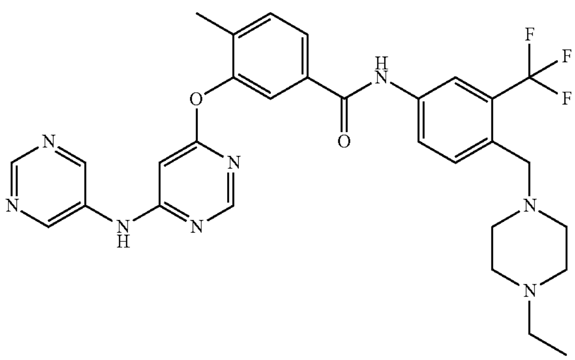 [SMILES: CCN1CCN(Cc2ccc(NC(=O)c3ccc(C)c(Oc4cc(Nc5cncnc5)ncn4)c3)cc2C(F)(F)F)CC1] | (A-8) | — | 889 | 487 |
| 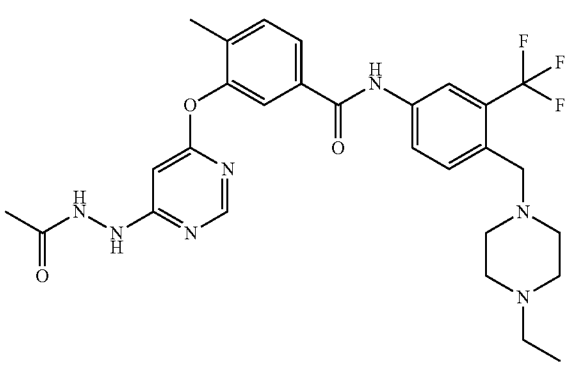 [SMILES: CCN1CCN(Cc2ccc(NC(=O)c3ccc(C)c(Oc4cc(NNC(C)=O)ncn4)c3)cc2C(F)(F)F)CC1] | (A-9) | — | >10000 | 7310 |
| 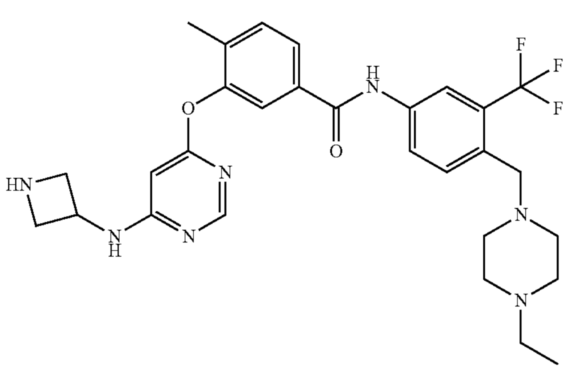 [SMILES: CCN1CCN(Cc2ccc(NC(=O)c3ccc(C)c(Oc4cc(NC5CNC5)ncn4)c3)cc2C(F)(F)F)CC1] | (A-10) | — | >10000 | >10000 |

TABLE 1a-continued

| Structure | Cpd. ID | BTK IC$_{50}$ (nM) | HCK IC$_{50}$ (nM) Inv | TAK1 IC$_{50}$ (nM) |
|---|---|---|---|---|
| 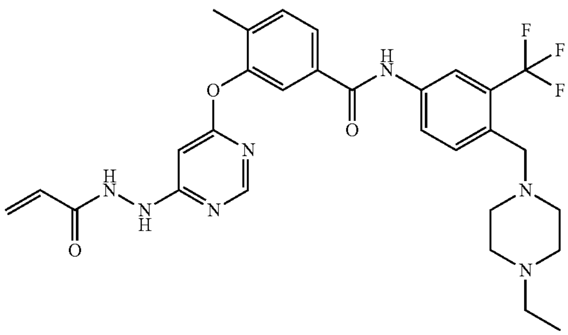 [SMILES: C=CC(=O)NNc1cc(Oc2cc(C(=O)Nc3ccc(CN4CCN(CC)CC4)c(C(F)(F)F)c3)ccc2C)ncn1] | (A-18) | — | 6980 | 1750 |
| 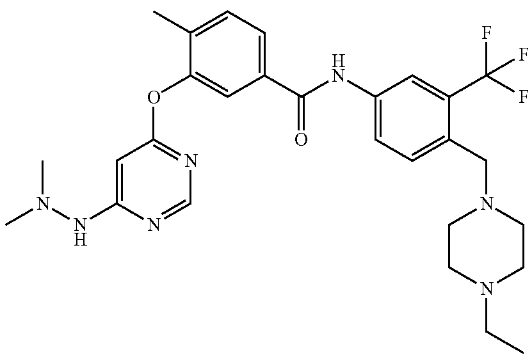 [SMILES: CCN1CCN(Cc2ccc(NC(=O)c3ccc(C)c(Oc4cc(NN(C)C)ncn4)c3)cc2C(F)(F)F)CC1] | (A-11) | — | >10000 | >10000 |
| 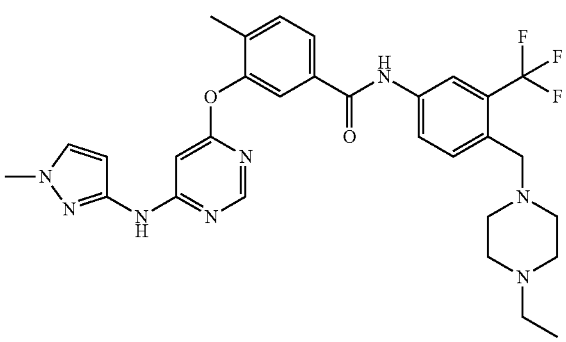 [SMILES: CCN1CCN(Cc2ccc(NC(=O)c3ccc(C)c(Oc4cc(Nc5ccn(C)n5)ncn4)c3)cc2C(F)(F)F)CC1] | (A-12) | — | 18 | 76.2 |
| 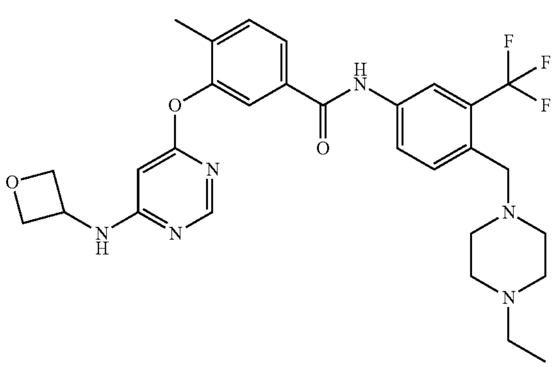 [SMILES: CCN1CCN(Cc2ccc(NC(=O)c3ccc(C)c(Oc4cc(NC5COC5)ncn4)c3)cc2C(F)(F)F)CC1] | (A-13) | — | 392 | 400 |

TABLE 1a-continued

| Structure | Cpd. ID | BTK IC$_{50}$ (nM) | HCK IC$_{50}$ (nM) Inv | TAK1 IC$_{50}$ (nM) |
|---|---|---|---|---|
| 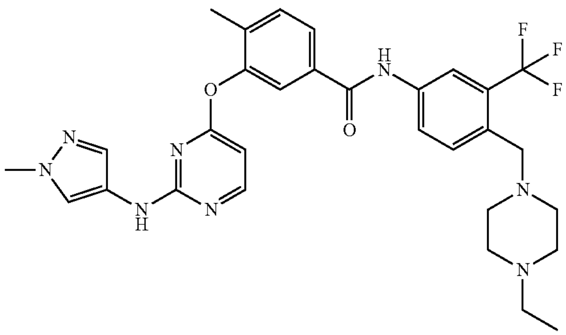 [SMILES: CCN1CCN(Cc2ccc(NC(=O)c3ccc(C)c(Oc4ccnc(Nc5cnn(C)c5)n4)c3)cc2C(F)(F)F)CC1] | (A-14) | — | 27.4 | 53.8 |
| 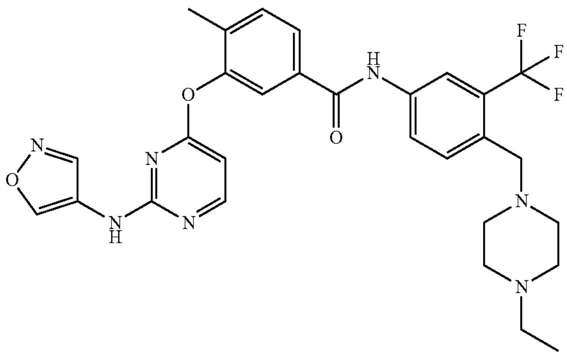 [SMILES: CCN1CCN(Cc2ccc(NC(=O)c3ccc(C)c(Oc4ccnc(Nc5cnoc5)n4)c3)cc2C(F)(F)F)CC1] | (A-15) | — | 116 | 136 |
| 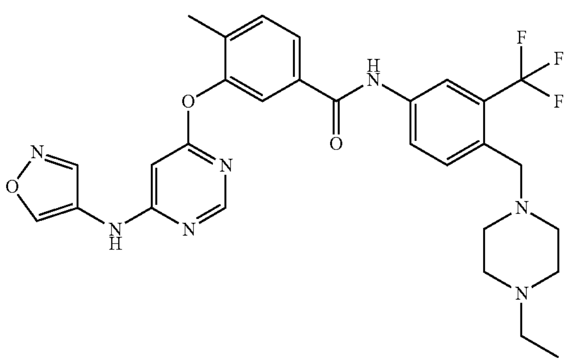 [SMILES: CCN1CCN(Cc2ccc(NC(=O)c3ccc(C)c(Oc4cc(Nc5cnoc5)ncn4)c3)cc2C(F)(F)F)CC1] | (A-16) | — | — | — |

TABLE 2

| Cpd. ID | BCWM.1 EC$_{50}$ (nM) | MWCL-1 EC$_{50}$ (nM) | RPCIWM-1 EC$_{50}$ (nM) | OCI-Ly3 EC$_{50}$ (nM) | Ramos EC$_{50}$ (nM) | OCI-Ly19 EC$_{50}$ (nM) | Mec1 EC$_{50}$ (nM) |
|---|---|---|---|---|---|---|---|
| (A-1) | 1720 | 3990 | — | 11500 | 9480 | 4980 | — |
| (A-2) | 42 | 1350 | — | 2960 | 5340 | 1750 | — |
| (A-3) | 50 | 910 | — | 480 | 2680 | 600 | — |
| (A-4) | 3010 | 1150 | — | 31900 | 21100 | 9430 | 14300 |
| (A-17) | 8 | 202 | — | 247 | 389 | 188 | — |

TABLE 2a

| Cpd. ID | BCWM.1 EC50 (nM) | MWCL-1 EC50 (nM) | TMD8 EC50 (nM) | OCI-Ly7 EC50 (nM) | OCI-Ly3 EC50 (nM) | Ramos EC50 (nM) | OCI-Ly19 EC50 (nM) |
|---|---|---|---|---|---|---|---|
| (A-5) | 51 | 73 | 132 | 655 | 4710 | 3000 | 173 |
|  | 72 | 242 |  |  |  | 6060 | 417 |
| (A-6) | 86 | 118 | — | — | 4770 | 3080 | 302 |
| (A-7) | 48 | 71 | — | — | 4000 | 3020 | 192 |
| (A-8) | 980 | 2660 | — | — | >10000 | 6180 | 1700 |
| (A-9) | 10800 | 18700 | — | — | 19600 | >20000 | >20000 |
|  | 6460 | >20000 |  |  | >20000 |  |  |
| (A-10) | 8250 | 24800 | — | — | 8370 | >20000 | >20000 |
|  | >20000 | >20000 |  |  | >20000 |  |  |
| (A-11) | 19700 | >20000 | — | — | >20000 | >20000 | >20000 |
| (A-12) | 38 | 75 | — | — | 156 | 2960 | 209 |
|  | 71 | 71 |  |  | 472 |  |  |
| (A-13) | 361 | 1760 | — | — | 1200 | 3260 | 2280 |
|  | 964 | 2860 |  |  | 1730 |  |  |
| (A-14) | 33 | 128 | 45 | 173 | — | 2090 | 179 |
| (A-15) | 185 | 718 | 392 | 786 | — | 4680 | 307 |
| (A-16) | 610 | 1710 | 856 | 1030 | — | 1310 | 777 |
| (A-18) | 1980 | 4090 | — | — | 1860 | 7240 | 2780 |
|  | 3750 | 6740 |  |  | 5030 |  |  |
| (I-11) | 4950 | 1440 | 3460 | 1120 | 9690 | 3890 | — |

Kinome Scan

Compounds (A-2) and (A-17) were run in the Kinome Scan™ (DiscoverRx) assay to determine the inhibition against a broad panel of known kinases.

Results

Table 3 shows the KinomeScan (an active site-directed competition binding assay to measure interactions between test compounds and individual kinases) data of each compound, II-1 and I-13. Lower values indicate a greater inhibition for a given kinase by the test compound. As is shown, II-1 and I-13 inhibited several other kinases include LOK, DDR1, JNK2, ZAK, IKK-alpha, BLK, p38-alpha, ABL1, LYN, and STK36 along with the key target HCK.

TABLE 3

| Kinases | A-2 (1 μM) | A-17 (1 μM) |
|---|---|---|
| TAOK 1 | 0.45 | 0.05 |
| LOK | 0.05 | 0.1 |
| TAOK3 | 0.45 | 0.1 |
| DDR1 | 0.35 | 0.25 |
| HCK | 1.5 | 0.3 |
| JNK2 | 0.15 | 0.3 |
| ZAK | 1.6 | 0.4 |
| IKK-alpha | 13 | 0.55 |
| BLK | 0.65 | 0.6 |
| p38-alpha | 0 | 0.75 |
| ABL1-nonphosphorylated | 1 | 0.8 |
| LYN | 3.6 | 0.8 |
| STK36 | 1 | 0.9 |
| LCK | 1.6 | 1 |
| FLT3 | 1.8 | 1.2 |
| MKK7 | 11 | 1.2 |
| MAP4K2 | 2.8 | 1.4 |
| p38-beta | 1.8 | 2.1 |
| PDGFRB | 5.1 | 2.5 |
| CSF1R | 3.2 | 2.6 |
| RET(M918T) | 7.4 | 2.8 |
| ABL2 | 2.9 | 2.9 |
| ABL1(E255K)-phosphorylated | 3.3 | 3 |
| CDC2L1 | 0.45 | 3.2 |
| EPHA8 | 5.4 | 3.6 |
| RET | 9.9 | 3.6 |
| CDC2L2 | 0.4 | 3.8 |
| KIT(L576P) | 2.2 | 3.9 |
| CDK8 | 12 | 4 |
| MAP4K4 | 6.4 | 4 |
| KIT(V559D) | 3.4 | 4.2 |
| MINK | 18 | 4.6 |
| MAP3K3 | 21 | 4.8 |
| TAOK2 | 0.15 | 4.8 |
| JAK3(JH1domain-catalytic) | 47 | 4.9 |
| JNK1 | 6.8 | 5 |
| KIT | 5.6 | 5.1 |
| FES | 4.1 | 5.2 |
| CDKL2 | 1.4 | 5.5 |
| TIE1 | 5.5 | 5.5 |
| ULK3 | 71 | 6 |
| HPK1 | 30 | 6.2 |
| CDK11 | 1.6 | 6.6 |
| CDKL3 | 1.6 | 6.8 |
| FGR | 13 | 7.7 |
| TNIK | 20 | 9 |
| CDC2L5 | 19 | 10 |
| MST3 | 36 | 10 |
| ABL1(M351T)-phosphorylated | 6 | 11 |
| DDR2 | 3 | 11 |
| FGFR1 | 21 | 12 |
| FLT3(N841I) | 14 | 12 |
| HIPK2 | 29 | 12 |
| NLK | 29 | 12 |
| SRC | 5.9 | 12 |
| HIPK3 | 13 | 13 |
| MAP4K5 | 29 | 14 |
| p38-gamma | 6.6 | 14 |
| RSK2(Kin. Dom. 2-C-terminal) | 97 | 15 |
| KIT(A829P) | 32 | 16 |
| KIT(V559D, T670I) | 11 | 16 |
| OSR1 | 79 | 16 |
| TNK1 | 33 | 16 |
| EPHB2 | 69 | 17 |
| YSK1 | 21 | 17 |
| EGFR(L747-E749del, A750P) | 21 | 18 |
| EPHA3 | 32 | 18 |
| FRK | 19 | 18 |
| MST4 | 38 | 18 |
| PCTK1 | 45 | 18 |
| RET(V804M) | 26 | 18 |
| TIE2 | 13 | 18 |
| PCTK2 | 10 | 20 |
| ULK1 | 100 | 20 |
| FGFR4 | 32 | 21 |
| BRAF(V600E) | 23 | 22 |
| HIPK1 | 32 | 22 |
| EGFR(L747-S752del, P753S) | 19 | 23 |
| FLT3(D835Y) | 23 | 23 |
| JNK3 | 15 | 23 |
| p38-delta | 15 | 23 |

TABLE 3-continued

| Kinases | A-2 (1 µM) | A-17 (1 µM) |
| --- | --- | --- |
| FLT3(D835H) | 23 | 24 |
| CAMK1 | 38 | 26 |
| CTK | 40 | 26 |
| FLT1 | 38 | 26 |
| MYO3A | 59 | 26 |
| SGK3 | 97 | 26 |
| YES | 24 | 27 |
| FGFR2 | 34 | 28 |
| NEK4 | 59 | 30 |
| SBK1 | 89 | 31 |
| ABL1(F317L)-phosphorylated | 3.9 | 33 |
| AURKA | 95 | 33 |
| MEK3 | 84 | 33 |
| CAMK1D | 73 | 34 |
| HIPK4 | 14 | 34 |
| ZAP70 | 69 | 35 |
| MUSK | 43 | 37 |
| ASK2 | 65 | 38 |
| EGFR(E746-A750del) | 28 | 38 |
| FLT4 | 54 | 38 |
| STK39 | 23 | 38 |
| TTK | 39 | 38 |
| FLT3(R834Q) | 64 | 39 |
| PAK3 | 61 | 39 |
| SLK | 17 | 39 |
| ABL1(T315I)-phosphorylated | 37 | 40 |
| CDK3 | 58 | 40 |
| CSK | 69 | 40 |
| PFTK1 | 27 | 40 |
| BRAF | 42 | 41 |
| FER | 30 | 42 |
| IKK-beta | 48 | 42 |
| PIK3CA(Q546K) | 85 | 42 |
| ABL1(T315I)-nonphosphorylated | 0 | 44 |
| MYLK2 | 63 | 44 |
| PRKCD | 39 | 44 |
| ROCK1 | 97 | 44 |
| CDKL1 | 45 | 45 |
| TYK2(JH1domain-catalytic) | 90 | 45 |
| GRK7 | 68 | 46 |
| PLK4 | 78 | 46 |
| ROCK2 | 100 | 46 |
| CDK2 | 43 | 47 |
| MAST1 | 59 | 47 |
| ABL1(F317I)-nonphosphorylated | 0 | 48 |
| EIF2AK1 | 62 | 48 |
| AURKB | 77 | 50 |
| MEK6 | 77 | 50 |
| ERBB2 | 46 | 51 |
| ERN1 | 58 | 51 |
| RET(V804L) | 62 | 51 |
| RPS6KA5(Kin. Dom. 1-N-terminal) | 78 | 51 |
| KIT(V559D, V654A) | 50 | 52 |
| PCTK3 | 32 | 52 |
| EGFR(L747-T751del, Sins) | 18 | 53 |
| EPHA2 | 40 | 53 |
| EGFR(L861Q) | 56 | 54 |
| MAP3K15 | 100 | 54 |
| SGK | 100 | 54 |
| FYN | 52 | 55 |
| PDGFRA | 25 | 55 |
| PIK3CA(C420R) | 100 | 55 |
| SRMS | 66 | 55 |
| CDK5 | 67 | 56 |
| IRAK1 | 97 | 56 |
| PIK3C2G | 81 | 56 |
| PKNB(M. tuberculosis) | 100 | 56 |
| QSK | 69 | 56 |
| YSK4 | 89 | 57 |
| CIT | 56 | 58 |
| EGFR(T790M) | 83 | 58 |
| JAK2(JH1domain-catalytic) | 74 | 58 |
| MAP3K1 | 60 | 58 |
| PIK3CA(E545A) | 89 | 58 |
| PIK3CG | 94 | 58 |
| NDR1 | 87 | 59 |
| PFPK5(P. falciparum) | 100 | 59 |
| SRPK1 | 70 | 59 |
| DYRK2 | 99 | 60 |
| EGFR | 55 | 60 |
| GSK3A | 40 | 60 |
| ABL1(F317L)-nonphosphorylated | 0 | 61 |
| CLK1 | 85 | 61 |
| PRKCQ | 55 | 61 |
| PAK1 | 96 | 62 |
| STK35 | 80 | 62 |
| ABL1(F317I)-phosphorylated | 7.9 | 63 |
| CAMK1G | 61 | 64 |
| CAMK4 | 100 | 64 |
| CDKL5 | 93 | 64 |
| CDK7 | 33 | 66 |
| PLK3 | 100 | 66 |
| PRKD1 | 87 | 66 |
| IRAK4 | 99 | 67 |
| PIK3CA(E545K) | 88 | 67 |
| EGFR(S752-I759del) | 37 | 68 |
| INSRR | 71 | 68 |
| PFTAIRE2 | 100 | 68 |
| MYLK | 100 | 69 |
| PIK3CA(I800L) | 83 | 70 |
| SYK | 21 | 70 |
| AURKC | 100 | 71 |
| CASK | 60 | 71 |
| CDK9 | 46 | 71 |
| CSNK1A1 | 83 | 71 |
| EPHB6 | 92 | 71 |
| PIK3CA | 100 | 71 |
| BMPR1B | 99 | 72 |
| FLT3-autoinhibited | 68 | 72 |
| PIK3CA(E542K) | 87 | 72 |
| PRKCI | 65 | 73 |
| ANKK1 | 100 | 74 |
| EPHA4 | 64 | 75 |
| EGFR(G719C) | 60 | 76 |
| EPHA5 | 86 | 76 |
| JAK1(JH1domain-catalytic) | 86 | 76 |
| MST2 | 82 | 76 |
| PRKCH | 94 | 76 |
| ARK5 | 96 | 77 |
| CLK4 | 66 | 77 |
| FGFR3 | 80 | 77 |
| GAK | 77 | 77 |
| MEK1 | 100 | 77 |
| MYO3B | 76 | 77 |
| WNK3 | 95 | 77 |
| DCAMKL1 | 77 | 78 |
| EPHA6 | 68 | 78 |
| FGFR3(G697C) | 81 | 78 |
| KIT(D816H) | 82 | 78 |
| RIPK5 | 90 | 78 |
| SNRK | 68 | 78 |
| ERBB4 | 88 | 79 |
| EGFR(L858R) | 83 | 80 |
| IKK-epsilon | 100 | 80 |
| TLK1 | 100 | 80 |
| TRKC | 100 | 80 |
| ERK2 | 100 | 81 |
| PRKD2 | 73 | 81 |
| ACVRL1 | 83 | 82 |
| BMPR2 | 86 | 82 |
| NEK10 | 100 | 82 |
| PAK2 | 78 | 82 |
| S6K1 | 54 | 82 |
| SIK | 73 | 82 |
| GSK3B | 83 | 83 |
| HUNK | 100 | 83 |
| MERTK | 100 | 83 |
| NIK | 62 | 83 |
| PIP5K2B | 100 | 83 |
| RIOK1 | 100 | 83 |
| VRK2 | 96 | 83 |
| CAMK2D | 92 | 84 |
| PAK6 | 100 | 84 |
| TBK1 | 95 | 84 |
| GCN2(Kin. Dom. 2, S808G) | 84 | 85 |
| PKN1 | 100 | 85 |

TABLE 3-continued

| Kinases | A-2 (1 μM) | A-17 (1 μM) |
| --- | --- | --- |
| SGK2 | 100 | 85 |
| TGFBR2 | 100 | 85 |
| WNK1 | 100 | 85 |
| ALK | 92 | 86 |
| DCAMKL3 | 97 | 86 |
| MEK2 | 83 | 86 |
| PIM1 | 100 | 86 |
| PRKCE | 92 | 86 |
| TAK1 | 3.2 | 86 |
| YANK2 | 100 | 86 |
| AXL | 68 | 87 |
| MKNK2 | 72 | 87 |
| NEK6 | 91 | 87 |
| PIP5K1A | 100 | 87 |
| ADCK3 | 100 | 88 |
| CLK2 | 100 | 88 |
| ERK8 | 100 | 88 |
| PIK3CB | 66 | 88 |
| PIM3 | 93 | 88 |
| RAF1 | 75 | 88 |
| AKT1 | 82 | 89 |
| BUB1 | 80 | 89 |
| MAP4K3 | 100 | 89 |
| BTK | 65 | 90 |
| ICK | 65 | 90 |
| PAK7 | 100 | 90 |
| PIK3CD | 100 | 90 |
| RIOK3 | 83 | 90 |
| BMX | 79 | 91 |
| CDK4-cyclinD1 | 94 | 91 |
| SNARK | 100 | 91 |
| TRKA | 90 | 91 |
| ALK(L1196M) | 90 | 92 |
| LATS2 | 100 | 92 |
| PRKG2 | 74 | 92 |
| NEK2 | 98 | 93 |
| TRKB | 85 | 93 |
| AAK1 | 94 | 94 |
| EGFR(L858R, T790M) | 80 | 94 |
| ERK3 | 93 | 94 |
| LRRK2(G2019S) | 100 | 94 |
| PAK4 | 95 | 94 |
| PIK3CA(H1047L) | 97 | 94 |
| RIPK4 | 88 | 94 |
| RPS6KA4(Kin. Dom. 1-N-terminal) | 96 | 94 |
| TESK1 | 81 | 94 |
| CSF1R-autoinhibited | 96 | 95 |
| LIMK2 | 94 | 95 |
| LRRK2 | 95 | 95 |
| PIK3CA(M1043I) | 83 | 95 |
| RPS6KA4(Kin. Dom. 2-C-terminal) | 100 | 95 |
| TNNI3K | 64 | 95 |
| HASPIN | 84 | 96 |
| MAP3K4 | 80 | 96 |
| PRP4 | 94 | 96 |
| YANK1 | 73 | 96 |
| ABL1(Y253F)-phosphorylated | 4.8 | 97 |
| EGFR(G719S) | 65 | 97 |
| MLK1 | 91 | 97 |
| NEK1 | 93 | 97 |
| PIK4CB | 98 | 97 |
| BIKE | 92 | 98 |
| RSK2(Kin. Dom. 1-N-terminal) | 100 | 98 |
| SRPK2 | 100 | 98 |
| STK16 | 100 | 98 |
| AMPK-alpha2 | 95 | 99 |
| CAMKK2 | 79 | 99 |
| EPHB4 | 87 | 99 |
| RSK4(Kin. Dom. 1-N-terminal) | 92 | 99 |
| ABL1(Q252H)-phosphorylated | 11 | 100 |
| ACVR1 | 100 | 100 |
| ACVR1B | 100 | 100 |
| ACVR2A | 100 | 100 |
| ACVR2B | 95 | 100 |
| ADCK4 | 100 | 100 |
| AKT2 | 90 | 100 |
| AKT3 | 100 | 100 |
| ALK(C1156Y) | 49 | 100 |
| AMPK-alpha1 | 85 | 100 |
| ASK1 | 96 | 100 |
| BMPR1A | 100 | 100 |
| BRK | 100 | 100 |
| BRSK1 | 100 | 100 |
| BRSK2 | 100 | 100 |
| CAMK2A | 92 | 100 |
| CAMK2B | 100 | 100 |
| CAMK2G | 86 | 100 |
| CAMKK1 | 100 | 100 |
| CDK4-cyclinD3 | 100 | 100 |
| CHEK1 | 100 | 100 |
| CHEK2 | 100 | 100 |
| CLK3 | 100 | 100 |
| CSNK1A1L | 99 | 100 |
| CSNK1D | 100 | 100 |
| CSNK1E | 100 | 100 |
| CSNK1G1 | 100 | 100 |
| CSNK1G2 | 100 | 100 |
| CSNK1G3 | 93 | 100 |
| CSNK2A1 | 100 | 100 |
| CSNK2A2 | 100 | 100 |
| DAPK1 | 100 | 100 |
| DAPK2 | 93 | 100 |
| DAPK3 | 100 | 100 |
| DCAMKL2 | 74 | 100 |
| DLK | 100 | 100 |
| DMPK | 100 | 100 |
| DMPK2 | 88 | 100 |
| DRAK1 | 100 | 100 |
| DRAK2 | 85 | 100 |
| DYRK1A | 92 | 100 |
| DYRK1B | 77 | 100 |
| EPHA1 | 90 | 100 |
| EPHA7 | 75 | 100 |
| EPHB1 | 78 | 100 |
| EPHB3 | 100 | 100 |
| ERBB3 | 100 | 100 |
| ERK1 | 100 | 100 |
| ERK4 | 96 | 100 |
| ERK5 | 98 | 100 |
| FAK | 100 | 100 |
| GRK1 | 77 | 100 |
| GRK4 | 100 | 100 |
| IGF1R | 100 | 100 |
| INSR | 100 | 100 |
| IRAK3 | 100 | 100 |
| ITK | 95 | 100 |
| JAK1(JH2domain-pseudokinase) | 90 | 100 |
| KIT(D816V) | 96 | 100 |
| KIT-autoinhibited | 65 | 100 |
| LATS1 | 100 | 100 |
| LIMK1 | 100 | 100 |
| LKB1 | 100 | 100 |
| LTK | 100 | 100 |
| LZK | 100 | 100 |
| MAK | 93 | 100 |
| MAP3K2 | 90 | 100 |
| MAPKAPK2 | 100 | 100 |
| MAPKAPK5 | 94 | 100 |
| MARK1 | 83 | 100 |
| MARK2 | 100 | 100 |
| MARK3 | 94 | 100 |
| MARK4 | 92 | 100 |
| MEK4 | 82 | 100 |
| MEK5 | 37 | 100 |
| MELK | 89 | 100 |
| MET | 100 | 100 |
| MET(M1250T) | 89 | 100 |
| MET(Y1235D) | 100 | 100 |
| MKNK1 | 94 | 100 |
| MLCK | 100 | 100 |
| MLK2 | 100 | 100 |
| MLK3 | 62 | 100 |
| MRCKA | 100 | 100 |
| MRCKB | 100 | 100 |
| MST1 | 80 | 100 |
| MST1R | 100 | 100 |

TABLE 3-continued

| Kinases | A-2 (1 μM) | A-17 (1 μM) |
|---|---|---|
| MTOR | 86 | 100 |
| MYLK4 | 100 | 100 |
| NDR2 | 100 | 100 |
| NEK11 | 100 | 100 |
| NEK3 | 65 | 100 |
| NEK5 | 85 | 100 |
| NEK7 | 100 | 100 |
| NEK9 | 100 | 100 |
| NIM1 | 100 | 100 |
| PDPK1 | 69 | 100 |
| PHKG1 | 100 | 100 |
| PHKG2 | 100 | 100 |
| PIK3C2B | 100 | 100 |
| PIK3CA(H1047Y) | 79 | 100 |
| PIM2 | 71 | 100 |
| PIP5K1C | 50 | 100 |
| PIP5K2C | 82 | 100 |
| PKAC-alpha | 72 | 100 |
| PKAC-beta | 100 | 100 |
| PKMYT1 | 100 | 100 |
| PKN2 | 89 | 100 |
| PLK1 | 100 | 100 |
| PLK2 | 100 | 100 |
| PRKD3 | 100 | 100 |
| PRKG1 | 100 | 100 |
| PRKR | 100 | 100 |
| PRKX | 100 | 100 |
| PYK2 | 97 | 100 |
| RIOK2 | 100 | 100 |
| RIPK1 | 54 | 100 |
| RIPK2 | 86 | 100 |
| ROS1 | 75 | 100 |
| RPS6KA5(Kin. Dom. 2-C-terminal) | 100 | 100 |
| RSK1(Kin. Dom. 1-N-terminal) | 100 | 100 |
| RSK1(Kin. Dom. 2-C-terminal) | 100 | 100 |
| RSK3(Kin. Dom. 1-N-terminal) | 100 | 100 |
| RSK3(Kin. Dom. 2-C-terminal) | 100 | 100 |
| RSK4(Kin. Dom. 2-C-terminal) | 100 | 100 |
| SgK110 | 100 | 100 |
| SIK2 | 100 | 100 |
| SRPK3 | 100 | 100 |
| STK33 | 97 | 100 |
| TEC | 82 | 100 |
| TGFBR1 | 100 | 100 |
| TLK2 | 100 | 100 |
| TNK2 | 100 | 100 |
| TRPM6 | 58 | 100 |
| TSSK1B | 83 | 100 |
| TXK | 89 | 100 |
| TYK2(JH2domain-pseudokinase) | 87 | 100 |
| TYRO3 | 92 | 100 |
| ULK2 | 81 | 100 |
| VEGFR2 | 28 | 100 |
| WEE1 | 100 | 100 |
| WEE2 | 100 | 100 |
| YANK3 | 88 | 100 |

Kinative

The kinase selectivity of compounds (A-5) and (A-14) were evaluated using a chemical proteomic approach named KiNativ which detects 260 kinases in A375 cells (ActivX Biosciences). To probe the intracellular targets of the compounds, A375 cells were incubated with the inhibitor at 1 μM final concentration and then looked for protection of labeling by an ATP-biotin probe that non-specifically labels conserved lysines on kinases and other nucleotide-dependent enzymes.

Results

Table 4 shows that compound (A-5) inhibits a number of kinases at 1 μM, including Abl (>90%), FYN (71.2%), LYN (87.8%), and ZAK (75.7%). Table 5 shows that compound (A-14) inhibits a number of kinases at 1 μM, including Abl (>90%), FYN (88.2%), LYN (85.7%), and ZAK (75.8%).

TABLE 4

| Kinase | Reference | Sequence | SEQ ID NO: | Labeling Site | Compound A-4 (1.0 μM) |
|---|---|---|---|---|---|
| ABL, ARG | UniRef100_P00519, UniRef100_P42684 | LMTGDTYTAHAGAKFPIK | 1 | Activation Loop | 95.5 |
| ACK | UniRef100_Q07912 | TVSVAVKCLKPDVLSQPEAMDDFIR | 2 | Lys1 | 4.9 |
| AGK | UniRef100_Q53H12 | ATVFLNPAACKGK | 3 | ATP | -31.4 |
| AMPKa1, AMPKa2 | UniRef100_P54646, UniRef100_Q13131 | DLKPENVLLDAHMNAK | 4 | Lys2 | 16.3 |
| ARAF | UniRef100_P10398 | DLKSNNIFLHEGLTVK | 5 | Lys2 | 12.2 |
| ATR | UniRef100_Q13535 | FYIMMCKPK | 6 | ATP | 23.0 |
| AurA | UniRef100_O14965 | FILALKVLFK | 7 | Lys1 | -16.0 |
| AurB | UniRef100_Q96GD4 | SHFIVALKVLFK | 8 | Lys1 | -51.1 |
| BARK1 | UniRef100_P25098 | DLKPANILLDEHGHVR | 9 | Lys2 | -13.4 |
| BRAF | UniRef100_P15056 | DLKSNNIFLHEDLTVK | 10 | Lys2 | 18.9 |
| BTK | UniRef100_Q06187 | YVLDDEYTSSVGSKFPVR | 11 | Activation Loop | -18.8 |
| CaMK1a | UniRef100_Q14012 | LVAIKCIAK | 12 | Lys1 | 12.4 |
| CaMK1d | UniRef100_Q8IU85 | LFAVKCIPK | 13 | Lys1 | -6.0 |
| CaMK2d | UniRef100_Q13557 | IPTGQEYAAKIINTKK | 14 | Lys1 | -8.1 |

TABLE 4-continued

| Kinase | Reference | Sequence | SEQ ID NO: | Labeling Site | Compound A-4 (1.0 μM) |
|---|---|---|---|---|---|
| CaMK2g | UniRef100_Q13555 | TSTQEYAAKIINTK | 15 | Lys1 | -23.1 |
| CaMK4 | UniRef100_Q16566 | DLKPENLLYATPAPDAPLK | 16 | Lys2 | 5.9 |
| CaMKK2 | UniRef100_Q96RR4 | DIKPSNLLVGEDGHIK | 17 | Lys2 | 6.2 |
| CASK | UniRef100_O14936, UniRef100_C9JGY0 | ETGQQFAVKIVDVAK | 18 | Lys1 | -28.1 |
| CDC2 | UniRef100_P06493 | DLKPQNLLIDDKGTIK | 19 | Lys2 | -2.3 |
| CDK11, CDK8 | UniRef100_P49336, UniRef100_Q9BWU1 | DLKPANILVMGEGPER | 20 | Lys2 | 50.0 |
| CDK2 | UniRef100_P24941 | DLKPQNLLINTEGAIK | 21 | Lys2 | -3.5 |
| CDK4 | UniRef100_P11802 | DLKPENILVTSGGTVK | 22 | Lys2 | 17.4 |
| CDK5 | UniRef100_Q00535 | DLKPQNLLINR | 23 | Lys2 | -27.3 |
| CDK6 | UniRef100_Q00534 | DLKPQNILVTSSGQIK | 24 | Lys2 | 13.1 |
| CDK7 | UniRef100_P50613 | DLKPNNLLLDENGVLK | 25 | Lys2 | 3.9 |
| CDK9 | UniRef100_P50750 | DMKAANVLITR | 26 | Lys2 | -16.2 |
| CHK1 | UniRef100_B5BTY6, UniRef100_O14757 | DIKPENLLLDER | 27 | Lys2 | -5.0 |
| CHK2 | UniRef100_O96017 | DLKPENVLLSSQEEDCLIK | 28 | Lys2 | -7.8 |
| CK1a | UniRef100_P48729, UniRef100_B4E1D9 | DIKPDNFLMGIGR | 29 | Lys2 | -0.6 |
| CK1g2 | UniRef100_P78368 | DVKPENFLVGRPGTK | 30 | Lys2 | -9.1 |
| CK2a2 | UniRef100_P19784 | DVKPHNVMIDHQQK | 31 | Lys2 | -18.2 |
| CLK3 | UniRef100_P49761 | YEIVGNLGEGTFGKVVECLDHAR | 32 | ATP Loop | -52.8 |
| CSK | UniRef100_P41240 | VSDFGLTKEASSTQDTGKLPVK | 33 | Activation Loop | 15.3 |
| DGKA | UniRef100_P23743 | IDPVPNTHPLLVFVNPKSGGK | 34 | ATP | -4.8 |
| DGKH | UniRef100_Q86XP1 | ATFSFCVSPLLVFVNSKSGDNQGVK | 35 | ATP | -6.3 |
| DGKQ | UniRef100_P52824 | GRLLTALVLPDLLHAKLPPDSCPLLVFVNPKSGGLK | 36 | ATP | 11.0 |
| DNAPK | UniRef100_P78527 | KGGSWIQEINVAEK | 37 | ATP | -61.5 |
| DNAPK | UniRef100_P78527 | EHPFLVKGGEDLR | 38 | ATP | -64.6 |
| eEF2K | UniRef100_O00418 | YIKYNSNSGFVR | 39 | ATP | -30.5 |
| EphB1 | UniRef100_P54762 | YLQDDTSDPTYTSSLGGKIPVR | 40 | Activation Loop | -1.7 |
| EphB2 | UniRef100_P29323 | FLEDDTSDPTYTSALGGKIPIR | 41 | Activation Loop | -12.8 |
| Erk1 | UniRef100_P27361 | DLKPSNLLINTTCDLK | 42 | Lys2 | -9.0 |
| Erk2 | UniRef100_P28482 | DLKPSNLLLNTTCDLK | 43 | Lys2 | -3.8 |
| Erk5 | UniRef100_Q13164 | DLKPSNLLVNENCELK | 44 | Lys2 | 25.9 |
| FER | UniRef100_P16591 | TSVAVKTCKEDLPQELK | 45 | Lys1 | 91.4 |
| FES | UniRef100_P07332 | LRADNTLVAVKSCR | 46 | Lys1 | 89.1 |

TABLE 4-continued

| Kinase | Reference | Sequence | SEQ ID NO: | Labeling Site | Compound A-4 (1.0 µM) |
|---|---|---|---|---|---|
| FGR | UniRef100_P09769 | LIKDDEYNPCQGSKFPIK | 47 | Activation Loop | 31.9 |
| FRAP | UniRef100_P42345 | IQSIAPSLQVITSKQRPR | 48 | ATP | -7.5 |
| FRK | UniRef100_P42685 | HEIKLPVK | 49 | Activation Loop | 91.1 |
| FYN, SRC, YES | UniRef100_P12931, UniRef100_P07947, UniRef100_P06241 | QGAKFPIKWTAPEAALYGR | 50 | Activation Loop | 71.2 |
| GCK | UniRef100_Q12851 | DIKGANLLLTLQGDVK | 51 | Lys2 | 94.9 |
| GCN2 | UniRef100_Q9P2K8 | DLKPVNIFLDSDDHVK | 52 | Lys2 | 20.8 |
| GSK3A | UniRef100_P49840 | DIKPQNLLVDPDTAVLK | 53 | Lys2 | 36.0 |
| GSK3B | UniRef100_P49841 | DIKPQNLLLDPDTAVLK | 54 | Lys2 | 0.5 |
| HPK1 | UniRef100_Q92918 | DIKGANILINDAGEVR | 55 | Lys2 | 68.1 |
| IKKa | UniRef100_O15111 | DLKPENIVLQDVGGK | 56 | Lys2 | -17.0 |
| IKKb | UniRef100_O14920 | DLKPENIVLQQGEQR | 57 | Lys2 | -12.6 |
| IKKe | UniRef100_Q14164 | SGELVAVKVFNTTSYLRPR | 58 | Lys1 | -9.9 |
| ILK | UniRef100_Q13418 | WQGNDIVVKVLK | 59 | Lys1 | 5.2 |
| IRAK1 | UniRef100_P51617 | AIQFLHQDSPSLIHGDIKSSNVLLDER | 60 | Lys2 | -3.5 |
| IRAK4 | UniRef100_Q9NWZ3 | DIKSANILLDEAFTAK | 61 | Lys2 | 1.9 |
| IRE1 | UniRef100_O75460 | DLKPHNILISMPNAHGK | 62 | Lys2 | -2.2 |
| ITPK1 | UniRef100_Q13572 | ESIFFNSHNVSKPESSSVLTELDKIEGVFERPSDEVIR | 63 | ATP | 1.2 |
| JAK1 | UniRef100_P23458 | QLASALSYLEDKDLVHGNVCTKNLLLAR | 64 | Protein Kinase Domain | 4.3 |
| JAK1 domain2 | UniRef100_P23458 | IGDFGLTKAIETDKEYYTVK | 65 | Activation Loop | -6.2 |
| JAK3 domain2 | UniRef100_P52333 | IADFGLAKLLPLDKDYYVVR | 66 | Activation Loop | 7.7 |
| JNK1, JNK2, JNK3 | UniRef100_P45983, UniRef100_P53779, UniRef100_P45984 | DLKPSNIVVK | 67 | Lys2 | 77.2 |
| KHS1 | UniRef100_Q9Y4K4 | NVHTGELAAVKIIK | 68 | Lys1 | 15.8 |
| KSR1 | UniRef100_Q8IVT5 | SKNVFYDNGKVVITDFGLFGISGVVR | 69 | Activation Loop | -22.0 |
| KSR1, KSR2 | UniRef100_Q6VAB6, UniRef100_Q8IVT5 | SKNVFYDNGK | 70 | Activation Loop | -10.0 |
| LATS1 | UniRef100_O95835 | ALYATKTLR | 71 | Lys1 | 5.4 |
| LATS2 | UniRef100_Q9NRM7 | DIKPDNILIDLDGHIK | 72 | Lys2 | -1.9 |
| LCK | UniRef100_P06239 | EGAKFPIKWTAPEAINYGTFTIK | 73 | Activation Loop | 92.3 |
| LKB1 | UniRef100_Q15831 | DIKPGNLLLTTGGTLK | 74 | Lys2 | -6.0 |
| LOK | UniRef100_O94804 | DLKAGNVLMTLEGDIR | 75 | Lys2 | 19.9 |
| LRRK2 | UniRef100_Q5S007 | DLKPHNVLLLYPNAAIIAK | 76 | Lys2 | -15.9 |

TABLE 4-continued

| Kinase | Reference | Sequence | SEQ ID NO: | Labeling Site | Compound A-4 (1.0 µM) |
|---|---|---|---|---|---|
| LYN | UniRef100_P07948 | VAVKTLKPGTMSVQAFLEEANLMK | 77 | Lys1 | 87.8 |
| MAP2K1 | UniRef100_Q02750 | IMHRDVKPSNILVNSR | 78 | Lys2 | 11.4 |
| MAP2K1, MAP2K2 | UniRef100_P36507, UniRef100_Q02750 | DVKPSNILVNSR | 79 | Lys2 | -16.3 |
| MAP2K3 | UniRef100_P46734 | DVKPSNVLINK | 80 | Lys2 | -1.0 |
| MAP2K4 | UniRef100_P45985 | DIKPSNILLDR | 81 | Lys2 | -14.1 |
| MAP2K5 | UniRef100_Q13163 | DVKPSNMLVNTR | 82 | Lys2 | 20.5 |
| MAP2K6 | UniRef100_P52564 | DVKPSNVLINALGQVK | 83 | Lys2 | 0.5 |
| MAP2K7 | UniRef100_O14733 | DVKPSNILLDER | 84 | Lys2 | -38.2 |
| MAP3K1 | UniRef100_Q13233 | DVKGANLLIDSTGQR | 85 | Lys2 | 26.9 |
| MAP3K2 | UniRef100_Q9Y2U5 | ELAVKQVQFDPDSPETSKEVNALECEIQLLK | 86 | Lys1 | 4.2 |
| MAP3K2, MAP3K3 | UniRef100_Q9Y2U5, UniRef100_Q99759 | DIKGANILR | 87 | Lys2 | 3.2 |
| MAP3K3 | UniRef100_Q99759 | ELASKQVQFDPDSPETSKEVSALECEIQLLK | 88 | Lys1 | 3.7 |
| MAP3K4 | UniRef100_Q9Y6R4 | DIKGANIFLTSSGLIK | 89 | Lys2 | 19.2 |
| MAP3K5 | UniRef100_Q99683 | DIKGDNVLINTYSGVLK | 90 | Lys2 | -30.4 |
| MAP3K6 | UniRef100_O95382 | DIKGDNVLINTFSGLLK | 91 | Lys2 | -25.0 |
| MARK2, MARK3 | UniRef100_P27448, UniRef100_Q7KZI7 | DLKAENLLLDADMNIK | 92 | Lys2 | 4.6 |
| MARK3 | UniRef100_P27448 | EVAIKIIDKTQLNPTSLQK | 93 | Lys1 | -26.1 |
| MARK3, MARK4 | UniRef100_Q96L34, UniRef100_P27448 | EVAIKIIDK | 94 | Lys1 | -16.2 |
| MARK4 | UniRef100_Q96L34 | DLKAENLLLDAEANIK | 95 | Lys2 | 2.9 |
| MAST1, MAST2 | UniRef100_Q6P0Q8, UniRef100_Q9Y2H9 | DLKPDNLLITSMGHIK | 96 | Lys2 | 35.6 |
| MAST3 | UniRef100_O60307 | DLKPDNLLITSLGHIK | 97 | Lys2 | -8.1 |
| MASTL | UniRef100_Q96GX5 | GAFGKVYLGQK | 98 | ATP Loop | 12.8 |
| MASTL | UniRef100_Q96GX5 | LYAVKVVK | 99 | Lys1 | 3.3 |
| MELK | UniRef100_Q14680 | DLKPENLLFDEYHK | 100 | Lys2 | -19.6 |
| MER | UniRef100_Q12866 | NCMLRDDMTVCVADFGLSKK | 101 | Activation Loop | 49.8 |
| MER, TYRO3 | UniRef100_Q06418, UniRef100_Q12866 | KIYSGDYYR | 102 | Activation Loop | 1.6 |
| MET | UniRef100_P08581 | DMYDKEYYSVHNK | 103 | Activation Loop | -21.0 |
| MLK3 | UniRef100_Q16584 | DLKSNNILLLQPIESDDMEHK | 104 | Lys2 | 20.7 |
| MLK4 | UniRef100_Q5TCX8 | DLKSSNILLLEK | 105 | Lys2 | -1.7 |
| MLKL | UniRef100_Q8NB16 | APVAIKVFK | 106 | Lys1 | -14.9 |
| MPSK1 | UniRef100_O75716 | DLKPTNILLGDEGQPVLMDLGSMNQACIHVEGSR | 107 | Lys2 | 16.1 |

TABLE 4-continued

| Kinase | Reference | Sequence | SEQ ID NO: | Labeling Site | Compound A-4 (1.0 µM) |
|---|---|---|---|---|---|
| MSK1 domain1 | UniRef100_O75582 | DIKLENILLDSNGHVVLTDFGLSK | 108 | Lys2 | 5.7 |
| MSK2 domain1 | UniRef100_O75676 | DLKLENVLLDSEGHIVLTDFGLSK | 109 | Lys2 | -64.9 |
| MST1 | UniRef100_Q13043 | ETGQIVAIKQVPVESDLQEIIK | 110 | Lys1 | -4.7 |
| MST2 | UniRef100_Q13188 | ESGQVVAIKQVPVESDLQEIIK | 111 | Lys1 | -6.2 |
| MST3 | UniRef100_Q9Y6E0 | DIKAANVLLSEHGEVK | 112 | Lys2 | -3.7 |
| MST4 | UniRef100_Q9P289 | TQQVVAIKIIDLEEAEDEIEDIQQEITVLSQCDSSYVTK | 113 | Lys1 | 6.2 |
| MST4, YSK1 | UniRef100_O00506, UniRef100_Q9P289 | DIKAANVLLSEQGDVK | 114 | Lys2 | 4.6 |
| MYO3A, MYO3B | UniRef100_Q8NEV4, UniRef100_Q8WXR4 | DVKGNNILLTTEGGVK | 115 | Lys2 | -15.3 |
| NDR1 | UniRef100_Q15208 | DIKPDNLLLDSK | 116 | Lys2 | 9.3 |
| NDR2 | UniRef100_Q9Y2H1 | DIKPDNLLLDAK | 117 | Lys2 | -10.9 |
| NEK1 | UniRef100_Q96PY6 | DIKSQNIFLTK | 118 | Lys2 | -3.0 |
| NEK2 | UniRef100_P51955 | DLKPANVFLDGK | 119 | Lys2 | -22.7 |
| NEK3 | UniRef100_P51956 | SKNIFLTQNGK | 120 | Activation Loop | 13.1 |
| NEK4 | UniRef100_P51957 | DLKTQNVFLTR | 121 | Lys2 | 1.5 |
| NEK6, NEK7 | UniRef100_Q8TDX7, UniRef100_Q9HC98 | DIKPANVFITATGVVK | 122 | Lys2 | -12.5 |
| NEK7 | UniRef100_Q8TDX7 | AACLLDGVPVALKK | 123 | Lys1 | -7.2 |
| NEK8 | UniRef100_Q86SG6 | DLKTQNILLDK | 124 | Lys2 | -11.4 |
| NEK9 | UniRef100_Q8TD19 | DIKTLNIFLTK | 125 | Lys2 | -1.2 |
| OSR1 | UniRef100_C9JIG9, UniRef100_O95747 | DVKAGNILLGEDGSVQIADFGVSAFLATGGDITR | 126 | Lys2 | -11.1 |
| p38a | UniRef100_Q16539 | DLKPSNLAVNEDCELK | 127 | Lys2 | 61.4 |
| p38a | UniRef100_Q16539 | QELNKTIWEVPER | 128 | Protein Kinase Domain | 92.2 |
| p38b | UniRef100_O15759 | QELNKTVWEVPQR | 129 | Protein Kinase Domain | 51.4 |
| p38d, p38g | UniRef100_O15264, UniRef100_P53778 | DLKPGNLAVNEDCELK | 130 | Lys2 | 62.5 |
| p70SEK | UniRef100_P23443 | DLKPENIMLNHQGHVK | 131 | Lys2 | -2.3 |
| p70S6Kb | UniRef100_Q9UBS0 | DLKPENIMLSSQGHIK | 132 | Lys2 | 8.2 |
| PAN3 | UniRef100_Q58A45 | VMDPTKILITGK | 133 | ATP | 12.1 |
| PCTAIRE1 | UniRef100_Q00536 | SKLTDNLVALKEIR | 134 | Lys1 | -3.5 |
| PCTAIRE2, PCTAIRE3 | UniRef100_Q00537, UniRef100_Q07002 | SKLTENLVALKEIR | 135 | Lys1 | 11.7 |
| PDK1 | UniRef100_O15530 | EYAIKILEK | 136 | Lys1 | 18.8 |
| PEK | UniRef100_Q9N2J5 | DLKPSNIFFTMDDVVK | 137 | Lys2 | 9.4 |

TABLE 4-continued

| Kinase | Reference | Sequence | SEQ ID NO: | Labeling Site | Compound A-4 (1.0 μM) |
|---|---|---|---|---|---|
| PFTAIRE1 | UniRef100_O94921 | LVALKVIR | 138 | Lys1 | 4.3 |
| PHKg1 | UniRef100_Q16816 | DLKPENILLDDNMNIK | 139 | Protein Kinase Domain | -49.0 |
| PHKg2 | UniRef100_P15735 | ATGHEFAVKIMEVTAER | 140 | Lys1 | 15.2 |
| PI4KA, PI4KAP2 | UniRef100_A4QPH2, UniRef100_P42356 | SGTPMQSAAKAPYLAK | 141 | ATP | 19.3 |
| PI4KB | UniRef100_Q9UBF8 | VPHTQAVVLNSKDK | 142 | ATP | -0.2 |
| PIK3C2B | UniRef100_O00750 | VIFKCGDDLRQDMLTLQMIR | 143 | ATP | 24.0 |
| PIK3C3 | UniRef100_Q8NEB9 | TEDGGKYPVIFKHGDDLR | 144 | ATP | -5.1 |
| PIK3CB | UniRef100_Q9BTS4, UniRef100_P42338 | VFGEDSVGVIFKNGDDLRQDMLTLQMLR | 145 | ATP | 27.8 |
| PIK3CD | UniRef100_O00329 | VNWLAHNVSKDNRQ | 146 | ATP | 2.2 |
| PIK3CG | UniRef100_P48736 | KKPLWLEFK | 147 | ATP | -21.1 |
| PIP4K2A | UniRef100_P48426 | AKELPTLKDNDFINEGQK | 148 | ATP | -26.7 |
| PIP4K2B | UniRef100_P78356 | AKDLPTFKDNDFLNEGQK | 149 | ATP | -44.7 |
| PIP4K2C | UniRef100_Q8TBX8 | TLVIKEVSSEDIADMHSNLSNYHQYIVK | 150 | ATP | 5.2 |
| PIP5K3 | UniRef100_Q9Y217 | GGKSGAAFYATEDDRFILK | 151 | ATP | 0.9 |
| PITSLRE | UniRef100_P21127 | DLKTSNLLLSHAGILK | 152 | Lys2 | -10.4 |
| PKCa, PKCb | UniRef100_P17252, UniRef100_P05771, UniRef100_B5BU22 | DLKLDNVMLDSEGHIK | 153 | Lys2 | 2.3 |
| PKD2 | UniRef100_Q9BZL6 | DVAVKVIDK | 154 | Lys1 | -6.9 |
| PKN1 | UniRef100_Q16512 | VLLSEFRPSGELFAIKALK | 155 | Lys1 | -32.1 |
| PKR | UniRef100_P19525 | DLKPSNIFLVDTK | 156 | Lys2 | -28.4 |
| PLK1 | UniRef100_P53350 | CFEISDADTEVFAGKIVPK | 157 | Lys1 | -9.1 |
| PRP4 | UniRef100_Q13523 | CNILHADIKPDNILVNESK | 158 | Lys2 | -20.1 |
| PRPK | UniRef100_Q96S44 | FLSGLELVKQGAEAR | 159 | ATP Loop | -13.7 |
| PYK2 | UniRef100_Q14289 | YIEDEDYYKASVTR | 160 | Activation Loop | 10.9 |
| RAF1 | UniRef100_P04049 | DMKSNNIFLHEGLTVK | 161 | Lys2 | 36.6 |
| RIPK3 | UniRef100_Q9Y572 | DLKPSNVLLDPELHVK | 162 | Lys2 | 32.6 |
| ROCK1, ROCK2 | UniRef100_O75116, UniRef100_Q13464 | DVKPDNMLLDK | 163 | Lys2 | 22.0 |
| RSK1 domain1 | UniRef100_Q15418 | DLKPENILLDEEGHIKLTDFGLSKEAIDHEK | 164 | Lys2 | -20.9 |
| RSK1 domain1, RSK2 domain1, RSK3 domain1 | UniRef100_Q15418, UniRef100_P51812, UniRef100_Q15349 | DLKPENILLDEEGHIK | 165 | Lys2 | -17.7 |
| RSK1 domain1 | UniRef100_Q15418 | DLKPSNILYVDESGNPECLR | 166 | Lys2 | -16.3 |

TABLE 4-continued

| Kinase | Reference | Sequence | SEQ ID NO: | Labeling Site | Compound A-4 (1.0 µM) |
|---|---|---|---|---|---|
| RSK2 domain1 | UniRef100_P51812 | DLKPENILLDEEGHIKLTDFGLSKESIDHEK | 167 | Lys2 | -3.3 |
| RSK2 domain2 | UniRef100_P51812 | DLKPSNILYVDESGNPESIR | 168 | Lys2 | -24.1 |
| RSK3 domain1 | UniRef100_O15349 | DLKPENILLDEEGHIKITDFGLSK | 169 | Lys2 | -32.6 |
| RSK4 domain1 | UniRef100_Q9UK32 | DLKPENILLDEIGHIK | 170 | Lys2 | 27.6 |
| RSKL1 | UniRef100_Q96S38 | VLGVIDKVLLVMDTR | 171 | ATP | 31.5 |
| SGK3 | UniRef100_Q96BR1 | FYAVKVLQK | 172 | Lys1 | -10.2 |
| SLK | UniRef100_Q9H2G2 | DLKAGNILFTLDGDIK | 173 | Lys2 | -14.3 |
| SMG1 | UniRef100_Q96Q15 | DTVTIHSVTITILPTKTKPK | 174 | ATP | -4.0 |
| SNRK | UniRef100_Q9NRH2 | DLKPENVVFFEK | 175 | Lys2 | 18.0 |
| SRC | UniRef100_P12931 | VAIKTLKPGTMSPEAFLQEAQVMKK | 176 | Lys1 | 76.1 |
| SRPK1 | UniRef100_Q96SB4 | IIHTDIKPENILLSVNEQYIR | 177 | Lys2 | -34.1 |
| STK33 | UniRef100_Q9BYT3 | DLKLENIMVK | 178 | Lys2 | 12.9 |
| STLK5 | UniRef100_Q7RTN6 | YSVKVLPWLSPEVLQQNLQGYDAK | 179 | Activation Loop | 5.0 |
| SYK | UniRef100_P43405 | ISDFGLSKALR | 180 | Activation Loop | 17.4 |
| TAK1 | UniRef100_O43318 | DLKPPNLLLVAGGTVLK | 181 | Lys2 | 32.0 |
| TAO1, TAO3 | UniRef100_Q9H2K8, UniRef100_Q7L7X3 | DIKAGNILLTEPGQVK | 182 | Lys2 | 76.5 |
| TAO2 | UniRef100_Q9UL54 | DVKAGNILLSEPGLVK | 183 | Lys2 | 86.0 |
| TBK1 | UniRef100_Q9UHD2 | TGDLFAIKVFNNISFLRPVDVQMR | 184 | Lys1 | 18.2 |
| TEC | UniRef100_P42680 | YVLDDQYTSSSGAKFPVK | 185 | Activation Loop | -12.8 |
| TLK1 | UniRef100_Q9UKI8 | YLNEIKPPIIHYDLKPGNILLVDGTACG | 186 | Lys2 | 4.9 |
| TLK2 | UniRef100_Q86UE8 | YLNEIKPPIIHYDLKPGNILLVNGTACGEIK | 187 | Lys2 | 7.1 |
| TYK2 domain2 | UniRef100_P29597 | IGDFGLAKAVPEGHEYYR | 188 | Activation Loop | -18.1 |
| ULK1 | UniRef100_O75385 | DLKPQNILLSNPAGR | 189 | Lys2 | -6.0 |
| ULK3 | UniRef100_D3DW67, UniRef100_Q6PHR2 | NISHLDLKPQNILLSSLEKPHLK | 190 | Lys2 | -4.4 |
| VRK2 | UniRef100_Q86Y07 | MLDVLEYIHENEYVHGDIKAANLLLGYK | 191 | Lys2 | 27.9 |
| Wee1 | UniRef100_P30291 | YIHSMSLVHDIKPSNIFISR | 192 | Lys2 | 23.2 |
| Wnk1, Wnk2 | UniRef100_Q9Y3S1, UniRef100_D3DUP1, UniRef100_Q9H4A3 | GSFKTVYK | 193 | ATP Loop | 24.2 |

TABLE 4-continued

| Kinase | Reference | Sequence | SEQ ID NO: | Labeling Site | Compound A-4 (1.0 µM) |
|---|---|---|---|---|---|
| Wnk1, Wnk2, Wnk3 | UniRef100_Q9Y3S1, UniRef100_D3DUP1, UniRef100_Q9BYP7, UniRef100_Q9H4A3 | DLKCDNIFITGPTGSVK | 194 | Lys2 | 0.2 |
| YANK3 | UniRef100_Q86UX6 | DVKPDNILLDER | 195 | Lys2 | 27.7 |
| ZAK | UniRef100_Q9NYL2 | WISQDKEVAVKK | 196 | Lys1 | 75.7 |
| ZAP70 | UniRef100_P43403 | ISDFGLSKALGADDSYYTAR | 197 | Activation Loop | 49.2 |
| ZC1/HGK, ZC2/TNIK, ZC3/MINK | UniRef100_O95819, UniRef100_Q9UKE5, UniRef100_Q8N4C8 | DIKGQNVLLTENAEVK | 198 | Lys2 | 19.2 |
| ZC2/TNIK | UniRef100_Q9UKE5 | TGQLAAIKVMDVTGDEEEEIKQEINMLKK | 199 | Lys1 | 23.9 |

TABLE 5

| Kinase | Reference | Sequence | SEQ ID NO: | Labeling Site | Cmpd. A-14 (1.0 µM) |
|---|---|---|---|---|---|
| ABL, ARG | UniRef100_P00519, UniRef100_P42684 | LMTGDTYTAHAGAKFPIK | 200 | Activation Loop | 98.4 |
| ACK | UniRef100_Q07912 | TVSVAVKCLKPDVLSQPEAMDDFIR | 201 | Lys1 | 8.5 |
| AGK | UniRef100_Q53H12 | ATVFLNPAACKGK | 202 | ATP | 5.9 |
| AKT1 | UniRef100_P31749 | GTFGKVILVK | 203 | ATP Loop | -23.9 |
| AKT2, AKT3 | UniRef100_Q9Y243, UniRef100_P31751 | GTFGKVILVR | 204 | ATP Loop | -19.7 |
| AMPKa1, AMPKa2 | UniRef100_P54646, UniRef100_Q96E92 | DLKPENVLLDAHMNAK | 205 | Lys2 | -17.5 |
| ANPa | UniRef100_P16066 | GMLFLHNGAICSHGNLKSSNCVVDGR | 206 | Lys2 | -5.3 |
| ARAF | UniRef100_P10398 | DLKSNNIFLHEGLTVK | 207 | Lys2 | 2.0 |
| ATR | UniRef100_Q13535 | FYIMMCKPK | 208 | ATP | -20.3 |
| AurA | UniRef100_O14965 | FILALKVLFK | 209 | Lys1 | 14.6 |
| AurA | UniRef100_O14965 | DIKPENLLLGSAGELK | 210 | Lys2 | 6.1 |
| AurA, AurB, AurC | UniRef100_O14965, UniRef100_Q9UQB9, UniRef100_Q96GD4 | GKFGNVYLAR | 211 | ATP Loop | -2.4 |
| AurB | UniRef100_Q96GD4 | SHFIVALKVLFK | 212 | Lys1 | 3.3 |
| BARK1 | UniRef100_P25098 | DLKPANILLDEHGHVR | 213 | Lys2 | -13.6 |
| BRAF | UniRef100_P15056 | DLKSNNIFLHEDLTVK | 214 | Lys2 | 18.9 |
| BTK | UniRef100_O06187 | YVLDDEYTSSVGSKFPVR | 215 | Activation Loop | -10.2 |
| CaMK1a | UniRef100_Q14012 | LVAIKCIAK | 216 | Lys1 | -5.4 |
| CaMK1d | UniRef100_Q8IU85 | LFAVKCIPK | 217 | Lys1 | -1.8 |
| CaMK2d | UniRef100_Q13557 | IPTGQEYAAKIINTKK | 218 | Lys1 | -7.3 |
| CaMK2g | UniRef100_Q13555 | TSTQEYAAKIINTK | 219 | Lys1 | 2.0 |
| CaMK4 | UniRef100_Q16566 | DLKPENLLYATPAPDAPLK | 220 | Lys2 | -2.0 |
| CaMKK2 | UniRef100_Q96RR4 | DIKPSNLLVGEDGHIK | 221 | Lys2 | 16.2 |

TABLE 5-continued

| Kinase | Reference | Sequence | SEQ ID NO: | Labeling Site | Cmpd. A-14 (1.0 µM) |
|---|---|---|---|---|---|
| CASK | UniRef100_O14936 | ETGQQFAVKIVDVAK | 222 | Lys1 | 7.1 |
| CDC2 | UniRef100_Q5H9N4 | DLKPQNLLIDDKGTIK | 223 | Lys2 | 9.0 |
| CDK11, CDK8 | UniRef100_P49336, UniRef100_Q9BWU1 | DLKPANILVMGEGPER | 224 | Lys2 | 49.2 |
| CDK2 | UniRef100_P24941 | DLKPQNLLINTEGAIK | 225 | Lys2 | 34.5 |
| CDK4 | UniRef100_P11802 | DLKPENILVTSGGTVK | 226 | Lys2 | 11.4 |
| CDK5 | UniRef100_Q00535 | DLKPQNLLINR | 227 | Lys2 | 11.3 |
| CDK6 | UniRef100_Q00534 | DLKPQNILVTSSGQIK | 228 | Lys2 | 13.6 |
| CDK7 | UniRef100_P50613 | DLKPNNLLLDENGVLK | 229 | Lys2 | -7.3 |
| CDK9 | UniRef100_P50750 | DMKAANVLITR | 230 | Lys2 | -13.1 |
| CHK1 | UniRef100_B4DT73 | DIKPENLLLDER | 231 | Lys2 | 12.2 |
| CHK2 | UniRef100_O96017 | DLKPENVLLSSQEEDCLIK | 232 | Lys2 | -1.6 |
| CK1a | UniRef100_P48729 | DIKPDNFLMGIGR | 233 | Lys2 | -19.6 |
| CK1d, CK1e | UniRef100_P49674, UniRef100_P48730 | DVKPDNFLMGLGKK | 234 | Lys2 | -9.3 |
| CK1g1, CK1g2, CK1g3 | UniRef100_Q9Y6M4, UniRef100_P78368, UniRef100_Q9HCP0 | KIGCGNFGELR | 235 | ATP Loop | 1.3 |
| CK1g2 | UniRef100_P78368 | DVKPENFLVGRPGTK | 236 | Lys2 | -23.3 |
| CLK2 | UniRef100_P49760 | LTHTDLKPENILFVNSDYELTYNLEK | 237 | Lys2 | -30.3 |
| CLK3 | UniRef100_P49761 | YEIVGNLGEGTFGKVVECLDHAR | 238 | ATP Loop | -4.0 |
| CSK | UniRef100_P41240 | VSDFGLTKEASSTQDTGKLPVK | 239 | Activation Loop | 20.0 |
| DGKA | UniRef100_P23743 | IDPVPNTHPLLVFVNPKSGGK | 240 | ATP | -16.3 |
| DGKH | UniRef100_Q86XP1 | ATFSFCVSPLLVFVNSKSGDNQGVK | 241 | ATP | 32.6 |
| DGKQ | UniRef100_P52824 | GRLLTALVLPDLLHAKLPPDSCPLLVFVNPKSGGLK | 242 | ATP | -23.2 |
| DNAPK | UniRef100_P78527 | KGGSWIQEINVAEK | 243 | ATP | -35.9 |
| DNAPK | UniRef100_P78527 | EHPFLVKGGEDLR | 244 | ATP | -63.7 |
| eEF2K | UniRef100_O00418 | YIKYNSNSGFVR | 245 | ATP | -22.0 |
| Erk1 | UniRef100_P27361 | DLKPSNLLINTTCDLK | 246 | Lys2 | -16.3 |
| Erk2 | UniRef100_P28482 | DLKPSNLLLNTTCDLK | 247 | Lys2 | -2.7 |
| Erk3 | UniRef100_Q16659 | DLKPANLFINTEDLVLK | 248 | Lys2 | 31.8 |
| Erk5 | UniRef100_Q13164 | DLKPSNLLVNENCELK | 249 | Lys2 | -42.7 |
| FER | UniRef100_P16591 | TSVAVKTCKEDLPQELK | 250 | Lys1 | 74.0 |
| FES | UniRef100_P07332 | LRADNTLVAVKSCR | 251 | Lys1 | 36.1 |
| FGR | UniRef100_P09769 | LIKDDEYNPCQGSKFPIK | 252 | Activation Loop | 70.3 |
| FRAP | UniRef100_P42345 | IQSIAPSLQVITSKQRPR | 253 | ATP | -3.3 |

TABLE 5-continued

| Kinase | Reference | Sequence | SEQ ID NO: | Labeling Site | Cmpd. A-14 (1.0 μM) |
|---|---|---|---|---|---|
| FRK | UniRef100_P42685 | HEIKLPVK | 254 | Activation Loop | 98.0 |
| FYN, SRC, YES | UniRef100_P12931, UniRef100_P07947, UniRef100_P06241 | QGAKFPIKWTAPEAALYGR | 255 | Activation Loop | 88.2 |
| GCK | UniRef100_Q12851 | DIKGANLLLTLQGDVK | 256 | Lys2 | 96.3 |
| GCN2 | UniRef100_Q9P2K8 | DLKPVNIFLDSDDHVK | 257 | Lys2 | 5.4 |
| GPRK6 | UniRef100_P43250 | DLKPENILLDDHGHIR | 258 | Lys2 | -1.9 |
| GSK3A | UniRef100_P49840 | DIKPQNLLVDPDTAVLK | 259 | Lys2 | 25.5 |
| GSK3B | UniRef100_P49841 | DIKPQNLLLDPDTAVLK | 260 | Lys2 | -3.5 |
| HPK1 | UniRef100_Q92918 | DIKGANILINDAGEVR | 261 | Lys2 | 88.2 |
| IKKa | UniRef100_O15111 | DLKPENIVLQDVGGK | 262 | Lys2 | -3.1 |
| IKKb | UniRef100_O14920 | DLKPENIVLQQGEQR | 263 | Lys2 | -12.2 |
| IKKe | UniRef100_Q14164 | SGELVAVKVFNTTSYLRPR | 264 | Lys1 | -3.9 |
| ILK | UniRef100_Q13418 | WQGNDIVVKVLK | 265 | Lys1 | -0.4 |
| ILK | UniRef100_Q13418 | ISMADVKFSFQCPGR | 266 | Protein Kinase Domain | 6.8 |
| IRAK1 | UniRef100_P51617 | AIQFLHQDSPSLIHGDIKSSNVLLDER | 267 | Lys2 | 7.6 |
| IRAK3 | UniRef100_Q9Y616 | VEIQNLTYAVKLFK | 268 | Lys1 | -7.1 |
| IRAK4 | UniRef100_Q9NWZ3 | DIKSANILLDEAFTAK | 269 | Lys2 | 6.3 |
| IRE1 | UniRef100_O75460 | DLKPHNILISMPNAHGK | 270 | Lys2 | -0.6 |
| ITPK1 | UniRef100_Q13572 | ESIFFNSHNVSKPESSSVLTELDKIEGVFERPSDEVIR | 271 | ATP | -16.2 |
| JAK1 domain1 | UniRef100_P23458 | QLASALSYLEDKDLVHGNVCTKNLLLAR | 272 | Protein Kinase Domain | 9.0 |
| JAK1 domain2 | UniRef100_P23458 | IGDFGLTKAIETDKEYYTVK | 273 | Activation Loop | 29.3 |
| JAK1 domain2 | UniRef100_P23458 | YDPEGDNTGEQVAVKSLKPESGGNHIADLKK | 274 | Lys1 | 24.0 |
| JAK3 domain2 | UniRef100_P52333 | IADFGLAKLLPLDKDYYVVR | 275 | Activation Loop | -4.3 |
| JNK1, JNK2, JNK3 | UniRef100_P45983, UniRef100_P53779, UniRef100_P45984 | DLKPSNIVVK | 276 | Lys2 | 31.5 |
| KHS1 | UniRef100_Q9Y4K4 | NVHTGELAAVKIIK | 277 | Lys1 | 33.9 |
| KHS2 | UniRef100_Q8IVH8 | NVNTGELAAIKVIK | 278 | Lys1 | 3.8 |
| KSR1 | UniRef100_Q8IVT5 | SKNVFYDNGKVVITDFGLFGISGVVR | 279 | Activation Loop | -0.2 |
| KSR1, KSR2 | UniRef100_Q6VAB6, UniRef100_Q8IVT5 | SKNVFYDNGK | 280 | Activation Loop | 1.4 |
| LATS1 | UniRef100_O95835 | ALYATKTLR | 281 | Lys1 | 15.8 |
| LATS2 | UniRef100_Q9NRM7 | DIKPDNILIDLDGHIK | 282 | Lys2 | 0.8 |
| LCK | UniRef100_P06239 | EGAKFPIKWTAPEAINYGTFTIK | 283 | Activation Loop | 83.8 |

TABLE 5-continued

| Kinase | Reference | Sequence | SEQ ID NO: | Labeling Site | Cmpd. A-14 (1.0 μM) |
|---|---|---|---|---|---|
| LKB1 | UniRef100_Q15831 | DIKPGNLLLTTGGTLK | 284 | Lys2 | 3.6 |
| LOK | UniRef100_O94804 | DLKAGNVLMTLEGDIR | 285 | Lys2 | 28.8 |
| LRRK2 | UniRef100_Q5S007 | DLKPHNVLLLYPNAAIIAK | 286 | Lys2 | -11.8 |
| LYN | UniRef100_P07948 | VAVKTLKPGTMSVQAFLEEANLMK | 287 | Lys1 | 85.7 |
| MAP2K1 | UniRef100_Q02750 | IMHRDVKPSNILVNSR | 288 | Lys2 | 6.6 |
| MAP2K1, MAP2K2 | UniRef100_P36507, UniRef100_Q02750 | KLIHLEIKPAIR | 289 | Lys1 | 9.4 |
| MAP2K1, MAP2K2 | UniRef100_P36507, UniRef100_Q02750 | DVKPSNILVNSR | 290 | Lys2 | 2.2 |
| MAP2K2 | UniRef100_P36507 | HQIMHRDVKPSNILVNSR | 291 | Lys2 | 3.9 |
| MAP2K3 | UniRef100_P46734 | DVKPSNVLINK | 292 | Lys2 | -1.0 |
| MAP2K4 | UniRef100_P45985 | DIKPSNILLDR | 293 | Lys2 | 0.4 |
| MAP2K5 | UniRef100_Q13163 | DVKPSNMLVNTR | 294 | Lys2 | -46.0 |
| MAP2K6 | UniRef100_P52564 | DVKPSNVLINALGQVK | 295 | Lys2 | 2.0 |
| MAP2K7 | UniRef100_O14733 | DVKPSNILLDER | 296 | Lys2 | 19.3 |
| MAP3K1 | UniRef100_Q13233 | DVKGANLLIDSTGQR | 297 | Lys2 | 27.5 |
| MAP3K2 | UniRef100_Q9Y2U5 | ELAVKQVQFDPDSPETSKEVNALECEIQLLK | 298 | Lys1 | -1.1 |
| MAP3K2, MAP3K3 | UniRef100_Q9Y2U5, UniRef100_Q99759 | DIKGANILR | 299 | Lys2 | 8.4 |
| MAP3K3 | UniRef100_Q99759 | ELASKQVQFDPDSPETSKEVSALECEIQLLK | 300 | Lys1 | 10.0 |
| MAP3K4 | UniRef100_Q9Y6R4 | DIKGANIFLTSSGLIK | 301 | Lys2 | 17.3 |
| MAP3K5 | UniRef100_Q99683 | DIKGDNVLINTYSGVLK | 302 | Lys2 | -10.2 |
| MAP3K6 | UniRef100_O95382 | DIKGDNVLINTFSGLLK | 303 | Lys2 | 2.1 |
| MARK2, MARK3 | UniRef100_P27448, UniRef100_Q7KZI7 | DLKAENLLLDADMNIK | 304 | Lys2 | -15.6 |
| MARK3 | UniRef100_P27448 | EVAIKIIDKTQLNPTSLQK | 305 | Lys1 | 2.6 |
| MARK3, MARK4 | UniRef100_Q96L34, UniRef100_P27448 | EVAIKIIDK | 306 | Lys1 | -7.5 |
| MARK4 | UniRef100_Q96L34 | DLKAENLLLDAEANIK | 307 | Lys2 | -28.5 |
| MAST1, MAST2 | UniRef100_Q6P0Q8, UniRef100_Q9Y2H9 | DLKPDNLLITSMGHIK | 308 | Lys2 | -24.8 |
| MAST3 | UniRef100_O60307 | DLKPDNLLITSLGHIK | 309 | Lys2 | -4.7 |
| MASTL | UniRef100_Q96GX5 | GAFGKVYLGQK | 310 | ATP Loop | 1.1 |
| MASTL | UniRef100_Q96GX5 | LYAVKVVK | 311 | Lys1 | -7.6 |
| MELK | UniRef100_Q14680 | DLKPENLLFDEYHK | 312 | Lys2 | -3.0 |
| MER, TYRO3 | UniRef100_Q06418, UniRef100_Q12866 | KIYSGDYYR | 313 | Activation Loop | 21.2 |
| MET | UniRef100_P08581 | DMYDKEYYSVHNK | 314 | Activation Loop | 5.7 |

TABLE 5-continued

| Kinase | Reference | Sequence | SEQ ID NO: | Labeling Site | Cmpd. A-14 (1.0 μM) |
|---|---|---|---|---|---|
| MLK3 | UniRef100_Q16584 | DLKSNNILLLQPIESDDMEIIK | 315 | Lys2 | -0.2 |
| MLK4 | UniRef100_Q5TCX8 | DLKSSNILLLEK | 316 | Lys2 | 1.5 |
| MLKL | UniRef100_Q8NB16 | APVAIKVFK | 317 | Lys1 | -5.5 |
| MPSK1 | UniRef100_O75716 | DLKPTNILLGDEGQPVLMDLGSMNQACIHVEGSR | 318 | Lys2 | -2.3 |
| MSK1 domain1 | UniRef100_O75582 | DIKLENILLDSNGHVVLTDFGLSK | 319 | Lys2 | -21.5 |
| MSK2 domain1 | UniRef100_O75676 | DLKLENVLLDSEGHIVLTDFGLSK | 320 | Lys2 | -8.1 |
| MST1 | UniRef100_Q13043 | ETGQIVAIKQPVESDLQEIIK | 321 | Lys1 | 7.5 |
| MST2 | UniRef100_Q13188 | ESGQVVAIKQVPVESDLQEIIK | 322 | Lys1 | 8.6 |
| MST3 | UniRef100_Q9Y6E0 | DIKAANVLLSEHGEVK | 323 | Lys2 | -8.9 |
| MST4 | UniRef100_Q9P289 | TQQVVAIKIIDLEEAEDEIEDIQQEITVLSQCDSSYVTK | 324 | Lys1 | -37.3 |
| MST4, YSK1 | UniRef100_O00506, UniRef100_Q9P289 | DIKAANVLLSEQGDVK | 325 | Lys2 | -2.4 |
| MYO3A, MYO3B | UniRef100_Q8NEV4, UniRef100_Q8WXR4 | DVKGNNILLTTEGGVK | 326 | Lys2 | 22.9 |
| NDR1 | UniRef100_Q15208 | DIKPDNLLLDSK | 327 | Lys2 | 2.3 |
| NDR2 | UniRef100_Q9Y2H1 | DIKPDNLLLDAK | 328 | Lys2 | 9.8 |
| NEK1 | UniRef100_Q96PY6 | DIKSQNIFLTK | 329 | Lys2 | -7.1 |
| NEK2 | UniRef100_P51955 | DLKPANVFLDGK | 330 | Lys2 | 12.5 |
| NEK3 | UniRef100_P51956 | SKNIFLTQNGK | 331 | Activation Loop | -8.6 |
| NEK4 | UniRef100_P51957 | DLKTQNVFLTR | 332 | Lys2 | 2.8 |
| NEK6, NEK7 | UniRef100_Q8TDX7, UniRef100_Q9HC98 | DIKPANVFITATGVVK | 333 | Lys2 | -1.8 |
| NEK7 | UniRef100_Q8TDX7 | AACLLDGVPVALKK | 334 | Lys1 | 2.7 |
| NEK8 | UniRef100_Q86SG6 | DLKTQNILLDK | 335 | Lys2 | -7.8 |
| NEK9 | UniRef100_Q8TD19 | DIKTLNIFLTK | 336 | Lys2 | -10.7 |
| NLK | UniRef100_Q9UBE8 | DIKPGNLLVNSNCVLK | 337 | Lys2 | 22.3 |
| OSR1 | UniRef100_C9JIG9, UniRef100_O95747 | DVKAGNILLGEDGSVQIADFGVSAFLATGGDITR | 338 | Lys2 | 32.2 |
| p38a | UniRef100_Q16539 | DLKPSNLAVNEDCELK | 339 | Lys2 | 76.1 |
| p38a | UniRef100_Q16539 | QELNKTIWEVPER | 340 | Protein Kinase Domain | 88.4 |
| p38d, p38g | UniRef100_O15264, UniRef100_P53778 | DLKPGNLAVNEDCELK | 341 | Lys2 | 51.5 |
| p70S6K | UniRef100_P23443 | DLKPENIMLNHQGHVK | 342 | Lys2 | -74.1 |
| p70S6Kb | UniRef100_Q9UBS0 | DLKPENIMLSSQGHIK | 343 | Lys2 | 3.5 |
| PAN3 | UniRef100_Q58A45 | VMDPTKILITGK | 344 | ATP | 7.3 |
| PCTAIRE1 | UniRef100_Q00536 | SKLTDNLVALKEIR | 345 | Lys1 | 53.3 |

TABLE 5-continued

| Kinase | Reference | Sequence | SEQ ID NO: | Labeling Site | Cmpd. A-14 (1.0 µM) |
|---|---|---|---|---|---|
| PCTAIRE2, PCTAIRE3 | UniRef100_Q00537, UniRef100_Q07002 | SKLTENLVALKEIR | 346 | Lys1 | 72.9 |
| PDHK1 | UniRef100_Q15118 | SPGQPIQVVYVPSHLYHMVFELFKNAMR | 347 | ATP | -23.7 |
| PEK | UniRef100_Q9NZJ5 | DLKPSNIFFTMDDVVK | 348 | Lys2 | -21.9 |
| PFTAIRE1 | UniRef100_O94921 | LVALKVIR | 349 | Lys1 | 64.0 |
| PHKg1 | UniRef100_Q16816 | DLKPENILLDDNMNIK | 350 | Protein Kinase Domain | -0.9 |
| PHKg2 | UniRef100_P15735 | ATGHEFAVKIMEVTAER | 351 | Lys1 | 7.1 |
| PI4K2B | UniRef100_Q8TCG2 | SEEPYGQLNPKWTK | 352 | ATP | 33.4 |
| PI4KA, PI4KAP2 | UniRef100_A4QPH2, UniRef100_P42356 | SGTPMQSAAKAPYLAK | 353 | ATP | 2.1 |
| PI4KB | UniRef100_Q9UBF8 | VPHTQAVVLNSKDK | 354 | ATP | 23.7 |
| PIK3C2B | UniRef100_O00750 | VIFKCGDDLRQDMLTLQMIR | 355 | ATP | -15.7 |
| PIK3C3 | UniRef100_Q8NEB9 | TEDGGKYPVIFKHGDDLR | 356 | ATP | -29.7 |
| PIK3CB | UniRef100_P42338 | VFGEDSVGVIFKNGDDLRQDMLTLQMLR | 357 | ATP | -3.9 |
| PIK3CD | UniRef100_O00329 | VNWLAHNVSKDNRQ | 358 | ATP | -22.8 |
| PIK3CG | UniRef100_P48736 | KKPLWLEFK | 359 | ATP | -20.1 |
| PIP4K2A | UniRef100_P48426 | AKELPTLKDNDFINEGQK | 360 | ATP | -19.5 |
| PIP4K2C | UniRef100_Q8TBX8 | TLVIKEVSSEDIADMHSNLSNYHQYIVK | 361 | ATP | -7.3 |
| PIP5K3 | UniRef100_Q9Y217 | GGKSGAAFYATEDDRFILK | 362 | ATP | 21.7 |
| PITSLRE | UniRef100_P21127 | DLKTSNLLLSHAGILK | 363 | Lys2 | 10.2 |
| PKCa, PKCb | UniRef100_P05771, UniRef100_P17252 | DLKLDNVMLDSEGHIK | 364 | Lys2 | -86.4 |
| PKCe | UniRef100_Q02156 | DLKLDNILLDAEGHCK | 365 | Lys2 | 27.7 |
| PKCi | UniRef100_P41743 | IYAMKVVK | 366 | Lys1 | -54.3 |
| PKD2 | UniRef100_Q9BZL6 | DVAVKVIDK | 367 | Lys1 | -5.4 |
| PKN1 | UniRef100_Q16512 | VLLSEFRPSGELFAIKALK | 368 | Lys1 | 1.8 |
| PKR | UniRef100_P19525 | DLKPSNIFLVDTKK | 369 | Lys2 | -1.7 |
| PLK1 | UniRef100_P53350 | CFEISDADTKEVFAGKIVPK | 370 | Lys1 | 18.8 |
| PLK4 | UniRef100_O00444 | AESIHTGLEVAIKMIDKK | 371 | Lys1 | -17.3 |
| PRP4 | UniRef100_Q13523 | CNILHADIKPDNILVNESK | 372 | Lys2 | -5.5 |
| PRPK | UniRef100_Q96544 | FLSGLELVKQGAEAR | 373 | ATP Loop | -16.0 |
| PYK2 | UniRef100_Q14289 | YIEDEDYYKASVTR | 374 | Activation Loop | 30.5 |
| RIPK1 | UniRef100_Q13546 | DLKPENILVDNDFHIK | 375 | Lys2 | 23.1 |
| RIPK3 | UniRef100_Q9Y572 | DLKPSNVLLDPELHVK | 376 | Lys2 | 70.2 |
| ROCK1, ROCK2 | UniRef100_O75116, UniRef100_Q13464 | DVKPDNMLLDK | 377 | Lys2 | -0.2 |

TABLE 5-continued

| Kinase | Reference | Sequence | SEQ ID NO: | Labeling Site | Cmpd. A-14 (1.0 µM) |
|---|---|---|---|---|---|
| RSK1 domain1 | UniRef100_Q15418 | DLKPENILLDEEGHIKLTDFGLSKEAIDHEK | 378 | Lys2 | -29.6 |
| RSK1 domain1, RSK2 domain1, RSK3 domain1 | UniRef100_P51812, UniRef100_Q15418, UniRef100_Q15349 | DLKPENILLDEEGHIK | 379 | Lys2 | -25.1 |
| RSK1 domain2 | UniRef100_Q15418 | DLKPSNILYVDESGNPECLR | 380 | Lys2 | 1.0 |
| RSK2 domain1 | UniRef100_P51812 | DLKPENILLDEEGHIKLTDFGLSKESIDHEK | 381 | Lys2 | -36.7 |
| RSK2 domain2 | UniRef100_P51812 | DLKPSNILYVDESGNPESIR | 382 | Lys2 | 2.8 |
| RSK3 domain1 | UniRef100_O15349 | DLKPENILLDEEGHIKITDFGLSK | 383 | Lys2 | -37.8 |
| RSKL1 | UniRef100_Q96S38 | VLGVIDKVLLVMDTR | 384 | ATP | 21.8 |
| SGK3 | UniRef100_Q96BR1 | FYAVKVLQK | 385 | Lys1 | 16.6 |
| SLK | UniRef100_Q9H2G2 | DLKAGNILFTLDGDIK | 386 | Lys2 | 13.8 |
| SMG1 | UniRef100_Q96Q15 | DTVTIHSVTITILPTKTKPK | 387 | ATP | -3.6 |
| SNRK | UniRef100_Q9NRH2 | DLKPENVVFFEK | 388 | Lys2 | 24.5 |
| SRC | UniRef100_P12931 | VAIKTLKPGTMSPEAFLQEAQVMKK | 389 | Lys1 | 82.7 |
| SRPK1 | UniRef100_Q96SB4 | IIHTDIKPENILLSVNEQYIR | 390 | Lys2 | -9.1 |
| SRPK1, SRPK2 | UniRef100_P78362, UniRef100_Q96SB4 | FVAMKVVK | 391 | Lys1 | -38.7 |
| STK33 | UniRef100_Q9BYT3 | DLKLENIMVK | 392 | Lys2 | -8.0 |
| STLK5 | UniRef100_Q7RTN6 | YSVKVLPWLSPEVLQQNLQGYDAK | 393 | Activation Loop | 12.0 |
| SYK | UniRef100_P43405 | ISDFGLSKALR | 394 | Activation Loop | 6.6 |
| TAK1 | UniRef100_O43318 | DLKPPNLLLVAGGTVLK | 395 | Lys2 | 0.4 |
| TAO1, TAO3 | UniRef100_Q7L7X3, UniRef100_Q9H2K8 | DIKAGNILLTEPGQVK | 396 | Lys2 | 87.1 |
| TAO2 | UniRef100_Q9UL54 | DVKAGNILLSEPGLVK | 397 | Lys2 | 92.0 |
| TBK1 | UniRef100_Q9UHD2 | TGDLFAIKVFNNISFLRPVDVQMR | 398 | Lys1 | -18.0 |
| TEC | UniRef100_P42680 | YVLDDQYTSSSGAKFPVK | 399 | Activation Loop | 20.6 |
| TLK1 | UniRef100_Q9UKI8 | YLNEIKPPIIHYDLKPGNILLVDGTACGEIK | 400 | Lys2 | 11.5 |
| TLK2 | UniRef100_Q86UE8 | YLNEIKPPIIHYDLKPGNILLVNGTACGEIK | 401 | Lys2 | 10.2 |

TABLE 5-continued

| Kinase | Reference | Sequence | SEQ ID NO: | Labeling Site | Cmpd. A-14 (1.0 μM) |
|---|---|---|---|---|---|
| ULK1 | UniRef100_O75385 | DLKPQNILLSNPAGR | 402 | Lys2 | 8.8 |
| ULK3 | UniRef100_D3DW67 | NISHLDLKPQNILLSSLEKPHLK | 403 | Lys2 | 27.1 |
| VRK2 | UniRef100_Q86Y07 | MLDVLEYIHENEYVHGDIKAANLLLGYK | 404 | Lys2 | -1.2 |
| Wnk1, Wnk2 | UniRef100_Q9Y3S1, UniRef100_D3DUP1 | GSFKTVYK | 405 | ATP Loop | 11.2 |
| Wnk1, Wnk2, Wnk3 | UniRef100_Q9Y3S1, UniRef100_D3DUP1, UniRef100_Q9BYP7 | DLKCDNIFITGPTGSVK | 406 | Lys2 | -1.1 |
| YANK3 | UniRef100_Q86UX6 | DVKPDNILLDER | 407 | Lys2 | -43.1 |
| ZAK | UniRef100_Q9NYL2 | WISQDKEVAVKK | 408 | Lys1 | 75.8 |
| ZAP70 | UniRef100_P43403 | ISDFGLSKALGADDSYYTAR | 409 | Activation Loop | 10.7 |
| ZC1/HGK, ZC2/TNIK, ZC3/MINK | UniRef100_O95819, UniRef100_Q9UKE5, UniRef100_Q8N4C8 | DIKGQNVLLTENAEVK | 410 | Lys2 | 57.5 |
| ZC2/TNIK | UniRef100_Q9UKE5 | TGQLAAIKVMDVTGDEEEEIKQEINMLKK | 411 | Lys1 | 46.0 |

Example 3. p-BTK and p-Hck Inhibition

Protocol for PhosFlow Studies

PhosFlow was performed to detect levels of phosphorylation for BTK-pY223 (BD Biosciences) and Hck-pY410 (Abcam) in BCWM.1 cells, in BCWM cells that stably overexpress HCK (BCWM.1_HCK-wt) and in BCWM.1 cells that stably overexpress the T338M mutant of HCK (BCWM.1_HCK-mu). Cells were fixed with BD Phosflow Fix Buffer I (BD Biosciences) at 37° C. for 10 min, then washed twice with BD Phosflow Perm/Wash Buffer I (BD Biosciences). Cells were suspended in BD Phosflow Perm/Wash Buffer I at 10 million/ml and antibodies aliquoted to flow tubes with 100 μl cells. Cells were incubated at room temperature for 30 min in the dark. Cells were washed twice with BD Phosflow Perm/Wash Buffer I before performing flow analysis using a BD™ FACSCanto II flow cytometer.

Protocol for Apoptosis Analysis

Apoptosis analysis of WM patient primary lymphoplasmacytic cells (LPCs) was preformed following A-5 and A-14 treatment of Bone marrow mononuclear cells (BMMC) from WM patients for 24 hours. Apoptosis analysis was performed using Annexin V/Propidium iodide staining with the Apoptosis Detection Kit I (BD Pharmingen) in CD19-APC-cy7 antibody (BD Pharmingen) gated LPCs population.

Results

PhosFlow studies indicate both A-5 and A-14 inhibit Hck and BTK phosphorylation in BCWM.1 cells and BCWM.1 cells with genetic engineered expression of Hck wild type (-wt) and T338M gatekeeper mutant (-mu) with both 0.5 μM and 0.1 μM doses (shown by Table 6 and Table 7, respectively). In addition, the expression of Hck-wt or Hck-mu increased the resistance to the inhibition of both Hck and BTK phosphorylations by A-5 and A-14, with more resistance presented in Hck-mu expressing BCWM.1 cells. Both A-5 and A-14 induced significant apoptosis in WM patient primary LPCs compared with DMSO control, as shown in Table 8.

TABLE 6

| Relative MFI % (0.5 μM drugs) | p-BTK | | | | | | p-Hck | | | | | |
|---|---|---|---|---|---|---|---|---|---|---|---|---|
| | BCW M.1 | | _Hck-BCWM.1 wt | | _Hck-BCWM.1 mu | | BCW M.1 | | _Hck-BCWM.1 wt | | _Hck-BCWM.1 mu | |
| | 15 min | 90 min | 15 min | 90 min | 15 min | 90 min | 15 min | 90 min | 15 min | 90 min | 15 min | 90 min |
| DMSO | 100 | 100 | 100 | 100 | 100 | 100 | 100 | 100 | 100 | 100 | 100 | 100 |
| A-5 | 56.3 | 42.3 | 73.6 | 69.9 | 100.7 | 90.4 | 68.2 | 49 | 80.4 | 77.7 | 102.2 | 81.1 |
| A-14 | 51.5 | 27.4 | 65.6 | 29.7 | 112.1 | 83.9 | 59.3 | 35.6 | 68.6 | 41.5 | 89.7 | 52.3 |

TABLE 7

| Relative MFI % (0.1 µM drugs) | p-BTK | | | | | | p-Hck | | | | | |
|---|---|---|---|---|---|---|---|---|---|---|---|---|
| | BCW M.1 | | Hck-BCWM.1 wt | | Hck-BCWM.1 mu | | BCW M.1 | | Hck-BCWM.1 wt | | Hck-BCWM.1 mu | |
| | 15 min | 90 min | 15 min | 90 min | 15 min | 90 min | 15 min | 90 min | 15 min | 90 min | 15 min | 90 min |
| DMSO | 100 | 100 | 100 | 100 | 100 | 100 | 100 | 100 | 100 | 100 | 100 | 100 |
| A-5 | 68.1 | 52.7 | 82.1 | 78.3 | 70.9 | 70.4 | 76.3 | 50.5 | 76 | 80.6 | 95.3 | 69.6 |
| A-14 | 81.8 | 50.1 | 76.3 | 72 | 75.3 | 61.2 | 73.6 | 57.8 | 75.8 | 78.9 | 83.1 | 63.7 |

TABLE 8

| | Treatments | Dose (1.0 µM) | | Dose (0.5 µM) | | Dose (0.2 µM) | |
|---|---|---|---|---|---|---|---|
| | | Apoptosis (%) | Apoptosis Relative to DMSO | Apoptosis (%) | Apoptosis Relative to DMSO | Apoptosis (%) | Apoptosis Relative to DMSO |
| Patient 1 | Untreated | 40.9 | 114.30% | | | | |
| | DMSO | 39.2 | 100% | | | | |
| | A-5 | 57.7 | 147.20% | | | | |
| Patient 2 | N | 14.2 | 97.30% | | | | |
| | DMSO | 14.6 | 100% | | | | |
| | A-5 | 28.9 | 197.90% | | | | |
| Patient 3 | N | 14.529 | 95.49% | | | | |
| | DMSO | 15.216 | 100.00% | | | | |
| | A-5 | 29.48 | 193.70% | | | | |
| Patient 4 | N | 29.83 | 103.00% | | | | |
| | DMSO | 29.75 | 100.00% | | | | |
| | A-5 | 48.56 | 163.20% | | | | |
| Patient 5 | N | 18.69 | 110.70% | | | | |
| | DMSO | 16.89 | 100% | | | | |
| | A-5 | 30.5 | 180.60% | 23.25 | 137.70% | | |
| | A-14 | 46.86 | 277.40% | 39.24 | 232.30% | | |
| Patient 6 | N | 8.66 | 117.50% | | | | |
| | DMSO | 7.37 | 100% | | | | |
| | A-5 | 17.82 | 241.80% | | | | |
| | A-14 | 20.88 | 283.30% | | | | |
| Patient 7 | DMSO | 6.46 | 100.00% | | | | |
| | A-5 | 18.2 | 281.70% | 17.23 | 266.70% | | |
| | A-14 | 31.51 | 487.80% | 22.62 | 350.20% | | |
| Patient 8 | DMSO | 5.38 | 100.00% | | | | |
| | A-5 | 17.31 | 321.75% | 11.04 | 205.20% | | |
| | A-14 | 31.58 | 586.99% | 12.9 | 239.78% | | |
| Patient 9 | DMSO | 7.6 | 100.00% | | | | |
| | A-14 | 43.7 | 575.00% | | | 24.8 | 326.32% |
| Patient 10 | N | 17.6 | 113.50% | | | | |
| | DMSO | 15.5 | 100% | | | | |
| | A-5 | 28.7 | 185.20% | | | 21.5 | 138.70% |
| | A-14 | 52 | 335.50% | | | 27.9 | 180.00% |
| Patient 11 | N | 26.2 | 112.70% | | | | |
| | DMSO | 25.5 | 100% | | | | |
| | A-5 | 47 | 184.30% | | | 30.2 | 118.40% |
| | A-14 | 71.8 | 281.60% | | | 53.1 | 208.20% |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (A):

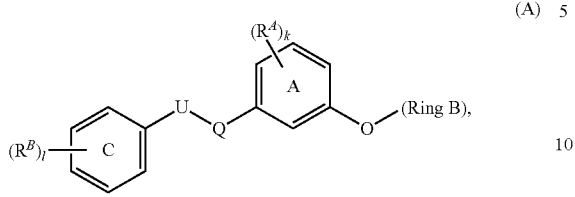

or a pharmaceutically acceptable salt, solvate, hydrate, tautomer, stereoisomer, or isotopically labeled derivative, thereof;

wherein:

each instance of $R^A$ is independently hydrogen, halogen, optionally substituted alkyl, optionally substituted carbocyclyl, $OR^{A1}$, $N(R^{A1})_2$, —CN, —C(=O)$R^{A1}$, —C(=O)O$R^{A1}$, —C(=O)N($R^{A1}$)$_2$, —NO$_2$, —N$R^{A1}$C(=O)$R^{A1}$, —N$R^{A1}$C(=O)O$R^{A1}$, —N$R^{A1}$S(=O)$_2$$R^{A1}$, —S(=O)$_2$$R^{A1}$, or —S(=O)$_2$N($R^{A1}$)$_2$;

each instance of $R^B$ is independently hydrogen, halogen, optionally substituted alkyl, optionally substituted carbocyclyl, optionally substituted heterocyclyl, optionally substituted aryl, optionally substituted heteroaryl, —O$R^{A1}$, —N($R^{A1}$)$_2$, —CN, —C(=O)$R^{A1}$, —C(=O)O$R^{A1}$, —C(=O)N($R^{A1}$)$_2$, —NO$_2$, —N$R^{A1}$C(=O)$R^{A1}$, —N$R^{A1}$C(=O)O$R^{A1}$, —N$R^{A1}$S(=O)$_2$$R^{A1}$, —S(=O)$_2$$R^{A1}$, or —S(=O)$_2$N($R^{A1}$)$_2$, provided that at least one instance of $R^B$ is optionally substituted heterocyclyl, optionally substituted —(CH$_2$)(heterocyclyl), optionally substituted —(CH$_2$)$_2$(heterocyclyl), or optionally substituted —(CH$_2$)$_3$(heterocyclyl);

each instance of $R^{A1}$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, or a sulfur protecting group when attached to a sulfur atom, or two $R^{A1}$ groups are joined to form an optionally substituted heterocyclic ring;

Ring B is of the formula:

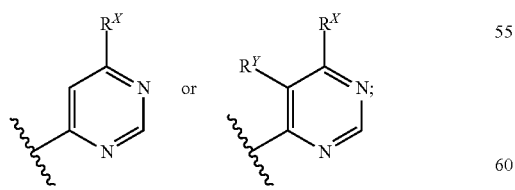

$R^Y$ is hydrogen, halogen, or substituted or unsubstituted C$_{1-6}$ alkyl;

$R^X$ is $R^D$, optionally substituted carbocyclyl, optionally substituted heterocyclyl, optionally substituted aryl, optionally substituted heteroaryl, or —N($R^{A1}$)($R^{Xa}$);

each instance of $R^{Xa}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)$R^{A1}$, —C(=O)O$R^{A1}$, —C(=O)N($R^{A1}$)$_2$, —S(=O)$R^{A1}$, —S(=O)N($R^{A1}$)$_2$, —S(=O)$_2$$R^{A1}$, —S(=O)$_2$O$R^{A1}$, —S(=O)$_2$N($R^{A1}$)$_2$, —N($R^{A1}$)$_2$, or a nitrogen protecting group;

k is 0, 1, 2, 3, or 4;

l is 1, 2, 3, 4, or 5;

-U-Q- is —N$R^A$(C=O)— or —(C=O)N$R^A$—; and $R^D$ is an electrophilic moiety of any one of Formulae (i-1) to (i-18):

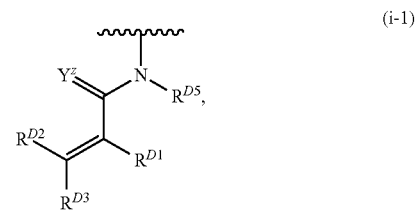

(i-1)

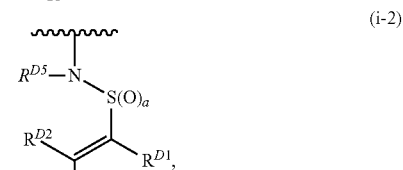

(i-2)

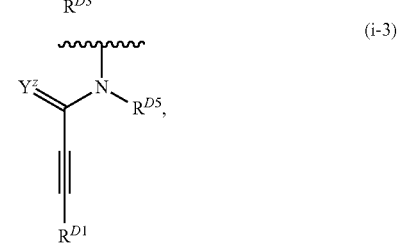

(i-3)

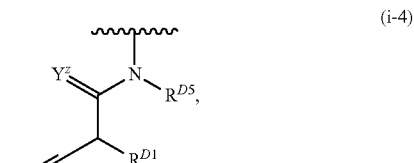

(i-4)

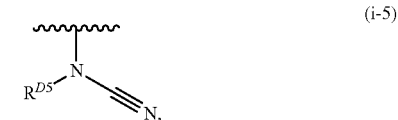

(i-5)

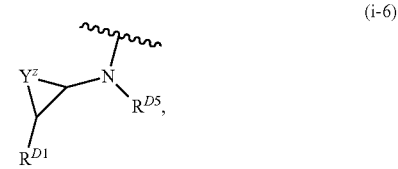

(i-6)

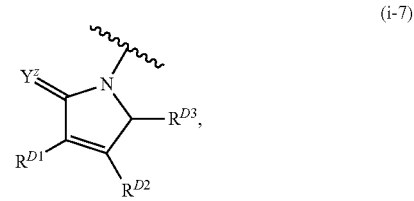

(i-7)

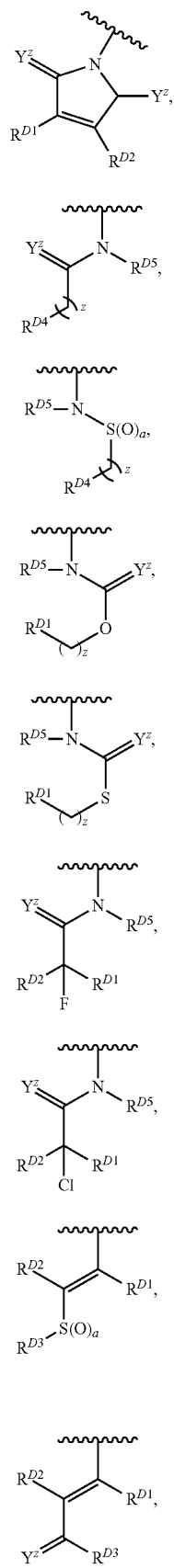

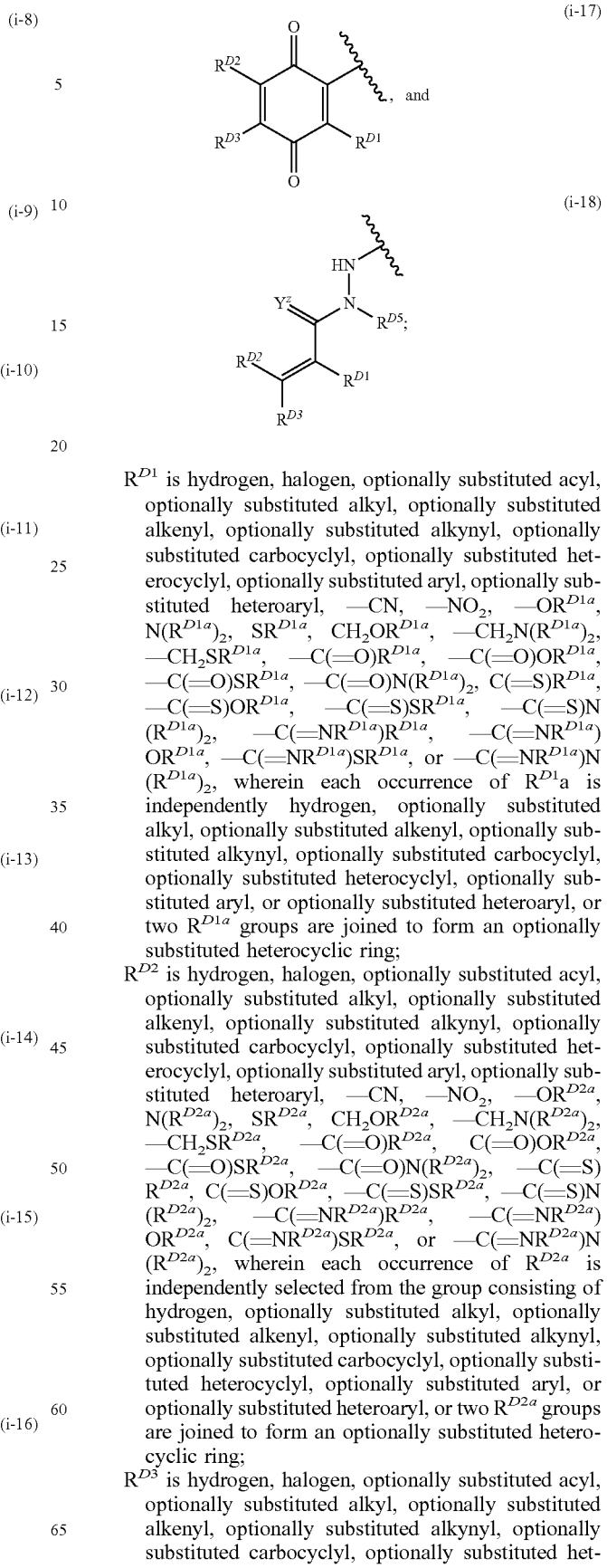

$R^{D1}$ is hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —NO$_2$, —OR$^{D1a}$, N(R$^{D1a}$)$_2$, SR$^{D1a}$, CH$_2$OR$^{D1a}$, —CH$_2$N(R$^{D1a}$)$_2$, —CH$_2$SR$^{D1a}$, —C(=O)R$^{D1a}$, —C(=O)OR$^{D1a}$, —C(=O)SR$^{D1a}$, —C(=O)N(R$^{D1a}$)$_2$, C(=S)R$^{D1a}$, —C(=S)OR$^{D1a}$, —C(=S)SR$^{D1a}$, —C(=S)N(R$^{D1a}$)$_2$, —C(=NR$^{D1a}$)R$^{D1a}$, —C(=NR$^{D1a}$)OR$^{D1a}$, —C(=NR$^{D1a}$)SR$^{D1a}$, or —C(=NR$^{D1a}$)N(R$^{D1a}$)$_2$, wherein each occurrence of R$^{D1a}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{D1a}$ groups are joined to form an optionally substituted heterocyclic ring;

$R^{D2}$ is hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —NO$_2$, —OR$^{D2a}$, N(R$^{D2a}$)$_2$, SR$^{D2a}$, CH$_2$OR$^{D2a}$, —CH$_2$N(R$^{D2a}$)$_2$, —CH$_2$SR$^{D2a}$, —C(=O)R$^{D2a}$, C(=O)OR$^{D2a}$, —C(=O)SR$^{D2a}$, —C(=O)N(R$^{D2a}$)$_2$, —C(=S)R$^{D2a}$, C(=S)OR$^{D2a}$, —C(=S)SR$^{D2a}$, —C(=S)N(R$^{D2a}$)$_2$, —C(=NR$^{D2a}$)R$^{D2a}$, —C(=NR$^{D2a}$)OR$^{D2a}$, C(=NR$^{D2a}$)SR$^{D2a}$, or —C(=NR$^{D2a}$)N(R$^{D2a}$)$_2$, wherein each occurrence of R$^{D2a}$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{D2a}$ groups are joined to form an optionally substituted heterocyclic ring;

$R^{D3}$ is hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —NO₂, —OR$^{D3a}$, —N(R$^{D3a}$)₂, —SR$^{D3a}$, —CH₂OR$^{D3a}$, —CH₂N(R$^{D3a}$)₂, —CH₂SR$^{D3a}$, —C(=O)R$^{D3a}$, —C(=O)OR$^{D3a}$, —C(=O)SR$^{D3a}$, —C(=O)N(R$^{D3a}$)₂, —C(=S)R$^{D3a}$, —C(=S)OR$^{D3a}$, —C(=S)SR$^{D3a}$, —C(=S)N(R$^{D3a}$)₂, —C(=NR$^{D3a}$)R$^{D3a}$, —C(=NR$^{D3a}$)OR$^{D3a}$, —C(=NR$^{D3a}$)SR$^{D3a}$, ands —C(=NR$^{D3}$a)N(R$^{D3}$a)₂, wherein each occurrence of R$^{D3}$a is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{D3a}$ groups are joined to form an optionally substituted heterocyclic ring;

optionally R$^{D1}$ and R$^{D3}$, or R$^{D2}$ and R$^{D3}$, or R$^{D1}$ and R$^{D2}$ are joined to form an optionally substituted carbocyclic or optionally substituted heterocyclic ring;

R$^{D4}$ is a leaving group;

R$^{D5}$ is hydrogen, C$_{1-6}$ alkyl, or a nitrogen protecting group;

Y$^Z$ is —O—, —S—, or —NR$^{D6}$—, wherein R$^{D6}$ is hydrogen, C$_{1-6}$ alkyl, or a nitrogen protecting group;

a is 1 or 2; and z is 0, 1, 2, 3, 4, 5, or 6;

wherein, unless otherwise provided:
each instance of the alkyl is independently C$_{1-6}$ alkyl;
each instance of the alkenyl is independently C$_{2-6}$ alkenyl;
each instance of the alkynyl is independently C$_{2-6}$ alkynyl;
each instance of the carbocyclyl and carbocyclic ring is independently 3- to 10-membered, monocyclic or bicyclic carbocyclyl;
each instance of the heterocyclyl and heterocyclic ring is independently 5- to 10-membered, monocyclic or bicyclic heterocyclyl;
each instance of the aryl is independently 6- or 10-membered, monocyclic or bicyclic aryl; and
each instance of the heteroaryl is independently 5- to 10-membered, monocyclic or bicyclic heteroaryl.

2. The compound of claim 1, or a pharmaceutically acceptable salt, solvate, hydrate, tautomer, stereoisomer, or isotopically labeled derivative thereof, wherein -U-Q- is

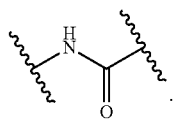 [SMILES: *NC(*)=O]

3. The compound of claim 1, wherein the compound is of Formula (A1):

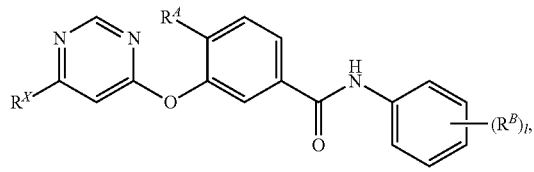

(A1)

or a pharmaceutically acceptable salt, solvate, hydrate, tautomer, stereoisomer, or isotopically labeled derivative thereof.

4. The compound of claim 3, wherein the compound is of Formula (A1-a), (A1-b), (A1-c), or (A1-d):

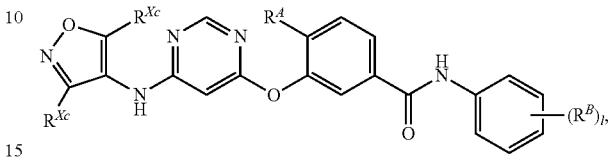

(A1-a)

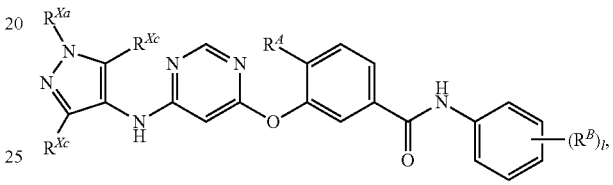

(A1-b)

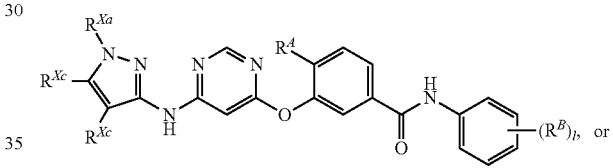

(A1-c)

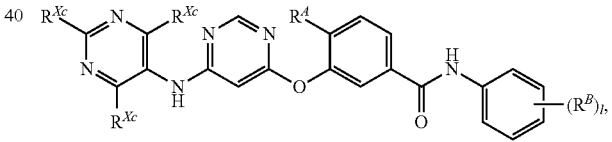

(A1-d)

or a pharmaceutically acceptable salt, solvate, hydrate, tautomer, stereoisomer, or isotopically labeled derivative thereof, wherein:
each instance of R$^{Xc}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{A1}$, —N(R$^{A1}$)₂, —SR$^{A1}$, —CN, —C(=O)R$^{A1}$, —C(=O)OR$^{A1}$, —C(=O)N(R$^{A1}$)₂, —NO₂, —N₃, —NR$^{A1}$C(=O)R$^{A1}$, —NR$^{A1}$C(=O)OR$^{A1}$, —NR$^{A1}$C(=O)N(R$^{A1}$)₂, —NR$^{A1}$S(=O)₂R$^{A1}$, —NR$^{A1}$S(=O)R$^{A1}$, —OC(=O)R$^{A1}$, —OC(=O)OR$^{A1}$, —OC(=O)N(R$^{A1}$)₂, —S(=O)R$^{A1}$, —S(=O)N(R$^{A1}$)₂, —S(=O)₂R$^{A1}$, or —S(=O)₂N(R$^{A1}$)₂.

5. The compound of claim 1, wherein the compound is of Formula (A3):

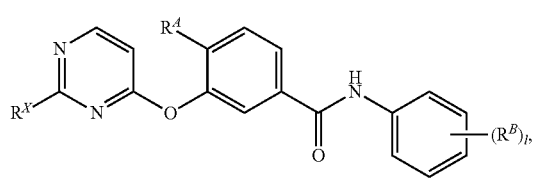

(A2)

or a pharmaceutically acceptable salt, solvate, hydrate, tautomer, stereoisomer, or isotopically labeled derivative thereof.

6. The compound of claim 5, or a pharmaceutically acceptable salt, solvate, hydrate, tautomer, stereoisomer, or isotopically labeled derivative thereof, wherein $R^D$ is selected from the group consisting of:

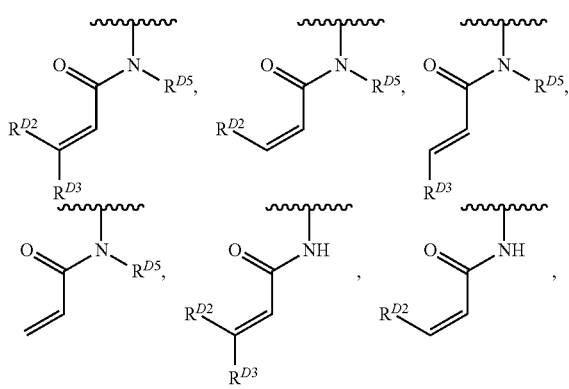

7. The compound of claim 1, or a pharmaceutically acceptable salt, solvate, hydrate, tautomer, stereoisomer, or isotopically labeled derivative thereof, wherein at least one instance of $R^A$ is substituted or unsubstituted, $C_{1-6}$ alkyl.

8. The compound of claim 1, or a pharmaceutically acceptable salt, solvate, hydrate, tautomer, stereoisomer, or isotopically labeled derivative thereof, wherein 1 is 1 or 2.

9. The compound of claim 1, or a pharmaceutically acceptable salt, solvate, hydrate, tautomer, stereoisomer, or isotopically labeled derivative thereof, wherein at least one instance of $R^B$ is substituted or unsubstituted, $C_{1-6}$ alkyl.

10. The compound of claim 1, or a pharmaceutically acceptable salt, solvate, hydrate, tautomer, stereoisomer, or isotopically labeled derivative thereof, wherein at least one instance of $R^B$ is substituted or unsubstituted —CH$_2$-(piperazinyl).

11. The compound of claim 1, or a pharmaceutically acceptable salt, solvate, hydrate, tautomer, stereoisomer, or isotopically labeled derivative thereof, wherein at least one instance of $R^B$ is $C_{1-6}$ haloalkyl.

12. The compound of claim 1, wherein the compound is of the formula:

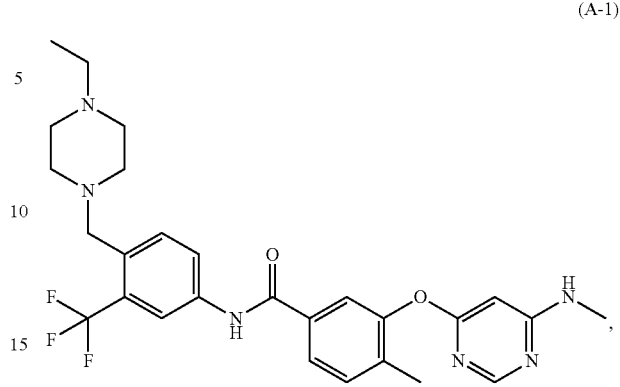

(A-5) 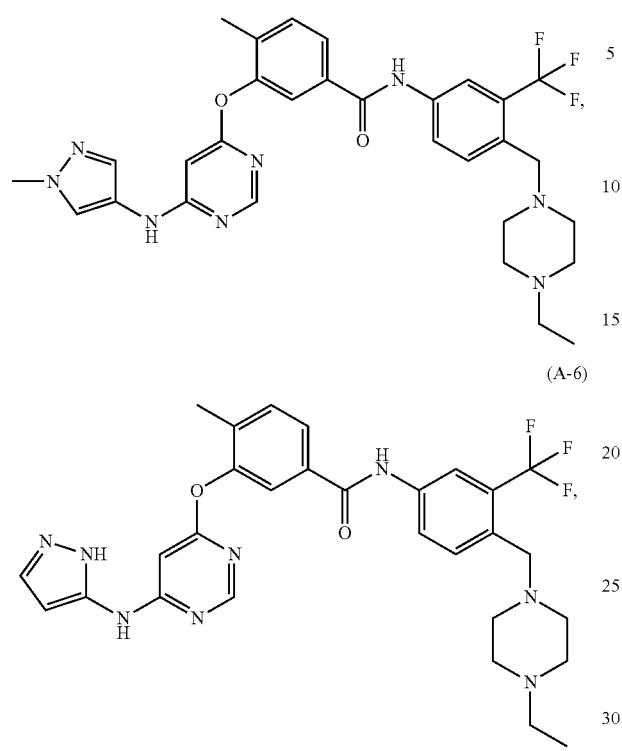
(A-6)
(A-7)
(A-8)
(A-9) 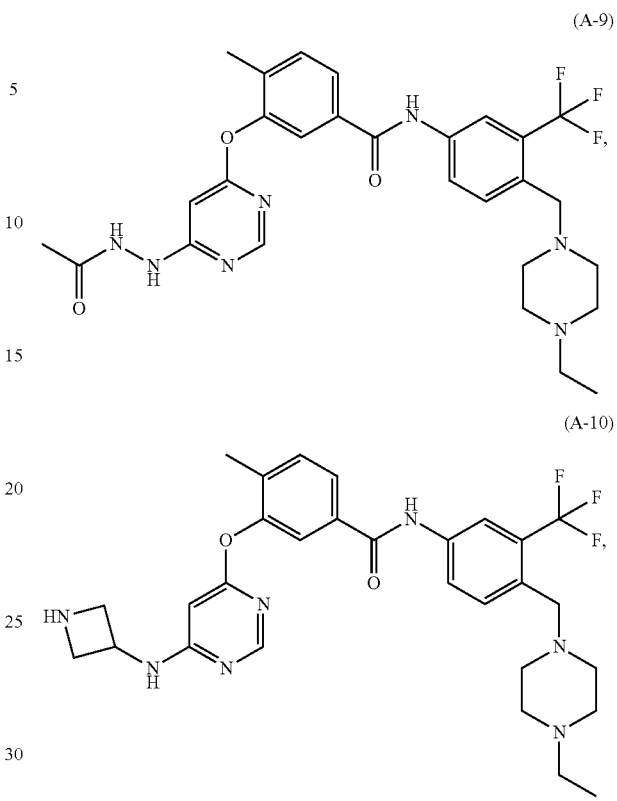
(A-10)
(A-11)
(A-12)

-continued

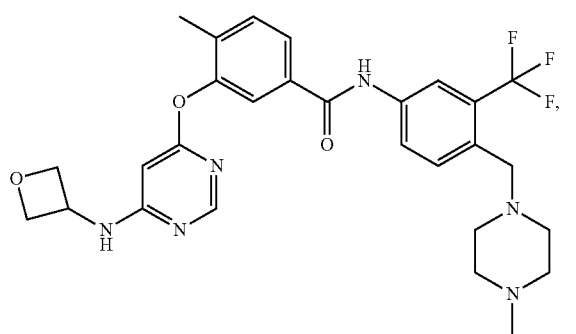
(A-13)

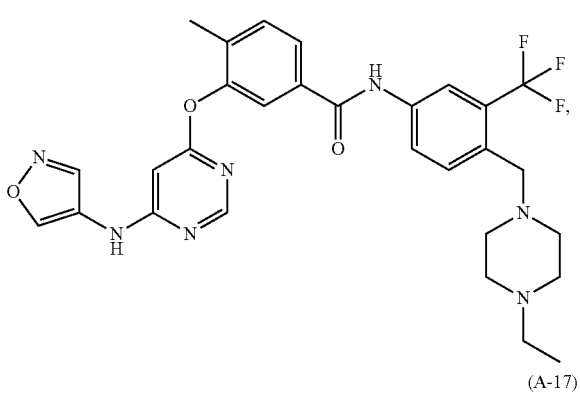
(A-16)

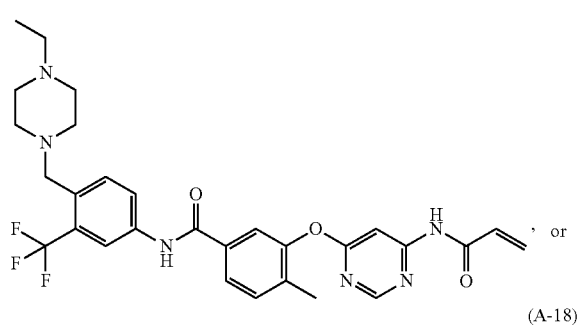
(A-17)

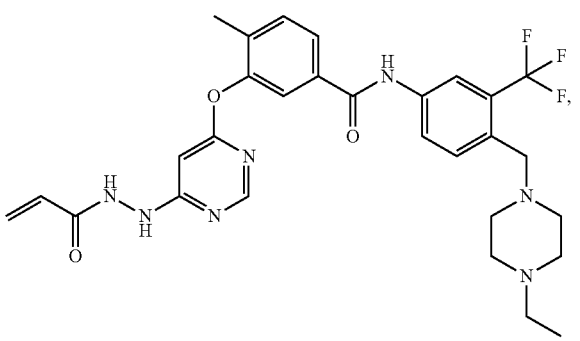
(A-18)

or a pharmaceutically acceptable salt, solvate, hydrate, tautomer, stereoisomer, or isotopically labeled derivative thereof.

13. A pharmaceutical composition comprising a compound of claim 1, or a pharmaceutically acceptable salt, solvate, hydrate, tautomer, stereoisomer, or isotopically labeled derivative thereof, and optionally a pharmaceutically acceptable excipient.

14. The compound of claim 1, or a pharmaceutically acceptable salt, solvate, hydrate, tautomer, stereoisomer, or isotopically labeled derivative thereof, wherein -U-Q-is

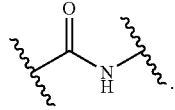 [SMILES: *NC(*)=O]

15. The compound of claim 1, or a pharmaceutically acceptable salt, solvate, hydrate, tautomer, stereoisomer, or isotopically labeled derivative thereof, wherein $R^X$ is $N(R^{A1})(R^{Xa})$.

16. The compound of claim 15, or a pharmaceutically acceptable salt, solvate, hydrate, tautomer, stereoisomer, or isotopically labeled derivative thereof, wherein $R^{A1}$ is hydrogen.

17. The compound of claim 16, or a pharmaceutically acceptable salt, solvate, hydrate, tautomer, stereoisomer, or isotopically labeled derivative thereof, wherein $R^{Xa}$ is optionally substituted alkyl or optionally substituted acyl.

18. The compound of claim 16, or a pharmaceutically acceptable salt, solvate, hydrate, tautomer, stereoisomer, or isotopically labeled derivative thereof, wherein $R^{Xa}$ is optionally substituted heterocyclyl or optionally substituted heteroaryl.

19. The compound of claim 16, or a pharmaceutically acceptable salt, solvate, hydrate, tautomer, stereoisomer, or isotopically labeled derivative thereof, wherein $R^{Xa}$ is $-N(R^{A1})_2$.

20. The compound of claim 1, or a pharmaceutically acceptable salt, solvate, hydrate, tautomer, stereoisomer, or isotopically labeled derivative thereof, wherein

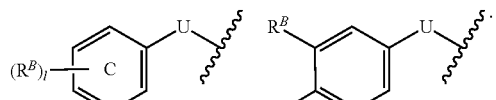

is of the formula:

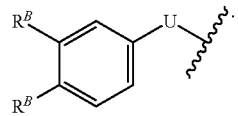

21. The compound of claim 1, or a pharmaceutically acceptable salt, solvate, hydrate, tautomer, stereoisomer, or isotopically labeled derivative thereof, provided that at least one instance of $R^B$ is optionally substituted —(CH$_2$)(heterocyclyl).

22. The compound of claim 1, or a pharmaceutically acceptable salt, solvate, hydrate, tautomer, stereoisomer, or isotopically labeled derivative thereof, wherein

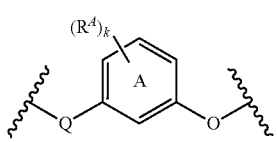

is of the formula:
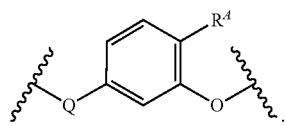
23. The compound of claim 1, wherein the compound is of the formula:
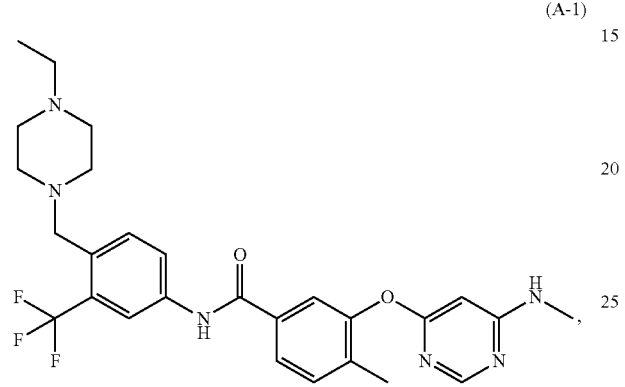
(A-1)
or a pharmaceutically acceptable salt thereof.
* * * * *

UNITED STATES PATENT AND TRADEMARK OFFICE
CERTIFICATE OF CORRECTION

PATENT NO.        : 9,856,223 B2                                     Page 1 of 2
APPLICATION NO.   : 15/104132
DATED             : January 2, 2018
INVENTOR(S)       : Steven P. Treon et al.

It is certified that error appears in the above-identified patent and that said Letters Patent is hereby corrected as shown below:

In the Claims

In Claim 1, at Column 377, Lines 15-16, the phrase:
"...or isotopically labeled derivative, thereof;"
Should be replaced with the phrase:
--or isotopically labeled derivative thereof;--.

In Claim 1, at Column 379, Lines 1-10, the formula:

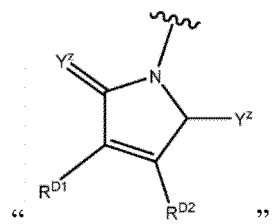
"                "

Should be replaced with the formula:

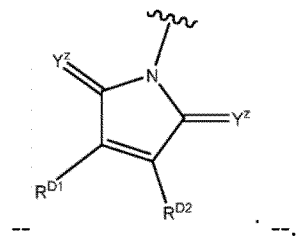
--                --.

In Claim 1, at Column 380, Line 34, the formula:
"$R^{D1}a$"
Should be replaced with the formula:
--$R^{D1a}$--.

Signed and Sealed this
Thirteenth Day of October, 2020

Andrei Iancu
*Director of the United States Patent and Trademark Office*

CERTIFICATE OF CORRECTION (continued)
U.S. Pat. No. 9,856,223 B2

In Claim 1, at Column 381, Lines 7-9, the phrase:
"ands $-C(=NR^{D3a})N(R^{D3a})_2$, wherein each occurrence of $R^{D3}a$ is"
Should be replaced with the phrase:
--or $-C(=NR^{D3a})N(R^{D3a})_2$, wherein each occurrence of $R^{D3a}$ is--.

In Claim 5, at Column 383, Lines 1-10, formula:

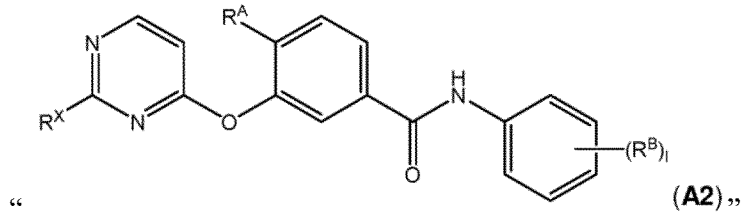
"                                                                 (A2)"

Should be replaced with the formula:

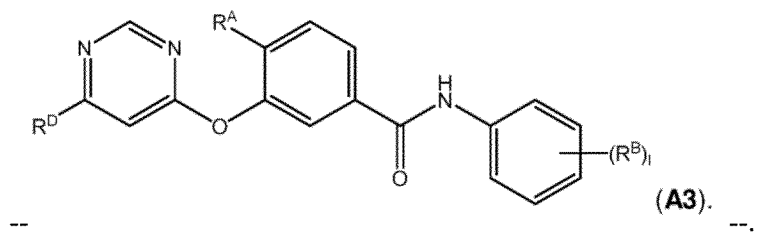
--                                                                (A3).--

In Claim 15, at Column 388, Lines 14-15, the phrase:
"$R^X$ is $N(R^{A1})(R^{Xa})$"
Should be replaced with the phrase:
--$R^X$ is $-N(R^{A1})(R^{Xa})$--.

In Claim 20, at Column 388, Lines 35-40, the formula:

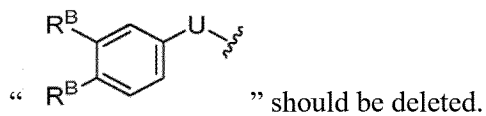
"                        " should be deleted.

```
                           SEQUENCE LISTING

<160> NUMBER OF SEQ ID NOS: 411

<210> SEQ ID NO 1
<211> LENGTH: 18
<212> TYPE: PRT
<213> ORGANISM: Homo sapiens

<400> SEQUENCE: 1

Leu Met Thr Gly Asp Thr Tyr Thr Ala His Ala Gly Ala Lys Phe Pro
1               5                   10                  15

Ile Lys

<210> SEQ ID NO 2
<211> LENGTH: 25
<212> TYPE: PRT
<213> ORGANISM: Homo sapiens

<400> SEQUENCE: 2

Thr Val Ser Val Ala Val Lys Cys Leu Lys Pro Asp Val Leu Ser Gln
1               5                   10                  15

Pro Glu Ala Met Asp Asp Phe Ile Arg
            20                  25

<210> SEQ ID NO 3
<211> LENGTH: 13
<212> TYPE: PRT
<213> ORGANISM: Homo sapiens

<400> SEQUENCE: 3

Ala Thr Val Phe Leu Asn Pro Ala Ala Cys Lys Gly Lys
1               5                   10

<210> SEQ ID NO 4
<211> LENGTH: 16
<212> TYPE: PRT
<213> ORGANISM: Homo sapiens

<400> SEQUENCE: 4

Asp Leu Lys Pro Glu Asn Val Leu Leu Asp Ala His Met Asn Ala Lys
1               5                   10                  15

<210> SEQ ID NO 5
<211> LENGTH: 16
<212> TYPE: PRT
<213> ORGANISM: Homo sapiens
```

```
<400> SEQUENCE: 5

Asp Leu Lys Ser Asn Asn Ile Phe Leu His Glu Gly Leu Thr Val Lys
1               5                   10                  15

<210> SEQ ID NO 6
<211> LENGTH: 9
<212> TYPE: PRT
<213> ORGANISM: Homo sapiens

<400> SEQUENCE: 6

Phe Tyr Ile Met Met Cys Lys Pro Lys
1               5

<210> SEQ ID NO 7
<211> LENGTH: 10
<212> TYPE: PRT
<213> ORGANISM: Homo sapiens

<400> SEQUENCE: 7

Phe Ile Leu Ala Leu Lys Val Leu Phe Lys
1               5                   10

<210> SEQ ID NO 8
<211> LENGTH: 12
<212> TYPE: PRT
<213> ORGANISM: Homo sapiens

<400> SEQUENCE: 8

Ser His Phe Ile Val Ala Leu Lys Val Leu Phe Lys
1               5                   10

<210> SEQ ID NO 9
<211> LENGTH: 16
<212> TYPE: PRT
<213> ORGANISM: Homo sapiens

<400> SEQUENCE: 9

Asp Leu Lys Pro Ala Asn Ile Leu Leu Asp Glu His Gly His Val Arg
1               5                   10                  15

<210> SEQ ID NO 10
<211> LENGTH: 16
<212> TYPE: PRT
<213> ORGANISM: Homo sapiens

<400> SEQUENCE: 10

Asp Leu Lys Ser Asn Asn Ile Phe Leu His Glu Asp Leu Thr Val Lys
1               5                   10                  15

<210> SEQ ID NO 11
<211> LENGTH: 18
<212> TYPE: PRT
<213> ORGANISM: Homo sapiens

<400> SEQUENCE: 11

Tyr Val Leu Asp Asp Glu Tyr Thr Ser Ser Val Gly Ser Lys Phe Pro
1               5                   10                  15

Val Arg

<210> SEQ ID NO 12
<211> LENGTH: 9
<212> TYPE: PRT
<213> ORGANISM: Homo sapiens
```

```
<400> SEQUENCE: 12

Leu Val Ala Ile Lys Cys Ile Ala Lys
1               5

<210> SEQ ID NO 13
<211> LENGTH: 9
<212> TYPE: PRT
<213> ORGANISM: Homo sapiens

<400> SEQUENCE: 13

Leu Phe Ala Val Lys Cys Ile Pro Lys
1               5

<210> SEQ ID NO 14
<211> LENGTH: 16
<212> TYPE: PRT
<213> ORGANISM: Homo sapiens

<400> SEQUENCE: 14

Ile Pro Thr Gly Gln Glu Tyr Ala Ala Lys Ile Ile Asn Thr Lys Lys
1               5                   10                  15

<210> SEQ ID NO 15
<211> LENGTH: 14
<212> TYPE: PRT
<213> ORGANISM: Homo sapiens

<400> SEQUENCE: 15

Thr Ser Thr Gln Glu Tyr Ala Ala Lys Ile Ile Asn Thr Lys
1               5                   10

<210> SEQ ID NO 16
<211> LENGTH: 19
<212> TYPE: PRT
<213> ORGANISM: Homo sapiens

<400> SEQUENCE: 16

Asp Leu Lys Pro Glu Asn Leu Leu Tyr Ala Thr Pro Ala Pro Asp Ala
1               5                   10                  15

Pro Leu Lys

<210> SEQ ID NO 17
<211> LENGTH: 16
<212> TYPE: PRT
<213> ORGANISM: Homo sapiens

<400> SEQUENCE: 17

Asp Ile Lys Pro Ser Asn Leu Leu Val Gly Glu Asp Gly His Ile Lys
1               5                   10                  15

<210> SEQ ID NO 18
<211> LENGTH: 15
<212> TYPE: PRT
<213> ORGANISM: Homo sapiens

<400> SEQUENCE: 18

Glu Thr Gly Gln Gln Phe Ala Val Lys Ile Val Asp Val Ala Lys
1               5                   10                  15

<210> SEQ ID NO 19
<211> LENGTH: 16
<212> TYPE: PRT
<213> ORGANISM: Homo sapiens
```

<400> SEQUENCE: 19

Asp Leu Lys Pro Gln Asn Leu Leu Ile Asp Asp Lys Gly Thr Ile Lys
1               5                   10                  15

<210> SEQ ID NO 20
<211> LENGTH: 16
<212> TYPE: PRT
<213> ORGANISM: Homo sapiens

<400> SEQUENCE: 20

Asp Leu Lys Pro Ala Asn Ile Leu Val Met Gly Glu Gly Pro Glu Arg
1               5                   10                  15

<210> SEQ ID NO 21
<211> LENGTH: 16
<212> TYPE: PRT
<213> ORGANISM: Homo sapiens

<400> SEQUENCE: 21

Asp Leu Lys Pro Gln Asn Leu Leu Ile Asn Thr Glu Gly Ala Ile Lys
1               5                   10                  15

<210> SEQ ID NO 22
<211> LENGTH: 16
<212> TYPE: PRT
<213> ORGANISM: Homo sapiens

<400> SEQUENCE: 22

Asp Leu Lys Pro Glu Asn Ile Leu Val Thr Ser Gly Gly Thr Val Lys
1               5                   10                  15

<210> SEQ ID NO 23
<211> LENGTH: 11
<212> TYPE: PRT
<213> ORGANISM: Homo sapiens

<400> SEQUENCE: 23

Asp Leu Lys Pro Gln Asn Leu Leu Ile Asn Arg
1               5                   10

<210> SEQ ID NO 24
<211> LENGTH: 16
<212> TYPE: PRT
<213> ORGANISM: Homo sapiens

<400> SEQUENCE: 24

Asp Leu Lys Pro Gln Asn Ile Leu Val Thr Ser Ser Gly Gln Ile Lys
1               5                   10                  15

<210> SEQ ID NO 25
<211> LENGTH: 16
<212> TYPE: PRT
<213> ORGANISM: Homo sapiens

<400> SEQUENCE: 25

Asp Leu Lys Pro Asn Asn Leu Leu Leu Asp Glu Asn Gly Val Leu Lys
1               5                   10                  15

<210> SEQ ID NO 26
<211> LENGTH: 11
<212> TYPE: PRT
<213> ORGANISM: Homo sapiens

<400> SEQUENCE: 26

Asp Met Lys Ala Ala Asn Val Leu Ile Thr Arg
1               5                   10

<210> SEQ ID NO 27
<211> LENGTH: 12
<212> TYPE: PRT
<213> ORGANISM: Homo sapiens

<400> SEQUENCE: 27

Asp Ile Lys Pro Glu Asn Leu Leu Leu Asp Glu Arg
1               5                   10

<210> SEQ ID NO 28
<211> LENGTH: 19
<212> TYPE: PRT
<213> ORGANISM: Homo sapiens

<400> SEQUENCE: 28

Asp Leu Lys Pro Glu Asn Val Leu Leu Ser Ser Gln Glu Glu Asp Cys
1               5                   10                  15

Leu Ile Lys

<210> SEQ ID NO 29
<211> LENGTH: 13
<212> TYPE: PRT
<213> ORGANISM: Homo sapiens

<400> SEQUENCE: 29

Asp Ile Lys Pro Asp Asn Phe Leu Met Gly Ile Gly Arg
1               5                   10

<210> SEQ ID NO 30
<211> LENGTH: 15
<212> TYPE: PRT
<213> ORGANISM: Homo sapiens

<400> SEQUENCE: 30

Asp Val Lys Pro Glu Asn Phe Leu Val Gly Arg Pro Gly Thr Lys
1               5                   10                  15

<210> SEQ ID NO 31
<211> LENGTH: 14
<212> TYPE: PRT
<213> ORGANISM: Homo sapiens

<400> SEQUENCE: 31

Asp Val Lys Pro His Asn Val Met Ile Asp His Gln Gln Lys
1               5                   10

<210> SEQ ID NO 32
<211> LENGTH: 23
<212> TYPE: PRT
<213> ORGANISM: Homo sapiens

<400> SEQUENCE: 32

Tyr Glu Ile Val Gly Asn Leu Gly Glu Gly Thr Phe Gly Lys Val Val
1               5                   10                  15

Glu Cys Leu Asp His Ala Arg
            20

<210> SEQ ID NO 33
<211> LENGTH: 22
<212> TYPE: PRT
<213> ORGANISM: Homo sapiens

```
<400> SEQUENCE: 33

Val Ser Asp Phe Gly Leu Thr Lys Glu Ala Ser Ser Thr Gln Asp Thr
1               5                   10                  15

Gly Lys Leu Pro Val Lys
            20

<210> SEQ ID NO 34
<211> LENGTH: 21
<212> TYPE: PRT
<213> ORGANISM: Homo sapiens

<400> SEQUENCE: 34

Ile Asp Pro Val Pro Asn Thr His Pro Leu Leu Val Phe Val Asn Pro
1               5                   10                  15

Lys Ser Gly Gly Lys
            20

<210> SEQ ID NO 35
<211> LENGTH: 25
<212> TYPE: PRT
<213> ORGANISM: Homo sapiens

<400> SEQUENCE: 35

Ala Thr Phe Ser Phe Cys Val Ser Pro Leu Leu Val Phe Val Asn Ser
1               5                   10                  15

Lys Ser Gly Asp Asn Gln Gly Val Lys
            20                  25

<210> SEQ ID NO 36
<211> LENGTH: 36
<212> TYPE: PRT
<213> ORGANISM: Homo sapiens

<400> SEQUENCE: 36

Gly Arg Leu Leu Thr Ala Leu Val Leu Pro Asp Leu Leu His Ala Lys
1               5                   10                  15

Leu Pro Pro Asp Ser Cys Pro Leu Leu Val Phe Val Asn Pro Lys Ser
            20                  25                  30

Gly Gly Leu Lys
        35

<210> SEQ ID NO 37
<211> LENGTH: 14
<212> TYPE: PRT
<213> ORGANISM: Homo sapiens

<400> SEQUENCE: 37

Lys Gly Gly Ser Trp Ile Gln Glu Ile Asn Val Ala Glu Lys
1               5                   10

<210> SEQ ID NO 38
<211> LENGTH: 13
<212> TYPE: PRT
<213> ORGANISM: Homo sapiens

<400> SEQUENCE: 38

Glu His Pro Phe Leu Val Lys Gly Gly Glu Asp Leu Arg
1               5                   10

<210> SEQ ID NO 39
<211> LENGTH: 12
```

```
<212> TYPE: PRT
<213> ORGANISM: Homo sapiens

<400> SEQUENCE: 39

Tyr Ile Lys Tyr Asn Ser Asn Ser Gly Phe Val Arg
1               5                   10

<210> SEQ ID NO 40
<211> LENGTH: 22
<212> TYPE: PRT
<213> ORGANISM: Homo sapiens

<400> SEQUENCE: 40

Tyr Leu Gln Asp Asp Thr Ser Asp Pro Thr Tyr Thr Ser Ser Leu Gly
1               5                   10                  15

Gly Lys Ile Pro Val Arg
            20

<210> SEQ ID NO 41
<211> LENGTH: 22
<212> TYPE: PRT
<213> ORGANISM: Homo sapiens

<400> SEQUENCE: 41

Phe Leu Glu Asp Asp Thr Ser Asp Pro Thr Tyr Thr Ser Ala Leu Gly
1               5                   10                  15

Gly Lys Ile Pro Ile Arg
            20

<210> SEQ ID NO 42
<211> LENGTH: 16
<212> TYPE: PRT
<213> ORGANISM: Homo sapiens

<400> SEQUENCE: 42

Asp Leu Lys Pro Ser Asn Leu Leu Ile Asn Thr Thr Cys Asp Leu Lys
1               5                   10                  15

<210> SEQ ID NO 43
<211> LENGTH: 16
<212> TYPE: PRT
<213> ORGANISM: Homo sapiens

<400> SEQUENCE: 43

Asp Leu Lys Pro Ser Asn Leu Leu Leu Asn Thr Thr Cys Asp Leu Lys
1               5                   10                  15

<210> SEQ ID NO 44
<211> LENGTH: 16
<212> TYPE: PRT
<213> ORGANISM: Homo sapiens

<400> SEQUENCE: 44

Asp Leu Lys Pro Ser Asn Leu Leu Val Asn Glu Asn Cys Glu Leu Lys
1               5                   10                  15

<210> SEQ ID NO 45
<211> LENGTH: 17
<212> TYPE: PRT
<213> ORGANISM: Homo sapiens

<400> SEQUENCE: 45

Thr Ser Val Ala Val Lys Thr Cys Lys Glu Asp Leu Pro Gln Glu Leu
1               5                   10                  15
```

Lys

<210> SEQ ID NO 46
<211> LENGTH: 14
<212> TYPE: PRT
<213> ORGANISM: Homo sapiens

<400> SEQUENCE: 46

Leu Arg Ala Asp Asn Thr Leu Val Ala Val Lys Ser Cys Arg
1               5                   10

<210> SEQ ID NO 47
<211> LENGTH: 18
<212> TYPE: PRT
<213> ORGANISM: Homo sapiens

<400> SEQUENCE: 47

Leu Ile Lys Asp Asp Glu Tyr Asn Pro Cys Gln Gly Ser Lys Phe Pro
1               5                   10                  15

Ile Lys

<210> SEQ ID NO 48
<211> LENGTH: 18
<212> TYPE: PRT
<213> ORGANISM: Homo sapiens

<400> SEQUENCE: 48

Ile Gln Ser Ile Ala Pro Ser Leu Gln Val Ile Thr Ser Lys Gln Arg
1               5                   10                  15

Pro Arg

<210> SEQ ID NO 49
<211> LENGTH: 8
<212> TYPE: PRT
<213> ORGANISM: Homo sapiens

<400> SEQUENCE: 49

His Glu Ile Lys Leu Pro Val Lys
1               5

<210> SEQ ID NO 50
<211> LENGTH: 19
<212> TYPE: PRT
<213> ORGANISM: Homo sapiens

<400> SEQUENCE: 50

Gln Gly Ala Lys Phe Pro Ile Lys Trp Thr Ala Pro Glu Ala Ala Leu
1               5                   10                  15

Tyr Gly Arg

<210> SEQ ID NO 51
<211> LENGTH: 16
<212> TYPE: PRT
<213> ORGANISM: Homo sapiens

<400> SEQUENCE: 51

Asp Ile Lys Gly Ala Asn Leu Leu Leu Thr Leu Gln Gly Asp Val Lys
1               5                   10                  15

<210> SEQ ID NO 52
<211> LENGTH: 16
<212> TYPE: PRT

```
<213> ORGANISM: Homo sapiens

<400> SEQUENCE: 52

Asp Leu Lys Pro Val Asn Ile Phe Leu Asp Ser Asp His Val Lys
1               5                   10                  15

<210> SEQ ID NO 53
<211> LENGTH: 17
<212> TYPE: PRT
<213> ORGANISM: Homo sapiens

<400> SEQUENCE: 53

Asp Ile Lys Pro Gln Asn Leu Leu Val Asp Pro Asp Thr Ala Val Leu
1               5                   10                  15

Lys

<210> SEQ ID NO 54
<211> LENGTH: 17
<212> TYPE: PRT
<213> ORGANISM: Homo sapiens

<400> SEQUENCE: 54

Asp Ile Lys Pro Gln Asn Leu Leu Leu Asp Pro Asp Thr Ala Val Leu
1               5                   10                  15

Lys

<210> SEQ ID NO 55
<211> LENGTH: 16
<212> TYPE: PRT
<213> ORGANISM: Homo sapiens

<400> SEQUENCE: 55

Asp Ile Lys Gly Ala Asn Ile Leu Ile Asn Asp Ala Gly Glu Val Arg
1               5                   10                  15

<210> SEQ ID NO 56
<211> LENGTH: 15
<212> TYPE: PRT
<213> ORGANISM: Homo sapiens

<400> SEQUENCE: 56

Asp Leu Lys Pro Glu Asn Ile Val Leu Gln Asp Val Gly Gly Lys
1               5                   10                  15

<210> SEQ ID NO 57
<211> LENGTH: 15
<212> TYPE: PRT
<213> ORGANISM: Homo sapiens

<400> SEQUENCE: 57

Asp Leu Lys Pro Glu Asn Ile Val Leu Gln Gln Gly Glu Gln Arg
1               5                   10                  15

<210> SEQ ID NO 58
<211> LENGTH: 19
<212> TYPE: PRT
<213> ORGANISM: Homo sapiens

<400> SEQUENCE: 58

Ser Gly Glu Leu Val Ala Val Lys Val Phe Asn Thr Thr Ser Tyr Leu
1               5                   10                  15

Arg Pro Arg
```

```
<210> SEQ ID NO 59
<211> LENGTH: 12
<212> TYPE: PRT
<213> ORGANISM: Homo sapiens

<400> SEQUENCE: 59

Trp Gln Gly Asn Asp Ile Val Val Lys Val Leu Lys
1               5                   10

<210> SEQ ID NO 60
<211> LENGTH: 27
<212> TYPE: PRT
<213> ORGANISM: Homo sapiens

<400> SEQUENCE: 60

Ala Ile Gln Phe Leu His Gln Asp Ser Pro Ser Leu Ile His Gly Asp
1               5                   10                  15

Ile Lys Ser Ser Asn Val Leu Leu Asp Glu Arg
            20                  25

<210> SEQ ID NO 61
<211> LENGTH: 16
<212> TYPE: PRT
<213> ORGANISM: Homo sapiens

<400> SEQUENCE: 61

Asp Ile Lys Ser Ala Asn Ile Leu Leu Asp Glu Ala Phe Thr Ala Lys
1               5                   10                  15

<210> SEQ ID NO 62
<211> LENGTH: 17
<212> TYPE: PRT
<213> ORGANISM: Homo sapiens

<400> SEQUENCE: 62

Asp Leu Lys Pro His Asn Ile Leu Ile Ser Met Pro Asn Ala His Gly
1               5                   10                  15

Lys

<210> SEQ ID NO 63
<211> LENGTH: 38
<212> TYPE: PRT
<213> ORGANISM: Homo sapiens

<400> SEQUENCE: 63

Glu Ser Ile Phe Phe Asn Ser His Asn Val Ser Lys Pro Glu Ser Ser
1               5                   10                  15

Ser Val Leu Thr Glu Leu Asp Lys Ile Glu Gly Val Phe Glu Arg Pro
            20                  25                  30

Ser Asp Glu Val Ile Arg
        35

<210> SEQ ID NO 64
<211> LENGTH: 28
<212> TYPE: PRT
<213> ORGANISM: Homo sapiens

<400> SEQUENCE: 64

Gln Leu Ala Ser Ala Leu Ser Tyr Leu Glu Asp Lys Asp Leu Val His
1               5                   10                  15

Gly Asn Val Cys Thr Lys Asn Leu Leu Leu Ala Arg
            20                  25
```

```
<210> SEQ ID NO 65
<211> LENGTH: 20
<212> TYPE: PRT
<213> ORGANISM: Homo sapiens

<400> SEQUENCE: 65

Ile Gly Asp Phe Gly Leu Thr Lys Ala Ile Glu Thr Asp Lys Glu Tyr
1               5                   10                  15

Tyr Thr Val Lys
            20

<210> SEQ ID NO 66
<211> LENGTH: 20
<212> TYPE: PRT
<213> ORGANISM: Homo sapiens

<400> SEQUENCE: 66

Ile Ala Asp Phe Gly Leu Ala Lys Leu Leu Pro Leu Asp Lys Asp Tyr
1               5                   10                  15

Tyr Val Val Arg
            20

<210> SEQ ID NO 67
<211> LENGTH: 10
<212> TYPE: PRT
<213> ORGANISM: Homo sapiens

<400> SEQUENCE: 67

Asp Leu Lys Pro Ser Asn Ile Val Val Lys
1               5                   10

<210> SEQ ID NO 68
<211> LENGTH: 14
<212> TYPE: PRT
<213> ORGANISM: Homo sapiens

<400> SEQUENCE: 68

Asn Val His Thr Gly Glu Leu Ala Ala Val Lys Ile Ile Lys
1               5                   10

<210> SEQ ID NO 69
<211> LENGTH: 26
<212> TYPE: PRT
<213> ORGANISM: Homo sapiens

<400> SEQUENCE: 69

Ser Lys Asn Val Phe Tyr Asp Asn Gly Lys Val Val Ile Thr Asp Phe
1               5                   10                  15

Gly Leu Phe Gly Ile Ser Gly Val Val Arg
            20                  25

<210> SEQ ID NO 70
<211> LENGTH: 10
<212> TYPE: PRT
<213> ORGANISM: Homo sapiens

<400> SEQUENCE: 70

Ser Lys Asn Val Phe Tyr Asp Asn Gly Lys
1               5                   10

<210> SEQ ID NO 71
<211> LENGTH: 9
```

```
<212> TYPE: PRT
<213> ORGANISM: Homo sapiens

<400> SEQUENCE: 71

Ala Leu Tyr Ala Thr Lys Thr Leu Arg
1               5

<210> SEQ ID NO 72
<211> LENGTH: 16
<212> TYPE: PRT
<213> ORGANISM: Homo sapiens

<400> SEQUENCE: 72

Asp Ile Lys Pro Asp Asn Ile Leu Ile Asp Leu Asp Gly His Ile Lys
1               5                   10                  15

<210> SEQ ID NO 73
<211> LENGTH: 23
<212> TYPE: PRT
<213> ORGANISM: Homo sapiens

<400> SEQUENCE: 73

Glu Gly Ala Lys Phe Pro Ile Lys Trp Thr Ala Pro Glu Ala Ile Asn
1               5                   10                  15

Tyr Gly Thr Phe Thr Ile Lys
            20

<210> SEQ ID NO 74
<211> LENGTH: 16
<212> TYPE: PRT
<213> ORGANISM: Homo sapiens

<400> SEQUENCE: 74

Asp Ile Lys Pro Gly Asn Leu Leu Leu Thr Thr Gly Gly Thr Leu Lys
1               5                   10                  15

<210> SEQ ID NO 75
<211> LENGTH: 16
<212> TYPE: PRT
<213> ORGANISM: Homo sapiens

<400> SEQUENCE: 75

Asp Leu Lys Ala Gly Asn Val Leu Met Thr Leu Glu Gly Asp Ile Arg
1               5                   10                  15

<210> SEQ ID NO 76
<211> LENGTH: 21
<212> TYPE: PRT
<213> ORGANISM: Homo sapiens

<400> SEQUENCE: 76

Asp Leu Lys Pro His Asn Val Leu Leu Phe Thr Leu Tyr Pro Asn Ala
1               5                   10                  15

Ala Ile Ile Ala Lys
            20

<210> SEQ ID NO 77
<211> LENGTH: 24
<212> TYPE: PRT
<213> ORGANISM: Homo sapiens

<400> SEQUENCE: 77

Val Ala Val Lys Thr Leu Lys Pro Gly Thr Met Ser Val Gln Ala Phe
1               5                   10                  15
```

```
Leu Glu Glu Ala Asn Leu Met Lys
            20
```

<210> SEQ ID NO 78
<211> LENGTH: 16
<212> TYPE: PRT
<213> ORGANISM: Homo sapiens

<400> SEQUENCE: 78

```
Ile Met His Arg Asp Val Lys Pro Ser Asn Ile Leu Val Asn Ser Arg
1               5                   10                  15
```

<210> SEQ ID NO 79
<211> LENGTH: 12
<212> TYPE: PRT
<213> ORGANISM: Homo sapiens

<400> SEQUENCE: 79

```
Asp Val Lys Pro Ser Asn Ile Leu Val Asn Ser Arg
1               5                   10
```

<210> SEQ ID NO 80
<211> LENGTH: 11
<212> TYPE: PRT
<213> ORGANISM: Homo sapiens

<400> SEQUENCE: 80

```
Asp Val Lys Pro Ser Asn Val Leu Ile Asn Lys
1               5                   10
```

<210> SEQ ID NO 81
<211> LENGTH: 11
<212> TYPE: PRT
<213> ORGANISM: Homo sapiens

<400> SEQUENCE: 81

```
Asp Ile Lys Pro Ser Asn Ile Leu Leu Asp Arg
1               5                   10
```

<210> SEQ ID NO 82
<211> LENGTH: 12
<212> TYPE: PRT
<213> ORGANISM: Homo sapiens

<400> SEQUENCE: 82

```
Asp Val Lys Pro Ser Asn Met Leu Val Asn Thr Arg
1               5                   10
```

<210> SEQ ID NO 83
<211> LENGTH: 16
<212> TYPE: PRT
<213> ORGANISM: Homo sapiens

<400> SEQUENCE: 83

```
Asp Val Lys Pro Ser Asn Val Leu Ile Asn Ala Leu Gly Gln Val Lys
1               5                   10                  15
```

<210> SEQ ID NO 84
<211> LENGTH: 12
<212> TYPE: PRT
<213> ORGANISM: Homo sapiens

<400> SEQUENCE: 84

```
Asp Val Lys Pro Ser Asn Ile Leu Leu Asp Glu Arg
```

```
                1               5                   10
```

<210> SEQ ID NO 85
<211> LENGTH: 15
<212> TYPE: PRT
<213> ORGANISM: Homo sapiens

<400> SEQUENCE: 85

```
Asp Val Lys Gly Ala Asn Leu Leu Ile Asp Ser Thr Gly Gln Arg
1               5                   10                  15
```

<210> SEQ ID NO 86
<211> LENGTH: 31
<212> TYPE: PRT
<213> ORGANISM: Homo sapiens

<400> SEQUENCE: 86

```
Glu Leu Ala Val Lys Gln Val Gln Phe Asp Pro Asp Ser Pro Glu Thr
1               5                   10                  15

Ser Lys Glu Val Asn Ala Leu Glu Cys Glu Ile Gln Leu Leu Lys
            20                  25                  30
```

<210> SEQ ID NO 87
<211> LENGTH: 9
<212> TYPE: PRT
<213> ORGANISM: Homo sapiens

<400> SEQUENCE: 87

```
Asp Ile Lys Gly Ala Asn Ile Leu Arg
1               5
```

<210> SEQ ID NO 88
<211> LENGTH: 31
<212> TYPE: PRT
<213> ORGANISM: Homo sapiens

<400> SEQUENCE: 88

```
Glu Leu Ala Ser Lys Gln Val Gln Phe Asp Pro Asp Ser Pro Glu Thr
1               5                   10                  15

Ser Lys Glu Val Ser Ala Leu Glu Cys Glu Ile Gln Leu Leu Lys
            20                  25                  30
```

<210> SEQ ID NO 89
<211> LENGTH: 16
<212> TYPE: PRT
<213> ORGANISM: Homo sapiens

<400> SEQUENCE: 89

```
Asp Ile Lys Gly Ala Asn Ile Phe Leu Thr Ser Ser Gly Leu Ile Lys
1               5                   10                  15
```

<210> SEQ ID NO 90
<211> LENGTH: 17
<212> TYPE: PRT
<213> ORGANISM: Homo sapiens

<400> SEQUENCE: 90

```
Asp Ile Lys Gly Asp Asn Val Leu Ile Asn Thr Tyr Ser Gly Val Leu
1               5                   10                  15

Lys
```

<210> SEQ ID NO 91
<211> LENGTH: 17

```
<212> TYPE: PRT
<213> ORGANISM: Homo sapiens

<400> SEQUENCE: 91

Asp Ile Lys Gly Asp Asn Val Leu Ile Asn Thr Phe Ser Gly Leu Leu
1               5                   10                  15

Lys

<210> SEQ ID NO 92
<211> LENGTH: 16
<212> TYPE: PRT
<213> ORGANISM: Homo sapiens

<400> SEQUENCE: 92

Asp Leu Lys Ala Glu Asn Leu Leu Leu Asp Ala Asp Met Asn Ile Lys
1               5                   10                  15

<210> SEQ ID NO 93
<211> LENGTH: 19
<212> TYPE: PRT
<213> ORGANISM: Homo sapiens

<400> SEQUENCE: 93

Glu Val Ala Ile Lys Ile Ile Asp Lys Thr Gln Leu Asn Pro Thr Ser
1               5                   10                  15

Leu Gln Lys

<210> SEQ ID NO 94
<211> LENGTH: 9
<212> TYPE: PRT
<213> ORGANISM: Homo sapiens

<400> SEQUENCE: 94

Glu Val Ala Ile Lys Ile Ile Asp Lys
1               5

<210> SEQ ID NO 95
<211> LENGTH: 16
<212> TYPE: PRT
<213> ORGANISM: Homo sapiens

<400> SEQUENCE: 95

Asp Leu Lys Ala Glu Asn Leu Leu Leu Asp Ala Glu Ala Asn Ile Lys
1               5                   10                  15

<210> SEQ ID NO 96
<211> LENGTH: 16
<212> TYPE: PRT
<213> ORGANISM: Homo sapiens

<400> SEQUENCE: 96

Asp Leu Lys Pro Asp Asn Leu Leu Ile Thr Ser Met Gly His Ile Lys
1               5                   10                  15

<210> SEQ ID NO 97
<211> LENGTH: 16
<212> TYPE: PRT
<213> ORGANISM: Homo sapiens

<400> SEQUENCE: 97

Asp Leu Lys Pro Asp Asn Leu Leu Ile Thr Ser Leu Gly His Ile Lys
1               5                   10                  15
```

```
<210> SEQ ID NO 98
<211> LENGTH: 11
<212> TYPE: PRT
<213> ORGANISM: Homo sapiens

<400> SEQUENCE: 98

Gly Ala Phe Gly Lys Val Tyr Leu Gly Gln Lys
1               5                   10

<210> SEQ ID NO 99
<211> LENGTH: 8
<212> TYPE: PRT
<213> ORGANISM: Homo sapiens

<400> SEQUENCE: 99

Leu Tyr Ala Val Lys Val Val Lys
1               5

<210> SEQ ID NO 100
<211> LENGTH: 14
<212> TYPE: PRT
<213> ORGANISM: Homo sapiens

<400> SEQUENCE: 100

Asp Leu Lys Pro Glu Asn Leu Leu Phe Asp Glu Tyr His Lys
1               5                   10

<210> SEQ ID NO 101
<211> LENGTH: 20
<212> TYPE: PRT
<213> ORGANISM: Homo sapiens

<400> SEQUENCE: 101

Asn Cys Met Leu Arg Asp Asp Met Thr Val Cys Val Ala Asp Phe Gly
1               5                   10                  15

Leu Ser Lys Lys
            20

<210> SEQ ID NO 102
<211> LENGTH: 9
<212> TYPE: PRT
<213> ORGANISM: Homo sapiens

<400> SEQUENCE: 102

Lys Ile Tyr Ser Gly Asp Tyr Tyr Arg
1               5

<210> SEQ ID NO 103
<211> LENGTH: 13
<212> TYPE: PRT
<213> ORGANISM: Homo sapiens

<400> SEQUENCE: 103

Asp Met Tyr Asp Lys Glu Tyr Tyr Ser Val His Asn Lys
1               5                   10

<210> SEQ ID NO 104
<211> LENGTH: 21
<212> TYPE: PRT
<213> ORGANISM: Homo sapiens

<400> SEQUENCE: 104

Asp Leu Lys Ser Asn Asn Ile Leu Leu Leu Gln Pro Ile Glu Ser Asp
1               5                   10                  15
```

```
Asp Met Glu His Lys
            20

<210> SEQ ID NO 105
<211> LENGTH: 12
<212> TYPE: PRT
<213> ORGANISM: Homo sapiens

<400> SEQUENCE: 105

Asp Leu Lys Ser Ser Asn Ile Leu Leu Glu Lys
1               5                   10

<210> SEQ ID NO 106
<211> LENGTH: 9
<212> TYPE: PRT
<213> ORGANISM: Homo sapiens

<400> SEQUENCE: 106

Ala Pro Val Ala Ile Lys Val Phe Lys
1               5

<210> SEQ ID NO 107
<211> LENGTH: 34
<212> TYPE: PRT
<213> ORGANISM: Homo sapiens

<400> SEQUENCE: 107

Asp Leu Lys Pro Thr Asn Ile Leu Leu Gly Asp Glu Gly Gln Pro Val
1               5                   10                  15

Leu Met Asp Leu Gly Ser Met Asn Gln Ala Cys Ile His Val Glu Gly
            20                  25                  30

Ser Arg

<210> SEQ ID NO 108
<211> LENGTH: 24
<212> TYPE: PRT
<213> ORGANISM: Homo sapiens

<400> SEQUENCE: 108

Asp Ile Lys Leu Glu Asn Ile Leu Leu Asp Ser Asn Gly His Val Val
1               5                   10                  15

Leu Thr Asp Phe Gly Leu Ser Lys
            20

<210> SEQ ID NO 109
<211> LENGTH: 24
<212> TYPE: PRT
<213> ORGANISM: Homo sapiens

<400> SEQUENCE: 109

Asp Leu Lys Leu Glu Asn Val Leu Leu Asp Ser Glu Gly His Ile Val
1               5                   10                  15

Leu Thr Asp Phe Gly Leu Ser Lys
            20

<210> SEQ ID NO 110
<211> LENGTH: 22
<212> TYPE: PRT
<213> ORGANISM: Homo sapiens

<400> SEQUENCE: 110

Glu Thr Gly Gln Ile Val Ala Ile Lys Gln Val Pro Val Glu Ser Asp
1               5                   10                  15
```

Leu Gln Glu Ile Ile Lys
            20

<210> SEQ ID NO 111
<211> LENGTH: 22
<212> TYPE: PRT
<213> ORGANISM: Homo sapiens

<400> SEQUENCE: 111

Glu Ser Gly Gln Val Val Ala Ile Lys Gln Val Pro Val Glu Ser Asp
1               5                   10                  15

Leu Gln Glu Ile Ile Lys
            20

<210> SEQ ID NO 112
<211> LENGTH: 16
<212> TYPE: PRT
<213> ORGANISM: Homo sapiens

<400> SEQUENCE: 112

Asp Ile Lys Ala Ala Asn Val Leu Leu Ser Glu His Gly Glu Val Lys
1               5                   10                  15

<210> SEQ ID NO 113
<211> LENGTH: 39
<212> TYPE: PRT
<213> ORGANISM: Homo sapiens

<400> SEQUENCE: 113

Thr Gln Gln Val Val Ala Ile Lys Ile Ile Asp Leu Glu Glu Ala Glu
1               5                   10                  15

Asp Glu Ile Glu Asp Ile Gln Gln Glu Ile Thr Val Leu Ser Gln Cys
            20                  25                  30

Asp Ser Ser Tyr Val Thr Lys
        35

<210> SEQ ID NO 114
<211> LENGTH: 16
<212> TYPE: PRT
<213> ORGANISM: Homo sapiens

<400> SEQUENCE: 114

Asp Ile Lys Ala Ala Asn Val Leu Leu Ser Glu Gln Gly Asp Val Lys
1               5                   10                  15

<210> SEQ ID NO 115
<211> LENGTH: 16
<212> TYPE: PRT
<213> ORGANISM: Homo sapiens

<400> SEQUENCE: 115

Asp Val Lys Gly Asn Asn Ile Leu Leu Thr Thr Glu Gly Gly Val Lys
1               5                   10                  15

<210> SEQ ID NO 116
<211> LENGTH: 12
<212> TYPE: PRT
<213> ORGANISM: Homo sapiens

<400> SEQUENCE: 116

Asp Ile Lys Pro Asp Asn Leu Leu Leu Asp Ser Lys
1               5                   10

```
<210> SEQ ID NO 117
<211> LENGTH: 12
<212> TYPE: PRT
<213> ORGANISM: Homo sapiens

<400> SEQUENCE: 117

Asp Ile Lys Pro Asp Asn Leu Leu Leu Asp Ala Lys
1               5                   10

<210> SEQ ID NO 118
<211> LENGTH: 11
<212> TYPE: PRT
<213> ORGANISM: Homo sapiens

<400> SEQUENCE: 118

Asp Ile Lys Ser Gln Asn Ile Phe Leu Thr Lys
1               5                   10

<210> SEQ ID NO 119
<211> LENGTH: 12
<212> TYPE: PRT
<213> ORGANISM: Homo sapiens

<400> SEQUENCE: 119

Asp Leu Lys Pro Ala Asn Val Phe Leu Asp Gly Lys
1               5                   10

<210> SEQ ID NO 120
<211> LENGTH: 11
<212> TYPE: PRT
<213> ORGANISM: Homo sapiens

<400> SEQUENCE: 120

Ser Lys Asn Ile Phe Leu Thr Gln Asn Gly Lys
1               5                   10

<210> SEQ ID NO 121
<211> LENGTH: 11
<212> TYPE: PRT
<213> ORGANISM: Homo sapiens

<400> SEQUENCE: 121

Asp Leu Lys Thr Gln Asn Val Phe Leu Thr Arg
1               5                   10

<210> SEQ ID NO 122
<211> LENGTH: 16
<212> TYPE: PRT
<213> ORGANISM: Homo sapiens

<400> SEQUENCE: 122

Asp Ile Lys Pro Ala Asn Val Phe Ile Thr Ala Thr Gly Val Val Lys
1               5                   10                  15

<210> SEQ ID NO 123
<211> LENGTH: 14
<212> TYPE: PRT
<213> ORGANISM: Homo sapiens

<400> SEQUENCE: 123

Ala Ala Cys Leu Leu Asp Gly Val Pro Val Ala Leu Lys Lys
1               5                   10

<210> SEQ ID NO 124
```

```
<211> LENGTH: 11
<212> TYPE: PRT
<213> ORGANISM: Homo sapiens

<400> SEQUENCE: 124

Asp Leu Lys Thr Gln Asn Ile Leu Leu Asp Lys
1               5                   10

<210> SEQ ID NO 125
<211> LENGTH: 11
<212> TYPE: PRT
<213> ORGANISM: Homo sapiens

<400> SEQUENCE: 125

Asp Ile Lys Thr Leu Asn Ile Phe Leu Thr Lys
1               5                   10

<210> SEQ ID NO 126
<211> LENGTH: 34
<212> TYPE: PRT
<213> ORGANISM: Homo sapiens

<400> SEQUENCE: 126

Asp Val Lys Ala Gly Asn Ile Leu Leu Gly Glu Asp Gly Ser Val Gln
1               5                   10                  15

Ile Ala Asp Phe Gly Val Ser Ala Phe Leu Ala Thr Gly Gly Asp Ile
            20                  25                  30

Thr Arg

<210> SEQ ID NO 127
<211> LENGTH: 16
<212> TYPE: PRT
<213> ORGANISM: Homo sapiens

<400> SEQUENCE: 127

Asp Leu Lys Pro Ser Asn Leu Ala Val Asn Glu Asp Cys Glu Leu Lys
1               5                   10                  15

<210> SEQ ID NO 128
<211> LENGTH: 13
<212> TYPE: PRT
<213> ORGANISM: Homo sapiens

<400> SEQUENCE: 128

Gln Glu Leu Asn Lys Thr Ile Trp Glu Val Pro Glu Arg
1               5                   10

<210> SEQ ID NO 129
<211> LENGTH: 13
<212> TYPE: PRT
<213> ORGANISM: Homo sapiens

<400> SEQUENCE: 129

Gln Glu Leu Asn Lys Thr Val Trp Glu Val Pro Gln Arg
1               5                   10

<210> SEQ ID NO 130
<211> LENGTH: 16
<212> TYPE: PRT
<213> ORGANISM: Homo sapiens

<400> SEQUENCE: 130

Asp Leu Lys Pro Gly Asn Leu Ala Val Asn Glu Asp Cys Glu Leu Lys
1               5                   10                  15
```

```
<210> SEQ ID NO 131
<211> LENGTH: 16
<212> TYPE: PRT
<213> ORGANISM: Homo sapiens

<400> SEQUENCE: 131

Asp Leu Lys Pro Glu Asn Ile Met Leu Asn His Gln Gly His Val Lys
1               5                   10                  15

<210> SEQ ID NO 132
<211> LENGTH: 16
<212> TYPE: PRT
<213> ORGANISM: Homo sapiens

<400> SEQUENCE: 132

Asp Leu Lys Pro Glu Asn Ile Met Leu Ser Ser Gln Gly His Ile Lys
1               5                   10                  15

<210> SEQ ID NO 133
<211> LENGTH: 12
<212> TYPE: PRT
<213> ORGANISM: Homo sapiens

<400> SEQUENCE: 133

Val Met Asp Pro Thr Lys Ile Leu Ile Thr Gly Lys
1               5                   10

<210> SEQ ID NO 134
<211> LENGTH: 14
<212> TYPE: PRT
<213> ORGANISM: Homo sapiens

<400> SEQUENCE: 134

Ser Lys Leu Thr Asp Asn Leu Val Ala Leu Lys Glu Ile Arg
1               5                   10

<210> SEQ ID NO 135
<211> LENGTH: 14
<212> TYPE: PRT
<213> ORGANISM: Homo sapiens

<400> SEQUENCE: 135

Ser Lys Leu Thr Glu Asn Leu Val Ala Leu Lys Glu Ile Arg
1               5                   10

<210> SEQ ID NO 136
<211> LENGTH: 9
<212> TYPE: PRT
<213> ORGANISM: Homo sapiens

<400> SEQUENCE: 136

Glu Tyr Ala Ile Lys Ile Leu Glu Lys
1               5

<210> SEQ ID NO 137
<211> LENGTH: 16
<212> TYPE: PRT
<213> ORGANISM: Homo sapiens

<400> SEQUENCE: 137

Asp Leu Lys Pro Ser Asn Ile Phe Phe Thr Met Asp Asp Val Val Lys
1               5                   10                  15
```

<210> SEQ ID NO 138
<211> LENGTH: 8
<212> TYPE: PRT
<213> ORGANISM: Homo sapiens

<400> SEQUENCE: 138

Leu Val Ala Leu Lys Val Ile Arg
1               5

<210> SEQ ID NO 139
<211> LENGTH: 16
<212> TYPE: PRT
<213> ORGANISM: Homo sapiens

<400> SEQUENCE: 139

Asp Leu Lys Pro Glu Asn Ile Leu Leu Asp Asp Asn Met Asn Ile Lys
1               5                   10                  15

<210> SEQ ID NO 140
<211> LENGTH: 17
<212> TYPE: PRT
<213> ORGANISM: Homo sapiens

<400> SEQUENCE: 140

Ala Thr Gly His Glu Phe Ala Val Lys Ile Met Glu Val Thr Ala Glu
1               5                   10                  15

Arg

<210> SEQ ID NO 141
<211> LENGTH: 16
<212> TYPE: PRT
<213> ORGANISM: Homo sapiens

<400> SEQUENCE: 141

Ser Gly Thr Pro Met Gln Ser Ala Ala Lys Ala Pro Tyr Leu Ala Lys
1               5                   10                  15

<210> SEQ ID NO 142
<211> LENGTH: 14
<212> TYPE: PRT
<213> ORGANISM: Homo sapiens

<400> SEQUENCE: 142

Val Pro His Thr Gln Ala Val Leu Asn Ser Lys Asp Lys
1               5                   10

<210> SEQ ID NO 143
<211> LENGTH: 20
<212> TYPE: PRT
<213> ORGANISM: Homo sapiens

<400> SEQUENCE: 143

Val Ile Phe Lys Cys Gly Asp Asp Leu Arg Gln Asp Met Leu Thr Leu
1               5                   10                  15

Gln Met Ile Arg
            20

<210> SEQ ID NO 144
<211> LENGTH: 18
<212> TYPE: PRT
<213> ORGANISM: Homo sapiens

<400> SEQUENCE: 144

Thr Glu Asp Gly Gly Lys Tyr Pro Val Ile Phe Lys His Gly Asp Asp

-continued

```
1               5                   10                  15
Leu Arg

<210> SEQ ID NO 145
<211> LENGTH: 28
<212> TYPE: PRT
<213> ORGANISM: Homo sapiens

<400> SEQUENCE: 145

Val Phe Gly Glu Asp Ser Val Gly Val Ile Phe Lys Asn Gly Asp Asp
1               5                   10                  15

Leu Arg Gln Asp Met Leu Thr Leu Gln Met Leu Arg
            20                  25

<210> SEQ ID NO 146
<211> LENGTH: 14
<212> TYPE: PRT
<213> ORGANISM: Homo sapiens

<400> SEQUENCE: 146

Val Asn Trp Leu Ala His Asn Val Ser Lys Asp Asn Arg Gln
1               5                   10

<210> SEQ ID NO 147
<211> LENGTH: 9
<212> TYPE: PRT
<213> ORGANISM: Homo sapiens

<400> SEQUENCE: 147

Lys Lys Pro Leu Trp Leu Glu Phe Lys
1               5

<210> SEQ ID NO 148
<211> LENGTH: 18
<212> TYPE: PRT
<213> ORGANISM: Homo sapiens

<400> SEQUENCE: 148

Ala Lys Glu Leu Pro Thr Leu Lys Asp Asn Asp Phe Ile Asn Glu Gly
1               5                   10                  15

Gln Lys

<210> SEQ ID NO 149
<211> LENGTH: 18
<212> TYPE: PRT
<213> ORGANISM: Homo sapiens

<400> SEQUENCE: 149

Ala Lys Asp Leu Pro Thr Phe Lys Asp Asn Phe Leu Asn Glu Gly
1               5                   10                  15

Gln Lys

<210> SEQ ID NO 150
<211> LENGTH: 28
<212> TYPE: PRT
<213> ORGANISM: Homo sapiens

<400> SEQUENCE: 150

Thr Leu Val Ile Lys Glu Val Ser Ser Glu Asp Ile Ala Asp Met His
1               5                   10                  15

Ser Asn Leu Ser Asn Tyr His Gln Tyr Ile Val Lys
            20                  25
```

<210> SEQ ID NO 151
<211> LENGTH: 19
<212> TYPE: PRT
<213> ORGANISM: Homo sapiens

<400> SEQUENCE: 151

Gly Gly Lys Ser Gly Ala Ala Phe Tyr Ala Thr Glu Asp Arg Phe
1               5                   10                  15

Ile Leu Lys

<210> SEQ ID NO 152
<211> LENGTH: 16
<212> TYPE: PRT
<213> ORGANISM: Homo sapiens

<400> SEQUENCE: 152

Asp Leu Lys Thr Ser Asn Leu Leu Ser His Ala Gly Ile Leu Lys
1               5                   10                  15

<210> SEQ ID NO 153
<211> LENGTH: 16
<212> TYPE: PRT
<213> ORGANISM: Homo sapiens

<400> SEQUENCE: 153

Asp Leu Lys Leu Asp Asn Val Met Leu Asp Ser Glu Gly His Ile Lys
1               5                   10                  15

<210> SEQ ID NO 154
<211> LENGTH: 9
<212> TYPE: PRT
<213> ORGANISM: Homo sapiens

<400> SEQUENCE: 154

Asp Val Ala Val Lys Val Ile Asp Lys
1               5

<210> SEQ ID NO 155
<211> LENGTH: 19
<212> TYPE: PRT
<213> ORGANISM: Homo sapiens

<400> SEQUENCE: 155

Val Leu Leu Ser Glu Phe Arg Pro Ser Gly Glu Leu Phe Ala Ile Lys
1               5                   10                  15

Ala Leu Lys

<210> SEQ ID NO 156
<211> LENGTH: 13
<212> TYPE: PRT
<213> ORGANISM: Homo sapiens

<400> SEQUENCE: 156

Asp Leu Lys Pro Ser Asn Ile Phe Leu Val Asp Thr Lys
1               5                   10

<210> SEQ ID NO 157
<211> LENGTH: 20
<212> TYPE: PRT
<213> ORGANISM: Homo sapiens

<400> SEQUENCE: 157

```
Cys Phe Glu Ile Ser Asp Ala Asp Thr Lys Glu Val Phe Ala Gly Lys
1               5                   10                  15

Ile Val Pro Lys
            20
```

<210> SEQ ID NO 158
<211> LENGTH: 19
<212> TYPE: PRT
<213> ORGANISM: Homo sapiens

<400> SEQUENCE: 158

```
Cys Asn Ile Leu His Ala Asp Ile Lys Pro Asp Asn Ile Leu Val Asn
1               5                   10                  15

Glu Ser Lys
```

<210> SEQ ID NO 159
<211> LENGTH: 15
<212> TYPE: PRT
<213> ORGANISM: Homo sapiens

<400> SEQUENCE: 159

```
Phe Leu Ser Gly Leu Glu Leu Val Lys Gln Gly Ala Glu Ala Arg
1               5                   10                  15
```

<210> SEQ ID NO 160
<211> LENGTH: 14
<212> TYPE: PRT
<213> ORGANISM: Homo sapiens

<400> SEQUENCE: 160

```
Tyr Ile Glu Asp Glu Asp Tyr Tyr Lys Ala Ser Val Thr Arg
1               5                   10
```

<210> SEQ ID NO 161
<211> LENGTH: 16
<212> TYPE: PRT
<213> ORGANISM: Homo sapiens

<400> SEQUENCE: 161

```
Asp Met Lys Ser Asn Asn Ile Phe Leu His Glu Gly Leu Thr Val Lys
1               5                   10                  15
```

<210> SEQ ID NO 162
<211> LENGTH: 16
<212> TYPE: PRT
<213> ORGANISM: Homo sapiens

<400> SEQUENCE: 162

```
Asp Leu Lys Pro Ser Asn Val Leu Leu Asp Pro Glu Leu His Val Lys
1               5                   10                  15
```

<210> SEQ ID NO 163
<211> LENGTH: 11
<212> TYPE: PRT
<213> ORGANISM: Homo sapiens

<400> SEQUENCE: 163

```
Asp Val Lys Pro Asp Asn Met Leu Leu Asp Lys
1               5                   10
```

<210> SEQ ID NO 164
<211> LENGTH: 31
<212> TYPE: PRT
<213> ORGANISM: Homo sapiens -continued

```
<400> SEQUENCE: 164

Asp Leu Lys Pro Glu Asn Ile Leu Leu Asp Glu Glu Gly His Ile Lys
1               5                   10                  15

Leu Thr Asp Phe Gly Leu Ser Lys Glu Ala Ile Asp His Glu Lys
            20                  25                  30

<210> SEQ ID NO 165
<211> LENGTH: 16
<212> TYPE: PRT
<213> ORGANISM: Homo sapiens

<400> SEQUENCE: 165

Asp Leu Lys Pro Glu Asn Ile Leu Leu Asp Glu Glu Gly His Ile Lys
1               5                   10                  15

<210> SEQ ID NO 166
<211> LENGTH: 20
<212> TYPE: PRT
<213> ORGANISM: Homo sapiens

<400> SEQUENCE: 166

Asp Leu Lys Pro Ser Asn Ile Leu Tyr Val Asp Glu Ser Gly Asn Pro
1               5                   10                  15

Glu Cys Leu Arg
            20

<210> SEQ ID NO 167
<211> LENGTH: 31
<212> TYPE: PRT
<213> ORGANISM: Homo sapiens

<400> SEQUENCE: 167

Asp Leu Lys Pro Glu Asn Ile Leu Leu Asp Glu Glu Gly His Ile Lys
1               5                   10                  15

Leu Thr Asp Phe Gly Leu Ser Lys Glu Ser Ile Asp His Glu Lys
            20                  25                  30

<210> SEQ ID NO 168
<211> LENGTH: 20
<212> TYPE: PRT
<213> ORGANISM: Homo sapiens

<400> SEQUENCE: 168

Asp Leu Lys Pro Ser Asn Ile Leu Tyr Val Asp Glu Ser Gly Asn Pro
1               5                   10                  15

Glu Ser Ile Arg
            20

<210> SEQ ID NO 169
<211> LENGTH: 24
<212> TYPE: PRT
<213> ORGANISM: Homo sapiens

<400> SEQUENCE: 169

Asp Leu Lys Pro Glu Asn Ile Leu Leu Asp Glu Glu Gly His Ile Lys
1               5                   10                  15

Ile Thr Asp Phe Gly Leu Ser Lys
            20

<210> SEQ ID NO 170
<211> LENGTH: 16
```

```
<212> TYPE: PRT
<213> ORGANISM: Homo sapiens

<400> SEQUENCE: 170

Asp Leu Lys Pro Glu Asn Ile Leu Leu Asp Glu Ile Gly His Ile Lys
1               5                   10                  15

<210> SEQ ID NO 171
<211> LENGTH: 15
<212> TYPE: PRT
<213> ORGANISM: Homo sapiens

<400> SEQUENCE: 171

Val Leu Gly Val Ile Asp Lys Val Leu Leu Val Met Asp Thr Arg
1               5                   10                  15

<210> SEQ ID NO 172
<211> LENGTH: 9
<212> TYPE: PRT
<213> ORGANISM: Homo sapiens

<400> SEQUENCE: 172

Phe Tyr Ala Val Lys Val Leu Gln Lys
1               5

<210> SEQ ID NO 173
<211> LENGTH: 16
<212> TYPE: PRT
<213> ORGANISM: Homo sapiens

<400> SEQUENCE: 173

Asp Leu Lys Ala Gly Asn Ile Leu Phe Thr Leu Asp Gly Asp Ile Lys
1               5                   10                  15

<210> SEQ ID NO 174
<211> LENGTH: 22
<212> TYPE: PRT
<213> ORGANISM: Homo sapiens

<400> SEQUENCE: 174

Asp Thr Val Thr Ile His Ser Val Gly Gly Thr Ile Thr Ile Leu Pro
1               5                   10                  15

Thr Lys Thr Lys Pro Lys
            20

<210> SEQ ID NO 175
<211> LENGTH: 12
<212> TYPE: PRT
<213> ORGANISM: Homo sapiens

<400> SEQUENCE: 175

Asp Leu Lys Pro Glu Asn Val Val Phe Phe Glu Lys
1               5                   10

<210> SEQ ID NO 176
<211> LENGTH: 25
<212> TYPE: PRT
<213> ORGANISM: Homo sapiens

<400> SEQUENCE: 176

Val Ala Ile Lys Thr Leu Lys Pro Gly Thr Met Ser Pro Glu Ala Phe
1               5                   10                  15

Leu Gln Glu Ala Gln Val Met Lys Lys
            20                  25
```

```
<210> SEQ ID NO 177
<211> LENGTH: 21
<212> TYPE: PRT
<213> ORGANISM: Homo sapiens

<400> SEQUENCE: 177

Ile Ile His Thr Asp Ile Lys Pro Glu Asn Ile Leu Leu Ser Val Asn
1               5                   10                  15

Glu Gln Tyr Ile Arg
            20

<210> SEQ ID NO 178
<211> LENGTH: 10
<212> TYPE: PRT
<213> ORGANISM: Homo sapiens

<400> SEQUENCE: 178

Asp Leu Lys Leu Glu Asn Ile Met Val Lys
1               5                   10

<210> SEQ ID NO 179
<211> LENGTH: 24
<212> TYPE: PRT
<213> ORGANISM: Homo sapiens

<400> SEQUENCE: 179

Tyr Ser Val Lys Val Leu Pro Trp Leu Ser Pro Glu Val Leu Gln Gln
1               5                   10                  15

Asn Leu Gln Gly Tyr Asp Ala Lys
            20

<210> SEQ ID NO 180
<211> LENGTH: 11
<212> TYPE: PRT
<213> ORGANISM: Homo sapiens

<400> SEQUENCE: 180

Ile Ser Asp Phe Gly Leu Ser Lys Ala Leu Arg
1               5                   10

<210> SEQ ID NO 181
<211> LENGTH: 17
<212> TYPE: PRT
<213> ORGANISM: Homo sapiens

<400> SEQUENCE: 181

Asp Leu Lys Pro Pro Asn Leu Leu Val Ala Gly Gly Thr Val Leu
1               5                   10                  15

Lys

<210> SEQ ID NO 182
<211> LENGTH: 16
<212> TYPE: PRT
<213> ORGANISM: Homo sapiens

<400> SEQUENCE: 182

Asp Ile Lys Ala Gly Asn Ile Leu Leu Thr Glu Pro Gly Gln Val Lys
1               5                   10                  15

<210> SEQ ID NO 183
<211> LENGTH: 16
<212> TYPE: PRT
```

<213> ORGANISM: Homo sapiens

<400> SEQUENCE: 183

Asp Val Lys Ala Gly Asn Ile Leu Leu Ser Glu Pro Gly Leu Val Lys
1               5                   10                  15

<210> SEQ ID NO 184
<211> LENGTH: 24
<212> TYPE: PRT
<213> ORGANISM: Homo sapiens

<400> SEQUENCE: 184

Thr Gly Asp Leu Phe Ala Ile Lys Val Phe Asn Asn Ile Ser Phe Leu
1               5                   10                  15

Arg Pro Val Asp Val Gln Met Arg
            20

<210> SEQ ID NO 185
<211> LENGTH: 18
<212> TYPE: PRT
<213> ORGANISM: Homo sapiens

<400> SEQUENCE: 185

Tyr Val Leu Asp Asp Gln Tyr Thr Ser Ser Ser Gly Ala Lys Phe Pro
1               5                   10                  15

Val Lys

<210> SEQ ID NO 186
<211> LENGTH: 31
<212> TYPE: PRT
<213> ORGANISM: Homo sapiens

<400> SEQUENCE: 186

Tyr Leu Asn Glu Ile Lys Pro Pro Ile Ile His Tyr Asp Leu Lys Pro
1               5                   10                  15

Gly Asn Ile Leu Leu Val Asp Gly Thr Ala Cys Gly Glu Ile Lys
            20                  25                  30

<210> SEQ ID NO 187
<211> LENGTH: 31
<212> TYPE: PRT
<213> ORGANISM: Homo sapiens

<400> SEQUENCE: 187

Tyr Leu Asn Glu Ile Lys Pro Pro Ile Ile His Tyr Asp Leu Lys Pro
1               5                   10                  15

Gly Asn Ile Leu Leu Val Asn Gly Thr Ala Cys Gly Glu Ile Lys
            20                  25                  30

<210> SEQ ID NO 188
<211> LENGTH: 18
<212> TYPE: PRT
<213> ORGANISM: Homo sapiens

<400> SEQUENCE: 188

Ile Gly Asp Phe Gly Leu Ala Lys Ala Val Pro Glu Gly His Glu Tyr
1               5                   10                  15

Tyr Arg

<210> SEQ ID NO 189
<211> LENGTH: 15
<212> TYPE: PRT

<213> ORGANISM: Homo sapiens

<400> SEQUENCE: 189

Asp Leu Lys Pro Gln Asn Ile Leu Leu Ser Asn Pro Ala Gly Arg
1               5                   10                  15

<210> SEQ ID NO 190
<211> LENGTH: 23
<212> TYPE: PRT
<213> ORGANISM: Homo sapiens

<400> SEQUENCE: 190

Asn Ile Ser His Leu Asp Leu Lys Pro Gln Asn Ile Leu Leu Ser Ser
1               5                   10                  15

Leu Glu Lys Pro His Leu Lys
            20

<210> SEQ ID NO 191
<211> LENGTH: 28
<212> TYPE: PRT
<213> ORGANISM: Homo sapiens

<400> SEQUENCE: 191

Met Leu Asp Val Leu Glu Tyr Ile His Glu Asn Glu Tyr Val His Gly
1               5                   10                  15

Asp Ile Lys Ala Ala Asn Leu Leu Leu Gly Tyr Lys
            20                  25

<210> SEQ ID NO 192
<211> LENGTH: 21
<212> TYPE: PRT
<213> ORGANISM: Homo sapiens

<400> SEQUENCE: 192

Tyr Ile His Ser Met Ser Leu Val His Met Asp Ile Lys Pro Ser Asn
1               5                   10                  15

Ile Phe Ile Ser Arg
            20

<210> SEQ ID NO 193
<211> LENGTH: 8
<212> TYPE: PRT
<213> ORGANISM: Homo sapiens

<400> SEQUENCE: 193

Gly Ser Phe Lys Thr Val Tyr Lys
1               5

<210> SEQ ID NO 194
<211> LENGTH: 17
<212> TYPE: PRT
<213> ORGANISM: Homo sapiens

<400> SEQUENCE: 194

Asp Leu Lys Cys Asp Asn Ile Phe Ile Thr Gly Pro Thr Gly Ser Val
1               5                   10                  15

Lys

<210> SEQ ID NO 195
<211> LENGTH: 12
<212> TYPE: PRT
<213> ORGANISM: Homo sapiens

```
<400> SEQUENCE: 195

Asp Val Lys Pro Asp Asn Ile Leu Leu Asp Glu Arg
1               5                   10

<210> SEQ ID NO 196
<211> LENGTH: 12
<212> TYPE: PRT
<213> ORGANISM: Homo sapiens

<400> SEQUENCE: 196

Trp Ile Ser Gln Asp Lys Glu Val Ala Val Lys Lys
1               5                   10

<210> SEQ ID NO 197
<211> LENGTH: 20
<212> TYPE: PRT
<213> ORGANISM: Homo sapiens

<400> SEQUENCE: 197

Ile Ser Asp Phe Gly Leu Ser Lys Ala Leu Gly Ala Asp Asp Ser Tyr
1               5                   10                  15

Tyr Thr Ala Arg
            20

<210> SEQ ID NO 198
<211> LENGTH: 16
<212> TYPE: PRT
<213> ORGANISM: Homo sapiens

<400> SEQUENCE: 198

Asp Ile Lys Gly Gln Asn Val Leu Leu Thr Glu Asn Ala Glu Val Lys
1               5                   10                  15

<210> SEQ ID NO 199
<211> LENGTH: 29
<212> TYPE: PRT
<213> ORGANISM: Homo sapiens

<400> SEQUENCE: 199

Thr Gly Gln Leu Ala Ala Ile Lys Val Met Asp Val Thr Gly Asp Glu
1               5                   10                  15

Glu Glu Glu Ile Lys Gln Glu Ile Asn Met Leu Lys Lys
            20                  25

<210> SEQ ID NO 200
<211> LENGTH: 18
<212> TYPE: PRT
<213> ORGANISM: Homo sapiens

<400> SEQUENCE: 200

Leu Met Thr Gly Asp Thr Tyr Thr Ala His Ala Gly Ala Lys Phe Pro
1               5                   10                  15

Ile Lys

<210> SEQ ID NO 201
<211> LENGTH: 25
<212> TYPE: PRT
<213> ORGANISM: Homo sapiens

<400> SEQUENCE: 201

Thr Val Ser Val Ala Val Lys Cys Leu Lys Pro Asp Val Leu Ser Gln
1               5                   10                  15
```

```
Pro Glu Ala Met Asp Asp Phe Ile Arg
            20              25
```

<210> SEQ ID NO 202
<211> LENGTH: 13
<212> TYPE: PRT
<213> ORGANISM: Homo sapiens

<400> SEQUENCE: 202

```
Ala Thr Val Phe Leu Asn Pro Ala Ala Cys Lys Gly Lys
1               5                   10
```

<210> SEQ ID NO 203
<211> LENGTH: 10
<212> TYPE: PRT
<213> ORGANISM: Homo sapiens

<400> SEQUENCE: 203

```
Gly Thr Phe Gly Lys Val Ile Leu Val Lys
1               5                   10
```

<210> SEQ ID NO 204
<211> LENGTH: 10
<212> TYPE: PRT
<213> ORGANISM: Homo sapiens

<400> SEQUENCE: 204

```
Gly Thr Phe Gly Lys Val Ile Leu Val Arg
1               5                   10
```

<210> SEQ ID NO 205
<211> LENGTH: 16
<212> TYPE: PRT
<213> ORGANISM: Homo sapiens

<400> SEQUENCE: 205

```
Asp Leu Lys Pro Glu Asn Val Leu Leu Asp Ala His Met Asn Ala Lys
1               5                   10                  15
```

<210> SEQ ID NO 206
<211> LENGTH: 26
<212> TYPE: PRT
<213> ORGANISM: Homo sapiens

<400> SEQUENCE: 206

```
Gly Met Leu Phe Leu His Asn Gly Ala Ile Cys Ser His Gly Asn Leu
1               5                   10                  15

Lys Ser Ser Asn Cys Val Val Asp Gly Arg
            20                  25
```

<210> SEQ ID NO 207
<211> LENGTH: 16
<212> TYPE: PRT
<213> ORGANISM: Homo sapiens

<400> SEQUENCE: 207

```
Asp Leu Lys Ser Asn Asn Ile Phe Leu His Glu Gly Leu Thr Val Lys
1               5                   10                  15
```

<210> SEQ ID NO 208
<211> LENGTH: 9
<212> TYPE: PRT
<213> ORGANISM: Homo sapiens

<400> SEQUENCE: 208

```
Phe Tyr Ile Met Met Cys Lys Pro Lys
1               5
```

<210> SEQ ID NO 209
<211> LENGTH: 10
<212> TYPE: PRT
<213> ORGANISM: Homo sapiens

<400> SEQUENCE: 209

```
Phe Ile Leu Ala Leu Lys Val Leu Phe Lys
1               5                   10
```

<210> SEQ ID NO 210
<211> LENGTH: 16
<212> TYPE: PRT
<213> ORGANISM: Homo sapiens

<400> SEQUENCE: 210

```
Asp Ile Lys Pro Glu Asn Leu Leu Gly Ser Ala Gly Glu Leu Lys
1               5                   10                  15
```

<210> SEQ ID NO 211
<211> LENGTH: 10
<212> TYPE: PRT
<213> ORGANISM: Homo sapiens

<400> SEQUENCE: 211

```
Gly Lys Phe Gly Asn Val Tyr Leu Ala Arg
1               5                   10
```

<210> SEQ ID NO 212
<211> LENGTH: 12
<212> TYPE: PRT
<213> ORGANISM: Homo sapiens

<400> SEQUENCE: 212

```
Ser His Phe Ile Val Ala Leu Lys Val Leu Phe Lys
1               5                   10
```

<210> SEQ ID NO 213
<211> LENGTH: 16
<212> TYPE: PRT
<213> ORGANISM: Homo sapiens

<400> SEQUENCE: 213

```
Asp Leu Lys Pro Ala Asn Ile Leu Leu Asp Glu His Gly His Val Arg
1               5                   10                  15
```

<210> SEQ ID NO 214
<211> LENGTH: 16
<212> TYPE: PRT
<213> ORGANISM: Homo sapiens

<400> SEQUENCE: 214

```
Asp Leu Lys Ser Asn Asn Ile Phe Leu His Glu Asp Leu Thr Val Lys
1               5                   10                  15
```

<210> SEQ ID NO 215
<211> LENGTH: 18
<212> TYPE: PRT
<213> ORGANISM: Homo sapiens

<400> SEQUENCE: 215

```
Tyr Val Leu Asp Asp Glu Tyr Thr Ser Ser Val Gly Ser Lys Phe Pro
```

```
1               5                  10                  15

Val Arg

<210> SEQ ID NO 216
<211> LENGTH: 9
<212> TYPE: PRT
<213> ORGANISM: Homo sapiens

<400> SEQUENCE: 216

Leu Val Ala Ile Lys Cys Ile Ala Lys
1               5

<210> SEQ ID NO 217
<211> LENGTH: 9
<212> TYPE: PRT
<213> ORGANISM: Homo sapiens

<400> SEQUENCE: 217

Leu Phe Ala Val Lys Cys Ile Pro Lys
1               5

<210> SEQ ID NO 218
<211> LENGTH: 16
<212> TYPE: PRT
<213> ORGANISM: Homo sapiens

<400> SEQUENCE: 218

Ile Pro Thr Gly Gln Glu Tyr Ala Ala Lys Ile Ile Asn Thr Lys Lys
1               5                   10                  15

<210> SEQ ID NO 219
<211> LENGTH: 14
<212> TYPE: PRT
<213> ORGANISM: Homo sapiens

<400> SEQUENCE: 219

Thr Ser Thr Gln Glu Tyr Ala Ala Lys Ile Ile Asn Thr Lys
1               5                   10

<210> SEQ ID NO 220
<211> LENGTH: 19
<212> TYPE: PRT
<213> ORGANISM: Homo sapiens

<400> SEQUENCE: 220

Asp Leu Lys Pro Glu Asn Leu Leu Tyr Ala Thr Pro Ala Pro Asp Ala
1               5                   10                  15

Pro Leu Lys

<210> SEQ ID NO 221
<211> LENGTH: 16
<212> TYPE: PRT
<213> ORGANISM: Homo sapiens

<400> SEQUENCE: 221

Asp Ile Lys Pro Ser Asn Leu Leu Val Gly Glu Asp Gly His Ile Lys
1               5                   10                  15

<210> SEQ ID NO 222
<211> LENGTH: 15
<212> TYPE: PRT
<213> ORGANISM: Homo sapiens

<400> SEQUENCE: 222
```

```
Glu Thr Gly Gln Gln Phe Ala Val Lys Ile Val Asp Val Ala Lys
1               5                   10                  15

<210> SEQ ID NO 223
<211> LENGTH: 16
<212> TYPE: PRT
<213> ORGANISM: Homo sapiens

<400> SEQUENCE: 223

Asp Leu Lys Pro Gln Asn Leu Leu Ile Asp Asp Lys Gly Thr Ile Lys
1               5                   10                  15

<210> SEQ ID NO 224
<211> LENGTH: 16
<212> TYPE: PRT
<213> ORGANISM: Homo sapiens

<400> SEQUENCE: 224

Asp Leu Lys Pro Ala Asn Ile Leu Val Met Gly Glu Gly Pro Glu Arg
1               5                   10                  15

<210> SEQ ID NO 225
<211> LENGTH: 16
<212> TYPE: PRT
<213> ORGANISM: Homo sapiens

<400> SEQUENCE: 225

Asp Leu Lys Pro Gln Asn Leu Leu Ile Asn Thr Glu Gly Ala Ile Lys
1               5                   10                  15

<210> SEQ ID NO 226
<211> LENGTH: 16
<212> TYPE: PRT
<213> ORGANISM: Homo sapiens

<400> SEQUENCE: 226

Asp Leu Lys Pro Glu Asn Ile Leu Val Thr Ser Gly Gly Thr Val Lys
1               5                   10                  15

<210> SEQ ID NO 227
<211> LENGTH: 11
<212> TYPE: PRT
<213> ORGANISM: Homo sapiens

<400> SEQUENCE: 227

Asp Leu Lys Pro Gln Asn Leu Leu Ile Asn Arg
1               5                   10

<210> SEQ ID NO 228
<211> LENGTH: 16
<212> TYPE: PRT
<213> ORGANISM: Homo sapiens

<400> SEQUENCE: 228

Asp Leu Lys Pro Gln Asn Ile Leu Val Thr Ser Ser Gly Gln Ile Lys
1               5                   10                  15

<210> SEQ ID NO 229
<211> LENGTH: 16
<212> TYPE: PRT
<213> ORGANISM: Homo sapiens

<400> SEQUENCE: 229

Asp Leu Lys Pro Asn Asn Leu Leu Leu Asp Glu Asn Gly Val Leu Lys
```

```
<210> SEQ ID NO 230
<211> LENGTH: 11
<212> TYPE: PRT
<213> ORGANISM: Homo sapiens

<400> SEQUENCE: 230

Asp Met Lys Ala Ala Asn Val Leu Ile Thr Arg
1               5                   10

<210> SEQ ID NO 231
<211> LENGTH: 12
<212> TYPE: PRT
<213> ORGANISM: Homo sapiens

<400> SEQUENCE: 231

Asp Ile Lys Pro Glu Asn Leu Leu Leu Asp Glu Arg
1               5                   10

<210> SEQ ID NO 232
<211> LENGTH: 19
<212> TYPE: PRT
<213> ORGANISM: Homo sapiens

<400> SEQUENCE: 232

Asp Leu Lys Pro Glu Asn Val Leu Leu Ser Ser Gln Glu Glu Asp Cys
1               5                   10                  15

Leu Ile Lys

<210> SEQ ID NO 233
<211> LENGTH: 13
<212> TYPE: PRT
<213> ORGANISM: Homo sapiens

<400> SEQUENCE: 233

Asp Ile Lys Pro Asp Asn Phe Leu Met Gly Ile Gly Arg
1               5                   10

<210> SEQ ID NO 234
<211> LENGTH: 14
<212> TYPE: PRT
<213> ORGANISM: Homo sapiens

<400> SEQUENCE: 234

Asp Val Lys Pro Asp Asn Phe Leu Met Gly Leu Gly Lys Lys
1               5                   10

<210> SEQ ID NO 235
<211> LENGTH: 11
<212> TYPE: PRT
<213> ORGANISM: Homo sapiens

<400> SEQUENCE: 235

Lys Ile Gly Cys Gly Asn Phe Gly Glu Leu Arg
1               5                   10

<210> SEQ ID NO 236
<211> LENGTH: 15
<212> TYPE: PRT
<213> ORGANISM: Homo sapiens

<400> SEQUENCE: 236

Asp Val Lys Pro Glu Asn Phe Leu Val Gly Arg Pro Gly Thr Lys
```

```
1               5                   10                  15
```

<210> SEQ ID NO 237
<211> LENGTH: 26
<212> TYPE: PRT
<213> ORGANISM: Homo sapiens

<400> SEQUENCE: 237

```
Leu Thr His Thr Asp Leu Lys Pro Glu Asn Ile Leu Phe Val Asn Ser
1               5                   10                  15

Asp Tyr Glu Leu Thr Tyr Asn Leu Glu Lys
            20                  25
```

<210> SEQ ID NO 238
<211> LENGTH: 23
<212> TYPE: PRT
<213> ORGANISM: Homo sapiens

<400> SEQUENCE: 238

```
Tyr Glu Ile Val Gly Asn Leu Gly Glu Gly Thr Phe Gly Lys Val Val
1               5                   10                  15

Glu Cys Leu Asp His Ala Arg
            20
```

<210> SEQ ID NO 239
<211> LENGTH: 22
<212> TYPE: PRT
<213> ORGANISM: Homo sapiens

<400> SEQUENCE: 239

```
Val Ser Asp Phe Gly Leu Thr Lys Glu Ala Ser Ser Thr Gln Asp Thr
1               5                   10                  15

Gly Lys Leu Pro Val Lys
            20
```

<210> SEQ ID NO 240
<211> LENGTH: 21
<212> TYPE: PRT
<213> ORGANISM: Homo sapiens

<400> SEQUENCE: 240

```
Ile Asp Pro Val Pro Asn Thr His Pro Leu Leu Val Phe Val Asn Pro
1               5                   10                  15

Lys Ser Gly Gly Lys
            20
```

<210> SEQ ID NO 241
<211> LENGTH: 25
<212> TYPE: PRT
<213> ORGANISM: Homo sapiens

<400> SEQUENCE: 241

```
Ala Thr Phe Ser Phe Cys Val Ser Pro Leu Leu Val Phe Val Asn Ser
1               5                   10                  15

Lys Ser Gly Asp Asn Gln Gly Val Lys
            20                  25
```

<210> SEQ ID NO 242
<211> LENGTH: 36
<212> TYPE: PRT
<213> ORGANISM: Homo sapiens

<400> SEQUENCE: 242

```
Gly Arg Leu Leu Thr Ala Leu Val Leu Pro Asp Leu Leu His Ala Lys
1               5                   10                  15

Leu Pro Pro Asp Ser Cys Pro Leu Leu Val Phe Val Asn Pro Lys Ser
            20                  25                  30

Gly Gly Leu Lys
        35

<210> SEQ ID NO 243
<211> LENGTH: 14
<212> TYPE: PRT
<213> ORGANISM: Homo sapiens

<400> SEQUENCE: 243

Lys Gly Gly Ser Trp Ile Gln Glu Ile Asn Val Ala Glu Lys
1               5                   10

<210> SEQ ID NO 244
<211> LENGTH: 13
<212> TYPE: PRT
<213> ORGANISM: Homo sapiens

<400> SEQUENCE: 244

Glu His Pro Phe Leu Val Lys Gly Gly Glu Asp Leu Arg
1               5                   10

<210> SEQ ID NO 245
<211> LENGTH: 12
<212> TYPE: PRT
<213> ORGANISM: Homo sapiens

<400> SEQUENCE: 245

Tyr Ile Lys Tyr Asn Ser Asn Ser Gly Phe Val Arg
1               5                   10

<210> SEQ ID NO 246
<211> LENGTH: 16
<212> TYPE: PRT
<213> ORGANISM: Homo sapiens

<400> SEQUENCE: 246

Asp Leu Lys Pro Ser Asn Leu Leu Ile Asn Thr Thr Cys Asp Leu Lys
1               5                   10                  15

<210> SEQ ID NO 247
<211> LENGTH: 16
<212> TYPE: PRT
<213> ORGANISM: Homo sapiens

<400> SEQUENCE: 247

Asp Leu Lys Pro Ser Asn Leu Leu Leu Asn Thr Thr Cys Asp Leu Lys
1               5                   10                  15

<210> SEQ ID NO 248
<211> LENGTH: 17
<212> TYPE: PRT
<213> ORGANISM: Homo sapiens

<400> SEQUENCE: 248

Asp Leu Lys Pro Ala Asn Leu Phe Ile Asn Thr Glu Asp Leu Val Leu
1               5                   10                  15

Lys
```

```
<210> SEQ ID NO 249
<211> LENGTH: 16
<212> TYPE: PRT
<213> ORGANISM: Homo sapiens

<400> SEQUENCE: 249

Asp Leu Lys Pro Ser Asn Leu Leu Val Asn Glu Asn Cys Glu Leu Lys
1               5                   10                  15

<210> SEQ ID NO 250
<211> LENGTH: 17
<212> TYPE: PRT
<213> ORGANISM: Homo sapiens

<400> SEQUENCE: 250

Thr Ser Val Ala Val Lys Thr Cys Lys Glu Asp Leu Pro Gln Glu Leu
1               5                   10                  15

Lys

<210> SEQ ID NO 251
<211> LENGTH: 14
<212> TYPE: PRT
<213> ORGANISM: Homo sapiens

<400> SEQUENCE: 251

Leu Arg Ala Asp Asn Thr Leu Val Ala Val Lys Ser Cys Arg
1               5                   10

<210> SEQ ID NO 252
<211> LENGTH: 18
<212> TYPE: PRT
<213> ORGANISM: Homo sapiens

<400> SEQUENCE: 252

Leu Ile Lys Asp Asp Glu Tyr Asn Pro Cys Gln Gly Ser Lys Phe Pro
1               5                   10                  15

Ile Lys

<210> SEQ ID NO 253
<211> LENGTH: 18
<212> TYPE: PRT
<213> ORGANISM: Homo sapiens

<400> SEQUENCE: 253

Ile Gln Ser Ile Ala Pro Ser Leu Gln Val Ile Thr Ser Lys Gln Arg
1               5                   10                  15

Pro Arg

<210> SEQ ID NO 254
<211> LENGTH: 8
<212> TYPE: PRT
<213> ORGANISM: Homo sapiens

<400> SEQUENCE: 254

His Glu Ile Lys Leu Pro Val Lys
1               5

<210> SEQ ID NO 255
<211> LENGTH: 19
<212> TYPE: PRT
<213> ORGANISM: Homo sapiens

<400> SEQUENCE: 255
```

```
Gln Gly Ala Lys Phe Pro Ile Lys Trp Thr Ala Pro Glu Ala Ala Leu
1               5                   10                  15

Tyr Gly Arg

<210> SEQ ID NO 256
<211> LENGTH: 16
<212> TYPE: PRT
<213> ORGANISM: Homo sapiens

<400> SEQUENCE: 256

Asp Ile Lys Gly Ala Asn Leu Leu Leu Thr Leu Gln Gly Asp Val Lys
1               5                   10                  15

<210> SEQ ID NO 257
<211> LENGTH: 16
<212> TYPE: PRT
<213> ORGANISM: Homo sapiens

<400> SEQUENCE: 257

Asp Leu Lys Pro Val Asn Ile Phe Leu Asp Ser Asp Asp His Val Lys
1               5                   10                  15

<210> SEQ ID NO 258
<211> LENGTH: 16
<212> TYPE: PRT
<213> ORGANISM: Homo sapiens

<400> SEQUENCE: 258

Asp Leu Lys Pro Glu Asn Ile Leu Leu Asp Asp His Gly His Ile Arg
1               5                   10                  15

<210> SEQ ID NO 259
<211> LENGTH: 17
<212> TYPE: PRT
<213> ORGANISM: Homo sapiens

<400> SEQUENCE: 259

Asp Ile Lys Pro Gln Asn Leu Leu Val Asp Pro Asp Thr Ala Val Leu
1               5                   10                  15

Lys

<210> SEQ ID NO 260
<211> LENGTH: 17
<212> TYPE: PRT
<213> ORGANISM: Homo sapiens

<400> SEQUENCE: 260

Asp Ile Lys Pro Gln Asn Leu Leu Asp Pro Asp Thr Ala Val Leu
1               5                   10                  15

Lys

<210> SEQ ID NO 261
<211> LENGTH: 16
<212> TYPE: PRT
<213> ORGANISM: Homo sapiens

<400> SEQUENCE: 261

Asp Ile Lys Gly Ala Asn Ile Leu Ile Asn Asp Ala Gly Glu Val Arg
1               5                   10                  15

<210> SEQ ID NO 262
<211> LENGTH: 15
<212> TYPE: PRT
```

```
<213> ORGANISM: Homo sapiens

<400> SEQUENCE: 262

Asp Leu Lys Pro Glu Asn Ile Val Leu Gln Asp Val Gly Gly Lys
1               5                   10                  15

<210> SEQ ID NO 263
<211> LENGTH: 15
<212> TYPE: PRT
<213> ORGANISM: Homo sapiens

<400> SEQUENCE: 263

Asp Leu Lys Pro Glu Asn Ile Val Leu Gln Gln Gly Glu Gln Arg
1               5                   10                  15

<210> SEQ ID NO 264
<211> LENGTH: 19
<212> TYPE: PRT
<213> ORGANISM: Homo sapiens

<400> SEQUENCE: 264

Ser Gly Glu Leu Val Ala Val Lys Val Phe Asn Thr Thr Ser Tyr Leu
1               5                   10                  15

Arg Pro Arg

<210> SEQ ID NO 265
<211> LENGTH: 12
<212> TYPE: PRT
<213> ORGANISM: Homo sapiens

<400> SEQUENCE: 265

Trp Gln Gly Asn Asp Ile Val Val Lys Val Leu Lys
1               5                   10

<210> SEQ ID NO 266
<211> LENGTH: 15
<212> TYPE: PRT
<213> ORGANISM: Homo sapiens

<400> SEQUENCE: 266

Ile Ser Met Ala Asp Val Lys Phe Ser Phe Gln Cys Pro Gly Arg
1               5                   10                  15

<210> SEQ ID NO 267
<211> LENGTH: 27
<212> TYPE: PRT
<213> ORGANISM: Homo sapiens

<400> SEQUENCE: 267

Ala Ile Gln Phe Leu His Gln Asp Ser Pro Ser Leu Ile His Gly Asp
1               5                   10                  15

Ile Lys Ser Ser Asn Val Leu Leu Asp Glu Arg
            20                  25

<210> SEQ ID NO 268
<211> LENGTH: 14
<212> TYPE: PRT
<213> ORGANISM: Homo sapiens

<400> SEQUENCE: 268

Val Glu Ile Gln Asn Leu Thr Tyr Ala Val Lys Leu Phe Lys
1               5                   10
```

-continued

<210> SEQ ID NO 269
<211> LENGTH: 16
<212> TYPE: PRT
<213> ORGANISM: Homo sapiens

<400> SEQUENCE: 269

Asp Ile Lys Ser Ala Asn Ile Leu Leu Asp Glu Ala Phe Thr Ala Lys
1               5                   10                  15

<210> SEQ ID NO 270
<211> LENGTH: 17
<212> TYPE: PRT
<213> ORGANISM: Homo sapiens

<400> SEQUENCE: 270

Asp Leu Lys Pro His Asn Ile Leu Ile Ser Met Pro Asn Ala His Gly
1               5                   10                  15

Lys

<210> SEQ ID NO 271
<211> LENGTH: 38
<212> TYPE: PRT
<213> ORGANISM: Homo sapiens

<400> SEQUENCE: 271

Glu Ser Ile Phe Phe Asn Ser His Asn Val Ser Lys Pro Glu Ser Ser
1               5                   10                  15

Ser Val Leu Thr Glu Leu Asp Lys Ile Glu Gly Val Phe Glu Arg Pro
            20                  25                  30

Ser Asp Glu Val Ile Arg
        35

<210> SEQ ID NO 272
<211> LENGTH: 28
<212> TYPE: PRT
<213> ORGANISM: Homo sapiens

<400> SEQUENCE: 272

Gln Leu Ala Ser Ala Leu Ser Tyr Leu Glu Asp Lys Asp Leu Val His
1               5                   10                  15

Gly Asn Val Cys Thr Lys Asn Leu Leu Leu Ala Arg
            20                  25

<210> SEQ ID NO 273
<211> LENGTH: 20
<212> TYPE: PRT
<213> ORGANISM: Homo sapiens

<400> SEQUENCE: 273

Ile Gly Asp Phe Gly Leu Thr Lys Ala Ile Glu Thr Asp Lys Glu Tyr
1               5                   10                  15

Tyr Thr Val Lys
            20

<210> SEQ ID NO 274
<211> LENGTH: 31
<212> TYPE: PRT
<213> ORGANISM: Homo sapiens

<400> SEQUENCE: 274

Tyr Asp Pro Glu Gly Asp Asn Thr Gly Glu Gln Val Ala Val Lys Ser
1               5                   10                  15

Leu Lys Pro Glu Ser Gly Gly Asn His Ile Ala Asp Leu Lys Lys
            20                  25                  30

<210> SEQ ID NO 275
<211> LENGTH: 20
<212> TYPE: PRT
<213> ORGANISM: Homo sapiens

<400> SEQUENCE: 275

Ile Ala Asp Phe Gly Leu Ala Lys Leu Leu Pro Leu Asp Lys Asp Tyr
1               5                   10                  15

Tyr Val Val Arg
            20

<210> SEQ ID NO 276
<211> LENGTH: 10
<212> TYPE: PRT
<213> ORGANISM: Homo sapiens

<400> SEQUENCE: 276

Asp Leu Lys Pro Ser Asn Ile Val Val Lys
1               5                   10

<210> SEQ ID NO 277
<211> LENGTH: 14
<212> TYPE: PRT
<213> ORGANISM: Homo sapiens

<400> SEQUENCE: 277

Asn Val His Thr Gly Glu Leu Ala Ala Val Lys Ile Ile Lys
1               5                   10

<210> SEQ ID NO 278
<211> LENGTH: 14
<212> TYPE: PRT
<213> ORGANISM: Homo sapiens

<400> SEQUENCE: 278

Asn Val Asn Thr Gly Glu Leu Ala Ala Ile Lys Val Ile Lys
1               5                   10

<210> SEQ ID NO 279
<211> LENGTH: 26
<212> TYPE: PRT
<213> ORGANISM: Homo sapiens

<400> SEQUENCE: 279

Ser Lys Asn Val Phe Tyr Asp Asn Gly Lys Val Val Ile Thr Asp Phe
1               5                   10                  15

Gly Leu Phe Gly Ile Ser Gly Val Val Arg
            20                  25

<210> SEQ ID NO 280
<211> LENGTH: 10
<212> TYPE: PRT
<213> ORGANISM: Homo sapiens

<400> SEQUENCE: 280

Ser Lys Asn Val Phe Tyr Asp Asn Gly Lys
1               5                   10

<210> SEQ ID NO 281
<211> LENGTH: 9
<212> TYPE: PRT

<213> ORGANISM: Homo sapiens

<400> SEQUENCE: 281

Ala Leu Tyr Ala Thr Lys Thr Leu Arg
1               5

<210> SEQ ID NO 282
<211> LENGTH: 16
<212> TYPE: PRT
<213> ORGANISM: Homo sapiens

<400> SEQUENCE: 282

Asp Ile Lys Pro Asp Asn Ile Leu Ile Asp Leu Asp Gly His Ile Lys
1               5                   10                  15

<210> SEQ ID NO 283
<211> LENGTH: 23
<212> TYPE: PRT
<213> ORGANISM: Homo sapiens

<400> SEQUENCE: 283

Glu Gly Ala Lys Phe Pro Ile Lys Trp Thr Ala Pro Glu Ala Ile Asn
1               5                   10                  15

Tyr Gly Thr Phe Thr Ile Lys
            20

<210> SEQ ID NO 284
<211> LENGTH: 16
<212> TYPE: PRT
<213> ORGANISM: Homo sapiens

<400> SEQUENCE: 284

Asp Ile Lys Pro Gly Asn Leu Leu Leu Thr Thr Gly Gly Thr Leu Lys
1               5                   10                  15

<210> SEQ ID NO 285
<211> LENGTH: 16
<212> TYPE: PRT
<213> ORGANISM: Homo sapiens

<400> SEQUENCE: 285

Asp Leu Lys Ala Gly Asn Val Leu Met Thr Leu Glu Gly Asp Ile Arg
1               5                   10                  15

<210> SEQ ID NO 286
<211> LENGTH: 21
<212> TYPE: PRT
<213> ORGANISM: Homo sapiens

<400> SEQUENCE: 286

Asp Leu Lys Pro His Asn Val Leu Leu Phe Thr Leu Tyr Pro Asn Ala
1               5                   10                  15

Ala Ile Ile Ala Lys
            20

<210> SEQ ID NO 287
<211> LENGTH: 24
<212> TYPE: PRT
<213> ORGANISM: Homo sapiens

<400> SEQUENCE: 287

Val Ala Val Lys Thr Leu Lys Pro Gly Thr Met Ser Val Gln Ala Phe
1               5                   10                  15

Leu Glu Glu Ala Asn Leu Met Lys
            20

<210> SEQ ID NO 288
<211> LENGTH: 16
<212> TYPE: PRT
<213> ORGANISM: Homo sapiens

<400> SEQUENCE: 288

Ile Met His Arg Asp Val Lys Pro Ser Asn Ile Leu Val Asn Ser Arg
1               5                   10                  15

<210> SEQ ID NO 289
<211> LENGTH: 12
<212> TYPE: PRT
<213> ORGANISM: Homo sapiens

<400> SEQUENCE: 289

Lys Leu Ile His Leu Glu Ile Lys Pro Ala Ile Arg
1               5                   10

<210> SEQ ID NO 290
<211> LENGTH: 12
<212> TYPE: PRT
<213> ORGANISM: Homo sapiens

<400> SEQUENCE: 290

Asp Val Lys Pro Ser Asn Ile Leu Val Asn Ser Arg
1               5                   10

<210> SEQ ID NO 291
<211> LENGTH: 18
<212> TYPE: PRT
<213> ORGANISM: Homo sapiens

<400> SEQUENCE: 291

His Gln Ile Met His Arg Asp Val Lys Pro Ser Asn Ile Leu Val Asn
1               5                   10                  15

Ser Arg

<210> SEQ ID NO 292
<211> LENGTH: 11
<212> TYPE: PRT
<213> ORGANISM: Homo sapiens

<400> SEQUENCE: 292

Asp Val Lys Pro Ser Asn Val Leu Ile Asn Lys
1               5                   10

<210> SEQ ID NO 293
<211> LENGTH: 11
<212> TYPE: PRT
<213> ORGANISM: Homo sapiens

<400> SEQUENCE: 293

Asp Ile Lys Pro Ser Asn Ile Leu Leu Asp Arg
1               5                   10

<210> SEQ ID NO 294
<211> LENGTH: 12
<212> TYPE: PRT
<213> ORGANISM: Homo sapiens

<400> SEQUENCE: 294

```
Asp Val Lys Pro Ser Asn Met Leu Val Asn Thr Arg
1               5                  10
```

<210> SEQ ID NO 295
<211> LENGTH: 16
<212> TYPE: PRT
<213> ORGANISM: Homo sapiens

<400> SEQUENCE: 295

```
Asp Val Lys Pro Ser Asn Val Leu Ile Asn Ala Leu Gly Gln Val Lys
1               5                  10                  15
```

<210> SEQ ID NO 296
<211> LENGTH: 12
<212> TYPE: PRT
<213> ORGANISM: Homo sapiens

<400> SEQUENCE: 296

```
Asp Val Lys Pro Ser Asn Ile Leu Leu Asp Glu Arg
1               5                  10
```

<210> SEQ ID NO 297
<211> LENGTH: 15
<212> TYPE: PRT
<213> ORGANISM: Homo sapiens

<400> SEQUENCE: 297

```
Asp Val Lys Gly Ala Asn Leu Leu Ile Asp Ser Thr Gly Gln Arg
1               5                  10                  15
```

<210> SEQ ID NO 298
<211> LENGTH: 31
<212> TYPE: PRT
<213> ORGANISM: Homo sapiens

<400> SEQUENCE: 298

```
Glu Leu Ala Val Lys Gln Val Gln Phe Asp Pro Asp Ser Pro Glu Thr
1               5                  10                  15

Ser Lys Glu Val Asn Ala Leu Glu Cys Glu Ile Gln Leu Leu Lys
                20                  25                  30
```

<210> SEQ ID NO 299
<211> LENGTH: 9
<212> TYPE: PRT
<213> ORGANISM: Homo sapiens

<400> SEQUENCE: 299

```
Asp Ile Lys Gly Ala Asn Ile Leu Arg
1               5
```

<210> SEQ ID NO 300
<211> LENGTH: 31
<212> TYPE: PRT
<213> ORGANISM: Homo sapiens

<400> SEQUENCE: 300

```
Glu Leu Ala Ser Lys Gln Val Gln Phe Asp Pro Asp Ser Pro Glu Thr
1               5                  10                  15

Ser Lys Glu Val Ser Ala Leu Glu Cys Glu Ile Gln Leu Leu Lys
                20                  25                  30
```

<210> SEQ ID NO 301
<211> LENGTH: 16
<212> TYPE: PRT

<213> ORGANISM: Homo sapiens

<400> SEQUENCE: 301

Asp Ile Lys Gly Ala Asn Ile Phe Leu Thr Ser Ser Gly Leu Ile Lys
1               5                   10                  15

<210> SEQ ID NO 302
<211> LENGTH: 17
<212> TYPE: PRT
<213> ORGANISM: Homo sapiens

<400> SEQUENCE: 302

Asp Ile Lys Gly Asp Asn Val Leu Ile Asn Thr Tyr Ser Gly Val Leu
1               5                   10                  15

Lys

<210> SEQ ID NO 303
<211> LENGTH: 17
<212> TYPE: PRT
<213> ORGANISM: Homo sapiens

<400> SEQUENCE: 303

Asp Ile Lys Gly Asp Asn Val Leu Ile Asn Thr Phe Ser Gly Leu Leu
1               5                   10                  15

Lys

<210> SEQ ID NO 304
<211> LENGTH: 16
<212> TYPE: PRT
<213> ORGANISM: Homo sapiens

<400> SEQUENCE: 304

Asp Leu Lys Ala Glu Asn Leu Leu Leu Asp Ala Asp Met Asn Ile Lys
1               5                   10                  15

<210> SEQ ID NO 305
<211> LENGTH: 19
<212> TYPE: PRT
<213> ORGANISM: Homo sapiens

<400> SEQUENCE: 305

Glu Val Ala Ile Lys Ile Ile Asp Lys Thr Gln Leu Asn Pro Thr Ser
1               5                   10                  15

Leu Gln Lys

<210> SEQ ID NO 306
<211> LENGTH: 9
<212> TYPE: PRT
<213> ORGANISM: Homo sapiens

<400> SEQUENCE: 306

Glu Val Ala Ile Lys Ile Ile Asp Lys
1               5

<210> SEQ ID NO 307
<211> LENGTH: 16
<212> TYPE: PRT
<213> ORGANISM: Homo sapiens

<400> SEQUENCE: 307

Asp Leu Lys Ala Glu Asn Leu Leu Leu Asp Ala Glu Ala Asn Ile Lys
1               5                   10                  15

<210> SEQ ID NO 308
<211> LENGTH: 16
<212> TYPE: PRT
<213> ORGANISM: Homo sapiens

<400> SEQUENCE: 308

Asp Leu Lys Pro Asp Asn Leu Leu Ile Thr Ser Met Gly His Ile Lys
1               5                   10                  15

<210> SEQ ID NO 309
<211> LENGTH: 16
<212> TYPE: PRT
<213> ORGANISM: Homo sapiens

<400> SEQUENCE: 309

Asp Leu Lys Pro Asp Asn Leu Leu Ile Thr Ser Leu Gly His Ile Lys
1               5                   10                  15

<210> SEQ ID NO 310
<211> LENGTH: 11
<212> TYPE: PRT
<213> ORGANISM: Homo sapiens

<400> SEQUENCE: 310

Gly Ala Phe Gly Lys Val Tyr Leu Gly Gln Lys
1               5                   10

<210> SEQ ID NO 311
<211> LENGTH: 8
<212> TYPE: PRT
<213> ORGANISM: Homo sapiens

<400> SEQUENCE: 311

Leu Tyr Ala Val Lys Val Val Lys
1               5

<210> SEQ ID NO 312
<211> LENGTH: 14
<212> TYPE: PRT
<213> ORGANISM: Homo sapiens

<400> SEQUENCE: 312

Asp Leu Lys Pro Glu Asn Leu Leu Phe Asp Glu Tyr His Lys
1               5                   10

<210> SEQ ID NO 313
<211> LENGTH: 9
<212> TYPE: PRT
<213> ORGANISM: Homo sapiens

<400> SEQUENCE: 313

Lys Ile Tyr Ser Gly Asp Tyr Tyr Arg
1               5

<210> SEQ ID NO 314
<211> LENGTH: 13
<212> TYPE: PRT
<213> ORGANISM: Homo sapiens

<400> SEQUENCE: 314

Asp Met Tyr Asp Lys Glu Tyr Tyr Ser Val His Asn Lys
1               5                   10

<210> SEQ ID NO 315

```
<211> LENGTH: 21
<212> TYPE: PRT
<213> ORGANISM: Homo sapiens

<400> SEQUENCE: 315

Asp Leu Lys Ser Asn Asn Ile Leu Leu Gln Pro Ile Glu Ser Asp
1               5                   10                  15

Asp Met Glu His Lys
            20

<210> SEQ ID NO 316
<211> LENGTH: 12
<212> TYPE: PRT
<213> ORGANISM: Homo sapiens

<400> SEQUENCE: 316

Asp Leu Lys Ser Ser Asn Ile Leu Leu Leu Glu Lys
1               5                   10

<210> SEQ ID NO 317
<211> LENGTH: 9
<212> TYPE: PRT
<213> ORGANISM: Homo sapiens

<400> SEQUENCE: 317

Ala Pro Val Ala Ile Lys Val Phe Lys
1               5

<210> SEQ ID NO 318
<211> LENGTH: 34
<212> TYPE: PRT
<213> ORGANISM: Homo sapiens

<400> SEQUENCE: 318

Asp Leu Lys Pro Thr Asn Ile Leu Leu Gly Asp Gly Gln Pro Val
1               5                   10                  15

Leu Met Asp Leu Gly Ser Met Asn Gln Ala Cys Ile His Val Glu Gly
            20                  25                  30

Ser Arg

<210> SEQ ID NO 319
<211> LENGTH: 24
<212> TYPE: PRT
<213> ORGANISM: Homo sapiens

<400> SEQUENCE: 319

Asp Ile Lys Leu Glu Asn Ile Leu Leu Asp Ser Asn Gly His Val Val
1               5                   10                  15

Leu Thr Asp Phe Gly Leu Ser Lys
            20

<210> SEQ ID NO 320
<211> LENGTH: 24
<212> TYPE: PRT
<213> ORGANISM: Homo sapiens

<400> SEQUENCE: 320

Asp Leu Lys Leu Glu Asn Val Leu Leu Asp Ser Glu Gly His Ile Val
1               5                   10                  15

Leu Thr Asp Phe Gly Leu Ser Lys
            20
```

```
<210> SEQ ID NO 321
<211> LENGTH: 22
<212> TYPE: PRT
<213> ORGANISM: Homo sapiens

<400> SEQUENCE: 321

Glu Thr Gly Gln Ile Val Ala Ile Lys Gln Val Pro Val Glu Ser Asp
1               5                   10                  15

Leu Gln Glu Ile Ile Lys
            20

<210> SEQ ID NO 322
<211> LENGTH: 22
<212> TYPE: PRT
<213> ORGANISM: Homo sapiens

<400> SEQUENCE: 322

Glu Ser Gly Gln Val Val Ala Ile Lys Gln Val Pro Val Glu Ser Asp
1               5                   10                  15

Leu Gln Glu Ile Ile Lys
            20

<210> SEQ ID NO 323
<211> LENGTH: 16
<212> TYPE: PRT
<213> ORGANISM: Homo sapiens

<400> SEQUENCE: 323

Asp Ile Lys Ala Ala Asn Val Leu Leu Ser Glu His Gly Glu Val Lys
1               5                   10                  15

<210> SEQ ID NO 324
<211> LENGTH: 39
<212> TYPE: PRT
<213> ORGANISM: Homo sapiens

<400> SEQUENCE: 324

Thr Gln Gln Val Val Ala Ile Lys Ile Ile Asp Leu Glu Glu Ala Glu
1               5                   10                  15

Asp Glu Ile Glu Asp Ile Gln Gln Glu Ile Thr Val Leu Ser Gln Cys
            20                  25                  30

Asp Ser Ser Tyr Val Thr Lys
        35

<210> SEQ ID NO 325
<211> LENGTH: 16
<212> TYPE: PRT
<213> ORGANISM: Homo sapiens

<400> SEQUENCE: 325

Asp Ile Lys Ala Ala Asn Val Leu Leu Ser Glu Gln Gly Asp Val Lys
1               5                   10                  15

<210> SEQ ID NO 326
<211> LENGTH: 16
<212> TYPE: PRT
<213> ORGANISM: Homo sapiens

<400> SEQUENCE: 326

Asp Val Lys Gly Asn Asn Ile Leu Leu Thr Thr Glu Gly Gly Val Lys
1               5                   10                  15

<210> SEQ ID NO 327
```

```
<211> LENGTH: 12
<212> TYPE: PRT
<213> ORGANISM: Homo sapiens

<400> SEQUENCE: 327

Asp Ile Lys Pro Asp Asn Leu Leu Leu Asp Ser Lys
1               5                   10

<210> SEQ ID NO 328
<211> LENGTH: 12
<212> TYPE: PRT
<213> ORGANISM: Homo sapiens

<400> SEQUENCE: 328

Asp Ile Lys Pro Asp Asn Leu Leu Leu Asp Ala Lys
1               5                   10

<210> SEQ ID NO 329
<211> LENGTH: 11
<212> TYPE: PRT
<213> ORGANISM: Homo sapiens

<400> SEQUENCE: 329

Asp Ile Lys Ser Gln Asn Ile Phe Leu Thr Lys
1               5                   10

<210> SEQ ID NO 330
<211> LENGTH: 12
<212> TYPE: PRT
<213> ORGANISM: Homo sapiens

<400> SEQUENCE: 330

Asp Leu Lys Pro Ala Asn Val Phe Leu Asp Gly Lys
1               5                   10

<210> SEQ ID NO 331
<211> LENGTH: 11
<212> TYPE: PRT
<213> ORGANISM: Homo sapiens

<400> SEQUENCE: 331

Ser Lys Asn Ile Phe Leu Thr Gln Asn Gly Lys
1               5                   10

<210> SEQ ID NO 332
<211> LENGTH: 11
<212> TYPE: PRT
<213> ORGANISM: Homo sapiens

<400> SEQUENCE: 332

Asp Leu Lys Thr Gln Asn Val Phe Leu Thr Arg
1               5                   10

<210> SEQ ID NO 333
<211> LENGTH: 16
<212> TYPE: PRT
<213> ORGANISM: Homo sapiens

<400> SEQUENCE: 333

Asp Ile Lys Pro Ala Asn Val Phe Ile Thr Ala Thr Gly Val Val Lys
1               5                   10                  15

<210> SEQ ID NO 334
<211> LENGTH: 14
<212> TYPE: PRT
```

<213> ORGANISM: Homo sapiens

<400> SEQUENCE: 334

Ala Ala Cys Leu Leu Asp Gly Val Pro Val Ala Leu Lys Lys
1               5                   10

<210> SEQ ID NO 335
<211> LENGTH: 11
<212> TYPE: PRT
<213> ORGANISM: Homo sapiens

<400> SEQUENCE: 335

Asp Leu Lys Thr Gln Asn Ile Leu Leu Asp Lys
1               5                   10

<210> SEQ ID NO 336
<211> LENGTH: 11
<212> TYPE: PRT
<213> ORGANISM: Homo sapiens

<400> SEQUENCE: 336

Asp Ile Lys Thr Leu Asn Ile Phe Leu Thr Lys
1               5                   10

<210> SEQ ID NO 337
<211> LENGTH: 16
<212> TYPE: PRT
<213> ORGANISM: Homo sapiens

<400> SEQUENCE: 337

Asp Ile Lys Pro Gly Asn Leu Leu Val Asn Ser Asn Cys Val Leu Lys
1               5                   10                  15

<210> SEQ ID NO 338
<211> LENGTH: 34
<212> TYPE: PRT
<213> ORGANISM: Homo sapiens

<400> SEQUENCE: 338

Asp Val Lys Ala Gly Asn Ile Leu Leu Gly Glu Asp Gly Ser Val Gln
1               5                   10                  15

Ile Ala Asp Phe Gly Val Ser Ala Phe Leu Ala Thr Gly Gly Asp Ile
                20                  25                  30

Thr Arg

<210> SEQ ID NO 339
<211> LENGTH: 16
<212> TYPE: PRT
<213> ORGANISM: Homo sapiens

<400> SEQUENCE: 339

Asp Leu Lys Pro Ser Asn Leu Ala Val Asn Glu Asp Cys Glu Leu Lys
1               5                   10                  15

<210> SEQ ID NO 340
<211> LENGTH: 13
<212> TYPE: PRT
<213> ORGANISM: Homo sapiens

<400> SEQUENCE: 340

Gln Glu Leu Asn Lys Thr Ile Trp Glu Val Pro Glu Arg
1               5                   10

```
<210> SEQ ID NO 341
<211> LENGTH: 16
<212> TYPE: PRT
<213> ORGANISM: Homo sapiens

<400> SEQUENCE: 341

Asp Leu Lys Pro Gly Asn Leu Ala Val Asn Glu Asp Cys Glu Leu Lys
1               5                   10                  15

<210> SEQ ID NO 342
<211> LENGTH: 16
<212> TYPE: PRT
<213> ORGANISM: Homo sapiens

<400> SEQUENCE: 342

Asp Leu Lys Pro Glu Asn Ile Met Leu Asn His Gln Gly His Val Lys
1               5                   10                  15

<210> SEQ ID NO 343
<211> LENGTH: 16
<212> TYPE: PRT
<213> ORGANISM: Homo sapiens

<400> SEQUENCE: 343

Asp Leu Lys Pro Glu Asn Ile Met Leu Ser Ser Gln Gly His Ile Lys
1               5                   10                  15

<210> SEQ ID NO 344
<211> LENGTH: 12
<212> TYPE: PRT
<213> ORGANISM: Homo sapiens

<400> SEQUENCE: 344

Val Met Asp Pro Thr Lys Ile Leu Ile Thr Gly Lys
1               5                   10

<210> SEQ ID NO 345
<211> LENGTH: 14
<212> TYPE: PRT
<213> ORGANISM: Homo sapiens

<400> SEQUENCE: 345

Ser Lys Leu Thr Asp Asn Leu Val Ala Leu Lys Glu Ile Arg
1               5                   10

<210> SEQ ID NO 346
<211> LENGTH: 14
<212> TYPE: PRT
<213> ORGANISM: Homo sapiens

<400> SEQUENCE: 346

Ser Lys Leu Thr Glu Asn Leu Val Ala Leu Lys Glu Ile Arg
1               5                   10

<210> SEQ ID NO 347
<211> LENGTH: 28
<212> TYPE: PRT
<213> ORGANISM: Homo sapiens

<400> SEQUENCE: 347

Ser Pro Gly Gln Pro Ile Gln Val Val Tyr Val Pro Ser His Leu Tyr
1               5                   10                  15

His Met Val Phe Glu Leu Phe Lys Asn Ala Met Arg
            20                  25
```

<210> SEQ ID NO 348
<211> LENGTH: 16
<212> TYPE: PRT
<213> ORGANISM: Homo sapiens

<400> SEQUENCE: 348

Asp Leu Lys Pro Ser Asn Ile Phe Phe Thr Met Asp Val Val Lys
1               5                   10                  15

<210> SEQ ID NO 349
<211> LENGTH: 8
<212> TYPE: PRT
<213> ORGANISM: Homo sapiens

<400> SEQUENCE: 349

Leu Val Ala Leu Lys Val Ile Arg
1               5

<210> SEQ ID NO 350
<211> LENGTH: 16
<212> TYPE: PRT
<213> ORGANISM: Homo sapiens

<400> SEQUENCE: 350

Asp Leu Lys Pro Glu Asn Ile Leu Leu Asp Asp Met Asn Ile Lys
1               5                   10                  15

<210> SEQ ID NO 351
<211> LENGTH: 17
<212> TYPE: PRT
<213> ORGANISM: Homo sapiens

<400> SEQUENCE: 351

Ala Thr Gly His Glu Phe Ala Val Lys Ile Met Glu Val Thr Ala Glu
1               5                   10                  15
Arg

<210> SEQ ID NO 352
<211> LENGTH: 14
<212> TYPE: PRT
<213> ORGANISM: Homo sapiens

<400> SEQUENCE: 352

Ser Glu Glu Pro Tyr Gly Gln Leu Asn Pro Lys Trp Thr Lys
1               5                   10

<210> SEQ ID NO 353
<211> LENGTH: 16
<212> TYPE: PRT
<213> ORGANISM: Homo sapiens

<400> SEQUENCE: 353

Ser Gly Thr Pro Met Gln Ser Ala Ala Lys Ala Pro Tyr Leu Ala Lys
1               5                   10                  15

<210> SEQ ID NO 354
<211> LENGTH: 14
<212> TYPE: PRT
<213> ORGANISM: Homo sapiens

<400> SEQUENCE: 354

Val Pro His Thr Gln Ala Val Val Leu Asn Ser Lys Asp Lys
1               5                   10

<210> SEQ ID NO 355
<211> LENGTH: 20
<212> TYPE: PRT
<213> ORGANISM: Homo sapiens

<400> SEQUENCE: 355

Val Ile Phe Lys Cys Gly Asp Asp Leu Arg Gln Asp Met Leu Thr Leu
1               5                   10                  15

Gln Met Ile Arg
            20

<210> SEQ ID NO 356
<211> LENGTH: 18
<212> TYPE: PRT
<213> ORGANISM: Homo sapiens

<400> SEQUENCE: 356

Thr Glu Asp Gly Gly Lys Tyr Pro Val Ile Phe Lys His Gly Asp Asp
1               5                   10                  15

Leu Arg

<210> SEQ ID NO 357
<211> LENGTH: 28
<212> TYPE: PRT
<213> ORGANISM: Homo sapiens

<400> SEQUENCE: 357

Val Phe Gly Glu Asp Ser Val Gly Val Ile Phe Lys Asn Gly Asp Asp
1               5                   10                  15

Leu Arg Gln Asp Met Leu Thr Leu Gln Met Leu Arg
            20                  25

<210> SEQ ID NO 358
<211> LENGTH: 14
<212> TYPE: PRT
<213> ORGANISM: Homo sapiens

<400> SEQUENCE: 358

Val Asn Trp Leu Ala His Asn Val Ser Lys Asp Asn Arg Gln
1               5                   10

<210> SEQ ID NO 359
<211> LENGTH: 9
<212> TYPE: PRT
<213> ORGANISM: Homo sapiens

<400> SEQUENCE: 359

Lys Lys Pro Leu Trp Leu Glu Phe Lys
1               5

<210> SEQ ID NO 360
<211> LENGTH: 18
<212> TYPE: PRT
<213> ORGANISM: Homo sapiens

<400> SEQUENCE: 360

Ala Lys Glu Leu Pro Thr Leu Lys Asp Asn Asp Phe Ile Asn Glu Gly
1               5                   10                  15

Gln Lys

<210> SEQ ID NO 361
<211> LENGTH: 28

<212> TYPE: PRT
<213> ORGANISM: Homo sapiens

<400> SEQUENCE: 361

Thr Leu Val Ile Lys Glu Val Ser Ser Glu Asp Ile Ala Asp Met His
1               5                   10                  15

Ser Asn Leu Ser Asn Tyr His Gln Tyr Ile Val Lys
            20                  25

<210> SEQ ID NO 362
<211> LENGTH: 19
<212> TYPE: PRT
<213> ORGANISM: Homo sapiens

<400> SEQUENCE: 362

Gly Gly Lys Ser Gly Ala Ala Phe Tyr Ala Thr Glu Asp Asp Arg Phe
1               5                   10                  15

Ile Leu Lys

<210> SEQ ID NO 363
<211> LENGTH: 16
<212> TYPE: PRT
<213> ORGANISM: Homo sapiens

<400> SEQUENCE: 363

Asp Leu Lys Thr Ser Asn Leu Leu Ser His Ala Gly Ile Leu Lys
1               5                   10                  15

<210> SEQ ID NO 364
<211> LENGTH: 16
<212> TYPE: PRT
<213> ORGANISM: Homo sapiens

<400> SEQUENCE: 364

Asp Leu Lys Leu Asp Asn Val Met Leu Asp Ser Glu Gly His Ile Lys
1               5                   10                  15

<210> SEQ ID NO 365
<211> LENGTH: 16
<212> TYPE: PRT
<213> ORGANISM: Homo sapiens

<400> SEQUENCE: 365

Asp Leu Lys Leu Asp Asn Ile Leu Leu Asp Ala Glu Gly His Cys Lys
1               5                   10                  15

<210> SEQ ID NO 366
<211> LENGTH: 8
<212> TYPE: PRT
<213> ORGANISM: Homo sapiens

<400> SEQUENCE: 366

Ile Tyr Ala Met Lys Val Val Lys
1               5

<210> SEQ ID NO 367
<211> LENGTH: 9
<212> TYPE: PRT
<213> ORGANISM: Homo sapiens

<400> SEQUENCE: 367

Asp Val Ala Val Lys Val Ile Asp Lys
1               5

<210> SEQ ID NO 368
<211> LENGTH: 19
<212> TYPE: PRT
<213> ORGANISM: Homo sapiens

<400> SEQUENCE: 368

Val Leu Leu Ser Glu Phe Arg Pro Ser Gly Glu Leu Phe Ala Ile Lys
1               5                   10                  15

Ala Leu Lys

<210> SEQ ID NO 369
<211> LENGTH: 13
<212> TYPE: PRT
<213> ORGANISM: Homo sapiens

<400> SEQUENCE: 369

Asp Leu Lys Pro Ser Asn Ile Phe Leu Val Asp Thr Lys
1               5                   10

<210> SEQ ID NO 370
<211> LENGTH: 20
<212> TYPE: PRT
<213> ORGANISM: Homo sapiens

<400> SEQUENCE: 370

Cys Phe Glu Ile Ser Asp Ala Asp Thr Lys Glu Val Phe Ala Gly Lys
1               5                   10                  15

Ile Val Pro Lys
            20

<210> SEQ ID NO 371
<211> LENGTH: 18
<212> TYPE: PRT
<213> ORGANISM: Homo sapiens

<400> SEQUENCE: 371

Ala Glu Ser Ile His Thr Gly Leu Glu Val Ala Ile Lys Met Ile Asp
1               5                   10                  15

Lys Lys

<210> SEQ ID NO 372
<211> LENGTH: 19
<212> TYPE: PRT
<213> ORGANISM: Homo sapiens

<400> SEQUENCE: 372

Cys Asn Ile Leu His Ala Asp Ile Lys Pro Asp Asn Ile Leu Val Asn
1               5                   10                  15

Glu Ser Lys

<210> SEQ ID NO 373
<211> LENGTH: 15
<212> TYPE: PRT
<213> ORGANISM: Homo sapiens

<400> SEQUENCE: 373

Phe Leu Ser Gly Leu Glu Leu Val Lys Gln Gly Ala Glu Ala Arg
1               5                   10                  15

<210> SEQ ID NO 374
<211> LENGTH: 14
<212> TYPE: PRT

<213> ORGANISM: Homo sapiens

<400> SEQUENCE: 374

Tyr Ile Glu Asp Glu Asp Tyr Tyr Lys Ala Ser Val Thr Arg
1               5                   10

<210> SEQ ID NO 375
<211> LENGTH: 16
<212> TYPE: PRT
<213> ORGANISM: Homo sapiens

<400> SEQUENCE: 375

Asp Leu Lys Pro Glu Asn Ile Leu Val Asp Asn Asp Phe His Ile Lys
1               5                   10                  15

<210> SEQ ID NO 376
<211> LENGTH: 16
<212> TYPE: PRT
<213> ORGANISM: Homo sapiens

<400> SEQUENCE: 376

Asp Leu Lys Pro Ser Asn Val Leu Leu Asp Pro Glu Leu His Val Lys
1               5                   10                  15

<210> SEQ ID NO 377
<211> LENGTH: 11
<212> TYPE: PRT
<213> ORGANISM: Homo sapiens

<400> SEQUENCE: 377

Asp Val Lys Pro Asp Asn Met Leu Leu Asp Lys
1               5                   10

<210> SEQ ID NO 378
<211> LENGTH: 31
<212> TYPE: PRT
<213> ORGANISM: Homo sapiens

<400> SEQUENCE: 378

Asp Leu Lys Pro Glu Asn Ile Leu Leu Asp Glu Glu Gly His Ile Lys
1               5                   10                  15
Leu Thr Asp Phe Gly Leu Ser Lys Glu Ala Ile Asp His Glu Lys
                20                  25                  30

<210> SEQ ID NO 379
<211> LENGTH: 16
<212> TYPE: PRT
<213> ORGANISM: Homo sapiens

<400> SEQUENCE: 379

Asp Leu Lys Pro Glu Asn Ile Leu Leu Asp Glu Glu Gly His Ile Lys
1               5                   10                  15

<210> SEQ ID NO 380
<211> LENGTH: 20
<212> TYPE: PRT
<213> ORGANISM: Homo sapiens

<400> SEQUENCE: 380

Asp Leu Lys Pro Ser Asn Ile Leu Tyr Val Asp Glu Ser Gly Asn Pro
1               5                   10                  15
Glu Cys Leu Arg
            20

<210> SEQ ID NO 381
<211> LENGTH: 31
<212> TYPE: PRT
<213> ORGANISM: Homo sapiens

<400> SEQUENCE: 381

Asp Leu Lys Pro Glu Asn Ile Leu Leu Asp Glu Glu Gly His Ile Lys
1               5                   10                  15

Leu Thr Asp Phe Gly Leu Ser Lys Glu Ser Ile Asp His Glu Lys
            20                  25                  30

<210> SEQ ID NO 382
<211> LENGTH: 20
<212> TYPE: PRT
<213> ORGANISM: Homo sapiens

<400> SEQUENCE: 382

Asp Leu Lys Pro Ser Asn Ile Leu Tyr Val Asp Glu Ser Gly Asn Pro
1               5                   10                  15

Glu Ser Ile Arg
            20

<210> SEQ ID NO 383
<211> LENGTH: 24
<212> TYPE: PRT
<213> ORGANISM: Homo sapiens

<400> SEQUENCE: 383

Asp Leu Lys Pro Glu Asn Ile Leu Leu Asp Glu Glu Gly His Ile Lys
1               5                   10                  15

Ile Thr Asp Phe Gly Leu Ser Lys
            20

<210> SEQ ID NO 384
<211> LENGTH: 15
<212> TYPE: PRT
<213> ORGANISM: Homo sapiens

<400> SEQUENCE: 384

Val Leu Gly Val Ile Asp Lys Val Leu Leu Val Met Asp Thr Arg
1               5                   10                  15

<210> SEQ ID NO 385
<211> LENGTH: 9
<212> TYPE: PRT
<213> ORGANISM: Homo sapiens

<400> SEQUENCE: 385

Phe Tyr Ala Val Lys Val Leu Gln Lys
1               5

<210> SEQ ID NO 386
<211> LENGTH: 16
<212> TYPE: PRT
<213> ORGANISM: Homo sapiens

<400> SEQUENCE: 386

Asp Leu Lys Ala Gly Asn Ile Leu Phe Thr Leu Asp Gly Asp Ile Lys
1               5                   10                  15

<210> SEQ ID NO 387
<211> LENGTH: 22
<212> TYPE: PRT

<213> ORGANISM: Homo sapiens

<400> SEQUENCE: 387

Asp Thr Val Thr Ile His Ser Val Gly Gly Thr Ile Thr Ile Leu Pro
1               5                   10                  15

Thr Lys Thr Lys Pro Lys
            20

<210> SEQ ID NO 388
<211> LENGTH: 12
<212> TYPE: PRT
<213> ORGANISM: Homo sapiens

<400> SEQUENCE: 388

Asp Leu Lys Pro Glu Asn Val Val Phe Phe Glu Lys
1               5                   10

<210> SEQ ID NO 389
<211> LENGTH: 25
<212> TYPE: PRT
<213> ORGANISM: Homo sapiens

<400> SEQUENCE: 389

Val Ala Ile Lys Thr Leu Lys Pro Gly Thr Met Ser Pro Glu Ala Phe
1               5                   10                  15

Leu Gln Glu Ala Gln Val Met Lys Lys
            20                  25

<210> SEQ ID NO 390
<211> LENGTH: 21
<212> TYPE: PRT
<213> ORGANISM: Homo sapiens

<400> SEQUENCE: 390

Ile Ile His Thr Asp Ile Lys Pro Glu Asn Ile Leu Leu Ser Val Asn
1               5                   10                  15

Glu Gln Tyr Ile Arg
            20

<210> SEQ ID NO 391
<211> LENGTH: 8
<212> TYPE: PRT
<213> ORGANISM: Homo sapiens

<400> SEQUENCE: 391

Phe Val Ala Met Lys Val Val Lys
1               5

<210> SEQ ID NO 392
<211> LENGTH: 10
<212> TYPE: PRT
<213> ORGANISM: Homo sapiens

<400> SEQUENCE: 392

Asp Leu Lys Leu Glu Asn Ile Met Val Lys
1               5                   10

<210> SEQ ID NO 393
<211> LENGTH: 24
<212> TYPE: PRT
<213> ORGANISM: Homo sapiens

<400> SEQUENCE: 393

Tyr Ser Val Lys Val Leu Pro Trp Leu Ser Pro Glu Val Leu Gln Gln
1               5                   10                  15

Asn Leu Gln Gly Tyr Asp Ala Lys
            20

<210> SEQ ID NO 394
<211> LENGTH: 11
<212> TYPE: PRT
<213> ORGANISM: Homo sapiens

<400> SEQUENCE: 394

Ile Ser Asp Phe Gly Leu Ser Lys Ala Leu Arg
1               5                   10

<210> SEQ ID NO 395
<211> LENGTH: 17
<212> TYPE: PRT
<213> ORGANISM: Homo sapiens

<400> SEQUENCE: 395

Asp Leu Lys Pro Pro Asn Leu Leu Leu Val Ala Gly Gly Thr Val Leu
1               5                   10                  15

Lys

<210> SEQ ID NO 396
<211> LENGTH: 16
<212> TYPE: PRT
<213> ORGANISM: Homo sapiens

<400> SEQUENCE: 396

Asp Ile Lys Ala Gly Asn Ile Leu Leu Thr Glu Pro Gly Gln Val Lys
1               5                   10                  15

<210> SEQ ID NO 397
<211> LENGTH: 16
<212> TYPE: PRT
<213> ORGANISM: Homo sapiens

<400> SEQUENCE: 397

Asp Val Lys Ala Gly Asn Ile Leu Leu Ser Glu Pro Gly Leu Val Lys
1               5                   10                  15

<210> SEQ ID NO 398
<211> LENGTH: 24
<212> TYPE: PRT
<213> ORGANISM: Homo sapiens

<400> SEQUENCE: 398

Thr Gly Asp Leu Phe Ala Ile Lys Val Phe Asn Asn Ile Ser Phe Leu
1               5                   10                  15

Arg Pro Val Asp Val Gln Met Arg
            20

<210> SEQ ID NO 399
<211> LENGTH: 18
<212> TYPE: PRT
<213> ORGANISM: Homo sapiens

<400> SEQUENCE: 399

Tyr Val Leu Asp Asp Gln Tyr Thr Ser Ser Gly Ala Lys Phe Pro
1               5                   10                  15

Val Lys

```
<210> SEQ ID NO 400
<211> LENGTH: 31
<212> TYPE: PRT
<213> ORGANISM: Homo sapiens

<400> SEQUENCE: 400

Tyr Leu Asn Glu Ile Lys Pro Pro Ile Ile His Tyr Asp Leu Lys Pro
 1               5                  10                  15

Gly Asn Ile Leu Leu Val Asp Gly Thr Ala Cys Gly Glu Ile Lys
            20                  25                  30

<210> SEQ ID NO 401
<211> LENGTH: 31
<212> TYPE: PRT
<213> ORGANISM: Homo sapiens

<400> SEQUENCE: 401

Tyr Leu Asn Glu Ile Lys Pro Pro Ile Ile His Tyr Asp Leu Lys Pro
 1               5                  10                  15

Gly Asn Ile Leu Leu Val Asn Gly Thr Ala Cys Gly Glu Ile Lys
            20                  25                  30

<210> SEQ ID NO 402
<211> LENGTH: 15
<212> TYPE: PRT
<213> ORGANISM: Homo sapiens

<400> SEQUENCE: 402

Asp Leu Lys Pro Gln Asn Ile Leu Leu Ser Asn Pro Ala Gly Arg
 1               5                  10                  15

<210> SEQ ID NO 403
<211> LENGTH: 23
<212> TYPE: PRT
<213> ORGANISM: Homo sapiens

<400> SEQUENCE: 403

Asn Ile Ser His Leu Asp Leu Lys Pro Gln Asn Ile Leu Leu Ser Ser
 1               5                  10                  15

Leu Glu Lys Pro His Leu Lys
            20

<210> SEQ ID NO 404
<211> LENGTH: 28
<212> TYPE: PRT
<213> ORGANISM: Homo sapiens

<400> SEQUENCE: 404

Met Leu Asp Val Leu Glu Tyr Ile His Glu Asn Glu Tyr Val His Gly
 1               5                  10                  15

Asp Ile Lys Ala Ala Asn Leu Leu Leu Gly Tyr Lys
            20                  25

<210> SEQ ID NO 405
<211> LENGTH: 8
<212> TYPE: PRT
<213> ORGANISM: Homo sapiens

<400> SEQUENCE: 405

Gly Ser Phe Lys Thr Val Tyr Lys
 1               5
```

<210> SEQ ID NO 406
<211> LENGTH: 17
<212> TYPE: PRT
<213> ORGANISM: Homo sapiens

<400> SEQUENCE: 406

Asp Leu Lys Cys Asp Asn Ile Phe Ile Thr Gly Pro Thr Gly Ser Val
1               5                   10                  15

Lys

<210> SEQ ID NO 407
<211> LENGTH: 12
<212> TYPE: PRT
<213> ORGANISM: Homo sapiens

<400> SEQUENCE: 407

Asp Val Lys Pro Asp Asn Ile Leu Leu Asp Glu Arg
1               5                   10

<210> SEQ ID NO 408
<211> LENGTH: 12
<212> TYPE: PRT
<213> ORGANISM: Homo sapiens

<400> SEQUENCE: 408

Trp Ile Ser Gln Asp Lys Glu Val Ala Val Lys Lys
1               5                   10

<210> SEQ ID NO 409
<211> LENGTH: 20
<212> TYPE: PRT
<213> ORGANISM: Homo sapiens

<400> SEQUENCE: 409

Ile Ser Asp Phe Gly Leu Ser Lys Ala Leu Gly Ala Asp Asp Ser Tyr
1               5                   10                  15

Tyr Thr Ala Arg
            20

<210> SEQ ID NO 410
<211> LENGTH: 16
<212> TYPE: PRT
<213> ORGANISM: Homo sapiens

<400> SEQUENCE: 410

Asp Ile Lys Gly Gln Asn Val Leu Leu Thr Glu Asn Ala Glu Val Lys
1               5                   10                  15

<210> SEQ ID NO 411
<211> LENGTH: 29
<212> TYPE: PRT
<213> ORGANISM: Homo sapiens

<400> SEQUENCE: 411

Thr Gly Gln Leu Ala Ala Ile Lys Val Met Asp Val Thr Gly Asp Glu
1               5                   10                  15

Glu Glu Glu Ile Lys Gln Glu Ile Asn Met Leu Lys Lys
            20                  25